("(12) United States Patent") Miyazaki et al.

(10) Patent No.: US 7,879,616 B2
(45) Date of Patent: Feb. 1, 2011

(54) METHOD FOR ANALYZING C-TERMINAL AMINO ACID SEQUENCE OF PEPTIDE USING MASS SPECTROMETRY

(75) Inventors: Kenji Miyazaki, Tokyo (JP); Akira Tsugita, Tokyo (JP); Kenichi Kamijo, Tokyo (JP); Hiroaki Torii, Tokyo (JP)

(73) Assignee: NEC Corporation, Tokyo (JP)

( * ) Notice: Subject to any disclaimer, the term of this patent is extended or adjusted under 35 U.S.C. 154(b) by 769 days.

(21) Appl. No.: 10/540,814

(22) PCT Filed: Dec. 25, 2003

(86) PCT No.: PCT/JP03/16748

§ 371 (c)(1),
(2), (4) Date: Jan. 9, 2006

(87) PCT Pub. No.: WO2004/059323

PCT Pub. Date: Jul. 15, 2004

(65) Prior Publication Data

US 2006/0134720 A1 Jun. 22, 2006

(30) Foreign Application Priority Data

Dec. 26, 2002 (JP) ............................. 2002-378050
Feb. 13, 2003 (JP) ............................. 2003-034943

(51) Int. Cl.
*G01N 33/00* (2006.01)

(52) U.S. Cl. .............................. 436/89; 436/86; 436/90; 435/23; 530/345

(58) Field of Classification Search .................. None
See application file for complete search history.

(56) References Cited

U.S. PATENT DOCUMENTS 5,952,653 A * 9/1999 Covey et al. ................. 250/288

FOREIGN PATENT DOCUMENTS

| JP | 06-102251 | 4/1994 |
|---|---|---|
| JP | 2002-505740 | 2/2002 |
| JP | 2002-168869 | 6/2002 |
| JP | 2002-535659 | 10/2002 |
| WO | WO 03/081255 A1 | 10/2003 |

OTHER PUBLICATIONS

Tsugita, Akira et. al. , Additional possible tools for identification of proteins on one- or two-dimensional electrophoresis, 1998, Electrophoresis, vol. 19, pp. 928-938.*

(Continued)

*Primary Examiner*—Yelena G Gakh
*Assistant Examiner*—Robert Xu
(74) *Attorney, Agent, or Firm*—Scully, Scott, Murphy & Presser, P.C.

(57) ABSTRACT

The present invention provides a method for analyzing the C-terminal amino acid sequence of a peptide by using a reaction for successively releasing the C-terminal amino acids of the peptide, which method can suppress, when successively releasing the C-terminal amino acids of a peptide of long amino acid length, such a undesirable side reaction as cleavage of peptide bond in the intermediate position of the peptide and can carry out the chemical treatment thereof under widely applicable conditions; In the method, a dry sample of a peptide with long amino acid length is beforehand subjected to an N-acylation treatment; by using a reaction reagent where an alkanoic acid anhydride is combined with a small amount of a perfluoroalkanoic acid, successive release of C-terminal amino acids is conducted under mild conditions; a hydrolysis treatment is applied; then, selective fragmentization at site of arginine residue is performed by digestion by trypsin; thereafter, decreases in molecular weight are measured for the C-terminal side fragments derived from a series of reaction products with use of a MALDI-TOF-MS apparatus; thereby, the C-terminal amino acid sequence of the peptide sample is identified.

14 Claims, 9 Drawing Sheets

---

C-terminal Truncation Reaction

Sample: N-acetyl-Glu¹-Fibrino peptide
Ac-EGVNDNEEGFFSAR

Positive mode

Negative mode

OTHER PUBLICATIONS

Vogt, S. et al., Effective esterification of carboxymethyl cellulose in a new non-aqueous swelling system, 1996, Polymer Bulletin, vol. 36, p. 549-555.*

Xu, Naxing, et al., Structural characterization of peptidoglycan muropeptides by marix-assisted laser desorption ionization mass spectrometry and postsorce decay analysis, 1997, analytical biochemisry, vol. 248, pp. 7-14.*

Harris, William A., et al., Use of matrix clusters and trypsin autolysis fragments as mass calibrants in matrix-assisted laser desorption/ionizaton time-of-flight mass spectrometry, 2002, Rapid Communicaitons in Mass Spectrometry, vol. 16, pp. 1714-1722.*

Miyazaki K. et al., "'Musui Sakusan Joki Ni Yoru C Mattan Hairetsu Kaiseki', Seikagaku", 74(8):739 (2002).

Tsugita A. et al., "C-Terminal Sequencing of Protein-A Novel Partial Acid Hydrolysis and Analysis by Mass Spectrometry", *Eur. J. Biochem.* 206:691-696 (1992).

Tsugita A. et al., "Reaction of Pentafluoropropionic Anhydride Vapor on Polypeptide as Revealed by Mass Spectrometry. A Carboxypeptidase Mimetic Degradation", *Chemistry Letters*, 235-238 (1992).

Takamoto K. et al., "Carboxy-Terminal Degradation of Peptides Using Perfluoroacyl Anhydrides A C-Terminal Sequencing Method", *Eur. J. Biochem.*, 228:362-372 (1995).

Miyazaki Kenji et al., "C-terminal Sequencing Method for Proteins in Polyacrylamide Gel by the Reaction of Acetic Anhydride", Promotecs, vol. 6, pp. 2026-2033 (2006).

Torii H., et al., "An Algorithm for the MS Analysis of Successive C-terminal Amino Acid Truncation Reaction", SEIKAQ, vol. 76, No. 8, p. 995 (2004).

* cited by examiner

Fig. 2
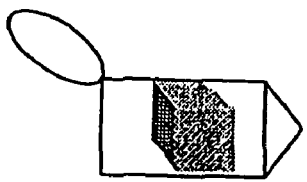
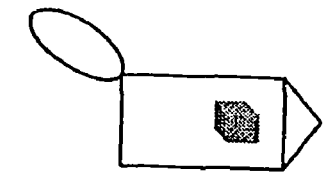
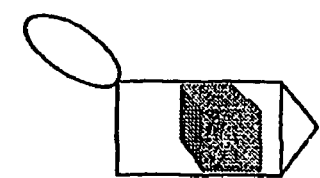

Fig. 7 myoglobin – horse

[1 – 153] mass = 17738.180
Cleavage at R

Small polar : D(7)    E(13)    N(3)    Q(6)
Large polar : K(19)   R(2)     H(11)
Small non-polar : S(5)    T(7)    A(15)   G(15)
Large non-polar : L(17)   I(9)    V(7)    M(2)   F(7)   Y(2)   W(2)
Special : C(0)    P(4)

| K[16] + 42.04  | K[42] + 42.04  | K[45] + 42.04  | K[47] + 42.04  |
| K[50] + 42.04  | K[56] + 42.04  | K[62] + 42.04  | K[63] + 42.04  |
| K[77] + 42.04  | K[78] + 42.04  | K[79] + 42.04  | K[87] + 42.04  |
| K[96] + 42.04  | K[98] + 42.04  | K[102] + 42.04 | K[118] + 42.04 |
| K[133] + 42.04 | K[145] + 42.04 | K[147] + 42.04 |                |

```
  1 G L S D G E W Q Q V L N V W G K V E A D I A G H G Q E V L I    30
 31 R l f t g h p e t l e K f d K f K h l K t e a e m K a s e d   60
 61 l K K h g t v v l t a l g g i l K K g h h e a e l K p l a     90
 91 q s h a t K h K i p i K y l e f i s d a i i h v l h s K h p  120
121 g n f g a d a q g a m t K a l e l f r N D I A A K Y K E L G  150
151 F Q G                                                        153
```

(1) [1-31] = 3444.742    (2) [32-139] = 12692.649    (3) [140-153] = 1636.809

Fig. 8
C-terminal Truncation Reaction
Sample: N-acetyl-Glu¹-Fibrino peptide
Ac-EGVNDNEEGFFSAR 
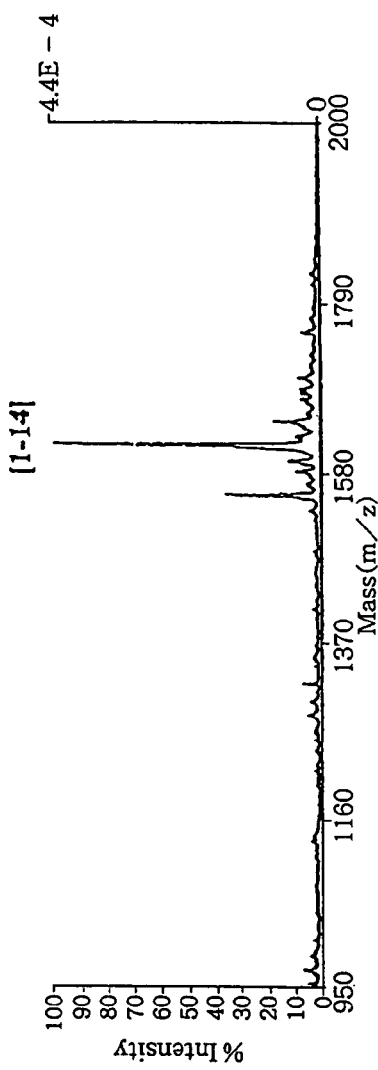
Positive mode
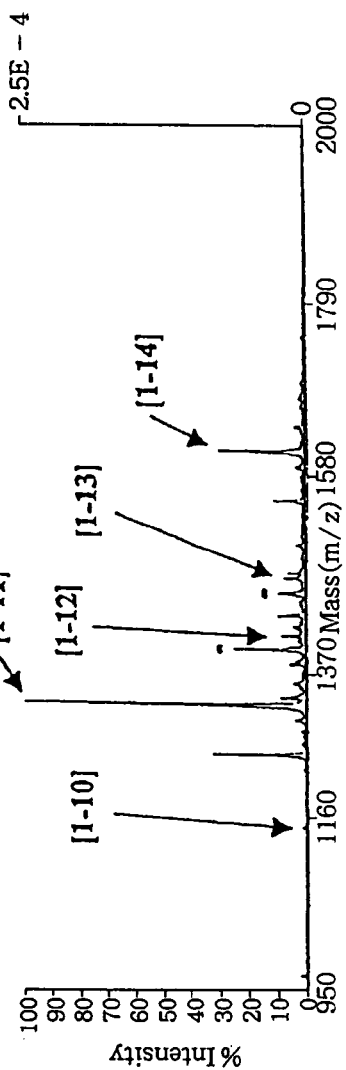
Negative mode

Fig. 9

List of Molecular weight (M+H)
of Fragment derived from Trypsin by Autolysis

| | |
|---|---|
| 758.4637 | 4860.3449 |
| 842.5100 | 4971.5791 |
| 906.5049 | 5152.3371 |
| 1006.4879 | 5228.5621 |
| 1045.5642 | 5501.8127 |
| 1469.7310 | 5618.6354 |
| 1736.8430 | 6039.8236 |
| 1768.7998 | 6139.8067 |
| 1859.0558 | |
| 2158.0313 | |
| 2211.1046 | |
| 2283.1807 | |
| 2457.2005 | |
| 2592.2914 | |
| 2624.3295 | |
| 2707.4168 | |
| 2950.5499 | |
| 3013.3243 | |
| 3145.5008 | |
| 3219.5124 | |
| 3309.7265 | |
| 3618.8372 | |
| 3900.8108 | |
| 4043.0040 | |
| 4133.2181 | |
| 4206.9820 | |
| 4475.2669 | |
| 4489.1168 | |
| 4596.2134 | |
| 4617.2117 | |
| 4732.2499 | | note: Further peaks may be optionally observed at M+H+14 or M+H+28 which are due to methylation on Lysine residue. In addition, M+H being more than 3,500 is generally out of detectable range, but ion species from autolysis products having such a large molecular weight may be occasionally detected as ion species with Z=2 or 3 within the range of 3,500 or less. Thus, the peaks with M+H > 3,500 are also summarized in the list.

METHOD FOR ANALYZING C-TERMINAL AMINO ACID SEQUENCE OF PEPTIDE USING MASS SPECTROMETRY

TECHNICAL FIELD

The present invention relates to a method for analysis of C-terminal amino acid sequence of peptide, more typically to a method comprising steps of releasing the C-terminal amino acids of a peptide successively by chemical technique, determining the molecular weights of the reaction products obtained therefrom by mass spectrometry, and identifying the C-terminal amino acid sequence of the peptide, for example, a peptide having a large number of amino acid residues, such as protein, based on the decreases in molecular weight that are caused by a series of amino acids eliminated successively. Particularly, the present invention relates to a technique for analysis of mass spectra, which can be usable, in the method for analysis of C-terminal amino acid sequence of peptide, for the process for assigning, based on the observed mass spectra, the peaks of the ion species derived from reaction products that show the decreases in molecular weight resulted from a series of amino acids eliminated successively to identify the C-terminal amino acid sequence of the peptide.

BACKGROUND ART

With respect to peptides and proteins collected from nature, the identification of their amino acid sequences are essential information to make a study of the biological properties and functions of the peptides and proteins in question. Currently, the full-length amino acid sequences for peptides and proteins are determined as deduced amino acid sequences, based on corresponding gene information thereof, for instance, nucleotide sequences of the genomic genes or c-DNAs produced from m-RNAs which encode their peptides. However, in identifying the genomic genes or the c-DNAs produced from m-RNAs which encode these peptides, the knowledge of partial amino acid sequences of the peptides is still required.

It is generally considered that, as the knowledge of the partial amino acid sequences of peptide, the N-terminal amino acid sequence and C-terminal amino acid sequence of peptide are particularly useful. Specifically, for example, in selecting a c-DNA which encodes an aimed peptide from a c-DNA library prepared from a large number of m-RNAs, if the N-terminal amino acid sequence and C-terminal amino acid sequence thereof are known, the aimed c-DNA can be selected by using nucleic acid probes that are produced based on said amino acid sequences of the two termini. Alternatively, the aimed c-DNA can be amplified selectively by applying PCR with use of oligonucleotide primers that are produced based on the amino acid sequences of the two termini.

As the method for analyzing the N-terminal amino acid sequence of a peptide, there has been conventionally used a method of subjecting a pure peptide sample obtained by isolation and purification to Edman degradation to successively degrade the N-terminal amino acids therefrom and identify the resulting amino acid derivatives. Meanwhile, as the method for analyzing the C-terminal amino acid sequence of a peptide, there has been proposed a method comprising steps of releasing the C-terminal amino acids successively from such a pure peptide sample by means of chemical technique and identifying the C-terminal amino acids released thereby, based on the molecular weight differences between the original peptide and truncated peptides that are obtained as reaction products therefrom. As the process for releasing the C-terminal amino acids successively by means of chemical technique, there is proposed, for example, a process comprising steps of allowing a vapor generated from a high concentration aqueous solution of pentafluoropropanoic acid ($CF_3CF_2COOH$) or a high concentration aqueous solution of heptafluorobutanoic acid ($CF_3CF_2CF_2COOH$), to act on a dried pure peptide sample under heating up condition of at 90° C., and thereby carrying out selective hydrolysis of the C-terminal amino acids, which is enhanced by said perfluoroalkanoic acid [Tsugita, A. et al., Eur. J. Biochem. 206, 691-696 (1992)]. In addition, there is also proposed a process using, in place of said high concentration aqueous solution of a perfluoroalkanoic acid, a solution of pentafluoropropanoic acid anhydride [$(CF_3CF_2CO)_2O$] in acetonitrile or a solution of heptafluorobutanoic acid anhydride [$(CF_3CF_2CF_2CO)_2O$] in acetonitrile, which process comprises steps of allowing a vapor generated from the solution, to act on a dried peptide under cooling down condition, for example, at −18° C., and thereby conducting selective release of the C-terminal amino acids, which is forced by said perfluoroalkanoic acid anhydride [Tsugita, A. et al., Chem. Lett. 1992, 235-238; Takamoto, K. et al., Eur. J. Biochem. 228, 362-372 (1995)].

In said method for selectively releasing the C-terminal amino acids by allowing a perfluoroalkanoic acid or a perfluoroalkanoic acid anhydride, which are supplied in vapor phase as a vapor thereof, to act on a dried pure peptide sample, it has been reported that an oxazolone ring structure is once formed from the C-terminal amino acids, as a reaction intermediate, through a dehydration reaction shown by the following reaction scheme (I):

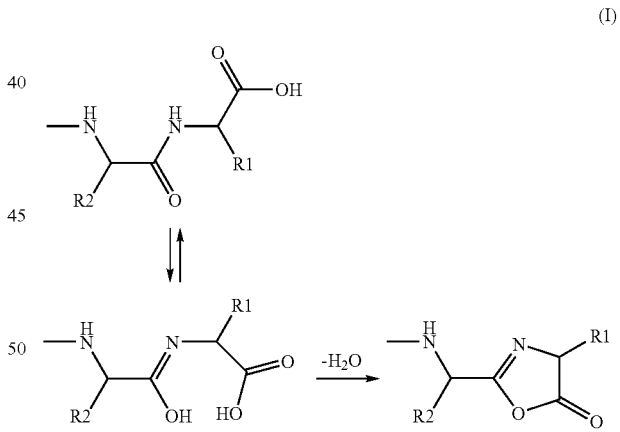

and then, the perfluoroalkanoic acid acts on the oxazolone ring to give rise to a reaction shown by the following reaction scheme (II):

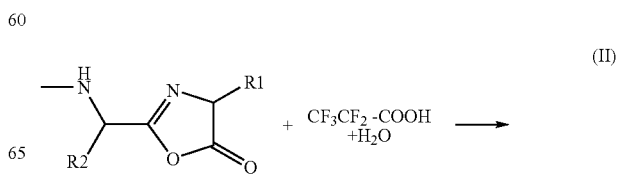

-continued

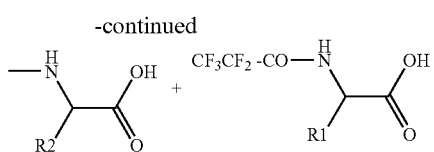

as a result, reaction of selectively releasing the C-terminal amino acids therefrom is achieved.

As the above reaction of selectively releasing the C-terminal amino acid proceeds successively, there is obtained, at a timing when a given treatment time has passed, a mixture comprising a series of reaction products in which one to ten odd amino acid residues have been removed from the C-terminus of the original peptide, respectively. This mixture comprising a series of reaction products is subjected to mass spectrometry to measure the masses of the ion species derived from the reaction products, whereby can be obtained a series of peaks exhibiting the mass differences, which reflect the C-terminal amino acid sequence. Specifically explaining, the individual reaction products are formed in reaction of successively releasing the C-terminal amino acids from the original peptide; hence, for example, a set of reaction products including several members in series, where up to several amino acid residues have been removed from the original peptide, are subjected to mass spectrometry and, thereby, the masses of corresponding ion species thereto can be analyzed collectively, which enables determination of C-terminal amino acid sequence of such several amino acid residues at one time.

Incidentally, for example, the information of C-terminal amino acid sequence used in production of nucleic acid probe or primer may originally be, in terms of the nucleotide sequence which codes such amino acid sequence, about 18 to 24 bases and accordingly about 6 to 8 amino acids. The identification of C-terminal amino acid sequence of up to ten odd amino acid residues is required only in very rare cases. Therefore, the above methods for preparation of treated sample comprising a series of reaction products, in which all the removals extending up to 10 odd amino acid residues are included, by the reaction of releasing the C-terminal amino acids from the dried peptide, where a vapor of a perfluoroalkanoic acid or a perfluoroalkanoic acid anhydride are supplied in vapor phase and allowed to act thereon, are suitable for the above-mentioned purposes.

DISCLOSURE OF THE INVENTION

Meanwhile, when a peptide to be examined is, for example, a peptide having a large number of amino acid residues such as a protein, the molecular weight of the original peptide per se exceeds an molecular weight range to which mass spectrometry is applicable, or the change in formula weight due to one amino acid residue is relatively small in relation to the large molecular weight of the original peptide per se, which leads to the decreased accuracy of measurement of differences in molecular weight; therefore, in such a case, the following idea has been studied. Specifically explaining, used is the idea in such a form that the mixture containing a series of reaction products obtained by the above-mentioned reaction for successive release of C-terminal amino acids, in which products one to ten odd amino acid residues have been removed respectively from the C-terminus of an original peptide, is subjected to enzymatic digestion of long peptide chain by using a protease having a site selectivity for cleavage, e.g. trypsin, which is applicable for selective cleavage of a peptide chain at the specific amino acid sites thereof; thereafter, the peptide fragments resulting from are subjected to analysis by mass spectrometry. That is, in the mixture of peptide fragments obtained by application of such enzymatic digestion thereto, are included a C-terminal peptide fragments derived from the original peptide, and a group of C-terminal peptide fragments derived from the series of said reaction products in which one to ten odd amino acid residues have been removed respectively from the C-terminus thereof; by applying mass spectrometry to the group of the C-terminal peptide fragments derived from the original peptide as well as the series of reaction products, to measure the mass of each of the ion species of the C-terminal peptide fragments derived from the reaction products, there can be measured, at a sufficiently high resolution for molecular weight, a series of peaks exhibiting the differences in mass, which may reflect the C-terminal amino acid sequence in question.

Meanwhile, the above-mentioned methods comprising such steps of supplying a vapor of a perfluoroalkanoic acid or a perfluoroalkanoic acid anhydride in vapor phase and allowing them to act on a dried peptide are useful technique for identifying the C-terminal amino acid sequence thereof; however, when extending application of the methods as a procedure for a wide use, the methods have been found to have various practical problems described below, in the case where a peptide to be examined is a peptide having a large number of amino acid residues, such a protein.

The first problem is described. In the above-mentioned method with use of a high concentration aqueous solution of a perfluoroalkanoic acid, which allows a vapor of the perfluoroalkanoic acid to act on a dried peptide under heating up condition, for example, at 90° C., there may occur a side reaction in which, at the serine residue [—NH—CH(CH$_2$OH)—CO—] in the peptide, an N,O-acyl rearrangement reaction proceeds between the amino group (—NH—) on its α-position and the hydroxyl group (—OH) on its β-position, subsequently, hydrolysis proceeds, which results in cleavage of peptide taking place at the N-terminus of the serine residue. Depending upon the conditions used, there may also occur a side reaction in which, at the threonine residue [—NH—CH(CH(CH$_3$)OH)—CO—] having a hydroxyl group (—OH) on its β-position, hydrolysis proceeds through a similar mechanism, which results in cleavage of peptide taking place at the N-terminus of the threonine residue. There may further occur a side reaction in which, at the aspartic acid residue [—NH—CH(CH$_2$COOH)—CO—] in the peptide, peptide bond rearrangement from C-terminal carboxy group to carboxy group on its β-position and subsequent hydrolysis proceed, which results in cleavage of peptide taking place at the C-terminus of the aspartic acid residue.

When the cleavage of long peptide chain due to such side reactions happens to occur, selective release of C-terminal amino acids progresses simultaneously even as for the resulting N-terminal peptide fragments therefrom. On some occasions, the co-existence of reaction products that are originated from these side reactions may be a factor interfering with the measurement, when conducting analysis of intended reaction products by mass spectrometry.

Further, even when there occurs no cleavage of original peptide chain but when there is formed a branched type peptide wherein the N-terminal portion of peptide is linked to the hydroxyl group (—OH) on the β-position thereof, which leads to loss of amide bond at the site, there is no formation of oxazolone ring structure therefrom, and accordingly selective release of C-terminal amino acid makes no further progress thereafter.

On the other hand, in the above-mentioned method with use of an acetonitrile solution of a perfluoroalkanoic acid anhydride, which allows a vapor of the perfluoroalkanoic acid anhydride generated from the solution to act on a dried peptide under cooling down condition, for example, at −18° C., no water molecule being vaporized from the solution is present in said system and, therefore, the method has such an advantage that the occurrence of the above-mentioned side reactions can be avoided effectively. However, since the reactivity of the perfluoroalkanoic acid anhydride used is high, effective suppression of undesired side reactions is more difficult when the treatment temperature rises higher; therefore, the treatment temperature is required to be kept at such a low temperature as, for example, −18° C. In other words, when the control of the treatment temperature is not enough, there is a high possibility that undesired side reactions are advanced thereby; therefore, in this view, it may be considered that the method still has somewhat weakness in the wide applicability and leaves a room to be improved further. In addition, when water condensation takes place in association with cooling, the resulting water gives rise to deterioration of the reagent used, i.e. deactivation of the perfluoroalkanoic acid anhydride used, which may result in a reduced reactivity on occasion, and thus there remains some anxiety that it may happen to become a serious problem in practical application.

The second problem is described. In the case where a peptide to be examined is a peptide having a large number of amino acid residues, such as a protein, it has been studied to employ such a manner in which after the reaction for releasing the C-terminal amino acids of the peptide selectively is finished, the treatment for enzymatic digestion by using a protease having a site selectivity for cleavage is added, and then measurement of the molecular weights of the C-terminal peptide fragments obtained is carried out. In this case, however, a plurality of the peptide fragments from the portion of the N-terminal side, which are inevitably side-produced by the enzymatic cleavage, will be observed coincidentally on the mass spectra measured. Therefore, there is looked forward to the proposal of a method for analysis of the mass spectra measured, which can distinguish, at a high accuracy, spectrum peaks for the C-terminal peptide fragments derived from the original peptide and a series of reaction products thereof, from spectrum peaks for N-terminal peptide fragments and subsequently can determine, at a high precision, the individual molecular weights for the C-terminal peptide fragments derived from the original peptide and the series of reaction products thereof. More particularly, there is looked forward to the proposal of a technique for analysis of mass spectra, which is effective to identify, on the mass spectra observed, the peaks of the individual ion species derived from the peptide fragments that are produced by enzymatic cleavage and then to distinguish, at a high accuracy, a group of ion species for the C-terminal fragments derived from the original peptide as well as the series of reaction products thereof, from a group of ion species for N-terminal peptide fragments.

The present invention solves the above-mentioned problems and aims at providing a method for reaction to release the C-terminal amino acids successively, with use of which method, when a reaction mechanism via formation of oxazolone ring structure as explained above is used to release the C-terminal amino acids from a long peptide chain, undesired side reactions such as cleavage of peptide bond somewhere along the peptide chain can be suppressed and further said chemical treatment itself can be carried out under widely applicable conditions. The present invention also aims at providing a method for easier analysis of C-terminal amino acid sequence of a long peptide chain, wherein there is combined, with the above-mentioned method for reaction to release the C-terminal amino acids successively, a treatment for enzymatic cleavage using such a protease as, when an original peptide and a series of reaction products obtained therefrom are subjected to an enzymatic cleavage treatment using a protease having a site selectivity for cleavage and the resulting peptide fragments are subjected to mass spectrometry, can distinguish more easily the intended peaks for the C-terminal peptide fragments derived from the original peptide and the series of reaction products thereof, from the peaks for other peptide fragments also obtained by enzymatic digestion. The present invention further aims at providing a technique for analysis of mass spectra, which gives rise to an increased accuracy of distinguishment when, in said analysis of C-terminal amino acid sequence, there are identified, on the mass spectra observed, the peaks of the ion species for the peptide fragments produced by a treatment for enzymatic digestion and then discrimination is made between the intended peaks for a group of the C-terminal peptide fragments derived from an original peptide and a series of reaction products thereof and the peaks for other peptide fragments due to the enzymatic digestion; and also a software for assistance of analysis, usable in a series of analytical operations conducted according to the technique for analysis.

The present inventors made an intensive study and examination continuously in order to solve the above-mentioned problems. As a result, it was concluded that the undesired reactions seen in the case of the method, where a high concentration aqueous solution of a perfluoroalkanoic acid is used to allow a vapor of the perfluoroalkanoic acid therefrom to act on a dried peptide under heating up conditions, for example, at 90° C., occur because the vapor of a perfluoroalkanoic acid as well as water molecule, both vaporized from the high concentration aqueous solution of the perfluoroalkanoic acid, are present in the reaction system, for example, at the serine residue [NH—CH(CH$_2$OH)—CO—] in the peptide, the N,O-acyl rearrangement reaction between the amino group (—NH—) on its α-position and the hydroxy group (—OH) on its β-position is promoted under said heating conditions and the hydrolysis of the ester formed thereby is also advanced by the help of water molecules co-existing in the reaction system. Meanwhile, in the case of the method, where an acetonitrile solution of a perfluoroalkanoic acid anhydride is used to allow a vapor of the perfluoroalkanoic acid anhydride therefrom to act on a dried peptide under cooling down conditions, for example, at −18° C., it has been confirmed that although there is no water molecule in the reaction system, such a high reactivity of the perfluoroalkanoic acid anhydride per se invites a rapid increase in the frequency of undesired side reactions relative to rising up of the treatment temperature.

Based on the above finding, the present inventors searched such reaction conditions as, without using any water solvent working as source for feeding water molecules to the reaction system and further without using any reagent with such high reactivity as perfluoroalkanoic acid anhydride, an oxazolone ring structure can be formed from the C-terminal amino acids of peptide, as an reaction intermediate and then reaction of selectively releasing the C-terminal amino acid can be completed in association with cleavage of the oxazolone ring. As a result, it was found that with use of a mixture obtained by adding a small amount of a perfluoroalkanoic acid to an alkanoic acid anhydride, when the perfluoroalkanoic acid and alkanoic acid anhydride, both of vapor phase, supplied from the mixture are allowed to act on a dried peptide, even at a treatment temperature such as 60° C. or less, the formation of oxazolone ring structure can be progressed, and subsequently followed by the reaction of selectively releasing the C-terminal amino acid therefrom, which is resulted from the cleavage of this oxazolone ring. It was also found that as the reactivity of alkanoic acid anhydride is significantly mild as compared with a perfluoroalkanoic acid anhydride, even in the presence of the perfluoroalkanoic acid, it is far from giving rise to any cleavage in the middle of peptide. Specifically explaining, the alkanoic acid anhydride acts, in the presence of the perfluoroalkanoic acid, on the hydroxy group present on the serine residue [—NH—CH(CH$_2$OH)—CO—] or threonine residue [—NH—CH(CH(CH$_3$)OH)—CO—] in the peptide to make progress preferentially in an O-acylation reaction, which leads to inhibiting the N,O-acyl rearrangement reaction competitively. It was also found that an N-acylation reaction to the amino group of N-terminus proceeds simultaneously and there also proceed, for example, an N-acylation reaction to the amino group on the ε-position of lysine residue [—NH—CH(CH$_2$CH$_2$CH$_2$CH$_2$NH$_2$)—CO—] and an O-acylation reaction to the phenolic hydroxy group of tyrosine residue [—NH—CH(CH$_2$—C$_6$H$_4$—OH)—CO—]. As a result, it was found that since the reactive functional groups such as hydroxy group or amino group on the side chain, which are involved in the rearrangement reaction such as N,O-acyl rearrangement reaction that initiates the cleavage in the middle of peptide, undergo protection and modification, undesired side reactions are avoided and, at a treatment temperature of, for example, 60° C. or less, there selectively proceed only reactions wherein the oxazolone ring structure is formed as the intended reaction intermediate from the C-terminal amino acid, and subsequently followed by the reaction of releasing the C-terminal amino acid in association with the cleavage of the oxazolone ring.

The present inventors further found that the above-mentioned reaction for selective release of C-terminal amino acids using a perfluoroalkanoic acid and an alkanoic acid anhydride, which comprises formation of an oxazolone ring structure and subsequent cleavage of the oxazolone ring, proceeds even when the perfluoroalkanoic acid and the alkanoic acid anhydride are dissolved in a dipolar aprotic solvent and are allowed to act on a target peptide in a liquid phase with no presence of water molecules in the reaction system, at a temperature of, for example, about 40° C. It was also found that the alkanoic acid anhydride acts on hydroxy group in the presence of the perfluoroalkanoic acid and, as a result, an O-acylation reaction proceeds preferentially, which leads to inhibiting the N,O-acyl rearrangement reaction competitively, and there also proceed an N-acylation reaction to amino group, an O-acylation reaction to phenolic hydroxy group, etc. As a result, it was found that since the reactive functional groups such as hydroxy group or amino group on the side chain, which are involved in the rearrangement reaction such as N,O-acyl rearrangement reaction that initiates the cleavage in the middle of peptide, undergo protection and modification, undesired side reactions are avoided and, at a treatment temperature of, for example, 40° C. or less, there selectively proceed only reactions wherein the oxazolone ring structure is formed as the intended reaction intermediate from the C-terminal amino acid, and subsequently followed by the reaction of releasing the C-terminal amino acid in association with the cleavage of the oxazolone ring. It was found that, for example, even a peptide subjected to gel electrophoresis and then bound on the gel carrier used can be subjected to a comparable liquid-phase reaction when the water impregnated into the gel carrier has been removed sufficiently and then there has been infiltrated, into the gel carrier for swelling of the gel, a solution obtained by dissolving a perfluoroalkanoic acid and an alkanoic acid anhydride in a dipolar aprotic solvent.

Further, the present inventors confirmed that, when reactive functional groups of peptide, such as hydroxy group and amino group on the side chain, which are involved in the rearrangement reaction such as N,O-acyl rearrangement reaction that initiates the cleavage in the middle of peptide, undergo protection and modification by O-acylation to hydroxy group and N-acylation to amino group and then there is carried out a reaction of selectively releasing the C-terminal amino acids of peptide with use of said perfluoroalkanoic acid and alkanoic acid anhydride, which occurs in association with the formation of oxazolone ring structure and subsequent cleavage of the oxazolone ring, undesired side reactions can be avoided more effectively. Specifically explaining, it was found that, when an alkanoic acid anhydride and an alkanoic acid both of vapor phase supplied from a mixture of the alkanoic acid anhydride with a small amount of the alkanoic acid is allowed to act on a dried peptide sample in a dried atmosphere at a temperature selected in a range of 10° C. to 60° C., it is possible to beforehand apply N-acylation by the acyl group derived from said alkanoic acid anhydride, to the N-terminal amino group of the peptide as well as to the side chain amino group of the lysine residue which may be present in the peptide, and O-acylation also by the same acyl group to the side chain hydroxy group of the peptide. It was also found that even for a peptide bound on a gel carrier, the N-acylation to said amino groups and the O-acylation to said hydroxy group are possible when the water impregnated into the gel carrier has been removed sufficiently and then a solution of an alkanoic acid anhydride dissolved in a dipolar aprotic solvent has been infiltrated into the gel carrier to give rise to swelling of the gel.

Also, the present inventors confirmed the following. That is, at a timing when the reaction for releasing the C-terminal amino acids of peptide is over, there are also present reaction intermediates generated in association with the formation of oxazolone ring structure and subsequent cleavage of the oxazolone ring; it is necessary for the mass spectrometry to be conducted later that the reaction intermediates are subjected to a hydrolysis treatment and the C-termini of reaction products are returned to a form in which carboxy group is exposed; and the hydrolysis treatment can be easily conducted, for example, by contacting the reaction products with an aqueous solution of a basic, nitrogen-containing, aromatic ring compound or a tertiary amine compound. It was also found that, in the hydrolysis treatment using the catalysis of such an organic base, there proceed, in addition to the hydrolysis reaction for cyclic ester in oxazolone ring structure, a hydrolysis reaction for ester in O-acylation-protected hydroxy group, that is, a deprotection in hydroxy group and, meanwhile, there occurs no deprotection in more stable N-acylation protection. Thus, when such a hydrolysis treatment is applied, there remain, in the original peptide chain, N-acylation protections of the N-terminal amino group and the side chain amino group of the lysine residue which may be present in the peptide chain; also in the peptide chain of each reaction product produced from the reaction for releasing C-terminal amino acids, there remain as well, N-acylation protections of the N-terminal amino group and the side chain amino group of the lysine residue which may be present in the peptide chain.

In addition to the above findings, the present inventors confirmed that, when a cleavage treatment is applied to a long peptide chain in which N-acylation protection has been made to the side chain amino group of the lysine group which may be present in the peptide chain, by using trypsin which has a site selectivity for cleavage of C-terminal side peptide bond of lysine or arginine residue, no cleavage of peptide takes place at the N-acylated lysine residue and there are obtained peptide fragments derived from cleavage at the arginine residue. More specifically explaining, by applying such a cleavage treatment by trypsin, there can be obtained, from a mixture of an original peptide chain and peptide chains of a series of the reaction products produced by a reaction for releasing C-terminal amino acids from the peptide chain, peptide fragments (which are common fragments) each having a partial amino acid sequence containing one arginine residue at the C-terminus and a group of C-terminal side peptide fragments each derived from C-terminal side partial amino acid sequence and containing no arginine residue. In this case, the present inventors concluded that, with respect to the average occurrence of arginine residue in peptide chain, for example, a long peptide chain of about 200 amino acids contain at least only 4 or more arginine residues and at most only about 10 arginine residues and that the common peptide fragments each having one arginine residue at the C-terminus are counted up to the number of about 4 to 10 and the C-terminal side peptide fragments derived from the original peptide contain at least 15 but 50 or less amino acids, at a high probability.

Moreover, the present inventors proved experimentally that, in the molecular weight measurement for various peptide fragments based on the cationic species and anionic species all generated from ionization treatments to the fragments, by means of mass spectrometry, for instance, of MALDI-TOF-MS (Matrix Assisted Laser Desorption Ionization Time-of-Flight Mass Spectrometry). there is apparently a general tendency that, when the peptide fragments have a cationic amino acid residue, particularly an arginine residue at the C-terminus, the peak intensity in the molecular weight measurement based on cationic species is significantly high relative to the corresponding peak intensity in the molecular weight measurement based on anionic species and, when the peptide fragments have no cationic amino acid residue at the C-terminus, the peak intensity in the molecular weight measurement based on anionic species is significantly high relative to the corresponding peak intensity in the molecular weight measurement based on cationic species. Further, the present inventors confirmed that, by utilizing the above general tendency proven experimentally, it is possible in the molecular weight measurement based on the cationic species and anionic species all generated from the ionization treatment, according to the MALDI-TOF-MS, to distinguish, with rationality, said common peptide fragments each having one arginine residue at the C-terminus, from said group of C-terminal side peptide fragments derived from C-terminal side partial amino acid sequence and containing no arginine residue, produced from the original peptide and a series of reaction products thereof. That is, the common peptide fragments each obtained by trypsin-induced cleavage and having one arginine residue at the C-terminus are observed as a single peak at a relatively high intensity in the molecular weight measurement based on cationic species and, in the molecular weight measurement based on anionic species, the intensity of the peak corresponding to the common peptide fragments is relatively low; however, by comparing the results of the two measurements, the common peptide fragments can be identified easily. Meanwhile, in the molecular weight measurement based on anionic species, said group of C-terminal side peptide fragments derived from C-terminal side partial amino acid sequence and containing no arginine residue, produced from the original peptide chain and a series of reaction products thereof, are observed as a series of peaks at a relatively high intensity and can be identified easily.

Based on a series of the above findings, the present inventors found the following matter; that is, even for a long peptide chain constituting, for example, a variety of proteins, analysis of its C-terminal amino acid sequence can be made more easily by employing a series of steps which comprise:

(1) applying N-acylation protection and O-acylation protection to a target peptide chain, (2) conducting a reaction for selectively releasing the C-terminal amino acids of the acylated peptide chain under the mild reaction conditions selected appropriately depending upon the state in which the acylated peptide chain is present, (3) then, conducting a hydrolysis reaction to the cyclic ester in oxazolone ring structure and a deprotection reaction to the O-acylation protection under mild conditions, (4) applying a trypsin-induced cleavage treatment to a mixture containing the original peptide chain and the peptide chains of a series of reaction products obtained by selective release of C-terminal amino acids of the peptide chain (in all of these peptide chains, N-acylation protection remains), to prepare peptide fragments (common peptide fragments) each having one arginine residue at the C-terminus and a series of C-terminal side peptide fragments derived from the C-terminal side partial amino acid sequence and containing no arginine residue, produced from the original peptide chain and the peptide chains of a series of reaction products thereof, (5) subjecting a mixture of these peptide fragments to mass spectrometry, in particular, MALDI-TOF-MS to conduct molecular weight measurements for the cationic species and anionic species all generated by an ionization treatment, and comparing the results of the two measurements to distinguish the common peptide fragments each having one arginine residue at the terminus, from said group of C-terminal side peptide fragments containing no arginine residue, produced from the original peptide chain and the peptide chains of a series of reaction products thereof, and (6) based on the differences in molecular weight between said group of the C-terminal side peptide fragments produced from the original peptide and the peptide chains of a series of reaction products thereof, identifying the C-terminal amino acid sequence of the long peptide chain. Further, the present inventors examined the usefulness of the above finding. As a result, the present invention has been completed.

The present invention has a plurality of different aspects depending upon the state in which a target peptide chain is present, although these aspects are based on a common technical concept. The present invention has a first aspect which is employed, for example, when the target peptide is an isolated dried sample, and a second aspect which is employed when the target peptide is a sample separated by gel electrophoresis and bound on the gel carrier used.

The method for analysis of C-terminal amino acid sequence of peptide according to the first aspect of the present invention is a method for analyzing the C-terminal amino acid sequence of a peptide to be examined, which method comprises the following steps:

a step of preparing a mixture containing a series of reaction products that are obtained from the peptide to be examined by releasing the C-terminal amino acids successively by chemical, a step of analyzing the differences in molecular weight between said series of reaction products and the original peptide by means of mass spectrometry to measure the decreases in molecular weight associated with the successive release of the C-terminal amino acids, and a step of identifying a series of the amino acids removed successively, based on a series of the measured decreases in molecular weight and arranging them from the C-terminus to obtain the information of the C-terminal amino acid sequence of the peptide, wherein said process for releasing the C-terminal amino acids successively comprises at least the following steps:

a pretreatment step, for providing the protection by means of N-acylation, of allowing an alkanoic acid anhydride and an alkanoic acid both of vapor phase, which are supplied from a mixture of the alkanoic acid anhydride with a small amount of the alkanoic acid added thereto, to act on a dry sample of said peptide to be examined in a dry atmosphere at a temperature selected in a range of 10° C. to 60° C. and, thereby, applying, to the N-terminal amino group of the peptide as well as to the amino group on the side chain of the lysine residue which may be included in the peptide, N-acylation by the acyl group derived from the alkanoic acid anhydride, a step of allowing an alkanoic acid anhydride and a perfluoroalkanoic acid both of vapor phase, which are supplied from a mixture of an alkanoic acid anhydride with a small amount of a perfluoroalkanoic acid added thereto, to act on the dry peptide sample after N-acylation protection in a dry atmosphere at a temperature selected in a range of 15° C. to 60° C. and, thereby, releasing the C-terminal amino acids successively in association with a process that at the C-terminus of the peptide, the formation of a 5-oxazolone structure represented by the following general formula (III):

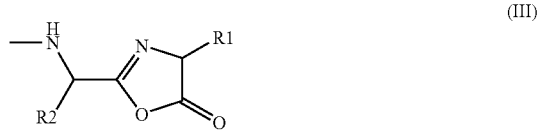

wherein R1 is a side chain of the C-terminal amino acid of the peptide and R2 is a side chain of the amino acid residue positioned just before the C-terminal amino acid, is followed by the cleavage of the 5-oxazolone ring, and a hydrolysis treatment step which comprises applying, to a mixture containing a series of reaction products obtained in said step of releasing the C-terminal amino acids successively, a post-treatment of removing the remaining alkanoic acid anhydride and perfluoroalkanoic acid in a dry state, and then supplying with a basic nitrogen-containing aromatic compound or a tertiary amine compound and water molecules, all of vapor phase, with use of an aqueous solution dissolving the basic nitrogen-containing, aromatic compound or the tertiary amine compound therein, to allow the water molecules to act on the peptides of the reaction products in the presence of the basic nitrogen-containing organic compound to give rise to a hydrolysis treatment, and after that conducting the re-dried up treatment by removing, from the mixture containing a series of reaction products, the remaining basic nitrogen-containing organic compound and water molecules to dry up the mixture, wherein said step of measuring the decreases in molecular weight associated with the successive release of the C-terminal amino acids employs a technique which comprises:

allowing trypsin to act on said mixture, after the re-dried up treatment, containing a series of the reaction products finished by hydrolysis treatment, in a buffer solution, to carry out the treatment for the enzymatic digestion specific to trypsin of said peptide chain which holds N-acylation protection as for the N-terminal amino group of the peptide chain as well as to the amino group on the side chain of the lysine residue that may be contained in the peptide chain, and thereby, conducting selective cleavage of the C-terminal side peptide bond of each arginine residue that present in the peptide chain to complete peptide fragmentization, applying a desalting treatment to remove the buffer solution component, followed by recovering and drying the peptide fragments after the digestion treatment by trypsin, followed by drying, next to that, conducting, as for the dried mixture containing said peptide fragments recovered after the digestion treatment by trypsin, molecular weight measurement for the cationic species as well as molecular weight measurement for anionic species, both of which are generated from the ionization treatment, by means of MALDI-TOF-MS, with respect to the corresponding ion species, which are measured in said molecular weight measurement for the cationic species as well as molecular weight measurement for anionic species, judging that the peaks of the peptide fragments each having an arginine residue at the C-terminus, which fragments are produced by said digestion treatment by trypsin, are peaks that give such intensities that the intensity in the molecular weight measurement for cationic species is relatively larger in comparison with the intensity in the molecular weight measurement for anionic species, and judging that the peaks of the C-terminal peptide fragment derived from the original peptide and the C-terminal peptide fragments derived from a series of the reaction products that are obtained by successive release of the C-terminal amino acids, which fragments are produced by said digestion treatment by trypsin, are peaks that give such intensities that the intensity in the molecular weight measurement for anionic species is relatively larger in comparison with the intensity in the molecular weight measurement for cationic species, and based on a series of the peaks that gives a relatively larger intensity in the molecular weight measurement for anionic species, measuring the decreases in molecular weight associated with the successive release of the C-terminal amino acids.

In the method for analysis according to the first aspect of the present invention, as the alkanoic acid anhydride contained in the mixture of an alkanoic acid anhydride with a small amount of a perfluoroalkanoic acid added thereto, there is preferably used a symmetric anhydride of an alkanoic acid having 2 to 4 carbon atoms. As said symmetric anhydride of an alkanoic acid having 2 to 4 carbon atoms, there is more preferably used a symmetric anhydride of a linear-chain alkanoic acid having 2 to 4 carbon atoms. As the alkanoic acid anhydride contained in said mixture of an alkanoic acid anhydride with a small amount of a perfluoroalkanoic acid added thereto, there is more preferably used, for example, acetic anhydride.

Meanwhile, as the perfluoroalkanoic acid contained in said mixture of an alkanoic acid anhydride with a small amount of a perfluoroalkanoic acid added thereto, there is preferably used a perfluoroalkanoic acid of which pKa is in a range of 0.3 to 2.5. As the perfluoroalkanoic acid contained in said mixture of an alkanoic acid anhydride with a small amount of a perfluoroalkanoic acid added thereto, there can be more preferably used a perfluoroalkanoic acid having 2 to 4 carbon atoms. As the perfluoroalkanoic acid having 2 to 4 carbon atoms, there is more preferably employed, for example, a linear-chain perfluoroalkanoic acid having 2 to 4 carbon atoms.

Further, in said mixture of an alkanoic acid anhydride with a small amount of a perfluoroalkanoic acid added thereto, the content of the perfluoroalkanoic acid is desirably selected in a range of 1 to 20% by volume relative to the total volume of the alkanoic acid anhydride and the perfluoroalkanoic acid. In the treatment using said mixture of an alkanoic acid anhydride with a small amount of a perfluoroalkanoic acid added thereto, said dry atmosphere is much more preferably in a state in which oxygen as well as water have been removed. The dry atmosphere is preferably achieved, for example, by, in an airtight vessel, vacuuming up the atmosphere contained therein. Additionally, in the treatment using said mixture of an alkanoic acid anhydride with a small amount of a perfluoroalkanoic acid added thereto, the temperature is set more desirably at a temperature selected in a range of 15° C. to 50° C.

Meanwhile, the method for analysis of C-terminal amino acid sequence of peptide according to the second aspect of the present invention is a method for analyzing the C-terminal amino acid sequence of a peptide to be examined, which method comprises the following steps:

a step of preparing a mixture containing a series of reaction products that are obtained from the peptide to be examined by releasing the C-terminal amino acids successively by chemical, a step of analyzing the differences in molecular weight between said series of reaction products and the original peptide by means of mass spectrometry to measure the decreases in molecular weight associated with the successive release of the C-terminal amino acids, and a step of identifying a series of the amino acids removed successively, based on a series of the measured decreases in molecular weight and arranging them from the C-terminus to obtain the information of the C-terminal amino acid sequence of the peptide, wherein said process for releasing the C-terminal amino acids successively, as for the sample of the target peptide that has been subjected to separation by gel electrophoresis and is maintained in a state that it is bound on a gel carrier, comprises the following steps:

a step of removing the water solvent impregnated into the gel carrier by dilution with use of a polar aprotic solvent having no solvency for the gel substance and having affinity for water, to conduct a dehydration treatment for the gel carrier, a pretreatment step for the target peptide sample that is still bound on the gel carrier after carrying out said step for dehydration treatment, in which pretreatment step applying N-acylation protection by the acyl group derived from the alkanoic acid constituting said alkanoic acid anhydride, to the N-terminal amino group of the target peptide with use of a solution of an alkanoic acid anhydride dissolved in a dipolar aprotic solvent that is capable of infiltrating into the gel substance and keeping it in a swollen state is conducted by immersing, at a temperature selected in a range of 30° C. to 80° C., the gel carrier in the solution of the alkanoic acid anhydride to allow the alkanoic acid anhydride to act on the target peptide sample that is kept in the bound state; and then removal of said solution is carried out by dilution with use of a polar aprotic solvent having no solvency for the gel substance and having affinity for the alkanoic acid anhydride as well as the dipolar aprotic solvent, to conduct termination of the N-acylation reaction and removal of the reaction reagent therefor;

a step of treatment as for the target peptide sample bound on the gel carrier, after the pretreatment step of N-acylation protection, comprising steps of:

immersing, at a temperature selected in a range of 30° C. to 80° C., the gel carrier in a mixed solution of an alkanoic acid anhydride added with a small amount of a perfluoroalkanoic acid in relative ratio thereto dissolved in a dipolar aprotic solvent that is capable of infiltrating into the gel substance and keeping it in a swollen state, to allow the alkanoic acid anhydride and the perfluoroalkanoic acid to act on the target peptide sample being kept in the bound state; thereby, successive release of the C-terminal amino acids results from the reaction process with use of the mixed solution in which formed is a 5-oxazolone-ring structure represented by the following general formula (III):

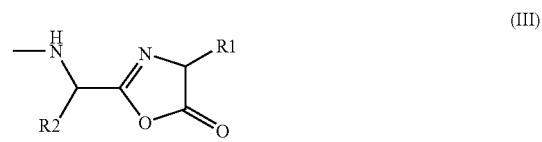

wherein R1 is a side chain of the C-terminal amino acid of the peptide and R2 is a side chain of the amino acid residue positioned just before the C-terminal amino acid, followed by the cleavage of the 5-oxazolone-ring, and removing the mixed solution used in the reaction for successive release of C-terminal amino acids, by dilution with use of a polar aprotic solvent having no solvency for the gel substance and having affinity for the perfluoroalkanoic acid and the alkanoic acid anhydride as well as the dipolar aprotic solvent, to conduct termination of the releasing reaction and removal of the reaction reagents therefor; and an additional step for hydrolysis treatment and then redehydration treatment, in which step the hydrolysis treatment for said mixture comprising a series of reaction products obtained by the reaction for successive release of C-terminal amino acids is conducted by immersing the gel carrier in an aqueous solution dissolving a basic nitrogen-containing aromatic compound or a tertiary amine compound therein to allow a water molecule to act, in the presence of said basic nitrogen-containing organic compound, on said peptides of the reaction products being still bound on the gel carrier, and then, the redehydration treatment for the gel carrier is performed by removing said aqueous solution infiltrated into the gel carrier by dilution with use of a polar aprotic solvent having no solvency for the gel substance and having affinity for water; and wherein said step of measuring the decreases in molecular weight associated with the successive release of the C-terminal amino acids employs a technique which comprises:

allowing trypsin being soluble in a buffer solution to act on said mixture, after the re-dehydration treatment, containing a series of the reaction products finished by hydrolysis treatment, to carry out the treatment for the enzymatic digestion specific to trypsin of said peptide chain which holds N-acylation protection as for the N-terminal amino group of the peptide chain as well as to the amino group on the side chain of the lysine residue that may be contained in the peptide chain, and thereby, conducting selective cleavage of the C-terminal side peptide bond of each arginine residue that present in the peptide chain to complete peptide fragmentization, applying a desalting treatment to remove the buffer solution component, followed by recovering and drying the peptide fragments after the digestion treatment by trypsin, followed by drying, next to that, conducting, as for the dried mixture containing said peptide fragments recovered after the digestion treatment by trypsin, molecular weight measurement for the cationic species as well as molecular weight measurement for anionic species, both of which are generated from the ionization treatment, by means of MALDI-TOF-MS, with respect to the corresponding ion species, which are measured in said molecular weight measurement for the cationic species as well as molecular weight measurement for anionic species, judging that the peaks of the peptide fragments each having an arginine residue at the C-terminus, which fragments are produced by said digestion treatment by trypsin, are peaks that give such intensities that the intensity in the molecular weight measurement for cationic species is relatively larger in comparison with the intensity in the molecular weight measurement for anionic species, and judging that the peaks of the C-terminal peptide fragment derived from the original peptide and the C-terminal peptide fragments derived from a series of the reaction products that are obtained by successive release of the C-terminal amino acids, which fragments are produced by said digestion treatment by trypsin, are peaks that give such intensities that the intensity in the molecular weight measurement for anionic species is relatively larger in comparison with the intensity in the molecular weight measurement for cationic species, and based on a series of the peaks that gives a relatively larger intensity in the molecular weight measurement for anionic species, measuring the decreases in molecular weight associated with the successive release of the C-terminal amino acids.

In the method for analysis according to the second aspect of the present invention, as the alkanoic acid anhydride contained in said mixed solution where a small amount of the perfluoroalkanoic acid in relative ratio to the alkanoic acid anhydride is dissolved, there is preferably used a symmetric anhydride of an alkanoic acid having 2 to 4 carbon atoms. As said symmetric anhydride of an alkanoic acid having 2 to 4 carbon atoms, there is more preferably used a symmetric anhydride of a linear-chain alkanoic acid having 2 to 4 carbon atoms. As the alkanoic acid anhydride contained in the mixed solution where a small amount of the perfluoroalkanoic acid in relative ratio to the alkanoic acid anhydride is dissolved, there is more preferably used, for example, acetic anhydride.

Meanwhile, as the perfluoroalkanoic acid contained in the mixed solution where a small amount of the perfluoroalkanoic acid in relative ratio to the alkanoic acid anhydride is dissolved, there is preferably used a perfluoroalkanoic acid of which pKa is in a range of 0.3 to 2.5. As the perfluoroalkanoic acid in the mixed solution where a small amount of the perfluoroalkanoic acid in relative ratio to the alkanoic acid anhydride is dissolved, there is preferably used a perfluoroalkanoic acid having 2 to 4 carbon atoms. As the perfluoroalkanoic acid having 2 to 4 carbon atoms, there is more preferably employed a linear-chain perfluoroalkanoic acid having 2 to 4 carbon atoms.

Further, in the mixed solution where a small amount of the perfluoroalkanoic acid in relative ratio to the alkanoic acid anhydride is dissolved, the content ratio of the alkanoic acid anhydride and the perfluoroalkanoic acid is selected more preferably in the range of 1 to 20 volumes of the perfluoroalkanoic acid per 100 volumes of the alkanoic acid anhydride.

In addition, the present inventors found that a common technique can be selected for the treatment for analyzing the spectra measured by the molecular weight measurements based on cationic species as well as by the molecular weight measurements based on anionic species by means of MALDI-TOF-MS, which are commonly employed in both the first aspect and the second aspect of the method for analysis of the C-terminal amino acid sequence of peptide according to the present invention, as for the aforementioned two steps (5) and (6):

Step (5): subjecting a mixture of the peptide fragments to molecular weight measurements for the cationic species and anionic species all generated by an ionization treatment by means of MALDI-TOF-MS, and comparing the results of the two measurements to distinguish the common peptide fragments each having one arginine residue at the C-terminus, from said group of C-terminal side peptide fragments containing no arginine residue, produced from the original peptide chain and the peptide chains of a series of reaction products thereof, and Step (6): based on the differences in molecular weight between said identified group of the C-terminal side peptide fragments produced from the original peptide and the peptide chains of a series of reaction products thereof, identifying the C-terminal amino acid sequence of the long peptide chain.

Specifically explaining, the present inventors found that the mixture of the peptide fragments to be measured include peptide fragments derived from trypsin, which are due to trypsin autolysis, in addition to the peptide fragments generated by the treatment for digestion by trypsin; of the ion species peaks remaining after the removal of the ion species peaks of said peptide fragments derived from trypsin, there are recognizable at least said common peptide fragments each having one arginine residue at the C-terminus and the C-terminal side peptide fragments of the original peptide chain having no arginine residue as distinct peaks; with respect to these ion species peaks clearly recognizable, by examining the presence of the ion species peaks derived from the peptide chains of a series of the reaction products which are produced therefrom in association with the successive release of the C-terminal amino acids, it is possible to carry out the distinguishment, at high rationality and reliability, between said common peptide fragments having one arginine residue at the C-terminus and a group of C-terminal side peptide fragments having no arginine residue which are derived from the original peptide chain and the peptide chains of a series of the reaction products.

The present inventors also found that, since the target peptide chain to be examined is subjected to the following steps (1) to (3) described above:

(1) a step of applying protection by N-acylation and O-acylation, (2) a step of a reaction for selective release of C-terminal amino acids, and (3) a step of hydrolysis of cyclic ester in oxazolone ring structure and deprotection for O-acylation protection, the ion species peaks derived from intended peptide fragments are often accompanied by the ion species peaks derived from secondary peptide fragments which retain the same peptide chain but have undergone additional modification reactions, such as those being substituted by excess of acyl groups or those undergoing unnecessary dehydration reactions; and, by examining the presence of such accompanying ion species peaks and referring to the relative ratio between the peak intensities thereof, the ion species peaks derived from the aimed peptide fragments can be identified at high rationality and reliability, and at the end, the present inventors have completed the method for analysis of spectra according to the present invention into which said criteria for judgment is incorporated.

Thus, the method for analysis of the spectra measured in the molecular weight measurements based on cationic species as well as the molecular weight measurements based on anionic species by means of mass spectrometry, particularly MALDI-TOF-MS, according to the present invention is a method for analysis of the spectra measured in the molecular weight measurements based on cationic species as well as on anionic species with use of mass spectrometry, particularly MALDI-TOF-MS, which method is usable, in the method for analysis of the C-terminal amino acid sequence of peptide according to the first or second aspect of the present invention, for measurement of the decreases in molecular weight associated with successive release of the C-terminal amino acids of the peptide;

said method for analysis of the spectra measured in the molecular weight measurements based on cationic species as well as on anionic species by means of MALDI-TOF-MS, wherein the step of analysis of the spectra, in which the range to be analyzed for the analysis operation of spectra is selected within m/z value of 4,000 or less, comprises the following Steps 1 to 9:

[Step 1] a step for identification of internal standard peaks derived from trypsin, which comprises:

with respect to the peptide fragments derived from the autolysis of trypsin having a known molecular weight, which are concomitant with the digestion treatment with trypsin used for peptide fragmentization, and incorporated into the dry mixture containing the peptide fragments, identifying the peaks of the cationic species due to the peptide fragments derived from trypsin autolysis, in a m/z value range of 4,000 to 500 of the result of the molecular weight measurements for cationic species, then, identifying the peaks of the corresponding anionic species due to the peptide fragments resulting from trypsin autolysis, in a m/z range of 4,000 to 500 of the result of the molecular weight measurements for anionic species;

[Step 2] a step for identification of major ion species peaks, which comprises:

excluding said peaks assigned for the cationic species peaks derived from trypsin from the result of molecular weight measurements for cationic species, identifying the highest peak of cationic species having the highest peak intensity, in a m/z value range of 4,000 to 500, and by using the peak intensity of the highest peak of cationic species as a basis, selecting peaks of cationic species each having a peak intensity of 1/40 or more relative to the basis to make up the first group of cationic species peaks therewith, next to that, excluding said peaks assigned for the anionic species peaks derived from trypsin from the result of molecular weight measurements for anionic species, identifying the highest peak of anionic species having the highest peak intensity, in a m/z value range of 4,000 to 500, and by using the peak intensity of the highest peak of anionic species as a basis, selecting anionic species peaks each having a peak intensity of 1/40 or more relative to the basis to make up the first group of anionic species peaks therewith,

[Step 3] a step for identification of counter ion species peaks for the major ion species peaks, which comprises:

identifying, in the result of the molecular weight measurements for anionic species, peaks due to anionic species each corresponding to each peak of said first group of cationic species peaks to make up the second group of anionic species peaks therewith, next to that, identifying, in the result of the molecular weight measurements for cationic species, peaks due to cationic species each corresponding to each peak of said first group of anionic species peaks to make up the second group of cationic species peaks therewith,

[Step 4] a step for identification of major ion species peaks having significant counter-ionic species, which comprises:

making up the overlapping group between the first group of anionic species peaks and the second group of anionic species peaks to define it as the third group of anionic species peaks, and also making up the sum group of the first group of anionic species peaks and the second group of anionic species peaks to define it as the fourth group of anionic species peaks, next to that, making up the overlapping group between the first group of cationic species peaks and the second group of cationic species peaks to define it as the third group of cationic species peaks, and also making up the sum group of the first group of cationic species peaks and the second group of cationic species peaks to define it as the fourth group of cationic species peaks, with respect to each cationic species peak corresponding to each peak of said third group of anionic species peaks, calculating the relative peak intensity on the basis of said peak intensity of the highest cationic species peak and, with respect to each anionic species peak of said third group of anionic species peaks, calculating the relative peak intensity on basis of said peak intensity of the highest anionic species peak, and comparing the two relative peak intensities with each other, identifying those corresponding cationic species peaks each having a relative intensity which is 3/2 or more relative to that of the peak of the third group of anionic species peaks to make up the fifth group of cationic species peaks therewith, meanwhile, identifying those anionic species peaks each having a relative intensity which is 3/2 or more relative to that of the corresponding cationic species peaks to make up the fifth group of anionic species peaks therewith,

[Step 5] a step for identification of major ion species peaks caused by peptide fragments derived from target peptide to be analyzed, which comprises:

based on the m/z value of each cationic species peak of the fourth group of cationic species peaks, calculating the differences in the m/z value between each adjacent peaks thereof, meanwhile, based on the m/z value of each anionic species peak of the fourth group of anionic species peaks, calculating the differences in the m/z value between each adjacent peaks thereof, with respect to each peak of the fifth group of cationic species peaks, examining said peak as to the following criteria:

(5a-1) a cationic species peak having a m/z value smaller than the m/z value of said peak by the molecular weight of 18 corresponding to loss of one water molecule is present in the fifth group of cationic species peaks;

(5a-2) a cationic species peak having a m/z value larger than the m/z value of said peak by the molecular weight excess equivalent to the formula weight of the acyl group used for said N-acylation protection is present in the fifth group of cationic species peaks; and (5a-3) a cationic species peak having a m/z value larger than the m/z value of said peak by the combination of the molecular weight decrease of 18 corresponding to loss of one water molecule and excess equivalent to the formula weight of the acyl group used for said N-acylation protection is present in the fifth group of cationic species peaks;

to select those cationic species peaks each satisfying at least one of said requirements (5a-1) to (5a-3), and then making up the sixth group of cationic species peaks therewith, meanwhile, with respect to each peak of the fifth group of anionic species peaks, examining said peak as to the following criteria:

(5b-1) an anionic species peak having a m/z value smaller than the m/z value of said peak by the molecular weight of 18 corresponding to loss of one water molecule is present in the fifth group of anionic species peaks;

(5b-2) an anionic species peak having a m/z value larger than the m/z value of said peak by the molecular weight excess equivalent to the formula weight of the acyl group used for said N-acylation protection is present in the fifth group of anionic species peaks; and (5b-3) an anionic species peak having a m/z value larger than the m/z value of said peak by the combination of the molecular weight decrease of 18 corresponding to loss of one water molecule and excess equivalent to the formula weight of the acyl group used for said N-acylation protection is present in the fifth group of anionic species peaks;

to select those anionic species peaks each satisfying at least one of said requirements (5b-1) to (5b-3), and then making up the sixth group of anionic species peaks therewith, judging that the sixth group of cationic species peaks selected thereby are a group of cationic species peaks caused by peptide fragments derived from the target peptide to be analyzed, and judging also that the six group of anionic species peaks selected thereby are a group of anionic species peaks caused by peptide fragments derived from the target peptide to be analyzed,

[Step 6] a step for identification of ion species peaks of peptide fragments per se derived from target peptide to be analyzed, which comprises:

with respect to each peak of the sixth group of cationic species peaks, in comparison with the relative intensities of its accompanying cationic species peaks that are relevant to at least one of said relationships (5a-1) to (5a-3) for said peak, selecting peaks whose relative intensities are superior to their accompanying cationic species peaks, and then from the group of the selected peaks, further selecting peaks which is not one of accompanying cationic species peaks that are relevant to at least one of said relationships (5a-1) to (5a-3) for other peak included in said group of the selected peaks and have an inferior relative intensity to other peak, and making up the seventh group of cationic species peaks therewith, meanwhile, with respect to each peak of the sixth group of anionic species peaks, in comparison with the relative intensities of its accompanying anionic species peaks that are relevant to at least one of said relationships (5b-1) to (5b-3) for said peak, selecting peaks whose relative intensities are superior to their accompanying anionic species peaks, and then from the group of the selected peaks, further selecting peaks which is not one of accompanying anionic species peaks that are relevant to at least one of said relationships (5b-1) to (5b-3) for other peak included in said group of the selected peaks and have an inferior relative intensity to other peak, and making up the seventh group of anionic species peaks therewith, judging that the seventh group of cationic species peaks are a group of cationic species peaks caused by peptide fragments per se derived from the target peptide to be analyzed, and judging also that the seventh group of anionic species peaks are a group of anionic species groups caused by peptide fragments per se derived from the target peptide to be analyzed,

[Step 7] a step for identification of peptide fragments each having arginine at the C-terminus of its peptide chain, produced by the digestion treatment by trypsin, which comprises:

selecting each anionic species peak which corresponds to each cationic species peak of the seventh group of cationic species peaks, from the peaks being present in the fourth group of anionic species peaks, to make up the eighth group of anionic species peaks therewith, with respect to each peak of the eighth group of anionic species peaks, selecting group of anionic species peaks of which a m/z value difference from the fiducial m/z value of the said anionic species peak is found within the range of less than 200, based on set of the m/z value differences between adjacent peaks that are calculated in the Step 5, from the peaks being present in the fourth group of anionic species peaks, and confirming that there is not present, in the thus-selected groups, any peak whose m/z value difference between those peaks is equivalent to the formula weight of natural chain a-amino acid residue: —NH—CH(R)—CO— (R is a side chain of said amino acid residue) or of a-amino acid residue protected by acylation wherein the hydroxy group or amino group of its side chain is modified by substitution with the acyl group used in said N-acylation protection, and thus judging that said eighth group of anionic species peaks are the group of anionic species peaks from peptide fragments each having arginine at the C-terminus of its peptide chain, which are derived from the target peptide to be examined and produced by the treatment for digestion by trypsin,

[Step 8] a step for identification of group of C-terminal side peptide fragments that are produced from target peptide and a series of reaction products thereof by the treatment for digestion by trypsin, which comprises:

with respect to each anionic species peak of the seventh group of anionic species peaks, selecting group of anionic species peaks of which a m/z value difference from the fiducial m/z value of the said anionic species peak is found within the range of less than 200, based on set of the m/z value differences between adjacent peaks that are calculated in the Step 5, from the peaks being present in the fourth group of anionic species peaks, and identifying those anionic species peaks being included in the seventh group of anionic species group, for which there is present, in the thus-selected groups, a peak whose m/z value difference between those peaks is equivalent to the formula weight of natural chain a-amino acid residue: —NH—CH(R)—CO— (R is a side chain of said amino acid residue) or of a-amino acid residue protected by acylation wherein the hydroxy group or amino group of its side chain is modified by substitution with the acyl group used in said N-acylation protection, and then making up the ninth group of anionic species peaks therewith, forming the summed-up group of each anionic species peak of the ninth group of anionic species peaks and each of said anionic species peaks being present in the fourth group of anionic species peaks whose m/z value difference between those peaks has been confirmed, in said operation of identification, to be equivalent to the formula weight of amino acid residue, and then defining the group as the tenth group of anionic species peaks, from said largest m/z peak, selecting, in the tenth group of anionic species peaks, an anionic species peak having the largest m/z value, successively identifying, from the tenth group of anionic species peaks, a series of anionic species peaks each having a m/z value difference between peaks that is equal to the formula weight of amino acid residue, by using, as the finducial point, the m/z value which the anionic species peak with the largest m/z value shows, and then judging that the series of thus-identified peaks as the group consisting of the anionic species peak of C-terminal peptide fragment derived from the original peptide and the anionic species peaks of C-terminal peptides derived from a series of reaction products that are obtained by successive release of C-terminal amino acids of original peptide, which fragments are all produced by the treatment for digestion by trypsin, and

[Step 9] a step for assignment of C-terminal amino acid sequence, which comprises:

according to a series of said formula weights of amino acid residues that are corresponding to the m/z differences between the anionic species peaks, which have been sequentially assigned in Step 8, based on the identified group consisting of the anionic species peaks of C-terminal peptide fragments that are derived from the original peptide and a series of reaction products resulted from successive release of C-terminal amino acids, which fragments are all produced by the treatment for digestion by trypsin, identifying the sequence of partial amino acids which have been released successively from the C-terminus thereof.

Further, after Step 1 being the step for identification of internal standard peaks derived from trypsin, it is preferred to employ a step for noise removal and smoothening treatment, which comprises:

with respect to each cationic species peak of the peptide fragments derived from trypsin autolysis, identified in the result of the molecular weight measurements for cationic species, determining its peak m/z value and calculating its apparent full-width of half maximum, by using said apparent full-width of half maximum calculated as the datum width, conducting, for the spectra of molecular weight measurement for cationic species peak, a treatment of removing noise peaks each showing an apparent full-width of half maximum which is ¼ or less of the datum width, then, conducting, for the spectra after the treatment for noise removal, a smoothing treatment such that the asymmetry of peak shape and the integrated intensity of peak as for each cationic species peak of the peptide fragments derived from trypsin autolysis can be well-retained, which are evaluated based on the determined peak m/z values and the two m/z values used in calculation of said apparent full-width of half maximum and, meanwhile, with respect to each anionic species peak of the peptide fragments derived from trypsin autolysis, identified in the result of the molecular weight measurements for anionic species, determining its peak m/z value and calculating its apparent full-width of half maximum, by using said apparent full-width of half maximum calculated as the datum width, conducting, for the spectra of molecular weight measurement for anionic species peak, a treatment of removing noise peaks each showing an apparent full-width of half maximum which is ¼ or less of the datum width, then, conducting, for the spectra after the treatment for noise removal, a smoothing treatment such that the asymmetry of peak shape and the integrated intensity of peak as for each anionic species peak of the peptide fragments derived from trypsin autolysis can be well-retained, which are evaluated based on the determined peak m/z values and the two m/z values used in calculation of said apparent full-width of half maximum.

Further, after Step 1 being the step for identification of internal standard peaks derived from trypsin, it is preferred also to employ a step for systematic error correction for peak m/z value, which comprises:

with respect to the cationic species peak of each peptide fragment derived from the trypsin autolysis, identified in the result of molecular weight measurements based on cationic species, calculating the m/z value of said cationic species based on the known molecular weight of said peptide fragment, comparing it with the peak m/z value measured therefor on the spectra and, based on their difference, making a correction of systematic error for the m/z value measured in spectra of the molecular weight measurements based on cationic species, meanwhile, with respect to the anionic species peak of each peptide fragment derived from the trypsin autolysis, identified in the result of molecular weight measurements based on anionic species, calculating the m/z value of said anionic species based on the known molecular weight of said peptide fragment, comparing it with the peak m/z value measured therefor on the spectra and, based on their difference, making a correction of systematic error for the m/z value measured in spectra of the molecular weight measurements based on anionic species.

In addition, as for Step 9 being the step for assignment of C-terminal amino acid sequence, in such case when the assigned sequence of partial amino acids which have been released successively from the C-terminus of original peptide, has arginine as the C-terminal amino acid, it is more preferable to optionally employ a step for reconfirming the assignment such that its C-terminal fragment is a peptide fragment having arginine at the C-terminus of its peptide chain, which comprises:

with respect to the anionic species peak having the largest m/z value in the tenth group of anionic species peaks, which is used as the finducial peak for the assignment of partial amino acid sequence, finding, in the result of the molecular weight measurement based on cationic species, a cationic species peak corresponding thereto, as for the corresponding cationic species peak, selecting group of cationic species peaks of which a m/z value is larger than the fiducial m/z value of the said anionic species peak and the m/z value difference therebetween is found within the range of less than 200, based on set of the m/z value differences between adjacent peaks that are calculated in the Step 5, from the peaks being present in the fourth group of cationic species peaks, and confirming that there is not present, in the thus-selected groups, any peak whose m/z value difference between those peaks is equivalent to the formula weight of natural chain a-amino acid residue: —NH—CH(R)—CO— (R is a side chain of said amino acid residue) or of a-amino acid residue protected by acylation wherein the hydroxy group or amino group of its side chain is modified by substitution with the acyl group used in said N-acylation protection.

BRIEF DESCRIPTION OF THE DRAWINGS

FIG. 2 is a drawing showing a process flow illustrating an example of the detailed operational procedures used when a peptide sample bound on the gel is subjected to a treatment for successive release of C-terminal amino acids according to the second aspect of the present invention.

FIG. 7 shows the cleavage sites at the C-terminal side peptide bond of each arginine residue due to the digestion by trypsin, and the lysine residues in which the cleavage at the C-terminal side peptide bond is prevented by the protection with use of N-acetylation, which are included in the amino acid sequences of a peptide chain that is a component of horse myoglobin.

FIG. 8 is a drawing showing a comparison of the MS spectra measured in anionic species detection mode (lower) and in cationic species detection mode (upper) by a MALDI-TOF-MS apparatus for mixture of the resulting reaction products that are obtained by using treatment conditions for successive release of C-terminal amino acids, which conditions are employed in the present invention, in which successive release of C-terminal amino acids of the globin peptide chain was conducted for an isolated dry peptide having an arginine residue at the C-terminus, i.e. an N-acetylated Glu$^1$-Fibrino peptide fragment, as described in Reference Example 1.

FIG. 9 shows a list of the molecular weights (M+H) of the cationic species corresponding to the fragments produced by autolysis of trypsin.

BEST MODE FOR CARRYING OUT THE INVENTION

Figure 1:
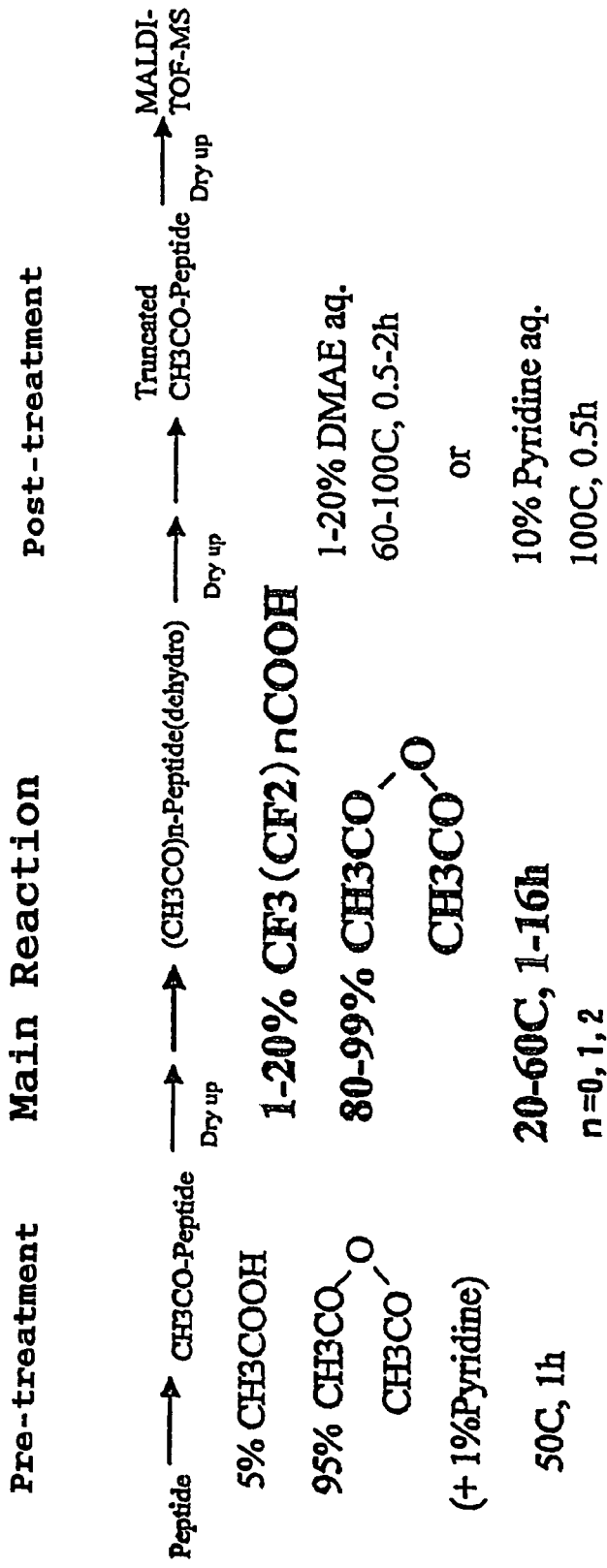
FIG. 1 is a drawing showing a process flow illustrating an example of the detailed operational procedures used when a dry peptide sample is subjected to a treatment for successive release of C-terminal amino acids according to the first aspect of the present invention.

The present invention is explained in more detail below.

The method for analysis of C-terminal amino acid sequence of peptide according to the present invention basically utilizes a technique which comprises steps of releasing, from a peptide to be examined, its C-terminal amino acids successively to prepare a series of reaction products each having a sequential truncation in peptide chain, and identifying the released amino acids based on the differences between the molecular weights of the C-terminal side peptide fragments derived from the series of reaction products and the molecular weight of the C-terminal side peptide fragment derived from the original peptide, which are discriminated from the fragments obtained by digestion of the series of reaction products and the original peptide by trypsin. More specifically explaining, these C-terminal side peptide fragments that are obtained by digestion by trypsin are terminated at the site specific to trypsin; MALDI-TOF-MS apparatus is employed as means for measuring the molecular weights of the C-terminal side peptide fragments derived from the series of reaction products and the molecular weight of the C-terminal side peptide fragment derived from the original peptide; its mechanism for ionization enables respective measurements for cationic species formed by addition of proton ($H^+$) to peptide fragment and for anionic species formed by detachment of proton ($H^+$) from peptide fragment. Since neither arginine residue nor lysine residue are included in the amino acid residues composing the C-terminal side peptide fragments, in which no mechanism for stabilizing the cationic species that is caused by arginine residue or lysine residue functions; when compared the results of measurement for cationic species with the results of measurement for anionic species, the relative intensities thereof show quite different behavior from that for other peptide fragments in whose amino acid residues an arginine residue or lysine residue is contained; such specific feature thereof is utilized for discrimination and identification of peaks that are attributed to a series of the C-terminal side peptide fragments, from the peaks of a plurality of species measured with use of a MALDI-TOF-MS apparatus.

Therefore, the greatest feature of the method for analysis according to the present invention lies in that, in the step of successively releasing the C-terminal amino acids of an original peptide, the side reaction of peptide bond degradation in the middle of the peptide chain is effectively suppressed and, thereby, there is prevented, into the mixture of all peptide fragments obtained by said treatment for digestion by trypsin, incorporation of peptide fragments resulting from said secondary reaction of peptide bond degradation, other than the common N-terminal side peptide fragments and the intended C-terminal side peptide fragments derived from the series of reaction products, which are all produced by digesting the original peptide with trypsin. It is also a major feature of the method for analysis according to the present invention that, in order to suppress said side reaction of peptide bond degradation in the middle of peptide chain, protection with N-acylation or O-acylation are beforehand applied to the target peptide chain and further, prior to the final digestion by trypsin, the protection with O-acylation is deprotected, while the N-acylation protection on lysine residue is left; thereby, fragmentization by digestion by trypsin is allowed to occur only at the C-terminal side peptide bond of arginine residue, formation of peptide fragments that are unnecessarily divided into small sizes is suppressed, and desired C-terminal side peptide fragments derived from a series of reaction products can have a molecular weight range suitable for measurement by means of MALDI-TOF-MS.

In the reaction for successively releasing C-terminal amino acids from a target peptide used in the present invention, employed is such a process in which, there is used, as a reaction agent, a combination of an alkanoic acid anhydride and a small amount of a perfluoroalkanoic acid, and the alkanoic acid anhydride is allowed to act as a reagent for activation of the C-terminal carboxy group of a target peptide, by means of catalytic function of the perfluoroalkanoic acid exhibiting a high proton donability, in a water-free environment under heated-up condition at a relatively low temperature; at the C-terminus of the peptide, there is once formed a 5-oxazolone structure represented by the following general formula (III):

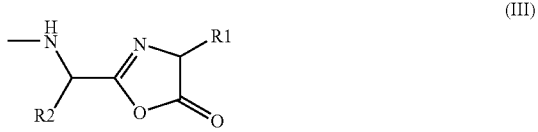
(III)

wherein R1 is a side chain of the C-terminal amino acid of the peptide; and R2 is a side chain of the amino acid residue positioned just before the C-terminal amino acid, and then the C-terminal amino acid is released in association with the cleavage of 5-oxazolone ring.

The reaction of the formation of said 5-oxazolone ring is expressed as a whole by the following reaction scheme (I):

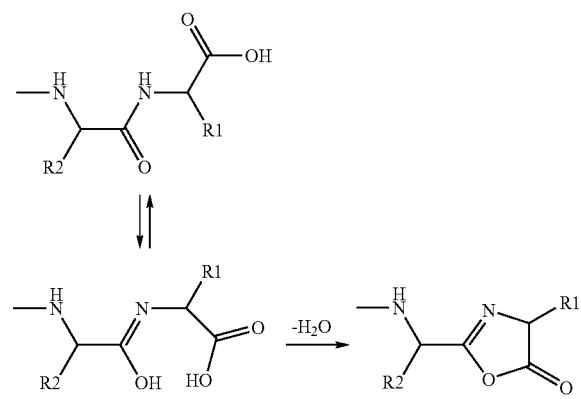
(I)

However, in the process for selectively releasing C-terminal amino acids according to the present invention, first, the perfluoroalkanoic acid present in a small amount is allowed to act as a proton donor on the dried peptide at the stage of keto-enol tautomerism represented by the following reaction scheme (Ia):

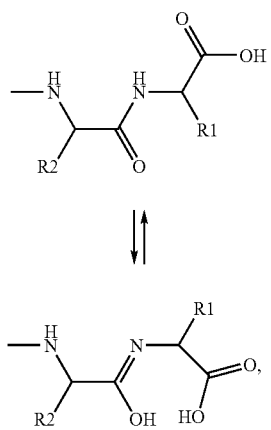
(Ia)

and thereby the ratio of enol form is heightened.

Then, an intramolecular ester bond is formed between the hydroxy group exposed in the enol type and the C-terminal carboxy group to complete the 5-oxazolone ring-formation. In this case, in the process for successive release of C-terminal amino acids according to the present invention, there is used an alkanoic acid anhydride as a reagent for activation of C-terminal carboxy group, and the enol form is converted into, for example, an asymmetric acid anhydride such as shown in the following reaction scheme (Ib):

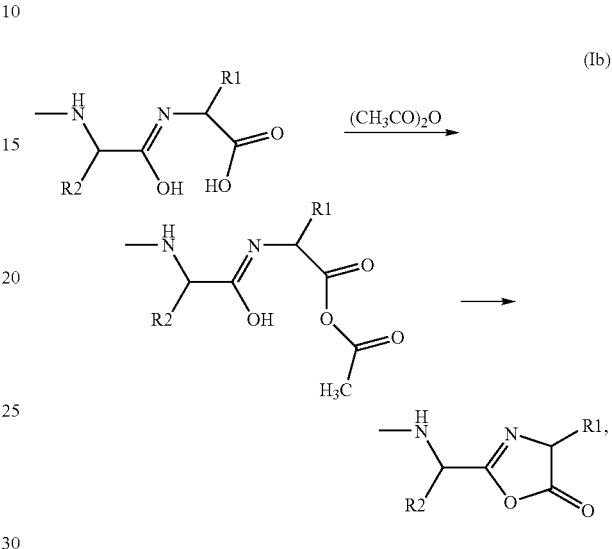
(Ib)

and thus the activated C-terminal carboxy group is involved in the reaction. As a result, such a reaction can proceed even under a mild temperature condition. Meanwhile, since the reaction system is maintained in a water-free state and the alkanoic acid anhydride of relatively low reactivity is used, initiation for the degradation of the peptide bond present in the middle of peptide chain is suppressed under such a mild temperature condition. In the process for selectively releasing C-terminal amino acids according to the present invention, it is understood that, from the once-formed 5-oxazolone ring, the separation of the C-terminal amino acid and the formation of the reaction intermediate for the next stage proceed, for instance, via such a reaction as shown by the following reaction scheme (II'):

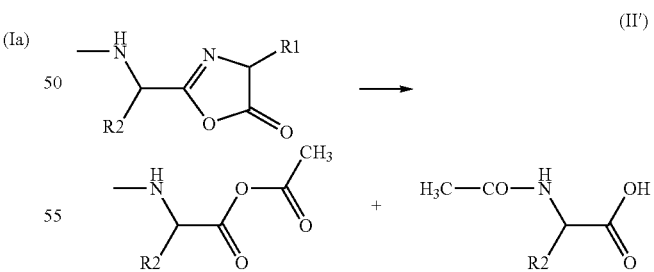
(II')

as a result, selective release of C-terminal amino acids is successively advanced in such a way.

Incidentally, there is a certain possibility that the serine residue [—NH—CH(CH$_2$OH)—CO—] and threonine residue [—NH—CH(CH(CH$_3$)OH)—CO—] in peptide chain may give rise to the following side reactions owing to the hydroxy group (—OH) on the side chain: for instance, a N,O-acyl rearrangement reaction between the α-position amino group (—NH—) and the β-position hydroxy group (—OH) is progressed; successively, hydrolysis of the ester bond formed thereby progresses, and thereby peptide cleavage takes place at the N-terminal side of serine residue; further, depending upon the condition, as for the threonine residue [—NH—CH(CH($CH_3$)OH)—CO—] having a hydroxy group (—OH) at the β-position, hydrolysis is advanced through the similar reaction mechanism that is caused by the N,O-acyl rearrangement reaction, and thereby peptide cleavage takes place at the N-terminal side of threonine residue. In addition, there is also anxiety that the lysine residue [—NH—CH(($CH_2$)$_4$—$NH_2$)—CO—] in peptide chain may give rise to the following side reaction owing to the amino group (—$NH_2$) on the side chain: when the exchange of amide bond takes place between the α-position amino group (—NH—) and the ε-position amino group (—$NH_2$) both of the lysine residue [—NH—CH($CH_2CH_2CH_2CH_2NH_2$)—CO—] under a heated-up condition, and successively, hydrolysis of the ε-position amide bond formed thereby is advanced, and thereby cleavage of peptide may occur at the N-terminal side of the lysine residue.

In the present invention, the reaction for successively releasing C-terminal amino acids is conducted in a dry state under a mild temperature condition; however, in order to more reliably avoid the above-mentioned side reactions in which the serine residue [—NH—CH($CH_2$OH)—CO—], threonine residue [—NH—CH(CH($CH_3$)OH)—CO—] and lysine residue [—NH—CH($CH_2CH_2CH_2CH_2NH_2$)—CO—] may be involved, there is conducted, prior to said reaction for successively releasing C-terminal amino acids, a pretreatment step of applying protection with N-acylation and O-acylation.

In the first aspect of the present invention, in this pretreatment step of applying protection with N-acylation and O-acylation, there is allowed to act, on a dry sample of a target peptide, an alkanoic acid anhydride and an alkanoic acid both of vapor phase and supplied from a mixture of an alkanoic acid anhydride and a small amount of an alkanoic acid, in a dry atmosphere at a temperature selected in a range of 10° C. to 60° C.; thereby, the reaction between the amino group (—$NH_2$) or hydroxy group (—OH) and the alkanoic acid anhydride is promoted by utilizing the proton donatability of the alkanoic acid, and N-acylation and O-acylation are achieved. In this case, since the proton donatability that the alkanoic acid has is inferior to the proton donatability that perfluoroalkanoic acid exhibits, it falls quite short of activity required for making progress of the reaction for formation of 5-oxazolone ring at the C-terminus of peptide chain.

In the second aspect of the present invention, a peptide sample bound on a gel carrier is beforehand subjected to a dehydration treatment; then, in the above-mentioned pretreatment step, the gel carrier is immersed, at a temperature selected in a range of 30° C. to 80° C., in a solution of alkanoic acid anhydride dissolved in a dipolar aprotic solvent that is infiltratable into the gel substance and capable of keeping it in swelling state; thereby, the alkanoic acid anhydride is allowed to act on the target peptide sample in a bound state to achieve N-acylation and O-acylation. This liquid-phase reaction in the dipolar aprotic solvent proceeds sufficiently even without utilizing the catalysis of an alkanoic acid having proton donability. In addition, an alkanoic acid is produced in the reaction system in association with the liquid-phase reaction, and the catalytic effect thereof is added, whereby the reaction is gradually promoted. However, since the proton donatability of the alkanoic acid derived in the system is inferior to the proton donatability that perfluoroalkanoic acid shows, it falls quite short of activity required for making progress of the reaction for formation of 5-oxazolone ring at the C-terminus of peptide chain.

In addition, in the present invention, by selecting, in the pretreatment step, such a condition that N-acylation is attained not only to the ε-position amino group (—$NH_2$) of the lysine residue [—NH—CH($CH_2CH_2CH_2CH_2NH_2$)—CO—] but also to the N-terminal amino group of peptide chain, it is possible to provide beforehand, for example, a guard against a case that, when, in the reaction for successive release of C-terminal amino acids, the C-terminal carboxy group has been activated, a reaction with the N-terminal amino group of adjacent peptide chain may happen to take place accidentally. Further, since, when the treatment for hydrolysis is conducted in the post-treatment step, there is selected such a hydrolysis condition that none of the protections with N-acylation to the ε-position amino group (—$NH_2$) of the lysine residue [—NH—CH(($CH_2$)$_4$—$NH_2$)—CO—] and to the N-terminal amino group of peptide chain is deprotected, no enzymatic digestion reaction by trypsin takes place, in the final treatment for digestion by trypsin, at the C-terminus of the lysine residue whose amino group on side chain is protected with N-acylation; and thus the peptide fragments obtained by digestion by trypsin are limited to those fragments obtained by digestion at the C-terminus of arginine residue.

In the present invention, made is good use of such merit that in final, the step of the treatment for digestion by trypsin is carried out in a state that the amino group on lysine residue side chain is protected with N-acylation; which avoids such occurrence of fragmentization into unnecessary large number of fragments, which results from the digestion of peptide chain at the two kinds of cleavage sites, i.e. arginine residue and lysine residue, and thus the long peptide chain can be divided into a plurality of peptide fragments by means of digestion by trypsin at the arginine residues that are contained at appropriate frequency in the peptide chain; as a result, a molecular weight of the resulting C-terminal side peptide fragment can be in a molecular weight range suitable for MALDI-TOF-MS measurement.

In the present invention, desalting treatment is conducted after the digestion treatment by trypsin, the resulting peptide fragments are recovered and dried, and then molecular weights of ion species that are derived from the mixture of the peptide fragments obtained by digestion treatment by trypsin are measured with use of a MALDI-TOF-MS apparatus. Incidentally, as desalting treatment is conducted after the digestion treatment by trypsin, the dried-up peptide fragments recovered are by no means fragments forming variety of salt forms but are peptide fragments per se. In the ionization stage thereof, there are generated a cationic species formed by addition with a proton ($H^+$) and an anionic species formed by detachment of proton ($H^+$); and these cationic species and anionic species are separately measured by selecting the detection mode. In the present invention, of the peptide fragments produced by digestion by trypsin, in a series of peptide fragments derived from the N-terminal side amino acid sequence that is common to the original peptide and the reaction products resulting from successive release of C-terminal amino acids, an arginine residue having a guanidino group with high proton ($H^+$) acceptability is present at the fragment C-terminus, which conduces to stabilization of a cationic species with addition of a proton ($H^+$). On the other hand, in the C-terminal side peptide fragments, such an arginine residue is not present, and thus there occurs no stabilization of a cationic species with addition of a proton ($H^+$) that is due to the presence of arginine residue. In connection with this difference, in the mass spectra for cationic species measured by the MALDI-TOF-MS apparatus, the peak intensities that are attributed to a series of peptide fragments derived from the common N-terminal side amino acid sequence, which have an arginine residue at the fragment C-termini thereof, are relatively high. Meanwhile, in the C-terminal side peptide fragments wherein no arginine residue is present, a carboxy group (—COOH) having proton ($H^+$) donatability is present at the C-terminus thereof, and thus in the mass spectra for anionic species measured by the MALDI-TOF-MS apparatus, the peak intensities that are attributed to the C-terminal side peptide fragments are relatively high.

In the present invention, the desalted and dried peptide fragments are subjected to measurement by MALDI-TOF-MS apparatus, and then the mass spectra for cationic species and for anionic species are compared with each other to find out the aforementioned differences in ralative intensities therebetween; and by using the differences in ralative intensities, there can be discriminated the peaks that are originated from the series of peptide fragments each having an arginine residue at the fragment C-terminus, which are derived from the common N-terminal side amino acid sequence, and further in the mass spectra for the anionic species, there can be easily distinguished the peaks that are originated from the series of the C-terminal side peptide fragments, which are ascribed to community in the N-terminal side amino acid sequence between the original peptide and the reaction products produced by the successive release of C-terminal amino acids.

In said molecular weight measurements for anionic species, there are measured the decreases in molecular weight associated with the successive release of C-terminal amino acids, based on a series of peaks each having a higher intensity, whereby the assignment of each amino acid giving a corresponding molecular weight change is determined. Incidentally, each of the C-terminal side peptide fragments each having no arginine residue, formed by digestion by trypsin has an α-position amino group (—$NH_2$) at the N-terminal amino acid residue and, therefore, shows a corresponding peak also in the mass spectra of cationic species; hence, the result of assignment of each amino acid can be reconfirmed by utilizing the molecular weight of the corresponding peak observed in the mass spectra of cationic species.

More detailed description is made below on each of the method for analysis of C-terminal amino acids of peptide according to the first aspect of the present invention and the method for analysis of C-terminal amino acids of peptide according to the second aspect of the present invention.

In the method for analysis of C-terminal amino acids of peptide according to the first aspect of the present invention, first, an isolated dry sample of peptide is subjected to the following treatment, in the step of subjecting a target peptide to a chemical means to successively release the C-terminal amino acids of the peptide to prepare a mixture containing a series of reaction products [this step is the steps (1) to (3) of the previously-mentioned steps (1) to (6) characterizing the present invention].

Prior to the step of successively releasing the C-terminal amino acids of target peptide, there is carried out a pretreatment (N-acylation protection) step of applying N-acylation by the acyl group of the above-mentioned alkanoic acid anhydride, to the N-terminal amino group of the peptide as well as to the side chain amino group of the lysine residue which may be contained in the peptide. The N-acylation protection to the side chain amino group of lysine residue, applied in the pretreatment step is carried out in order to prevent the cleavage in the C-terminal side peptide bond of lysine residue which occurs in the digestion by trypsin conducted finally; therefore, it is desired to select such an acyl group that the N-acylation protection on the side chain of lysine residue is not deprotected in the hydrolysis treatment described later but the O-acylation protection made simultaneously therewith is deprotected sufficiently. Therefore, in the first aspect of the present invention, there is used, as a reaction reagent which is supplied as a vapor and which can apply N-acylation protection and O-acylation protection to a dry sample of peptide, a combination of an alkanoic acid anhydride (which is an electrophilic acylating agent) and an alkanoic acid (which acts as a catalyst for promotion of acylation, owing to the proton donability).

The alkanoic acid anhydride and alkanoic acid used in the pretreatment step are allowed to act on the peptide chain in a dry atmosphere as a vapor having a particular partial pressure ratio; therefore, they are vaporized from a mixture of the alkanoic acid anhydride and a small amount of the alkanoic acid, in a air-tight reaction vessel which is maintained at a temperature selected in a range of 10 to 60° C. It is preferred to use a mixture capable of giving a desired partial pressure ratio at a temperature selected in a range of 10 to 60° C., specifically an alkanoic acid of 2 to 4 carbon atoms and a symmetric anhydride of said alkanoic acid of 2 to 4 carbon atoms. It is more preferred to use a linear-chain alkanoic acid of 2 to 4 carbon atoms and a symmetric anhydride of said linear-chain alkanoic acid of 2 to 4 carbon atoms. When the alkanoic acid anhydride and the alkanoic acid added in a small amount are the same kind, there is no case that different alkanoyl groups are present in the N-alkanoylation protection and O-alkanoylation protection achieved, even if an acyl exchange reaction has taken place in the course of N-alkanoylation and O-alkanoylation. Therefore, even when part of the O-alkanoylation protection remains protected in the hydrolysis treatment described later, the difference in molecular weight between deprotected molecule and protected molecule is known beforehand and the peak of the protected molecule can be identified easily. In the pretreatment step of applying N-acylation protection, it is ordinarily desired to use a combination of acetic anhydride and acetic acid.

Specifically explaining, in the pretreatment step of applying N-acylation protection, an alkanoic acid anhydride and an alkanoic acid are allowed to act on a dry sample of peptide in a vapor state; therefore, in order to obtain an appropriate vapor pressure, it is preferred that the alkanoic acid anhydride used in the pretreatment step is the same as the alkanoic acid anhydride used in the subsequent step of successively releasing C-terminal amino acids. This alkanoic acid anhydride has, in a dry atmosphere at a temperature selected in a range of 10 to 60° C., a reactivity too low to cause a side reaction such as cleavage of peptide; in the pretreatment step, the catalysis of the alkanoic acid used together with the alkanoic acid anhydride is far inferior to that of perfluoroalkanoic acid; therefore, N-acylation protection can be carried out without causing undesired side reactions.

When a peptide of long amino acid sequence, such as protein has a secondary structure or a tertiary structure, a defolding treatment is beforehand applied to convert the structure into a peptide chain which does not show such a higher order structure; thereby, N-acylation protection proceeds even to all the side chain amino groups of lysine residue present in the peptide, under the condition of applying N-acylation protection to the N-terminal amino group of the peptide. Further, O-acylation protection proceeds to the side chain hydroxy groups of serine residue and threonine residue present in the peptide, and these groups are protected. Furthermore, the side chain phenolic hydroxy group of tyrosine residue present in the peptide undergoes O-acylation partially although the reactivity differs. As a result of the pretreatment step where these plurality of acylation protections are made, all of the side chain amino group of lysine residue and the side chain hydroxy groups of serine residue and threonine residue undergo protection (modification) and the resulting groups are no longer able to take part in undesired side reactions.

Incidentally, there is substantially no fear that the combination of an alkanoic acid anhydride and an alkanoic acid, used in the pretreatment step, causes undesired side reactions such as cleavage of peptide in the middle. However, the temperature of the pretreatment is preferably a temperature selected in a range of 10 to 60° C., more preferably around room temperature or a temperature range slightly higher than room temperature. Specifically, the temperature is preferably selected in a range of 15 to 50° C. The proportion of the alkanoic acid in the mixture of the alkanoic acid anhydride and the alkanoic acid is preferably 2 to 10% by volume, specifically 5% by volume relative to the total volume of the alkanoic acid anhydride and the alkanoic acid.

Incidentally, the speed of N-acylation in the pretreatment step varies depending upon the partial pressures (gas-phase concentrations) of the alkanoic acid anhydride and alkanoic acid used and the temperature of the reaction (N-acylation). Therefore, the reaction time in the pretreatment step is desired to be appropriately selected depending mainly upon the reaction temperature. For example, when the reaction temperature is selected at 50° C., the reaction time is selected within 1 hour, for example, at 30 minutes, whereby N-acylation to the N-terminal amino group of peptide can be completed. At that time, it is preferred to add pyridine of catalytic amount, for example, 0.1 to 1.0% by volume relative to the total of the alkanoic acid anhydride and the alkanoic acid, in order to promote the acylation by the alkanoic acid anhydride and the alkanoic acid. This pyridine base, which functions as a proton acceptor, allows, for example, easier removal of the proton to be detached in association with the acylation of amino group.

When the target peptide forms, for example, a —S—S— bond of oxidized type with the cysteine of an adjacent peptide molecule or per se contains cysteine having a —S—S— bond, an ordinary reducing treatment is applied beforehand to remove such a bridge for conversion into a peptide containing cysteine of reduced type. When cysteine of reduced type is present in the target peptide, carboxymethylation, pyridylethylation or the like is applied to the side chain sulfanyl group (—SH) of the cysteine for protection thereof. Specifically explaining, when the target peptide is a peptide of long amino acid sequence, such as protein and has a secondary or tertiary structure and when its molecule may contain cysteine having a —S—S— bond, an ordinary reducing treatment is applied in the stage of applying a defolding treatment for conversion into a peptide chain not showing such a higher order structure, whereby such a bridge is removed and the original peptide is converted into a peptide containing cysteine of reduced type. In addition, to the cysteine of reduced type present in the original peptide is applied carboxymethylation, pyridylethylation or the like to the side chain sulfanyl group (—SH) of the cysteine for protection thereof.

As the procedure of such a pretreatment step, there can be mentioned a procedure which comprises placing a liquid mixture of an alkanoic acid anhydride and a small amount of an alkanoic acid in a sealable reactor, cooling this mixture once to reduce the vapor pressure thereof, degassing the reactor, and increasing the reactor-inside temperature to a reaction temperature to vaporize the alkanoic acid anhydride in the reactor. By employing such a procedure, there is another advantage that the leakage of water into the reactor can be prevented. Further, by conducting degassing so that no oxygen remains in the reaction system, for example, the sulfur present in methionine, which is included in amino acid residues constituting the target peptide, can be prevented from oxidation by oxygen and subsequent change of its scheme weight. In the method of present invention which is based on the measurement of molecular weights, such prevention of oxidation is preferred for achieving a higher accuracy. After the reaction of the pretreatment step has been over, the reaction reagent remaining in the reactor is removed and then the subsequent step for successively releasing the C-terminal amino acids of the original peptide is conducted.

In the reaction for successive release of the C-terminal amino acids of the original peptide according to the first aspect of the present invention, there are allowed to act, on the dry sample of the peptide after N-acylation protection, an alkanoic acid anhydride and a perfluoroalkanoic acid both of vapor phase and supplied from a mixture of an alkanoic acid anhydride and a small amount of a perfluoroalkanoic acid, in a dry atmosphere at a temperature selected in a range of 15 to 60° C.; and at the C-terminus of the peptide, the C-terminal amino acids are released successively in association with the formation of a 5-oxazolone structure represented by the following general scheme (III):

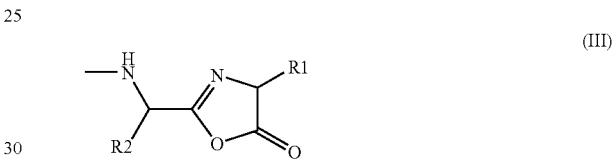

wherein R1 is a side chain of the C-terminal amino acid of the peptide and R2 is a side chain of the amino acid residue positioned just before the C-terminal amino acid, and the subsequent cleavage of the 5-oxazolone ring.

In this reaction for formation of 5-oxazolone ring, first, at the state of the keto-enol tautomerism represented by the following reaction scheme (Ia):

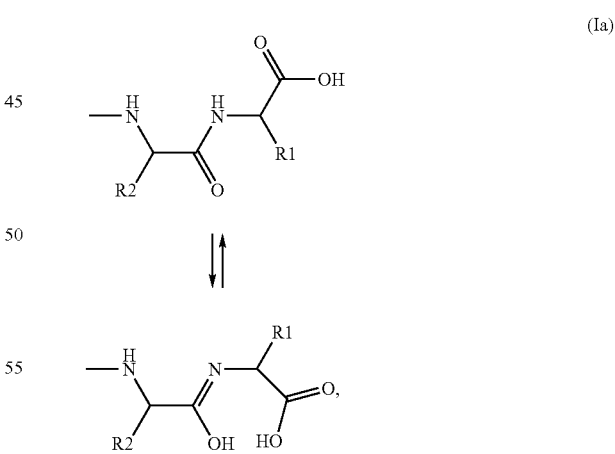

the ratio for staying in the enol state is heightened by allowing the perfluoroalkanoic acid of vapor phase to function as a proton donor toward the dried peptide, in a dry atmosphere.

Then, an intramolecular ester bond is formed, in the enol type, between the exposed hydroxy group and the C-terminal carboxy group to complete the formation of 5-oxazolone ring. It is estimated that, in this esterification reaction as well, the perfluoroalkanoic acid of vapor phase functions probably as a proton donor to induce the esterification reaction proceeding under an acid catalyst. In the first aspect of the present invention, an alkanoic acid anhydride is used as a reagent for activation of C-terminal carboxy group, for conversion into an asymmetric acid anhydride as illustrated by, for example, the following reaction scheme (Ib):

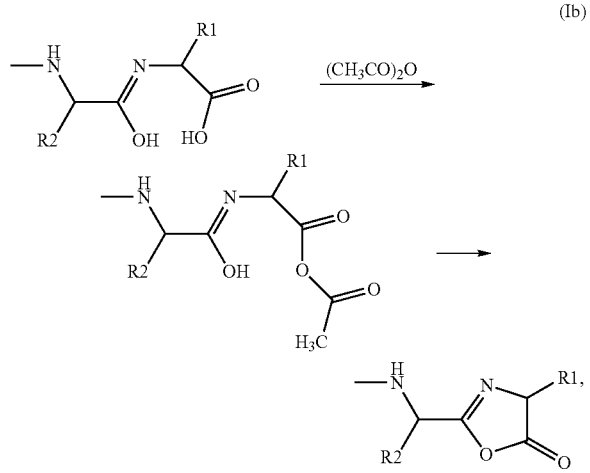

and thus the activated C-terminal carboxy group is involved in the reaction. As a result, such a reaction can proceed under a mild temperature condition and the reaction temperature can be selected in a range of 15° C. to 60° C. Incidentally, such a reaction temperature is selected preferably at around room temperature or in a temperature range slightly higher than room temperature, and more preferably in a specific range of 15° C. to 50° C.

In the treatment using the mixture of an alkanoic acid anhydride and a small amount of a perfluoroalkanoic acid, the alkanoic acid anhydride gives rise ordinarily to N-acylation to the N-terminal amino group of peptide and, therefore, N-acylation protection is achieved in the system; however, it is desired to apply a pretreatment aiming at N-acylation protection.

Thus, in the first aspect of the present invention, the high proton donatability of perfluoroalkanoic acid is utilized, and thus a perfluoroalkanoic acid of which pKa is within a range of 0.3 to 2.5 is preferably used. In addition, since this perfluoroalkanoic acid needs to be supplied to a dried peptide sample in a vapor phase, it is preferred that the perfluoroalkanoic acid is superior in volatility so that a desired vapor pressure is obtained at said temperature selected in a range of 15° C. to 60° C. From this standpoint as well, a perfluoroalkanoic acid having 2 to 4 carbon atoms is more suitable, and a linear-chain perfluoroalkanoic acid having 2 to 4 carbon atoms is particularly suitable. Specifically, use of trifluoroacetic acid ($CF_3COOH$), pentafluoropropanoic acid ($CF_3CF_2COOH$) or heptafluorobutanoic acid ($CF_3CF_2CF_2COOH$) is desired.

The alkanoic acid anhydride used as an activation reagent is consumed with the progress of the reaction; therefore, it is desired to conduct the reaction while the vapor pressure of the alkanoic acid anhydride supplied in a vapor phase is maintained at a given level. Examples of the means used for achieving the purpose include such a means that the reaction system is kept in a sealed state and thereby the vapor pressure of the alkanoic acid anhydride present in the system is stabilized. More particularly, exemplified is such a procedure in which a liquid mixture of an alkanoic acid anhydride and a small amount of a perfluoroalkanoic acid is placed in a sealable reactor; the liquid mixture is once cooled to reduce its vapor pressure; in this state, the reactor inside is evacuated and then sealed off; the alkanoic acid anhydride is vaporized in the reactor by heating up to a reaction temperature. By employing such a procedure, there is another advantage that the leakage of water into the reactor can be prevented. Further, when evacuation is conducted so that no oxygen remains in the reaction system, for example, the sulfur present in the methionine, which is included in the amino acid residues composing a target peptide, can be prevented from oxidation by oxygen and consequent change of its formula weight. In the method of the present invention based on the measurement of molecular weights, such prevention of oxidation is further preferred for achieving a higher accuracy.

As the alkanoic acid anhydride, variety of alkanoic acid anhydrides are usable as long as they can produce an appropriate vapor pressure when heated to the temperature of reaction. However, there is preferred an alkanoic acid anhydride which gives a sufficient vapor pressure when the reaction temperature is selected in the above-mentioned preferable range, for example, of 15° C. to 50° C. Therefore, a symmetric anhydride of an alkanoic acid having 2 to 4 carbon atoms is used preferably. As the symmetric acid anhydride, a symmetric anhydride of a linear-chain alkanoic acid having 2 to 4 carbon atoms is used more preferably, and a symmetric anhydride of a linear-chain alkanoic acid having 2 carbon atoms, i.e. acetic anhydride is used particularly preferably. Since such an alkanoic acid anhydride is used for the activation of C-terminal carboxy group, the anhydride is preferred to give minimum steric hindrance, and the above-mentioned acetic anhydride, etc. are very suitable in this respect as well.

The alkanoic acid anhydride and perfluoroalkanoic acid used in the successive release of C-terminal amino acids are allowed to act on a dried peptide sample in respective vapor states. The reaction is conducted in a dry atmosphere in order to avoid the hydrolysis of once-formed 5-oxazolone ring by the water incoming from outside of the system and its reversion to original structure. In this view, it is more desirable that the reaction is carried out generally in a sealed reactor. Incidentally, the mixture of the alkanoic acid anhydride and the perfluoroalkanoic acid, initially fed into the reactor is, at room temperature, a liquid mixture wherein the alkanoic acid anhydride and the perfluoroalkanoic acid are mixed uniformly. In this mixture containing the alkanoic acid anhydride and a small amount of the perfluoroalkanoic acid, the perfluoroalkanoic acid functioning as a catalyst is not consumed during the reaction in principle and therefore its content can be a small amount. Specifically explaining, the vapor of perfluoroalkanoic acid present in the vapor phase, as compared with the vapor of alkanoic acid anhydride co-existing, can be in a relatively low concentration. In other words, depending upon the kinds of the alkanoic acid anhydride and perfluoroalkanoic acid used, for instance, upon the respective saturated vapor pressures thereof at the reaction temperature, there is appropriately selected a liquid mixture having a mixing ratio which can achieve an intended partial pressure ration (a concentration ratio in vapor phase). The content of perfluoroalkanoic acid in the mixture of the alkanoic acid anhydride and a small amount of the perfluoroalkanoic acid, is desired to be selected, for example, in a range of 1 to 20% by volume, preferably in a range of 3 to 10% by volume relative to the total volume of the alkanoic acid anhydride and the perfluoroalkanoic acid.

In the first aspect of the present invention, it is judged that, from the once-formed 5-oxazolone ring, the separation of the C-terminal amino acid and the formation of the reaction intermediate for the next stage proceed, for instance, via such a reaction as shown by the following reaction scheme (II'):

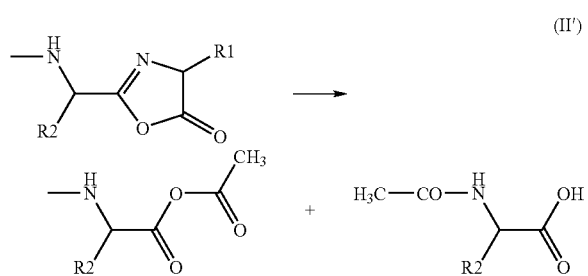

as a result, successive release of C-terminal amino acids is advanced. Therefore, the reaction products obtained after the completion of such reactions are a mixture comprising, in addition to those having a carboxy group exposed at the C-terminus, such as shown in the above reaction scheme (II), an intermediate product having the 5-oxazolone ring structure and a form of reaction intermediate in which its C-terminus has been converted into the form of asymmetric acid anhydride.

The reaction occurring in the step of successively releasing the C-terminal amino acids of peptide comprises at least two-stage elementary reactions, i.e. a stage of formation of 5-oxazolone ring structure as illustrated by the reaction scheme (Ib) and a stage of separation of C-terminal amino acid by the cleavage of 5-oxazolone ring structure, as illustrated by the reaction scheme (II'). Therefore, the overall reaction rate depends upon the reaction rates of the two stages, but depends mainly upon the partial pressures (concentrations in vapor phase) of the alkanoic acid anhydride and perfluoroalkanoic acid used as well as on the reaction temperature. In addition, since a series of reaction products are formed by successive reactions, the maximum length of C-terminal amino acid sequence removed by such successive reactions becomes longer as the treatment duration becomes longer. Hence, the treatment duration for the step of selectively releasing C-terminal amino acid in such a successive manner needs to be appropriately chosen depending mainly upon the partial pressures (concentrations in vapor phase) of the alkanoic acid anhydride and perfluoroalkanoic acid used and the reaction temperature employed and also in view of the intended length of the C-terminal amino acid sequence to be analyzed.

There is arranged a hydrolysis step as a post-treatment step in order to convert the forms of reaction intermediates each having no carboxy group exposed at the C-terminus, such as illustrated in the above reaction scheme (II'), formed in the step of successively releasing the selected C-terminal amino acids of peptide, into a form having a carboxy group exposed at the C-terminus. That is, in the first aspect of the present invention, in this hydrolysis step, after there have been removed, in a dry state, the alkanoic acid anhydride and perfluoroalkanoic acid remaining in the mixture containing a series of reaction products, obtained by said step of successively releasing the C-terminal amino acids of peptide, there are supplied a basic nitrogen-containing aromatic compound or a tertiary amine compound both of vapor phase and water molecules, from an aqueous solution of the basic nitrogen-containing aromatic compound or the tertiary amine compound; said water molecules are allowed to act on the above-mentioned reaction products in the presence of the basic nitrogen-containing organic compound, whereby are hydrolyzed the ester bond inside the 5-oxazolone ring and the C-terminal asymmetric acid anhydride structure which is one form of the reaction intermediates and each C-terminal amino acid residue is allowed to have a reproduced carboxy group (—COOH). By the action of water molecules in the presence of the basic nitrogen-containing, organic compound, there also occurs deprotection at the side chain hydroxy groups of serine residue and threonine residue and the side chain phenolic hydroxy group of tyrosine residue, all of which are present in the peptide chain and to all of which O-acylation has been applied in the pretreatment step. Meanwhile, the N-acylation protections to the side chain amino group of lysine residue as well as to the N-terminal amino acid group of peptide chain, are not deprotected and remain. After this hydrolysis, there is carried out a redrying post-treatment of removing the basic nitrogen-containing organic compound and water molecules remaining in the mixture containing a series of reaction products of hydrolysis and then conducting drying. By applying such hydrolysis, the side chain amino group of lysine residue is N-acylated in the original peptide and the series of reaction product peptides and the respective C-terminal carboxy groups are exposed. In this state, they are subjected to digestion by trypsin.

The basic nitrogen-containing aromatic compound or tertiary amine compound both of vapor phase, used in the hydrolysis has no ability to react with, for example, products having such a form in which its C-terminus has been turned into an asymmetric acid anhydride, or to form any amide bond therewith; and further, the basic nitrogen-containing aromatic compound or tertiary amine compound can be made into a uniform solution when made into an aqueous solution and is therefore suitable for use in the hydrolysis. As the basic nitrogen-containing aromatic compound which can be used, there is preferred a monocyclic, nitrogen-containing, aromatic compound which can give an appropriate vapor pressure, and, for example, pyridine can be more suitably used. As the tertiary amine compound which can be used, there is preferred one having the same weak basicity as shown by pyridine and, for instance, DMAE [$(CH_3)_2N$—$CH_2CH_2OH$] can be suitably used. When for example, pyridine is used, the pyridine content is preferably selected in a range of 5 to 15% by volume, specifically at 10% by volume relative to the whole volume of the aqueous solution thereof. When (dimethylamino)ethanol (DMAE) is used, the DMAE content is preferably selected in a range of 1 to 20% by volume, specifically at 10% by volume relative to the whole volume of the aqueous solution thereof.

The monocyclic nitrogen-containing aromatic compound or tertiary amine compound is allowed to act on a dried mixed sample containing the reaction products, in the vapor state together with water molecules. In this post-treatment as well, the reaction is desired to be conducted generally in a sealed reactor. In said post-treatment, since water molecules are used, their vapor pressure needs to be set at a certain level or higher. Therefore, the treatment temperature is desirably chosen, for example, at a temperature of 60° C. or more but, when the mechanical strength of the reactor is taken into consideration, in a range of 100° C. or lower. In order to complete the hydrolysis quickly, a temperature of 100° C. or slightly lower is desired to be selected.

In the selective release of C-terminal amino acids according to the first aspect of the present invention, it is very preferable to carry out the pretreatment step, the step of selectively releasing C-terminal amino acids and the post-treatment step, for example, in the same reactor and continuously. An example of the flow pattern of these steps is illustrated in FIG. 1. A drying-up operation is conducted in said flow when each step has been completed, so that the reagents used in each step do not remain in the peptide sample. This drying-up operation is generally conducted by vacuum distillation, and thereby the C-terminal amino acids released that are by-products in said reaction can be removed as well, in some cases. The flow pattern of steps of FIG. 1 illustrates a case wherein acetic anhydride of high availability in a very high purity is utilized as the alkanoic acid anhydride used therein.

On the other hand, in the flow pattern of steps illustrated in FIG. 1, as for the treatment duration in the step of selectively releasing C-terminal amino acids, there is shown a range of treatment time which is selected depending upon the proportions of the acetic anhydride and perfluoroalkanoic acid used and the treatment temperature employed, for a model case where the length of amino acids of the C-terminal amino acid sequence to be truncated in said step is intended to be ten odd amino acids as maximum case and 3 amino acids as minimum case. In general, when the proportion of the perfluoroalkanoic acid is larger and the treatment temperature is higher, the reaction rate is higher, and thereby it is possible to prepare, in a shorter duration, a series of reaction products wherein the intended maximum amount of truncation from amino acid sequence has been attained.

Furthermore, in the pretreatment step, N-acetylation to N-terminal amino group of peptide is carried out by using acetic anhydride and acetic acid both of vapor phase. Even in the case of such combination of acetic anhydride and acetic acid, there is, in some cases, a fear, maybe very small, that the activation reaction to C-terminal carboxy group expressed by the above-shown reaction scheme (Ia) and the side reaction caused thereby are induced. In order to suppress such a side reaction, a small amount of pyridine vapor can be allowed to co-exist to form a weak addition salt between the pyridine base and the C-terminal carboxy group of peptide, which may provide a protection effect against the occurrence of the undesired side reaction. Such an addition salt undergoes easy deprotection by conducting a drying-up operation upon completion of the pretreatment step to distill off the pyridine base under vacuum, and no problem occurs in the next step of selectively releasing C-terminal amino acids. From these standpoints, it is preferred to add, for the formation of addition salt, a small amount of a nitrogen-containing, heterocyclic, aromatic compound which can be easily distilled off under reduced pressure and has a weak basicity, such as pyridine. Further, since the formation of addition salt has a protection function also for the carboxy group on the side chain of amino acid, it can effectively prevent coincidentally even the undesired side reaction that is originated from the carboxy group on the side chain of amino acid.

In the first aspect of the present invention, there are determined the differences in the molecular weight between the series of reaction products prepared by successively releasing C-terminal amino acids and the original peptide, by using the measurement results obtained by mass spectrometry, and there are identified amino acids corresponding to the differences in molecular weight. Therefore, it is generally desired that the original peptide remains in the mixture subjected to the measurement by mass spectrometry, in such an amount as to enable the determination of its molecular weight.

Specifically explaining, the method for analysis of the C-terminal amino acid sequence of peptide, according to the first aspect of the present invention may be applied to such a case where the maximum length analyzed for the C-terminal amino acid sequence is as long as ten and odd amino acids. With respect to the contents of the series of reaction products of which kinds reach, as the maximum case, the number of ten and odd, the content of the minimum content reaction product is desired at least to be not smaller than about $\frac{1}{10}$ of the content of the maximum content reaction product. In addition, the remaining amount of the original peptide as well is desired at least to be not smaller than about $\frac{1}{10}$ of the content of the maximum content reaction product. Meanwhile, the required information of C-terminal amino acid sequence is within 10 amino acids in many cases and, when selecting the treatment time in which about 10 amino acids can be released, the above-mentioned requirements regarding the contents can be satisfied.

Next, with respect to the first aspect of the present invention, more detailed description is made on the steps (4) to (6) of the above-mentioned steps (1) to (6) characterizing the present invention, that is, on the step of analyzing, by mass spectrometry, the differences in molecular weight between the original peptide and said series of reaction products, to determine the decreases in molecular weight occurring in association with the successive release of C-terminal amino acids, as well as on the step of, based on the determined decreases in molecular weight, identifying the series of amino acids released successively and arranging these amino acids from the C-terminus of peptide to obtain the information of C-terminal amino acid sequence.

In the present invention, a MALDI-TOF-MS apparatus is used for the measurement of molecular weights; therefore, molecular weight measurement of high precision is possible even for a peptide of high molecular weight. However, even when there is used a MALDI-TOF-MS apparatus suitable for the measurement of molecules of large molecular weight such as peptide, there is an upper limit as to the molecular weight allowing for effective ionization, and therefore it is desired that the maximum amino acids of a peptide that is possibly subjected to measurement does not exceed 30 to 50 amino acids. In addition, amino acids corresponding are identified based on the measured differences in molecular weight; therefore, in order to distinguish two amino acid residues giving a formula weight difference of 1, such as Asn vs Asp, or Gln vs Glu, from each other at a high precision, the molecular weight of the longest peptide, i.e. the peptide with no release of C-terminal amino acid therefrom that is used as a datum point, is preferably in a range of no more than 4,000, more preferably in a range of no more than 3,000. When reduced to amino acids, it is length of preferably 40 amino acids at longest, more preferably in a range of no more than 30 amino acids.

In the first aspect of the present invention, in order to enable its application to a peptide of long amino acid sequence, which is far longer than the above-mentioned amino acid length, such as protein, a peptide chain is cleaved, prior to mass spectrometry, using trypsin which is a protease having a peptide cleavage ability at specific sites of peptide and showing an excellent enzymatic reaction efficiency; and, using the C-terminal peptide fragments obtained, there are measured the differences in molecular weight between the series of reaction products prepared by successive release of C-terminal amino acids and the original peptide.

In the digestion by trypsin, trypsin is allowed to act on a mixture containing the series of reaction products after hydrolysis and redrying, in a buffer solution; thereby, the peptide chains wherein each N-terminal amino group thereof and each side chain amino group of the lysine residue (which may be present therein) are N-acylated and protected, undergo specific-to-trypsin cleavage. In that case, since the side chain amino group of lysine residue is N-acylated and protected, the C-terminal side peptide bond of N-acylated lysine residue is not cleaved in the middle and the C-terminal side peptide bond of the arginine residue present in each peptide chain is selectively cleaved in the middle.

For example, if cleavage occurs at the lysine residue and also at the arginine residue, the total number of the resulting peptide fragments reaches a considerable number and, as a result, there appears a tendency that the average amino acid length of each fragment becomes short and peaks of a considerable number of peptide fragments concentrate in a narrow molecular weight range. If there is such concentration of peaks of a considerable number of peptide fragments, it is difficult, in some cases, to identify intended C-terminal side peptide fragments. In particular, the C-terminal side peptide fragments derived from the series of reaction products obtained by successive release of C-terminal amino acids are low in content when the number of amino acids eliminated is large and, when there are other peptide fragments adjacent thereto, it becomes a big obstacle, in some cases, for identification of intended C-terminal side peptide fragments. In the present invention, since the C-terminal side peptide bond of each arginine residue present in peptide chain is selectively cleaved in the middle, the total number of the resulting peptide fragments do not become unnecessarily large and, moreover, the amino acid length of each intended C-terminal side peptide fragment can be allowed to be in a range of amino acid number suitable for the above-mentioned measurement by using MALDI-TOF-MS apparatus.

After the digestion by trypsin; desalting is conducted, the above-mentioned buffer solution component is removed; the peptide fragments after the digestion by trypsin are recovered and dried; and the dried mixture containing the recovered peptide fragments after the digestion by trypsin are subjected to molecular weight measurements for the cationic species and anionic species generated by an ionization treatment, with use of MALDI-TOF-MS.

As already described, there is employed, in the present invention, a technique which comprises:

based on the results of the molecular weight measurements for cationic species and anionic species, obtained with use of a MALDI-TOF-MS apparatus, judging that the peaks of the peptide fragments each having an arginine residue at the C-terminus, obtained by digestion by trypsin show a higher intensity in the molecular weight measurement for cationic species than in the molecular weight measurement for anionic species, owing to the arginine residue possessed by each fragment, judging that the peaks of the C-terminal peptide fragments obtained by digestion by trypsin, derived from the original peptide and also from a series of the reaction products produced from successive release of the C-terminal amino acids of the peptide show a higher intensity in the molecular weight measurement for anionic species than in the molecular weight measurement for cationic species, owing to no presence of arginine residue in each fragment, and based on the molecular weights of the anionic species corresponding to a series of C-terminal peptide fragments and showing a higher intensity in the molecular weight measurement for anionic species, measuring the decreases in molecular weight which have occurred in association with the successive release of the C-terminal amino acids of the original peptide.

In the method for analysis of C-terminal amino acid sequence of peptide according to the first aspect of the present invention, the amino acids released successively are identified based on the differences in molecular weight. Therefore, distinction between leusine (Leu) residue and isoleusine (Ile) residue both having the same formula weight is impossible in principle, which is the same as in the conventional method for analysis of C-terminal amino acid sequence using mass spectrometry. Meanwhile, in the present invention, distinction between glutamine (Gln) residue and lysine (Lys) residue (they have the same formula weight) is possible because the side chain of the lysine (Lys) residue undergoes N-alkanoylation. Further, in the reaction for releasing C-terminal amino acids, conversion of amide bond into enol form and subsequent formation of 5-oxazolone ring structure are essential as shown in the reaction scheme (Ib), and thus no further reaction for release proceeds when cyclic amino acid proline (Pro), in which no imino group (—NH—) that forms an amide bond together with carbonyl group (C=O) is present, has become a C-terminal amino acid. In other words, by confirming that there occurs no further elimination of C-terminal amino acid even when the treatment duration therefor has been prolonged, it is possible to predict that the amino acid residue that is a main factor for such arrest is cyclic amino acid proline (Pro).

Meanwhile, in the present invention, an alkanoic acid anhydride and a perfluoroalkanoic acid are allowed to act in the reaction for subjecting a target peptide to chemical means to successively release the C-terminal amino acids from the peptide to obtain a series of reaction products; therefore, under such reaction condition for successive release of C-terminal amino acids, there proceed O-acylation and N-acylation reaction together to the hydroxy groups present in the serine residue [—NH—CH(CH$_2$OH)—CO—] and threonine residue [—NH—CH(CH(CH$_3$)OH)—CO—] of the peptide, the N-terminal amino group of the peptide, and the ε-position amino group of the lysine residue [—NH—CH(CH$_2$CH$_2$CH$_2$CH$_2$NH$_2$)—CO—] of the peptide, even if no pretreatment step for O-acylation protection and N-acylation protection is applied beforehand to the above groups. As a result, a competitive hindrance effect is obtained against the side reactions (e.g. N,O-acyl rearrangement reaction) caused by the hydroxy groups present in the serine residue [—NH—CH(CH$_2$OH)—CO—] and threonine residue [—NH—CH(CH(CH$_3$)OH)—CO—] of the peptide. In the present invention, however, since the molecular weights of peptide fragments are measured finally, it is necessary to very reliably prevent the in-the-middle cleavage of peptide fragments, caused, for example, by the hydroxy groups present in the serine residue [—NH—CH(CH$_2$OH)—CO—] and threonine residue [—NH—CH(CH(CH$_3$)OH)—CO—] of the peptide, and there is carried out, prior to the step for successive release of C-terminal amino acids, a pretreatment step of applying O-acylation protection and N-acylation protection.

If a number of acetylated forms of serine residue and threonine residue are included in the reaction products obtained finally, the molecular weight differences between such multi-acetylated product and deacetylated product are aligned in the integral times of formula weight 42, specifically 84, 126 and 168, and they are close to the formula weight 87 of serine residue [—NH—CH(CH$_2$OH)—CO—], the formula weight 128 of glutamine residue [—NH—CH(CH$_2$CH$_2$—CONH$_2$)—CO—] or the formula weight 129 of glutamic acid residue [—NH—CH(CH$_2$CH$_2$—COOH)—CO—] and the formula weight 170 of N-acetyllysine residue [—NH—CH(CH$_2$CH$_2$CH$_2$CH$_2$NH—COCH$_3$)—CO—], respectively. Therefore, there is some fear that the peaks for the multi-acetylated products may be mistaken as main peaks and the deacetylated products may be regarded as the above-mentioned amino-acid-eliminated products. In the present invention, a sufficient countermeasure is taken for such fear by selecting, in the post-treatment (hydrolysis) step, conditions in which deprotection of O-acylation protections to serine residue and threonine residue proceeds sufficiently. In addition, since the molecular weight measurement is made after peptide fragmentization, the measurement is conducted in such an analytical precision that the distinction between glutamine residue and glutamic acid residue, which differ in formula weight by only 1, is possible; since the formula weight difference related to the difference in number of remaining acetyl groups differs from the formula weight of an amino acid residue showing a similar formula weight at least with the formula weight difference of 2 to 3, the possibility of the mis-assignment mentioned above is eliminated in many cases.

The reactor vessel is provided with a liquid reagent-holding system that is capable of reserving the liquid reagent for said reaction or each of the liquid reagents combined in the component kit thereof respectively, capable of feeding the liquid reagents for said reactions at given rates to the peptide sample held in said sample container, and capable of maintaining such a state that their direct contact with each other is avoided, and the reactor vessel has a capacity to accommodate said sample container inside. Preferably, the reactor vessel is designed in such a form that the inside can be evacuated; the liquid reagents remaining therein after the completion of the reaction can be distilled off under reduced pressure, and the structure can be made air-tight during the reaction. In addition, the reactor vessel is required to be made of such a material that, when the vapor of the reagent is generated in the reactor vessel, no reaction takes place between the reagent and the wall of the vessel. Therefore, there is suitably used such a vessel formed by using a glass material that is widely used for reactors of chemical reaction. For the cocks used in a sealed-state operation, cocks made of such a material as Teflon® or the like is used suitably.

Successively, more detailed description is made on the method for analysis of C-terminal amino acid sequence of peptide, according to the second aspect of the present invention.

In the second aspect of the present invention, first, there is used a target peptide which has been separated by gel electrophoresis and bound on a gel carrier, in place of the isolated, dried peptide sample used in the first aspect of the present invention. When such a peptide bound on a gel carrier is subjected to a reaction for successive release of the C-terminal amino acids, it is impossible to effectively employ a solid-state reaction using a reaction reagent of vapor phase; therefore, there is employed a technique of infiltrating a reaction agent into the gel carrier to give rise to a liquid-phase reaction. In that case, in the steps (1) to (3) of the above-mentioned steps (1) to (6) characterizing the present invention, i.e. the step of subjecting a target peptide to chemical means to successively release the C-terminal amino acids of the peptide to prepare a mixture containing a series of reaction products, the target peptide is not isolated from the gel carrier and, in, that state, the C-terminal amino acids of the peptide are successively released.

That is, in the steps (1) to (3) of the above-mentioned steps (1) to (6) characterizing the present invention, i.e. the step of subjecting a target peptide to chemical means to successively release the C-terminal amino acids of the peptide, there are conducted:

a step of treatment for dehydration of gel carrier, in which the water included in a gel carrier is removed by dilution with a polar aprotic solvent which does not dissolve the gel and has affinity to water in order to eliminate beforehand the water that is an obstacle to the next-stage pretreatment step of carrying out acylation reaction as for a sample of target peptide bound on the gel carrier which is beforehand isolated by electrophoresis, a pretreatment step of applying acylation protection described below, a step of successively releasing the C-terminal amino acids of peptide, and a post-treatment step of applying hydrolysis to the reaction products obtained.

Incidentally, with respect to the gel substance used for peptide separation by gel electrophoresis, there are appropriately selected the conditions under which a plurality of different peptides falling in a particular molecular weight range can give respective spots (or bands) separated from each other, specifically, the sizes of the fine pores formed inside the gel by selecting the proportion of a polyacrylamide in the gel. As a result, there are present, in the spots (or bands) separated from each other, peptides different in electrophoresis speed owing to the differences in peptide chain molecular weight and electric charge amount on surface, in, for example, the SDS-PAGE method. Such peptides are held inside the fine pores formed in the gel; when only the water in the gel is diluted and dissolved by a polar aprotic solvent which does not dissolve the gel but has affinity to water, the peptides can remain bound on the gel carrier at the spots (or bands) separated from each other, even after such dehydration. That is, the polar aprotic solvent used in the dehydration is generally inferior to water in the affinity to the gel substance such as polyacrylamide; therefore, the volume of the gel decrease with the removal of the water which has maintained the sizes of the fine pores of gel and has had solvation with the pore surfaces. As preferable polar aprotic solvents used in the dehydration, there can be mentioned, for example, nitriles having 4 or less carbon atoms, such as acetonitrile ($CH_3CN$) and ketones having 4 or less carbon atoms, such as acetone, when there is used, for example, a polyacrylamide gel. These polar aprotic solvents used in the dehydration are more volatile than water and, when vaporized to dry-up, the gel decreases its volume, becoming a shrunk gel carrier.

In the second aspect of the present invention, in the pretreatment step of applying acylation protection to peptide chain, the gel carrier loading the peptide thereon is, after the above-mentioned dehydration, immersed in a solution of an alkanoic acid anhydride dissolved in a dipolar aprotic solvent capable of infiltrating into the gel substance and maintaining it in a swollen state, at a temperature selected in a range of 30° C. to 80° C.; thereby, the alkanoic acid anhydride is allowed to act on the target peptide sample bound on the gel carrier, to apply N-acylation protection by the acyl group derived from the alkanoic acid constituting said alkanoic acid anhydride, to the N-terminal amino group of the peptide as well as to the side chain amino group of the lysine residue which may be present in the peptide. This N-acylation protection to the side chain amino group of lysine residue, applied in the pretreatment step has an object of preventing, in the final digestion by trypsin, the in-the-middle cleavage of the C-terminal side peptide bond of lysine residue; therefore, it is desired to select such an acyl group that, in the hydrolysis described later, the N-acylation protection on the side chain of lysine residue is not deprotected but the deprotection of O-acylation protection proceeds sufficiently. In this case, in the second aspect of the present invention, the alkanoic acid anhydride, which is an electrophilic acylating agent, is polarized inside the molecule in a dipolar aprotic solvent, owing to the action of the solvent; when the acylating agent is allowed to act on a peptide, there proceed N-acylation and O-acylation to amino group and hydroxy group. When an alkanoic acid derived from said alkanoic acid anhydride is by-produced, such N-acylation and O-acylation are promoted by the catalysis of the alkanoic acid. That is, in the second aspect of the present invention, since the alkanoic acid by-produced in the gel carrier does not diffused or dissipated quickly, such an alkanoic acid remaining in the gel carrier can be utilized as a catalyst for promotion of reaction; therefore, an alkanoic acid anhydride alone is used as a reaction agent.

As the alkanoic acid anhydride used in the pretreatment step, there is preferred an alkanoic acid anhydride capable of achieving N-acylation protection to the side chain amino group of lysine residue at a temperature selected in a range of 30° C. to 80° C., specifically a symmetric anhydride derived from an alkanoic acid having 2 to 4 carbon atoms. Particularly preferred is a symmetric anhydride derived from a linear-chain alkanoic acid having 2 to 4 carbon atoms. When a symmetric alkanoic acid anhydride is used, an alkanoic acid of the same kind is formed as a by-product; therefore, there is no case that different alkanoyl groups are present in the N-alkanoylation protection and O-alkanoylation protection achieved, even if an acyl group exchange reaction has taken place in the course of N-alkanoylation and O-alkanoylation. Therefore, even when part of the O-alkanoylation protection remains protected in the hydrolysis treatment described later, the difference in molecular weight between deprotected molecule and protected molecule is known beforehand and the peak of the protected molecule can be identified easily. In the pretreatment step of applying N-acylation protection, it is ordinarily desired to use acetic anhydride.

In the dipolar aprotic solvent, the alkanoic acid anhydride gives rise to intramolecular polarization and acts as an electrophilic reaction reagent on said amino group of peptide; as a result, the N-acylation proceeds sufficiently even at a temperature of 30° C. or higher. The N-acylation temperature is preferably selected ordinarily at 50° C. or above for promotion of the reaction; however, since the reaction is carried out generally in a closed reactor, the reaction temperature is desirably selected at 100° C. or below in view of the mechanical strength of the reactor. An alkanoic acid is formed in association with the N-acylation; however its amount is slight and the side reaction caused by such an alkanoic acid having a proton donability and the alkanoic acid anhydride present together invites no problem ordinarily in the above-mentioned temperature range. Specifically explaining, the alkanoic acid formed in the reaction system is far inferior in acid catalysis to, for example, perfluoroalkanoic acids and, moreover, its amount is small; therefore, at the above-mentioned temperature condition, there is, as a side reaction, no formation of 5-oxazolone ring structure which is a main reaction in the step of successive release of C-terminal amino acids using a perfluoroalkanoic acid and an alkanoic acid anhydride. Further, in the pre-treatment step using an alkanoic acid anhydride alone, various side reactions, such as in-the-middle cleavage of peptide main chain bond (—CONH—), which are suppressed even in the step of successive release of C-terminal amino acids using a perfluoroalkanoic acid and an alkanoic acid anhydride, are suppressed to an even lower extent.

Meanwhile, the dipolar aprotic solvent, which gives rise to reswelling of gel, is preferably an organic solvent which can infiltrate into the gel substance and maintain it in a swollen state, has a relatively small molecular size, and has high affinity to the gel substance. In addition, the solvent is preferred to have such a high bipolarity as to allow the alkanoic acid anhydride to cause intramolecular polarization in the above-mentioned N-alkanoylation and O-alkanoylation and have excellent solvency toward an alkanoic acid formed as a by-product. A dipolar aprotic solvent low in vaporization at the above-mentioned reaction temperature is more preferred. For example, formamide ($HCONH_2$) satisfies all the requirements mentioned above, when a polyacrylamide gel is used.

When a given reaction time has passed, the alkanoic acid anhydride in the gel carrier is removed for termination of the reaction. Therefore, the whole gel carrier is washed using a polar aprotic solvent which gives rise to no dissolution of the gel substance and shows affinity to the alkanoic acid anhydride and the dipolar aprotic solvent. That is, by washing with the polar aprotic solvent, there are diluted and removed, by diffusion, the alkanoic acid anhydride and dipolar aprotic solvent which are present in the gel carrier by infiltration. As the polar aprotic solvent satisfying the requirements for the above washing, there can be mentioned, for example, nitriles having 4 or less carbon atoms, such as acetonitrile ($CH_3CN$) and ketones having 4 or less carbon atoms, such as acetone, when a polyacrylamide gel is used. As the polar aprotic solvent used for dilution and washing, there is ordinarily preferred the polar aprotic solvent used in the above-mentioned dehydration step. Further, the polar aprotic solvent used in such washing is more volatile than water; when it is vaporized, the gel is dried, reduces its volume, and becomes a shrunk gel carrier.

In the step of successive release of C-terminal amino acids in the second aspect of the present invention, the reaction is initiated ordinarily by infiltrating a reaction reagent solution into the shrunk gel carrier free of water. Therefore, after the pre-treatment step of N-acylation protection, the gel carrier having a peptide sample bound thereon is immersed, at a temperature selected in a range of 30° C. to 80° C., in a mixed solution obtained by dissolving an alkanoic acid anhydride and a small amount of a perfluoroalkanoic acid in a dipolar aprotic solvent infiltratable into the gel substance and capable of maintaining it in a swollen state, to allow the alkanoic acid anhydride and perfluoroalkanoic acid to act on the peptide sample bound on the gel carrier; at the C-terminus of the peptide, there arises successive release of the C-terminal amino acids of the peptide in association with formation of the 5-oxazolone structure represented by the following general formula (III):

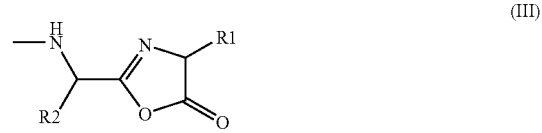

wherein R1 is a side chain of the C-terminal amino acid of the peptide and R2 is a side chain of the amino acid residue positioned just before said C-terminal amino acid, and subsequent cleavage of the 5-oxazolone ring.

In the reaction for formation of 5-oxazolone ring using a perfluoroalkanoic acid and an alkanoic acid anhydride, first, the perfluoroalkanoic acid is allowed to act as a proton donor on the peptide chain bound in the pores of the gel carrier, in the stage of keto-enol tautomerism represented by the following reaction scheme (Ia):

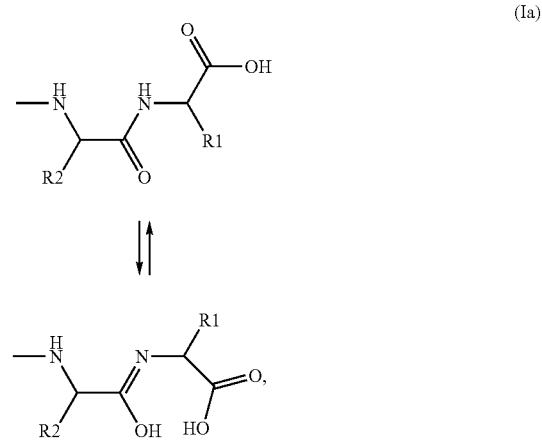

and thereby the ratio of enol form is heightened.

Then, to the enol form is allowed to act the alkanoic acid anhydride as a reagent capable of activating the C-terminal carboxy group of the enol form; thereby, the C-terminal carboxy group is converted into, for example, an asymmetric acid anhydride such as represented by the following reaction scheme (Ib):

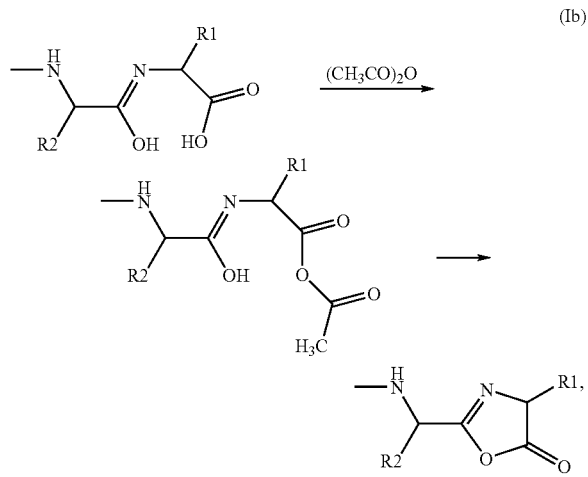

thus, for example, the reaction between the activated C-terminal carboxy group and the hydroxy group of enol form is involved in promotion of the formation of 5-oxazolone ring. In the dipolar aprotic solvent, the alkanoic acid anhydride is contained in a higher concentration than the perfluoroalkanoic acid; thereby, the above reaction can proceed under a mild temperature condition and the reaction temperature can be selected in a range of 30° C. to 80° C.

Meanwhile, in the second aspect of the present invention as well, the catalysis of the perfluoroalkanoic acid is brought about by its proton donatability. As the perfluoroalkanoic acid, there is preferred a perfluoroalkanoic acid whose pKa is in a range of 0.3 to 2.5. There is suitably used a perfluoroalkanoic acid having 2 to 4 carbon atoms, dissolvable uniformly in the dipolar aprotic solvent at the above-mentioned reaction temperature. More suitable is a linear-chain perfluoroalkanoic acid having 2 to 4 carbon atoms. Specifically desired are trifluoroacetic acid ($CF_3COOH$), pentafluoropropanoic acid ($CF_3CF_2COOH$) and heptafluorobutanoic acid ($CF_3CF_2CF_2COOH$).

As the alkanoic acid anhydride used for the activation of the C-terminal carboxy group, there is preferred one showing an appropriate reactivity when the reaction temperature has been reached. Therefore, it is preferred to use a symmetric anhydride of an alkanoic acid having 2 to 4 carbon atoms. Use of a symmetric anhydride of a linear-chain alkanoic acid having 2 to 4 carbon atoms is more preferred and, in particular, a symmetric anhydride of a linear-chain alkanoic acid having 2 carbon atoms, i.e. acetic anhydride is suitable. The alkanoic acid anhydride is preferred to further be able to form 5-oxazolone low in steric hindrance, and acetic anhydride is suitable in this respect as well.

The alkanoic acid anhydride used as an activating reagent is consumed with the progress of reaction; therefore, it is desired to dissolve the anhydride beforehand in the dipolar aprotic solvent used for swelling of gel, in a large excess relative to the amount consumed in the reaction with peptide, in order to suppress the reduction in concentration. Specifically, the ratio of alkanoic acid anhydride and perfluoroalkanoic acid in the mixed solution used for swelling of gel is selected desirably in a range of 1 to 20 volumes (perfluoroalkanoic acid) per 100 volumes of alkanoic acid anhydride and that the concentration of alkanoic acid anhydride in dipolar aprotic solvent is selected desirably in a range of 10 to 30% by volume. The reaction time is desired to be appropriately selected dependently upon the reaction temperature and the concentrations of alkanoic acid anhydride and perfluoroalkanoic acid in dipolar aprotic solvent and also in view of the time required for swelling of the gel carrier shrunk in association with the dehydration using a polar aprotic solvent. For example, the time in which a polyacrylamide gel (12.5% by mass) after dehydration using acetonitrile is immersed in a dipolar aprotic solvent such as formamide to achieve the reswelling of the gel carrier, needs to be, for example, about 3 hours at 40° C.; therefore, the overall reaction time is selected so as to be the sum of the above time of gel reswelling and a time required for selective release of intended amino acid residues, i.e. C-terminal amino acids.

Meanwhile, as the dipolar aprotic solvent used for reswelling of gel, there is preferred an organic solvent which can infiltrate into the gel substance and maintain it in a swollen state, has a relative small molecular size, and has excellent affinity to the gel substance. It is further preferred that the solvent shows such a high bipolarity as, in the stage of keto-enol tautomerism represented by the above-mentioned scheme (Ia), the ratio of enol form can be maintained and that the solvent has high solvency toward the alkanoic acid anhydride and perfluoroalkanoic acid (both are solutes) and the alkanoic acid, which is a by-product formed therefrom. A dipolar aprotic solvent low in volatility at the above-mentioned reaction temperature is more preferred. For example, formamide ($HCONH_2$) satisfies all the requirements mentioned above, when a polyacrylamide gel is used.

The dipolar aprotic solvent having high solvency toward the alkanoic acid anhydride and perfluoroalkanoic acid and the alkanoic acid, which is a by-product formed therefrom, can dissolve even water molecules easily. Therefore, in the reaction in the mixed solution containing such a dipolar aprotic solvent, the reaction system is preferably maintained in a dry atmosphere free of water. That is, the C-terminal carboxy group, which has been converted into a reaction intermediate represented by the above scheme (Ib), i.e. an asymmetric acid anhydride and has been activated, undergoes hydrolysis when water molecules come into the reaction system, and returns to the original carboxy group. In order to avoid such a deactivation stage, the reaction system is preferably maintained in a water-removed state.

For example, the sulfur which is present in methionine as one amino acid residue constituting a target peptide, may undergo oxidation by the oxygen incoming into the system and change its formula weight. Prevention of this oxidation by oxygen is preferred in the method of the present invention which is based on the measurement of molecular weights, in order to achieve a higher accuracy.

In order to maintain the reaction system in a dry atmosphere free of not only water and but also oxygen, it is desired, for example, to make the reaction system air-tight for prevention of the incoming of water and oxygen from outside the system and further conduct the addition and discharge of mixed solution in a dried inert gas, for example, a nitrogen atmosphere.

In the second aspect of the present invention as well, it is judged that, from the once-formed 5-oxazolone ring, the separation of the C-terminal amino acid and the formation of the reaction intermediate for the next stage proceed, for instance, via such a reaction as shown by the following reaction scheme (II')

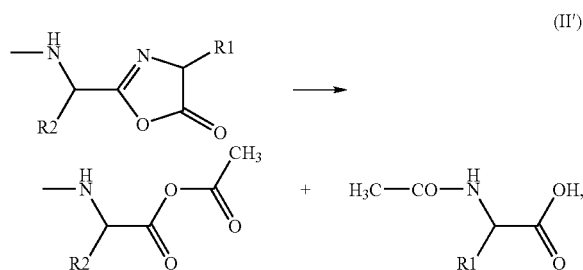

as a result, successive release of C-terminal amino acids is advanced. Therefore, the reaction products obtained after the completion of such reactions are a mixture comprising, in addition to those having a carboxy group exposed at the C-terminus, such as shown in the above reaction scheme (II), an intermediate product having the 5-oxazolone ring structure and a form of reaction intermediate in which its C-terminus has been converted into the form of asymmetric acid anhydride.

The reaction occurring in the step of successively releasing the C-terminal amino acids of peptide comprises at least two-stage elementary reactions, i.e. a stage of formation of 5-oxazolone ring structure as illustrated by the reaction scheme (Ib) and a stage of separation of C-terminal amino acid by the cleavage of 5-oxazolone ring structure, as illustrated by the reaction scheme (II'). Therefore, the overall reaction rate depends upon the reaction rates of the two stages, but depends mainly upon the concentrations of the alkanoic acid anhydride and perfluoroalkanoic acid used as well as on the reaction temperature. In addition, since a series of reaction products are formed by successive reactions, the maximum length of C-terminal amino acid sequence removed by such successive reactions becomes longer as the treatment duration becomes longer. Hence, the treatment duration for the step of selectively releasing C-terminal amino acid in such a successive manner needs to be appropriately chosen depending mainly upon the concentrations of the alkanoic acid anhydride and perfluoroalkanoic acid used and the reaction temperature employed and also in view of the intended length of the C-terminal amino acid sequence to be analyzed.

The termination of the reaction for successive release of selected C-terminal amino acids is conducted by lowering the temperature of the reaction system and diluting and removing the reaction reagent present in the gel carrier, i.e. the perfluoroalkanoic acid and the alkanoic acid anhydride. Specifically explaining, the termination of the reaction and the removal of the reaction reagent are conducted by diluting and removing the mixed solution used for the reaction for successive release of C-terminal amino acids, with a polar aprotic solvent which causes no dissolution of the gel substance and has affinity to the perfluoroalkanoic acid, the alkanoic acid anhydride and the dipolar aprotic solvent. The dilution and removal of the reaction reagent (the perfluoroalkanoic acid and the alkanoic acid anhydride) may be conducted by using the dipolar aprotic solvent used for preparation of the mixed solution. However, for termination of the formation of 5-oxazolone ring structure such as illustrated by the reaction scheme (Ib), it is more desirable to remove the perfluoroalkanoic acid, the alkanoic acid and the dipolar aprotic solvent by using a polar aprotic solvent which hardly contributes to stabilization of enol form intermediate. At least in the final stage of the dilution and removal of the reaction reagent, there is conducted dilution and removal using a polar aprotic solvent. When a polyacrylamide gel is used, there can be mentioned, as the polar aprotic solvent satisfying these conditions, for example, nitrites having 4 or less carbon atoms, such as acetonitrile ($CH_3CN$) and ketones having 4 or less carbon atoms, such as acetone.

In the second aspect of the present invention, the post-treatment of conducting hydrolysis to the series of reaction products obtained by successive release of C-terminal amino acids is carried out as well in a state that the peptide mixture containing the series of reaction products are bound on the gel carrier. That is, the hydrolysis is conducted by immersing the gel carrier loading thereon a mixture containing the series of reaction products obtained by successive release of C-terminal amino acids, in an aqueous solution of a basic nitrogen-containing aromatic compound or a tertiary amine compound, to allow water molecules to act on the reaction product peptides in the presence of the basic nitrogen-containing organic compound.

In this hydrolysis, the basic nitrogen-containing aromatic compound or tertiary amine compound catalyses the hydrolysis of the 5-oxazolone ring structure shown by the reaction scheme (II') and the next-stage reaction intermediate (acid anhydride form); however, the compound per se does not react with the 5-oxazolone ring structure or the reaction intermediate (acid anhydride form) to produce an undesired by-product but functions as an appropriate base catalyst. Specifically explaining, in the hydrolysis of the 5-oxazolone ring structure shown by the reaction scheme (II') and the nextstage reaction intermediate (acid anhydride form), the reaction products have an exposed carboxy group at the C-terminus of peptide chain, as shown in the following reaction scheme (IV).

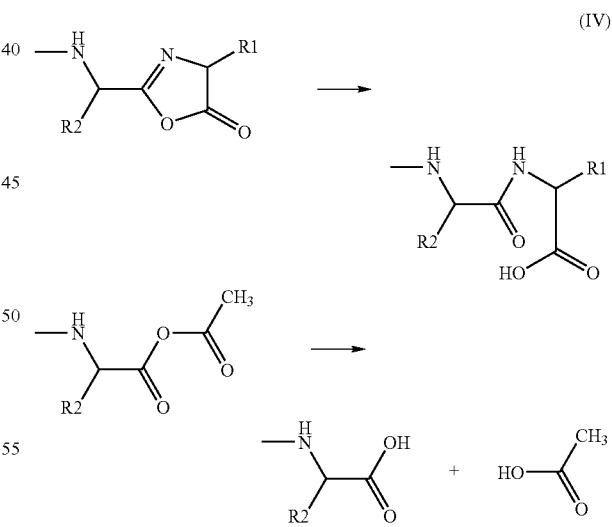

The basic nitrogen-containing aromatic compound or tertiary amine compound used in the hydrolysis is preferred because it does not react with, for example, the reaction intermediate whose C-terminus has been converted into an asymmetric acid anhydride, to form an amide bond and further, when made into an aqueous solution, can become a uniform solution. As the basic nitrogen-containing aromatic compound usable, preferred is a monocyclic, nitrogen-containing, aromatic compound highly soluble in polar aprotic solvents and, for example, pyridine is suitable. As the tertiary amine compound usable, preferred is a compound showing the same relatively weak basicity as pyridine and, for example, DMAE [(CH$_3$)$_2$N—CH$_2$CH$_2$OH] is suitable. When, for example, pyridine is used, the amount is preferably selected in a range of 5 to 15% by volume relative to the whole volume of the aqueous solution, specifically at 10% by volume. When DMAE [(dimethylamino)ethanol] is used, the amount is preferably selected in a range of 1 to 20% by volume relative to the whole volume of the aqueous solution, specifically at 10% by volume.

The monocyclic, nitrogen-containing, aromatic compound or tertiary amine compound is allowed to act on the gel loading the reaction products thereon, in the form of an aqueous solution. In this post-treatment, the aqueous solution containing such an organic base infiltrates into the highly hydrophilic gel substance quickly. The reaction temperature is selected preferably at 60° C. or above for quick completion of the hydrolysis. However, since the reaction is conducted in a closed reactor, the reaction temperature is desirably selected generally at 100° C. or below, in view of the mechanical strength of the reactor.

The hydrolysis using an aqueous solution containing the organic base is primarily intended to allow a carboxy group to be exposed at the C-terminus of each reaction product peptide chain, and the conditions thereof are selected so that there simultaneously occurs deprotection of the O-acylation protection made in the pre-treatment step but there occurs no deprotection of the N-acylation protections to N-terminal amino group or to the side chain amino group of lysine residue.

Incidentally, when there remains the basic nitrogen-containing aromatic compound or tertiary amine compound used in the hydrolysis, the remaining nitrogen base forms an addition salt with the carboxy group exposed at the C-terminus of each reaction product. Therefore, it is preferred that the aqueous solution present in the gel carrier is diluted and removed using a polar aprotic solvent which causes no dissolution of the gel substance and has affinity to water and, thereby, the gel carrier is redehydrated and the basic nitrogen-containing aromatic compound or tertiary amine compound used in the hydrolysis and the water are diluted and removed. Accordingly, the polar aprotic solvent used in the redehydration is preferably one having high solubility even to the basic nitrogen-containing aromatic compound or tertiary amine compound. When a polyacrylamide gel is used, there can be mentioned, as the polar aprotic solvent for redehydration, satisfying these requirements, for example, nitriles having 4 or less carbon atoms, such as acetonitrile (CH$_3$CN) and ketones having 4 or less carbon atoms, such as acetone.

The hydrolysis conducted after successive release of C-terminal amino acids can be carried out after the dilution and removal of the reaction reagent including the alkanoic acid anhydride and the perfluoroalkanoic acid by using the polar aprotic solvent. Alternatively, the successive release of C-terminal amino acids and the hydrolysis may be carried out continuously. Specifically explaining, when the aqueous solution containing the organic base is added while the temperature of the reaction for successive release of C-terminal amino acids is lowered to terminate the reaction, there occur the deactivation of the reaction reagent, which is a combination of the alkanoic acid anhydride and the perfluoroalkanoic acid, and its dissolution into the aqueous solution from the gel; and there arise the termination of the reaction for successive release of C-terminal amino acids and the deactivation and removal of the reaction reagent. Successively, the hydrolysis of reaction products is made and, by finally applying the redehydration using a polar aprotic solvent, there are conducted removal of the aqueous solution of organic base, the alkanoic acid corresponding to the alkanoic acid anhydride, the perfluoroalkanoic acid and the dipolar aprotic solvent, as well as redehydration; therefore, there is substantially no difference from the case in which the washing and removal operation using a polar aprotic solvent is employed in the middle.

In the step for measuring the decreases in molecular weight occurring in association with the successive release of C-terminal amino acids, according to the second aspect of the present invention, as in the same step of the first aspect of the present invention, as for the dry mixture containing the peptide fragments processed by digestion by trypsin, which are produced by performing treatment for digestion by trypsin to fragmentize peptide chains of long amino acid length and subsequently recovered, by means of MALDI-TOF-MS, measurement are carried out respectively for the molecular weights of the cationic species and for anionic species, which are both produced by the ionization treatment thereof.

One of the characteristics of the second aspect of the present invention lies in conducting the step of subjecting the above-mentioned mixture containing a series of reaction products after hydrolysis and subsequent redehydration, to digestion by trypsin in a state that the mixture after redehydration is still bound on a gel carrier. Specifically explaining, trypsin dissolved in a buffer solution is allowed to act on the mixture containing a series of reaction products after hydrolysis and subsequent redehyration, in a state that the mixture is still bound on the gel carrier, whereby specific-to-trypsin cleavage is applied to the peptide chains wherein the N-terminal amino group of each peptide chain and the side chain amino group of the lysine group (which may be present in each peptide chain) are protected by N-acylation, and the C-terminal side peptide bond of arginine residue present in each peptide chain is selectively cleaved in the middle and, as a result, peptide fragmentization takes place.

Generally, a gel carrier used for separation of molecular weights by gel electrophoresis such as two-dimensional electrophoresis or SDS-PAGE method is capable of holding peptide chains each having a certain or larger amino acid length, in the gel pores and gives a clear difference in the electrophoresis speeds of the peptide chains; however, when the amino acid lengths of peptide chains are smaller than the above range, the ability of the gel carrier for holding such peptide chains in the gel pores decreases quickly. In the second aspect of the present invention, this uniqueness shown by the gel carrier in gel electrophoresis is utilized; that is, a peptide chain of large amino acid length is subjected to successive release of C-terminal amino acids in a state that the peptide chain has been bound on a gel carrier, to prepare a series of reaction products, then, they are subjected to digestion by trypsin for peptide fragmentization, thereby, intended C-terminal side peptide fragments can be easily detached by dissolution and recovered from the gel carrier.

In the second aspect of the present invention as well, since, in the mixture containing a series of reaction products after hydrolysis, the N-terminal amino group of each peptide chain and the side chain amino group of the lysine group, which may be present in the peptide chain, are protected by N-acylation, there occurs, in the digestion by trypsin, no in-the-middle cleavage of the C-terminal side peptide bond of N-acylated lysine residue but there occurs the selected in-the-middle cleavage of the C-terminal side peptide bond of the arginine residue present in each peptide chain. As explained previously, when there occurs the selected in-the-middle cleavage of the C-terminal side peptide bond of the arginine residue present in each peptide chain, a plurality of peptide fragments are produced from each peptide chain of large amino acid length and, in this case, each of intended C-terminal side peptide fragments generally has such an amino acid length as to correspond to one fraction of the original peptide when divided into several fractions and they are detached from the gel carrier and dissolve in the trypsin solution. Other peptide fragments as well dissolve in the trypsin solution; when the buffer solution and the gel carrier are separated from each other, various peptide fragments detached are recovered in the buffer solution. Then, desalting is conducted, the buffer solution component is removed, and the peptide fragments obtained by digestion by trypsin are recovered and dried.

The later step, that is, the operation from the molecular weight measurements for the dry mixture containing the recovered peptide fragments after digestion by trypsin by, for example, MALDI-TOF-MS, to the determination of C-terminal amino acid sequence based on the results of the above measurements is conducted in the same manner as in the above-mentioned first aspect of the present invention.

As for a protein separated from a sample containing various kinds of proteins, by gel electrophoresis, e.g. two-dimensional electrophoresis or SDS-PAGE method, its rough molecular weight is estimated thereby, and it is composed of a large number of amino acids, in such a case, after the isolation and recovery of such a protein from the spot (or band) separated, there need to be carried out such a series of operations including production of C-terminal side peptide fragments therefrom by using the method according the first aspect of the present invention, measurement of their molecular weights and identification of its C-terminal amino acid sequence based on the results of measurement. The method of the second aspect of the present invention for analysis of C-terminal amino acid sequence of peptide is such method in which, in place of the isolation and recovery of such a protein from the spot (or band) separated, the gel portion containing said spot (or band) is cut out, and the protein is subjected to a series of chemical treatments in a state that the protein is still bound on the gel carrier. In the second aspect of the present invention, the operation of beforehand isolating and recovering a protein from its separated spot (or band) can be omitted and, moreover, the determination of C-terminal amino acid sequence can be carried out at the same accuracy without being affected by the yield in the isolation and recovery.

When there is used the method according to the second aspect of the present invention, the target peptide is made into a linear peptide and subjected to separation by gel electrophoresis to form a single spot bound on a gel carrier. The gel electrophoresis may be a conventional SDS-PAGE method wherein electrophoresis is made in a one-dimensional direction, but may also be a two-dimensional electrophoresis wherein migration is conducted on a gel in a two-dimensional direction for superior separation. With use of such two-dimensional electrophoresis, the separated peptide sample is free from impurities and, even when the sample amount is small, the C-terminal amino acid sequence of the peptide sample can be determined by the method of the second aspect of the present invention. When separation of peptide is made by gel electrophoresis, if the peptide has a —S—S—bond formed between the cysteine residues present in the molecule, it is preferred that there is beforehand added, to the peptide, a reducing reagent such as 2-sulfanylethanol (HS—$C_2H_2$—OH, 2-mercaptoethanol) or DTT (dithiothreitol, threo-1,4-disulfanyl-2,3-butanediol) and electrophoresis is conducted in a reduced state of the peptide to form a single spot. Or, it is preferred to beforehand reduce the —S—S— bond formed between the cysteine residues present in the molecule or to beforehand conduct modification of the reducing type cysteines, such as carboxymethylation using iodoacetic acid or the like, to form a single spot. Thus, by converting the original peptide into a linear peptide free from —S—S— bond formed between the cysteine residues in the molecule, digestion by trypsin can be carried out more efficiently.

Next, more detailed description is made on the method of the present invention for molecular weight measurements of cationic species and anionic species by mass spectrometry, particularly MALDI-TOF-MS.

In the present invention, a MALDI-TOF-MS apparatus is used for the measurement of molecular weights, i.e. m/z values of the ion species derived from the peptide fragments produced by digestion by trypsin; thereby, accurate molecular weight measurement is possible even for a peptide chain of high molecular weight. In a long peptide chain to be subjected to digestion by trypsin, the N-terminal amino group and the side chain amino group of lysine residue are replaced with an alkanoyl group introduced in the above-mentioned N-acylation; therefore, selective in-the-middle cleavage occurs only at the C-terminal side peptide bond of arginine residue. Accordingly, the long peptide chain to be analyzed is divided into a plurality of peptide fragments each containing one arginine residue at the C-terminus (the number or these fragments is the same as the number of the arginine residues contained in the original peptide chain) and a C-terminal side (of the original peptide) peptide fragment containing no arginine residue in the middle. Also, each of a series of reaction product peptide chains produced by successive release of C-terminal amino acids is divided into a plurality of common peptide fragments each containing one arginine residue at the C-terminus and C-terminal side (of each reaction product peptide chain) peptide fragments containing no arginine residue.

In the above-mentioned N-acylation protection, O-acylation protection proceeds as well for the hydroxy groups of serine residue, threonine residue, etc. and, in the hydrolysis, there is selected such a condition that deprotection even for the above O-acylation protection proceeds sufficiently; however, part of the O-acylation protections remains undeprotected often and O-acylated compounds are present in a small amount. Further, in the reaction for successive release of C-terminal amino acids, there slightly occur side reactions such as acyl group exchange reaction, the perfluoroalkanoyl group derived from the perfluoroalkanoic acid used is introduced and such compounds having the perfluoroalkanoyl group introduced are present in a small amount in some cases.

Therefore, when the mixture of peptide fragments produced by digestion by trypsin are subjected to molecular weight measurements of the cationic species and anionic species generated by ionization according to MALDI-TOF-MS, the major ion species are a plurality of common peptide fragments each containing one arginine residue at the C-terminus and a series of C-terminal side peptide fragments containing no arginine residue in the middle, reflecting the successive release of C-terminal amino acids. However, there are also present often, in a small amount, ion species derived from the peptide fragments replaced with an excessive amount of the above-mentioned alkanoyl group; or, in some cases, there are also present, in a small amount, ion species derived from the peptide fragments replaced with the above-mentioned perfluoroalkanoyl group in place of the alkanoyl group.

In the successive release of C-terminal amino acids, when there occur, for example, a reaction for conversion of carbamoyl group (—CO—NH$_2$) on the side chain into cyano group (—CN), shown by the following scheme (V):

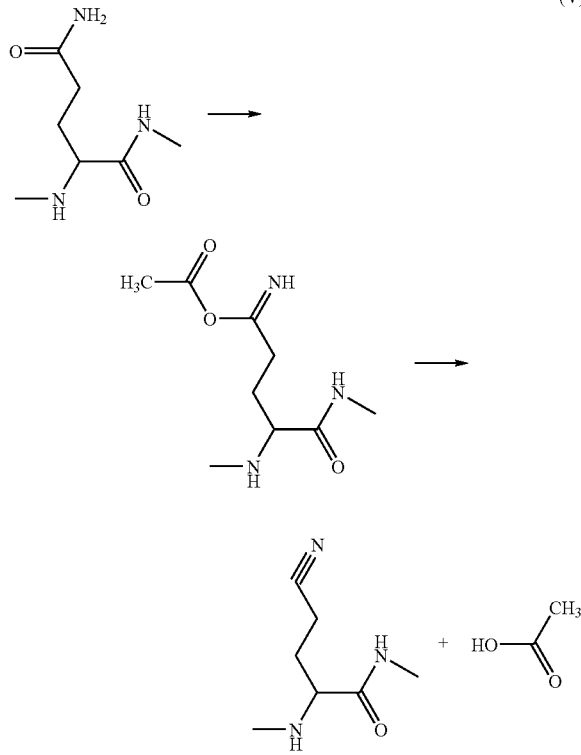

or dehydration such as dehydroxylation on the side chain of serine residue or threonine residue, which is raised from elimination of acetyloxy group from the side chain, shown by the following scheme (VI):

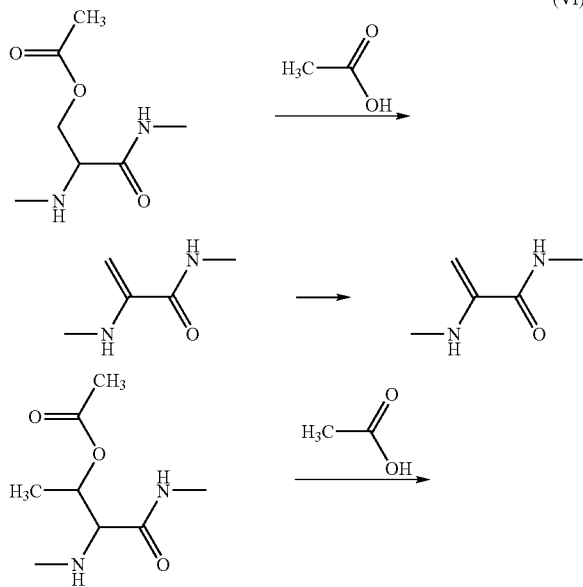

there takes place a reduction in molecular weight, corresponding to removal of water molecule. An ion species derived from a peptide fragment wherein such dehydration has taken place as a side reaction, is also present often in a small amount. Further, an ion species derived from a peptide fragment wherein the replacement with an excessive amount of alkanoyl group and the above dehydration as a side reaction have taken place, is present often in a small amount.

In the mixture of peptide fragments obtained by digestion by trypsin are also present unavoidably autolysis products of the trypsin used, that is, peptide fragments derived from trypsin, formed by trypsin cleavage by other trypsin molecule. Incidentally, since the amino acid sequence of trypsin is known, the molecular weight or m/z value of the ion species derived from each peptide fragment (autolysis product) of trypsin is known beforehand. Needless to say, as to each ion species derived from each peptide fragment (autolysis product) of trypsin, there is no ion species replaced with the above-mentioned alkanoyl group.

The major peptide fragments produced from a long peptide chain to be analyzed are a plurality of common peptide fragments each containing one arginine residue at the C-terminus and a series of C-terminal side peptide fragments containing no arginine residue in the middle, reflecting the successive release of C-terminal amino acids. When these major peptide fragments are subjected to MALDI-TOF-MS, each major peptide fragment is converted into a proton (H$^+$)-added cationic species and a proton (H$^+$)-detached anionic species, and the cationic species and the anionic species can be measured separately by selecting the measurement mode.

First, each of the common peptide fragments each containing one arginine residue at the C-terminus has, at the C-terminus, an arginine residue containing a guanidino group of high proton (H$^+$) acceptability and is stabilized by becoming a proton (H$^+$)-added cationic species; as a result, the fragment gives a clear intense peak on the spectra for molecular weight measurement by cationic species. Each common peptide fragment, which has an arginine residue at the C-terminus, has also a carboxy group (—COOH) of proton (H$^+$) donatability at the C-terminus; therefore, the fragment gives a significantly intense peak also on the spectra for molecular weight measurement by anionic species.

Meanwhile, with respect to the series of C-terminal side peptide fragments containing no arginine residue in the middle, reflecting the successive release of C-terminal amino acids, the total of their individual amounts is equal to the amount of each of the common peptide fragments each having one arginine residue at the C-terminus; however, the amount of each individual fragment constituting the series of C-terminal side peptide fragments becomes relatively smaller in inverse proportion to the increased steps of the reaction for successive release of C-terminal amino acids. While the C-terminal side peptide fragments of the original peptide chain per se may happen to contain an arginine residue at the C-terminus, the C-terminal side peptide fragments derived from the series of reaction products have no arginine residue. Each of these C-terminal side peptide fragments has, at the N-terminus, an amino group with proton (H$^+$) acceptability and, at the C-terminus, a carboxy group (—COOH) whit proton (H⁺) donatability. Each of these fragments gives a significantly intense peak on the spectra for molecular weight measurement by anionic species and also a significantly intense peak on the spectra for molecular weight measurement by cationic species.

Meanwhile, the ion species derived from the above-mentioned accompanying (present-together) peptide fragments, such as ion species showing an increase in molecular weight corresponding to excessive alkanoyl group, ion species showing a decrease in molecular weight corresponding to the loss water molecule and ion species showing an increase in molecular weight corresponding to the loss of water molecule and the addition of excessive alkanoyl group, generally give a significantly weak peak as compared with the ion species derived from the above-mentioned major peptide fragments. It is to be noted that when the cationic species derived from these accompanying peptide fragments give a significantly intense peak on the spectra for molecular weight measurement by cationic species, the corresponding anionic species should theoretically be confirmed even on the spectra for molecular weight measurement by anionic species, if examined precisely, even though their peaks may be weak. Similarly, it is to be noted that when the anionic species derived from these accompanying peptide fragments give a significantly intense peak on the spectra for molecular weight measurement by anionic species, the corresponding cationic species should theoretically be confirmed even on the spectra for molecular weight measurement by cationic species, if examined precisely, even though their peaks may be weak.

In the present invention, after digestion by trypsin and subsequent desalting, the resulting peptide fragments are recovered and dried, and the mixture containing peptide fragments is subjected to measurement of their ion species with use of a MALDI-TOF-MS apparatus. The characteristic of this MALDI-TOF-MS is that there are formed, in the ionization stage, a proton (H⁺)-added cationic species and a proton (H⁺)-detached anionic species of each peptide fragment but there are prevented the occurrence of secondary ionization, subsequent detachment of large fragment from parent ion species, and resultant formation of daughter ion species. Owing to this characteristic, when the mixture of peptide fragments is subjected to MALDI-TOF-MS for independent measurements of cationic species and anionic species using respective measurement modes and when attention is paid to common peptide fragments each containing one arginine residue, there is no case that, for example, daughter ion species formed by detachment of large fragment (atomic group) from parent ion species are measured as significantly intense peaks, in addition to the ion species derived from the common peptide fragments per se and the ion species having the same amino acid sequence, derived from the above-mentioned accompanying peptide fragments. In other words, a possibility is extremely low that the daughter ion species formed by detachment of large fragment (atomic group) corresponding to the formula weight of one amino acid residue, from parent ion species derived from peptide fragments per se, are measured as significantly intense peaks. Meanwhile, the ion species derived from the series of C-terminal side peptide fragments containing no arginine residue in the middle, reflecting the successive release of C-terminal amino acids are measured as peaks whose m/z values are different from each other by the formula weight of either one amino acid residue.

In the digestion by trypsin for fragmentization according to the present invention, of lysine residue and arginine residue which are specific cleavage sites, lysine residue is beforehand protected by N-alkanoylation at the side chain amino group; thereby, trypsin cleavage is allowed to occur only at arginine residue. As a result, the C-terminal side peptide fragments obtained by digestion by trypsin of peptide chains are allowed to be in a range not exceeding 40 amino acids, preferably in a range not exceeding 30 amino acids. Accordingly, when the ion species derived from the series of C-terminal side peptide fragments reflecting the successive release of intended C-terminal amino acids are analyzed and identified from the obtained spectra for molecular weight measurements by cationic species and anionic species according to MALDI-TOF-MS, the analysis can be limited generally to a m/z value range not exceeding 4,000.

With respect to the series of C-terminal side peptide fragments reflecting the successive release of C-terminal amino acids, the shortest C-terminal peptide fragments when C-terminal amino acids have been successively released, is desired to have at least a length of 5 to 6 amino acids when a sequence of at least 3 to 4 amino acid residues from C-terminus is determined. Accordingly, it is desired that at least one of the ion species derived from the series of C-terminal side peptide fragments gives a clear peak in a m/z value range of 500 or more.

In the method for analysis of C-terminal amino acid sequence of peptide according to the first aspect or the second aspect of the present invention, the technique for analysis of the spectra for molecular weight measurements of cationic species and anionic species by means of MALDI-TOF-MS according to the present invention is employed as a method for identifying the ion species derived from the series of C-terminal side peptide fragments, which gives reductions in molecular weight associated with the successive release of C-terminal amino acids, through the analysis by cross-comparison of the spectra for molecular weight measurement of cationic species and the spectra for molecular weight measurement of anionic species by means of MALDI-TOF-MS with each other. In this analysis, the above-mentioned features that are caused by the successive release of C-terminal amino acids and the fragmentization due to digestion by trypsin are utilized.

First, when the mixture of peptide fragments is measured for m/z values of ion species with use of a MALDI-TOF-MS apparatus, each of the common peptide fragments each containing one arginine residue at the C-terminus and each of the series of C-terminal side peptide fragments reflecting successive release of intended C-terminal amino acids are ionized into respective proton (H⁺)-added cationic species and proton (H⁺)-detached anionic species; however, the ratio of cationic species and anionic species is different in each peptide fragment and there is a fear that, in an analysis using only either of the spectra for molecular weight measurement by cationic species and the spectra for molecular weight measurement by anionic species, no clear intense peak is obtained, making identification impossible; therefore, in the spectral analysis according to the present invention, the two spectra are compared and analysis is progressed. In that case, the analysis of spectra is made in a m/z value range of 4,000 or less for the reasons mentioned above and ordinarily no problem is incurred thereby.

First, in the step 1, since ion species peaks derived from the peptide fragments produced by autolysis of trypsin are present in the spectra for molecular weight measurement of cationic species as well as in the spectra for molecular weight measurement of anionic species, obtained by MALDI-TOF-MS, these ion species peaks are identified. The peptide fragments produced by autolysis of trypsin include N-terminal side fragments each having a lysine residue or an arginine residue at the C-terminus and a C-terminal side fragment, and their molecular weights are known. Based on these known molecular weights, proton ($H^+$)-added cationic species peaks and proton ($H^+$)-detached anionic species peaks, all derived from the above-mentioned peptide fragments are identified in a m/z value range of 500 to 4,000.

These ion species peaks derived from trypsin can be used, for example, as internal standard peaks in conducting correction of systematic error of m/z value and also as a base for removal of noise peak by referring to the m/z values of internal standard peaks and their full-width of half maximums.

Then, in the step 2 for identification of major ion species peaks, after the ion species peaks derived from trypsin have been removed, ion species peaks showing a clear peak intensity are selected. Specifically explaining, in the ion species peaks remaining after the ion species peaks derived from trypsin have been removed, either one of the ion species derived from the common peptide fragments each having one arginine residue at the C-terminus and also from the series of C-terminal side peptide fragments reflecting the successive release of intended C-terminal amino acids, shows, in theory, the maximum peak intensity in the spectra for molecular weight measurements of cationic species as well as in the spectra for molecular weight measurements of anionic species.

Accordingly, after the ion species peaks derived from trypsin have been removed, the highest cationic species peak having the maximum peak intensity is identified in the result of molecular weight measurement of cationic species; cationic species peaks each having a peak intensity of 1/40 or more relative to the peak intensity of the highest cationic species peak are selected; and such cationic species peaks are designated as the first group of cationic species peaks. This first group of cationic species peaks comprise at least a group of cationic species peaks derived from the common peptide fragments each having one arginine residue at the C-terminus.

Meanwhile, after the ion species peaks derived from trypsin have been removed, the highest anionic species peak having the maximum peak intensity is identified in the result of molecular weight measurement of anionic species; anionic species peaks each having a peak intensity of 1/40 or more relative to the peak intensity of the highest anionic species peak are selected; and such anionic species peaks are designated as the first group of anionic species peaks. For example, when there are selected such reaction conditions and time as the maximum number of amino acid residues removed by successive release of C-terminal amino acids is 5, the proportion of reaction product formed by removal of 5 amino acid residues exceeds about 1/50; therefore, the first group of anionic species peaks ordinarily comprise at least all of the anionic species peaks derived from those peptide fragments (wherein the number of removed amino acid residues is 5 or less) of the series of C-terminal side peptide fragments reflecting the successive release of intended C-terminal amino acids.

In the step 3, first, in view of the fact that there are also present those peptide fragments which give clear peak intensities in the result of molecular weight measurement of cationic species but are low in the amount of corresponding anionic species and show no clear peak intensities in the result of molecular weight measurement of anionic species, there are identified corresponding anionic species peaks, with respect to the first group of cationic species peaks each giving a clear peak intensity, and such corresponding anionic species peaks are designated as the second group of anionic species peaks.

The cationic species which accompany the cationic species derived from the common peptide fragments each having one arginine residue at the C-terminus, for example, the cationic species showing an increase in molecular weight corresponding to the addition of excessive alkanoyl group, the cationic species showing a reduction in molecular weight corresponding to the loss of water molecule, and the cationic species showing an increase in molecular weight corresponding to the loss of water molecule and the addition of excessive alkanoyl group, generally give significantly lower peak intensities than the cationic species derived from the above-mentioned major peptide fragments; even when the peaks of these accompanying cationic species belong to the first group of cationic species peaks, the accompanying anionic species peaks corresponding to the above accompanying cationic species peaks show even lower peak intensities and are not included in the first group of anionic species peaks, in many cases. These accompanying anionic species peaks are confirmed to be significant anionic species peaks, in the operation for identification of the second group of anionic species peaks.

Then, in view of the fact that there are also present those peptide fragments which give clear peak intensities in the result of molecular weight measurement of anionic species but are low in the amount of corresponding cationic species and show no clear peak intensities in the result of molecular weight measurement of cationic species, there are identified corresponding cationic species peaks, with respect to the first group of anionic species peaks each giving a clear peak intensity, and such corresponding cationic species peaks are designated as the second group of cationic species peaks.

With respect to those peptide fragments of low proportions, of the series of C-terminal side peptide fragments reflecting the successive release of intended C-terminal amino acids, even when their anionic species peaks belong to the first group of anionic species peaks, their corresponding cationic species peaks give even lower peak intensities and are not included in the first group of cationic species peaks, in many cases. In said operation of identifying the second group of cationic species peaks, the cationic species peaks corresponding to these C-terminal side peptide fragments of low proportions provide confirmation of being significant anionic species peaks. Further, the anionic species peaks which accompany the anionic species peaks derived from the series of C-terminal side peptide fragments reflecting the successive release of intended C-terminal amino acids, generally give significantly lower peak intensities than the anionic species peaks derived from the above-mentioned major peptide fragments; even when the peaks of these accompanying anionic species belong to the first group of anionic species peaks, the accompanying cationic species peaks corresponding to the above accompanying anionic species peaks show even lower peak intensities and are not included in the first group of cationic species peaks, in many cases. These accompanying cationic species peaks are confirmed to be significant cationic species peaks, in the operation for identification of the second group of cationic species peaks.

In the step 4, the peaks overlapping between the first group of anionic species peaks and the second group of anionic species peaks, that is, the peaks of those anionic species which show clear peak intensities in the spectra for molecular weight measurement of anionic species and whose corresponding cationic species show also clear peak intensities in the spectra for molecular weight measurement of cationic species, are designated as the third group of anionic species peaks. The anionic species derived from those peptide fragments of large proportions, of the series of C-terminal side peptide fragments reflecting the successive release of intended C-terminal amino acids are ordinarily included in the third group of anionic species peaks.

Also, the sum of the first group of anionic species peaks and the second group of anionic species peaks is designated as the fourth group of anionic species peaks. The fourth group of anionic species peaks include at least the anionic species peaks of the common peptide fragments each having one arginine residue at the C-terminus and the series of C-terminal side peptide fragments reflecting the successive release of intended C-terminal amino acids and many of the anionic species peaks which accompany the above-mentioned anionic species peaks.

Meanwhile, the peaks overlapping between the first group of cationic species peaks and the second group of cationic species peaks, that is, the peaks of cationic species which show clear peak intensities in the spectra for molecular weight measurement of cationic species and whose corresponding anionic species show also clear peak intensities in the spectra for molecular weight measurement of anionic species, are designated as the third group of cationic species peaks. The cationic species derived from those peptide fragments of large proportions, of the common peptide fragments each having one arginine residue at the C-terminus and the series of C-terminal side peptide fragments reflecting the successive release of intended C-terminal amino acids are ordinarily included in the third group of cationic species peaks.

Also, the sum of the first group of cationic species peaks and the second group of cationic species peaks is designated as the fourth group of cationic species peaks. The fourth group of cationic species peaks include at least the cationic species peaks of the common peptide fragments each having one arginine residue at the C-terminus and the series of C-terminal side peptide fragments reflecting the successive release of intended C-terminal amino acids and many of the cationic species peaks which accompany the above-mentioned cationic species peaks.

Further, with respect to each anionic species peak contained in the third group of anionic species peak, there is calculated its relative peak intensity to the peak intensity of the highest anionic species peak and, with respect to each corresponding cationic species peak, there is calculated its relative peak intensity to the peak intensity of the highest cationic species peak. These two relative peak intensities are compared with each other, and there is examined whether the corresponding cationic species peak is more intense or the corresponding anionic species peak is more intense.

As described previously, in each peptide fragment having one arginine residue at the C-terminus, the arginine residue has, at its C-terminus, a guanidino group of high proton ($H^+$) acceptability; therefore, the peptide fragment tends to become a proton ($H^+$)-added cationic species which is stable. As a result, with respect to the peptide fragment, the proportion of cationic species formed is clearly higher than the proportion of corresponding anionic species formed. Meanwhile, in each C-terminal side peptide fragment having no arginine residue, there are, at the N-terminus, an amino group having a proton ($H^+$) acceptability and, at the C-terminus, a carboxy group (—COOH) having a proton ($H^+$) donatability; as a result, with respect to this peptide fragment, the proportion of anionic species formed is significantly higher than the proportion of corresponding cationic species formed.

In the present invention, according to this criterion, there are identified those corresponding cationic species peaks each having a relative peak intensity which is 3/2 or more relative to the relative peak intensity of the corresponding peak of the third group of anionic species peaks, and such cationic species peaks are designated as the fifth group of cationic species peaks; meanwhile, there are identified those anionic species peaks each having a relative peak intensity which is 3/2 or more relative to the relative peak intensity of the corresponding peak of the third group of cationic species peaks, and such anionic species peaks are designated as the fifth group of anionic species peaks.

The fifth group of cationic species peaks include at least cationic species peaks derived from the peptide fragments each having one arginine residue at the C-terminus, and the fifth group of anionic species peaks include at least anionic species peaks derived from those peptide fragments of relatively high proportions, of the series of C-terminal side peptide fragments having no arginine residue. These fifth groups include, in addition to the ion species peaks derived from the above-mentioned major peptide fragments, even those ion species peaks which accompany them but show clear peak intensities. Therefore, the fifth group of cationic species peaks and the fifth group of anionic species peaks are designated as peaks of major ion species having significant counter ions.

The fifth group of cationic species peaks and the fifth group of anionic species peaks are designated as peaks of major ion species having significant counter ions. As described previously, those peptide fragments present in high proportions, of the common peptide fragments each having one arginine residue at the C-terminus, and those peptide fragments present in relatively high proportions, of the series of C-terminal side peptide fragments containing no arginine residue, include, in addition to the ion species peaks derived from major peptide fragments, even those ion species peaks which accompany them but show clear peak intensities. Therefore, in the step 5, these accompanying ion species peaks are excluded and there are selected only the ion species peaks derived from those peptide fragments present in high proportions, of the common peptide fragments each having one arginine residue at the C-terminus, as well as from those peptide fragments present in relatively high proportions, of the series of C-terminal side peptide fragments containing no arginine residue.

Specifically explaining, there may be present those accompanying ion species peaks, which accompany the above-mentioned accompanying ion species peaks, for example, an ion species peak wherein two excessive alkanoyl groups remain. These secondary accompanying species peaks, however, are even lower in peak intensity and the possibility for the secondary accompanying species peaks to be included in the fifth group of cationic species peaks and the fifth group of anionic species peaks is nearly zero.

Hence, from the fifth group of cationic species peaks are selected those "parent cationic species peaks" having either of the following accompanying cationic species peaks:

(5a-1) cationic species peaks having a smaller m/z value than the m/z value of said peak by the molecular weight of 18 corresponding to loss of water molecule, (5a-2) cationic species peaks each having a larger m/z value than the m/z value of said peak by the molecular weight equivalent to excess of the formula weight of the acyl group used for said N-acylation protection, and (5a-3) cationic species peaks each having a larger m/z value than the m/z value of said peak by the molecular weight equivalent to the combination of the molecular weight decrease of 18 corresponding to loss of water molecule and excess of the formula weight of the acyl group used for said N-acylation protection, and these parent cationic species peaks present in the fifth group of cationic species peaks are designated as the sixth group of cationic species peaks. The cationic species peaks of the sixth group are derived from those peptide fragments produced by digestion by trypsin of a target peptide chain and present in high proportions.

Similarly, from the fifth group of anionic species peaks are selected those "parent anionic species peaks" having either of the following accompanying anionic species peaks:

(5b-1) anionic species peaks having a smaller m/z value than the m/z value of said peak by the molecular weight of 18 corresponding to loss of water molecule, (5b-2) anionic species peaks each having a larger m/z value than the m/z value of said peak by the molecular weight equivalent to excess of the formula weight of the acyl group used for said N-acylation protection, and (5b-3) anionic species peaks each having a larger m/z value than the m/z value of said peak by the molecular weight equivalent to the combination of the molecular weight decrease of 18 corresponding to loss of water molecule and excess of the formula weight of the acyl group used for said N-acylation protection, and these parent anionic species peaks present in the fifth group of anionic species peaks are designated as the sixth group of anionic species peaks. The anionic species peaks of the sixth group are derived from those peptide fragments produced by digestion by trypsin of a target peptide chain and present in high proportions.

Prior to the above judgement, in order to calculate the difference in m/z value between ion species peaks, there is calculated a difference in m/z value between adjacent peaks which become a basis therefor. In that case, there are excluded those ion species peaks which are low in peak intensity and give inaccuracy in the determination of m/z value of ion species peak, and only significant ion peaks derived from the peptide fragments produced by digestion by trypsin of a target peptide chain are used in the analytical operation described later. Therefore, with respect to each cationic species peak of the fourth group of cationic species peaks, its m/z value differences from adjacent peaks are calculated and, with respect to each anionic species peak of the fourth group of anionic species peaks, its m/z value differences from adjacent peaks are calculated.

When each "parent cationic species peak" is compared with its accompanying cationic species peak, the relative peak intensity of the "parent cationic species peak" is generally higher than the relative peak intensity of the accompanying cationic species peak. Similarly, when each "parent anionic species peak" is compared with its accompanying anionic species peak, the relative peak intensity of the "parent anionic species peak" is generally higher than the relative peak intensity of the accompanying anionic species peak. Accordingly, in the step 6, such comparison of relative peak intensities is made; there is selected, from each peak of the sixth group of cationic species peaks, a peak corresponding to the "parent cationic species peak", and the thus-selected peaks are designated as the seventh group of cationic species peaks; similarly, there is selected, from each peak of the sixth group of anionic species peaks, a peak corresponding to the "parent anionic species peak", and the thus-selected peaks are designated as the seventh group of anionic species peaks.

For example, when all of the accompanying cationic species peaks (5a-1) to (5a-3) are included in the fifth group of cationic species peaks, these accompanying cationic species peaks (5a-1) to (5a-3) are included also in the sixth group of cationic species peaks. However, by conducting the above comparison of relative peak intensities, it is possible to exclude the accompanying cationic peaks (5a-1) to (5a-3) and select only the peaks corresponding to the "parent cationic species peaks", that is, the cationic species peaks of the peptide fragments per se, derived from a target peptide. Similarly, when all of the accompanying anionic species peaks (5b-1) to (5b-3) are included in the fifth group of anionic species peaks, these accompanying anionic species peaks (5b-1) to (5b-3) are included also in the sixth group of anionic species peaks. However, by conducting the above comparison of relative peak intensities, it is possible to exclude the accompanying anionic peaks (5b-1) to (5b-3) and select only the peaks corresponding to the "parent anionic species peaks", that is, the anionic species peaks of the peptide fragments per se, derived from a target peptide.

The seventh group of cationic species peaks include mainly the cationic species peaks of the peptide fragments per se, each containing one arginine residue at the C-terminus and derived from a target peptide chain. When the target peptide chain per se happens to have an arginine residue at the C-terminus, there are also included, in the seventh group of cationic species peaks, the cationic species peaks derived from the C-terminal side peptide fragment having only one arginine residue at the C-terminus, produced by digestion by trypsin, in addition to the cationic species peaks derived from other peptide fragments each having one arginine residue at the C-terminus.

Meanwhile, the C-terminal side peptide fragment having one arginine residue at the C-terminus is accompanied by a series of C-terminal side peptide fragments formed by the successive cleavage of C-terminal amino acids; however, other peptide fragments formed by digestion by trypsin are not accompanied by the series of C-terminal side peptide fragments formed by the successive cleavage of C-terminal amino acids. With respect to the series of C-terminal side peptide fragments formed by the successive cleavage of C-terminal amino acids, the relative peak intensities of the corresponding anionic species peaks are generally higher and, therefore, these corresponding anionic species peaks appear on the spectra for molecular weight measurement of anionic species, in theory.

Based on this standpoint, there is selected each anionic species peak corresponding to each of the seventh group of cationic species peaks present in the fourth group of anionic species peaks; such anionic species peaks are designated as the eighth group of anionic species peaks; there is investigated whether or not these corresponding anionic species peaks are accompanied by anionic species peaks derived from the series of C-terminal side peptide fragments formed by the successive release of C-terminal amino acids. Specifically explaining, there is investigated whether or not there is present, for each of the eighth group of anionic species peaks, anionic species peaks each having, as a result of the successive release of C-terminal amino acids, a m/z value difference corresponding to the formula weight of natural linear α-amino acid residue: —NH—CH(R)—CO— (R is a side chain of said amino acid residue) or of acylated α-amino acid residue obtained by substituting the hydroxy group or amino group of said side chain with the acyl group used in the above-mentioned N-acylation protection. This investigation is conducted as follows. There are selected, for each of the eighth group of anionic species peaks, those anionic species peaks present in the fourth group of anionic species peaks, each having a m/z value difference of smaller than 200 and, when the acyl group used in N-acylation protection is, for example, an acetyl group, there is investigated whether or not there are anionic species peaks each having a m/z value difference corresponding to the formula weight shown in the following Table 1.

TABLE 1

| | Formula weight | Corresponding amino acid residue |
|---|---|---|
| 0 | 57 | -Gly- |
| 2 | 71 | -Ala- |
| 4 | 87 | -Ser- |
| 6 | 99 | -Val- |
| 7 | 101 | -Thr- |
| 8 | 103 | -Cys- |
| 9 | 113 | -Leu- |
| 10 | 113 | -Ile- |
| 11 | 114 | -Asn- |
| 12 | 115 | -Asp- |
| 13 | 128 | -Gln- |
| 14 | 129 | -Glu- |
| 17 | 131 | -Met- |
| 18 | 137 | -His- |
| 21 | 147 | -Phe- |
| 22 | 156 | -Arg- |
| 23 | 163 | -Tyr- |
| 24 | 170 | -Lys(Ac)- |
| 25 | (179) | (-His(Ac)-) |
| 26 | 186 | -Trp- |
| 27 | (205) | (-Tyr(Ac)-) |

After it is confirmed that said peak is not accompanying with any anionic species peak having a m/z value difference equivalent to one of the formula weights of amino acid residues, it is judged that said peak is included in the group of anionic species peaks of peptide fragments each having arginine at the C-terminus of the peptide chain, derived from a target peptide and produced by digestion by trypsin.

In the process for the successive release of C-terminal amino acids according to the present invention, there also occurs O-acylation protection to the hydroxy groups of side chain of serine and threonine in the N-acylation protection step as for the anionic species peaks of major C-terminal side peptide fragments; however, this O-acylation to the hydroxy groups of side chain of serine and threonine is deprotected in the hydrolysis step prior to the digestion by trypsin; as a result, the anionic species peaks each showing a m/z value difference equivalent to the formula weight of O-acylated amino acid residue are measured as accompanying anionic species peaks; therefore, said m/z value differences corresponding to the formula weights of amino acid residues listed in Table 1 do not include the formula weights of those O-acylated amino acid residues. However, since N-acylated histidine residue and O-acylated tyrosine residue are not sufficiently deprotected in the hydrolysis step, there is remained possibility that they may mix in a considerable amount in the anionic species peaks derived from major C-terminal side peptide fragments. Meanwhile, in the present invention, the N-acylated lysine residue is not deprotected, in the hydrolysis step, by adoption of an appropriate condition but, if the N-acylated lysine residue is deprotected, the resulting lysine residue undergoes digestion by trypsin at its C-terminal side peptide bond; accordingly, there is no case that the m/z value difference between anionic species peaks derived from major C-terminal side peptide fragments corresponds to the formula weight of lysine residue. Further, since there is no removal of proline residue in the successive release of C-terminal amino acids of the present invention, no m/z value difference corresponding to the formula weight of proline residue is naturally contained in the above Table 1.

Meanwhile, in the seventh group of anionic species peaks are generally contained at least anionic species peaks of the C-terminal side peptide fragments per se, derived from a target peptide chain. The C-terminal side peptide fragments of target peptide are accompanied by the series of C-terminal side peptide fragments formed by the successive release of C-terminal amino acids, and main anionic species peaks of these accompanying C-terminal side peptide fragments are also contained in the seventh group of anionic species peaks.

Those present in small proportions, of the series of C-terminal side peptide fragments, for example, the C-terminal side peptide fragments formed in later stages of successive release of C-terminal amino acids are observed as their anionic species peaks, in the spectra for molecular weight measurement of anionic species; however, their corresponding cationic species peaks are at a noise level and may not be identified.

In the step 8, there is investigated whether or not each of the seventh group of anionic species peaks is accompanied by anionic species peaks of the series of C-terminal side peptide fragments formed by the successive release of C-terminal amino acids. This investigation is conducted as follows. There are selected, for each peak of the seventh group of anionic species peaks, those anionic species peaks present in the fourth group of anionic species peaks, each having a m/z value difference of smaller than 200 and, when the acyl group used in N-acylation protection is, for example, an acetyl group, there is investigated whether or not there are anionic species peaks each having a m/z value difference corresponding to the formula weight shown in the above Table 1.

When, in the investigation, it has been confirmed that said peaks are accompanied by anionic species peaks each showing a m/z value difference corresponding to the formula weight of amino acid, and the ninth group of anionic species peaks is made up therewith. The sum of this ninth group of anionic species peaks and those anionic species peaks which are not included in the seventh group of anionic species peaks but are presumed to be anionic species peaks of the series of C-terminal side peptide fragments, is designated as the tenth group of anionic species peaks. This tenth group of anionic species peaks contains the anionic species peaks of the series of C-terminal side peptide fragments formed by the successive release of C-terminal side amino acids. It is possible that, in these anionic species peaks, an anionic species peak of largest m/z value is selected and subsequently each anionic species peak showing a m/z value difference corresponding to the above-shown formula weight of amino acid residue is identified successively.

Finally, in the step 9, it is reconfirmed that the m/z value difference of each of the anionic species peaks selected in the step 8 agrees with each of the above-shown formula weights of amino acid residues, that is, reflects the partial amino acid sequence cleaved successively from the C-terminus; then, a series of operations for spectra analysis is completed.

In the above step of spectral analysis, there are utilized the peak m/z values and peak intensities of the spectra for molecular weight measurement by cationic species peaks and molecular weight measurement by anionic species peaks, obtained by MALDI-TOF-MS. Generally, in the MALDI-TOF-MS apparatus, the number of ions entering the detector is integrated and each ion is digitalized and plotted against the corresponding m/z value (minute integral range). Accordingly, there can be easily determined the apparent peak intensity of each ion and the m/z value of the ion, and there can be easily calculated the apparent full-width of half maximum of the ion. Meanwhile, it is not rare that spike-shaped noise signals overlap on spectra. Prior to the analysis, it is desired to remove these spike-shaped noise signals. In order to judge whether the obtained peaks are of true signal peaks or of noise peaks, it is possible to utilize a fact that, in the noise peaks, the full-width of half maximums are extremely narrow as compared with those of true signal peaks. For example, after the identification (the step 1) of internal standard peaks derived from trypsin, there are calculated the apparent full-widths of half maximum of the ion species peaks of the peptide fragments derived from trypsin autolysis; peaks of extremely narrow full-width of half maximum as compared with said apparent full-width of half maximums are searched; and the peaks of extremely narrow full-widths of half maximum can be judged as noise peaks.

Systematic peak widening is seen often owing to the measurement mechanism of MALDI-TOF-MS apparatus. It is preferred that this systematic peak widening is evaluated for the ion species peaks of the peptide fragments derived from trypsin autolysis, the asymmetry of the shapes of these peaks and their integral peak intensities are subjected to a smoothening treatment, then, for true signal peaks, their peak intensities and peak m/z values are determined.

Trypsin-derived internal standard peaks are present in the spectra for molecular weight measurements of cationic species and anionic species according to the MALDI-TOF-MS of the present invention; therefore, the above-mentioned noise peaks removal and smoothening treatment can be similarly conducted to the spectra of the two kinds of peaks (anionic species peaks and cationic species peaks) with referring to the internal standard peaks.

In addition to the systematic peak widening, there are cases that each peak m/z value has a systematic error owing to the measurement mechanism of MALDI-TOF-MS. It is desired that, prior to analysis, the systematic error of m/z value is corrected. This correction of systematic error of m/z value can also be made by using the ion species peaks of the peptide fragments derived from trypsin autolysis, after the internal standard peaks derived from trypsin have been identified in the step 1.

As described previously, in the spectral analysis for molecular weight measurement of cationic species and molecular weight measurement of anionic species by the MALDI-TOF-MS of the present invention, it is aimed to identify the major anionic species peaks of the series of C-terminal side peptide fragments formed by the successive release of C-terminal amino acids and, in the course of the analysis, there are identified, as well, anionic species peaks which accompany these major anionic species peaks. Specifically explaining, in the step 5, the following anionic species peaks (5b-1) to (5b-3) which accompany each "parent anionic species peak", are identified:

(5b-1) anionic species peaks having a smaller m/z value than the m/z value of said peak by the molecular weight of 18 corresponding to loss of water molecule, (5b-2) anionic species peaks each having a larger m/z value than the m/z value of said peak by the molecular weight equivalent to excess of the formula weight of the acyl group used for N-acylation protection, and (5b-3) anionic species peaks each having a m/z larger than the m/z of said peak by the molecular weight equivalent to the combination of the molecular weight decrease of 18 corresponding to loss of water molecule and excess of the formula weight of the acyl group used for N-acylation protection.

Accordingly, with respect to the spectra for molecular weight measurement of anionic species peaks, there are also made the assignments of these accompanying anionic species peaks, in addition to the assignments of the major anionic species peaks of the series of C-terminal side peptide fragments formed by the successive release of C-terminal amino acids.

In addition to the assignments of the major anionic species peaks of the series of C-terminal side peptide fragments formed by the successive release of C-terminal amino acids, there can also be made the assignments of the major anionic species peaks derived from digestion by trypsin and the assignments of their accompanying anionic species peaks. Finally, even the correspondence to the major cationic species peaks of the spectra for molecular weight measurement of cationic species is confirmed and, thus, both of the spectra for molecular weight measurement of cationic species peaks and the spectra for molecular weight measurement of anionic species peaks are analyzed by the MALDI-TOF-MS.

There is shown below an example of the procedure for identification of peaks derived from a peptide to be analyzed and assignment thereof, used in determining the C-terminal amino acid sequence of the peptide using mass spectra.

In the following description are shown the criteria and procedure used in determining the assignments of the ion species which are obtained by conducting the following steps:

a step of a pre-treatment for protection with N-acylation, in which N-acylation by alkanoic acid anhydride-derived acyl group is applied to the N-terminal amino group of a target peptide and the side chain amino group of lysine group which may be present in the peptide, a step of applying, to the peptide, a reaction reagent which is a combination of an alkanoic acid anhydride and a small amount of a perfluoroalkanoic acid, under a mild condition, to give rise to formation of a 5-oxazolone structure represented by the following general formula (III):

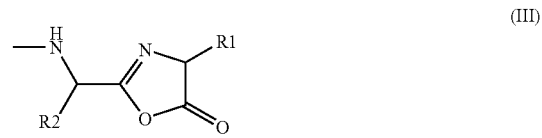

wherein R1 is a side chain of the C-terminal amino acid of the peptide and R2 is a side chain of the amino acid residue positioned just before the C-terminal amino acid, and then to conduct the release of C-terminal amino acid in association with cleavage of the 5-oxazolone ring, a hydrolysis step of removing the reaction reagent which is a combination of an alkanoic acid anhydride and a small amount of a perfluoroalkanoic acid, for inactivation and then regenerating the C-terminal carboxy group by the ring opening of remaining 5-oxazolone structure, and a step of conducting digestion by trypsin of peptide chain selectively at the arginine residue sites to obtain peptide fragments, and then by subjecting these peptide fragments to MALDI-TOF-MS by anionic species detection mode and cationic species detection mode to obtain respective mass spectra and selecting, from the monovalent ion species on the spectra, those ion species derived from the target peptide chain.

Description is made on a premise that, under actual conditions, as the alkanoic acid anhydride used in the pre-treatment step for protection with N-acylation and the step of releasing C-terminal amino acids, acetic anhydride [$(CH_3CO)_2O$] is used and, as the perfluoroalkanoic acid, trifluoroacetic acid ($CF_3COOH$) is used.

When the treatments proceed ideally under the above-mentioned conditions and when there are over the pre-treatment (N-acylation) step, the step of conducting the release of C-terminal amino acids and the subsequent hydrolysis step, N-acetylation remains at the N-terminal amino group and the side chain amino group of lysine residue; O-acetylation is completely deprotected, for example, at the side chain hydroxy group of serine residue, the side chain hydroxy group of threonine residue and the side chain phenolic hydroxy group of tyrosine residue; and the C-terminal carboxy group is regenerated from the C-terminal 5-oxazolone structure.

However, there are present, in the products obtained actually by the successive release of C-terminal amino acids, by-products derived from the side reactions taking place mainly in the step of conducting the release of C-terminal amino acids and the subsequent hydrolysis step.

When, in the hydrolysis, the deprotection of the O-acylation to the side chain hydroxy group of serine residue and the side chain hydroxy group of threonine residue is insufficient, there remain by-products wherein acetyl group is substituted on the amino acid residue. Meanwhile, when, in the hydrolysis, the regeneration of C-terminal carboxy group from C-terminal 5-oxazolone structure is not made, there remain by-products whose C-terminus is "dehydrated".

In the step of conducting the release of C-terminal amino acids, there are also formed by-products which are "dehydrated", for example, on the side chain of asparagine residue or glutamine residue, derived from a conversion reaction from carbamoyl group (CO—NH$_2$) on the side chain to cyano group (—CN), represented by the following scheme (V):

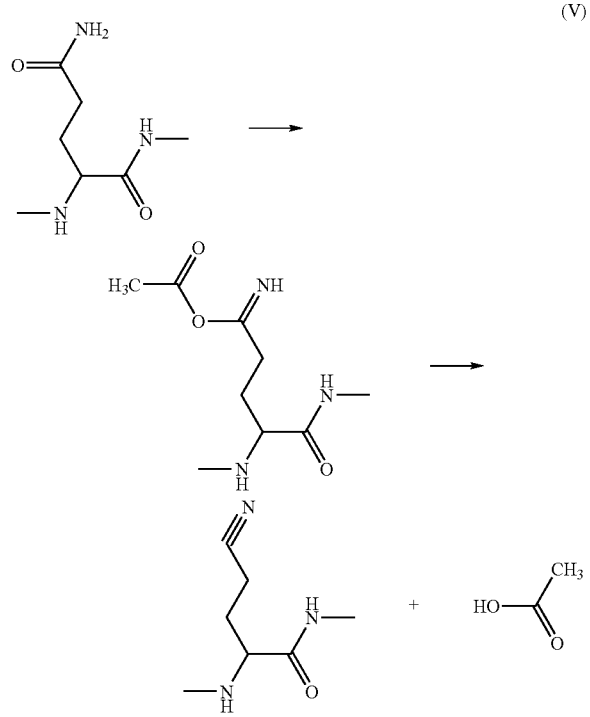

or on the side chain of serine residue or threonine residue, derived from the elimination of the acetyloxy group on the side chain, represented by the following general scheme (VI):

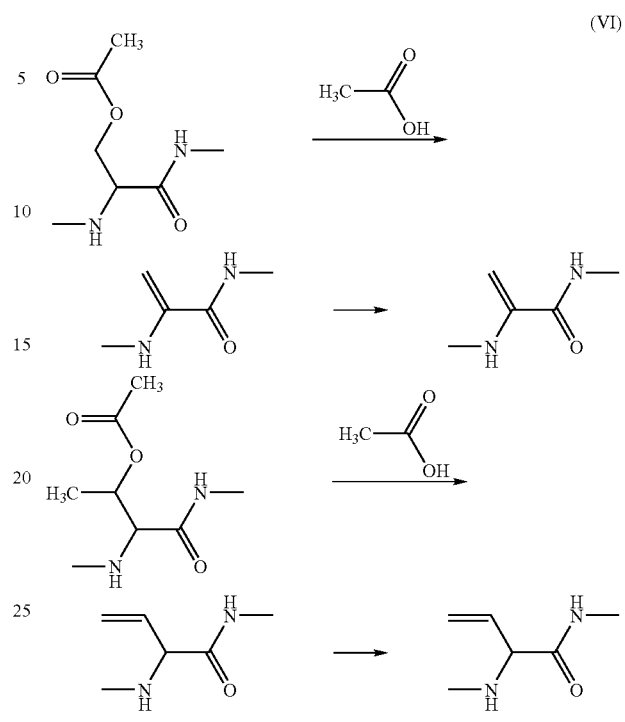

Meanwhile, when, in the pre-treatment step for protection by N-acylation and the step of conducting the release of C-terminal amino acids, acetylation proceeds even for the side chain phenolic hydroxy group of tyrosine residue and the imino nitrogen (—NH—) on the side chain imidazole ring of histidine residue, deprotection does not sufficiently proceed in the hydrolysis and there remain by-products wherein acetyl group is substituted on such amino acid residue.

Thus, in actual reaction products, there are often present, in addition to (i) ideal reaction products, (ii) secondary products having surplus acetylation, (iii) secondary products subjected to "dehydration", and (iv) secondary products subjected to "dehydration" and further having surplus acetylation.

In some cases, there are also present, in small amounts, secondary products wherein the trifluoroacetyl group derived from trifluoroacetic acid is not sufficiently deprotected and trifluoroacetylation remains. Therefore, there are, in some cases, also present, in small amounts, (v) seconadary products having trifluoroacetylation, and (vi) secondary products subjected to "dehydration" and further having trifluoroacetylation.

When the release of C-terminal amino acids is conducted under conventional reaction conditions, cleavage proceeds at various sites such as between Gly and Gly, the C-terminal side of Asp, particularly between Asp and Pro, and the N-terminal side of Ser or Thr, at certain frequencies. Meanwhile, in the release of the C-terminal amino acids according to the present invention, there are selected such reaction conditions that the cleavage in the middle of peptide chain is prevented; therefore, it is assumed for simplicity that, in the products after the release of C-terminal amino acids, there is no such unexpected by-product as formed by cleavage in the middle of peptide chain and subsequent successive release of C-terminal amino acids from each peptide fragment.

In the present invention, in the pre-treatment (N-acetylation protection) step and the step of conducting release of C-terminal amino acids, there are selected conditions which can effectively prevent formation of the secondary products (v) and (vi); however, there are often present, in certain amounts, the secondary products (ii) to (iv), in addition to the ideal reaction products (i). Prior to the measurement of mass spectra, the reaction products wherein the N-terminal amino group and the side chain amino group of lysine residue are acetylated, are subjected to digestion by trypsin for selective fragmentization of peptide chain at arginine residue sites; as a result, there are obtained N-terminal side fragments whose N-terminal amino group is acetylated and whose C-terminal amino acid is arginine, intermediate fragments whose two ends have been formed by digestion by trypsin, whose N-terminal amino group is not acetylated and whose C-terminal amino acid is arginine, and a series of C-terminal side fragments whose N-terminal amino group is not acetylated and whose C-terminal amino acid sequence has been subjected to successive cleavage of amino acids.

In the present invention, when it is assumed for simplicity that no cleavage occurs in the middle of peptide chain in the step of conducting successive release of C-terminal amino acids and when a sufficient time is taken for digestion by trypsin, the total number of the C-terminal side fragments becomes almost equal to the N-terminal side fragments and the intermediate fragments regarding the peptide fragments obtained from the original peptide. As mentioned previously, these peptide fragments are, at a high possibility, accompanied by at least the secondary products (ii) to (iv) in addition to the ideal reaction products (i); however, the proportions of these four kinds of reaction products (i) to (iv) are not constant for each peptide fragment and vary depending upon its amino acid sequence and the reaction conditions employed. For example, when this is contained no amino acid residue which can receive surplus acetylation, there is no formation of the secondary products (ii) and (iv). Further, in the measurement using, for example, a MALDI-TOF-MS apparatus, the proportions of anionic species and cationic species generated from each peptide fragment differ depending upon the amino acid sequence of the peptide fragment, the modification of amino acid residue of the peptide fragment, the ionization condition employed, etc.; of the monovalent ion species peaks appearing on the mass spectra obtained by anionic species detection mode and cationic species detection mode, some of the ion species of the four kinds of reaction products (i) to (iv) are not observed as peaks of significant intensity. For example, in those ion species low in amount produced, whose corresponding cationic species are extremely high in proportion, the corresponding anionic species are not observed as peaks of significant intensity on the mass spectra obtained by anionic species detection mode.

Below is shown an example of the procedure for reliably determining the assignments of those ion species giving a significantly intensive peak, of the ion species derived from the four kinds of reaction products (i) to (iv) even when only part of the ion species of the four kinds of reaction products (i) to (iv) is observed, by taking into consideration various possible cases such as mentioned above, to the maximum extent.

(Step 0) Recognition of Peaks on Spectra

Peaks are recognized on the spectra measured by anionic species detection mode as well as on the spectra measured by cationic species detection mode, and the apparent peak positions (m/z) and peak intensities of the recognized peaks are read.

Generally, peaks of ion species derived from peptide are accompanied by isotopic peaks that contain isotopes for the constituents atoms, for example, $^{13}C$ in place of $^{12}C$. However, the ratio of their intensities is roughly constant. Specifically explaining, as for each main peak of an ion species constituted by light atoms alone, there are present a plurality of isotopic ion species where the mass increases 1 by 1; however, the intensities for these isotopic peaks decrease in geometric series in approximate proportion to the natural isotopic abundance of $^{13}C$ relative to $^{12}C$, as the difference in mass increases by 1, 2 and 3.

With respect to the individual peaks recognized, there are calculated the intensities of isotopic peaks where the difference in mass increases by 1, 2 and 3, based on the above assumption; when there is, at a peak position (m/z) increased by 1 in mass number, a peak of other ion species overlapping with the isotopic peak, a correction is made to the apparent peak intensity therefor. A piling up operation including such correction is made to each recognized peak, and there are conducted recognition of ion species constituted by light atoms alone and reading of each peak position (m/z) and peak intensity.

The peak of each ion species constituted by light atoms alone is called Pi in the order of peak position (m/z).

Set of all the peaks recognized: A A $\equiv \{P_i| $ for $^{\forall}i\}$ (Step 1) Removal of Ion Species Peaks of Fragments Derived from Trypsin Autolysis In the digestion by trypsin, there are also formed peptide fragments derived from the autolysis of the trypsin used as an enzyme protein. Since the peak positions of the ion species of the peptide fragments derived from the autolysis of the trypsin are known beforehand, the set $A_t$ of the peaks of the ion species of the peptide fragments derived from the autolysis of the trypsin is removed from the peak set A and the remainder is designated as $A_p$ (a set of ion species peaks of fragments derived from peptide).

Set of ionic species peaks of fragments derived from trypsin autolysis: $A_t$

Set of ionic species peaks of fragments derived from peptide: $A_p$ $A_p \equiv A \backslash A_t$ Incidentally, a list of the peak positions of the ion species derived from the fragments obtained by trypsin autolysis is shown in FIG. 9.

(Step 2) Calculation of Distance between Peaks

For the peaks contained in the set $A_p$, there are calculated peak-to-peak distances of all the peaks.

Distance ($\Delta$m/z) between peak $P_i$ and $P_j$:$d_{ij}$

Incidentally, in the step 0, $P_i$ is arranged in the order of the peak position (m/z); it is desired that there is calculated a distance ($d_{ii+1}$) between adjacent peaks $P_i$ and $P_{i+1}$ and $d_{ij}$ is calculated as $d_{ij} = \{d_{ii+1} + \ldots + d_{j-1j}\}$.

(Step 3) Identification of m/z Range to be Analyzed

Sub-step 3-1 Selection of Significant Peaks Having a Peak Intensity of Threshold Value or Higher In the analysis which follows, it is essential that with respect to each of the fragments to be analyzed, i.e. the C-terminal side fragments, the N-terminal side fragments and the intermediate fragments, at least one of the ion species derived from the four kinds of reaction products (i) to (iv) shows a significantly intensive peak on the spectra.

In the peak set $A_p$, a peak having the maximum peak intensity is selected and the peak intensity is designated as $I_{max}$. A threshold peak intensity $I_{th}$ is set based on the peak intensity $I_{max}$. The threshold peak intensity $I_{th}$ is set at least at 1/40 of $I_{max}$.

In the peak set $A_p$, peaks of the threshold peak intensity $I_{th}$ or above are selected and are designated as main peak set M.

if intensity $I_i$ of peak $P_i > I_{th} \Rightarrow P_i \in M$

Sub-step 3-2 Identification or Resetting of m/Z Range to be Analyzed

When it is intended to analyze the C-terminal side fragments formed by successively releasing about 7 amino acid residues from the C-terminus of peptide, the difference in mass between these fragments is assumed to be ordinarily in a range of 600 to 1,200.

Taking this into consideration, there are selected, in the main peak set M, a peak $P_{Mmax}$ having the largest peak position (m/Z) and a peak $P_{Mmin}$ having the smallest peak position (m/Z). Regarding the distance ($\Delta$m/Z) between the peak $P_{Mmax}$ and the peak $P_{Mmin}$, it is confirmed that the difference in mass exceeds at least 600.

When, regarding the distance ($\Delta$m/Z) between the peak $P_{Mmax}$ and the peak $P_{Mmin}$, the difference in mass does not satisfy the above condition, the threshold peak intensity $I_{th}$ set in the Sub-step 3-1 is reset at a smaller value, selection of the main peak set M is remade, and it is confirmed that the new difference in mass satisfies the above condition.

There is finally set a m/Z range to be analyzed so that its upper limit is larger in mass by 100 than the peak position ($m_{max}$) of the peak $P_{max}$ and its lower limit is selected as smaller one from following two peak positions (m/z), smaller one by 100 in mass than the peak position ($m_{min}$) of the peak $P_{min}$ or smaller one by 1,000 in mass than the peak position ($m_{max}$) of the peak $P_{Mmax}$. In the peak set $A_p$, there are selected those peaks whose peak positions are contained in the thus-set m/Z range to be analyzed, and they are designated as peak set $S_0$. In the analysis which follows, there are analyzed the main peak set M and the element peaks of the peak set $S_0$ containing the main peak set M.

Bivalent ion species peaks [bivalent cationic species (m+2/2) and bivalent anionic species (m−2/2)] corresponding to the monovalent ion species peaks [cationic species (m+1/1) and anionic species (m−1/1)] contained in the main peak set M, may appear in a range of $m_{max}/2$ to $m_{min}/2$. There is beforehand confirmed the presence of peaks corresponding to bivalent ion species peaks corresponding to those monovalent ion species peaks contained in the main peak set M, of the peak set $S_0$ to be analyzed. Specifically explaining, since the proportions of bivalent ion species peaks corresponding to monovalent ion species peaks are significantly small or such ion species peaks are often not found, the presence of peaks corresponding to bivalent ion species peaks is beforehand confirmed in consideration of this fact.

(Step 4) Classification and Assignment of Ion Species Peaks of Peptide Fragments Obtained by Digestion by Trypsin of Four Kinds of Reaction Products (i) to (iv)

As described previously, in actual reaction, there are often formed, in addition to ideal reaction products (i), (ii) secondary products having surplus acetylation, (iii) secondary products subjected to "dehydration", and (iv) secondary products subjected to "dehydration" and further having surplus acetylation.

However, when there are considered the C-terminal side fragments, N-terminal side fragments and intermediate fragments all obtained by digestion by trypsin, for example, amino acid residue having surplus acetylation is present in the N-terminal side fragments but is not present in the C-terminal side fragments. Thus, with respect to each peptide fragment as well, only part of the following four kinds of peptide fragments may be obtained depending upon the amino acid sequence of the peptide fragment:

(i) ideal products: peptide fragments having neither amino acid residue having surplus acetylation nor amino acid residue subjected to "dehydration", (ii) peptide fragments containing an amino acid residue(s) having surplus acetylation but having no amino acid residue subjected to "dehydration", (iii) peptide fragments containing an amino acid residue(s) subjected to "dehydration" but having no amino acid residue having surplus acetylation, and (iv) peptide fragments containing an amino acid residue(s) having surplus acetylation and an amino acid residue(s) subjected to "dehydration".

As described previously, there are also anticipated peptide fragments into which trifluoroacetyl group has been introduced in place of acetyl group. However, their proportions are presumed to be sufficiently low and such fragments are not considered and are excluded here.

Hence, in order to know which ion species derived from the above-mentioned four kinds of peptide fragments having the same amino acid sequence are present in the ion species peaks of the peptide fragments obtained by digestion by trypsin, an example of the procedure for conducting grouping and assignment of peaks is explained below.

The sets of ion species peaks derived from the above-mentioned four kinds of peptide fragments (i) to (iv) are respectively designated as follows:

S (0): a set of ion species peaks derived from the peptide fragments (i),

S (+Ac): a set of ion species peaks derived from the peptide fragments (ii),

S (−$H_2O$): a set of ion species peaks derived from the peptide fragments (iii), and S (+Ac, −$H_2O$): a set of ion species peaks derived from the peptide fragments (iv).

The ion species peaks derived from the four kinds of peptide fragments (i) to (iv) are constituted by the same amino acid sequence and may give a group of peaks adjacent to each other.

TABLE 2

Values of specific peak shifts brought about by ion species peak side reactions derived from four kinds of peptide fragments (i) to (iv)

| Distance between peaks d | |
|---|---|
| 60 (42 + 18) | (ii)-(iii): acetylation ⇔ dehydration |
| 42 | (ii)-(i): acetylation ⇔ no side reaction |
| | (iv)-(iii): acetylation + dehydration ⇔ dehydration |
| 24 (42 − 18) | (iv)-(i): acetylation + dehydration ⇔ no side reaction |
| 18 | (i)-(iii): no side reaction ⇔ dehydration |
| | (ii)-(iv): acetylation ⇔ acetylation + dehydration |

Incidentally, the m/Z differences corresponding to the above 18, 24, 42 and 60 are not contained in the molecular weight reductions shown in Table 1, which occur in association with the successive release of C-terminal amino acids.

The cases in which any of the ion species of the four kinds of peptide fragments (i) to (iv) appear on the spectra obtained, are classified into the following 15 cases.

1. A case wherein the four kinds of peaks of the peptide fragments (i) to (iv) are observed.

2. A case wherein the three kinds of peaks of the peptide fragments (i), (ii) and (iii) are observed; that is, a case wherein the probabilities of surplus acetylation and "dehydration" are low and the peak of the peptide fragment (iv) having surplus acetylation and subjected to "dehydration" is below the measurement limit, or a case wherein both of a peptide fragment having surplus acetylation (this corresponds to an intermediate in the "dehydration" stage of the scheme (VI) and a peptide fragment subjected to "dehydration" are contained.

3. A case wherein the three kinds of peaks of the peptide fragments (i), (ii) and (iv) are observed; that is, a case wherein a peptide fragment having surplus acetylation is a main fragment, a peptide fragment having surplus acetylation and subjected to "dehydration" is observable, but a peptide fragment formed by "dehydration" of an ideal fragment (this ideal fragment is small in amount) is below the measurement limit.

4. A case wherein the three kinds of peaks of the peptide fragments (i), (iii) and (iv) are observed; that is, a case wherein a peptide fragment subjected to "dehydration" is a main fragment, a peptide fragment subjected to "dehydration" and having surplus acetylation is observable, but a peptide fragment formed by surplus acetylation of an ideal fragment (this ideal fragment left is small in amount) is below the measurement limit.

5. A case wherein the three kinds of peaks of the peptide fragments (ii), (iii) and (iv) are observed; that is, a case wherein a peptide fragment subjected to "dehydration" and a peptide fragment having surplus acetylation are main fragments and an ideal fragment not subjected to any of such side reactions is below the measurement limit.

6. A case wherein the two kinds of peaks of the peptide fragments (i) and (ii) are observed: that is, a case wherein an amino acid residue(s) subjectable to surplus acetylation is (are) contained but no amino acid residue subjectable to "dehydration" is contained.

7. A case wherein the two kinds of peaks of the peptide fragments (i) and (iii) are observed; that is, a case wherein an amino acid residue(s) subjectable to "dehydration" is (are) contained but no amino acid residue subjectable to surplus acetylation is contained, or a case wherein neither amino acid residue subjectable to surplus acetylation nor amino acid residue subjectable to "dehydration" is present but a peptide fragment not complete in hydrolysis of C-terminal 5-oxazolone structure remains.

8. A case wherein the two kinds of peaks of the peptide fragments (ii) and (iv) are observed; that is, a peptide fragment having surplus acetylation is a main fragment, a peptide fragment having surplus acetylation and subjected to "dehydration" can be observed, but both an ideal peptide fragment and a "dehydrated" peptide fragment are below the measurement limit.

9. A case wherein the two kinds of peaks of the peptide fragments (ii) and (iii) are observed; that is, a case wherein no amino acid residue subjectable to surplus acetylation is contained but a "dehydration" stage as seen in the formula (VI) has proceeded at a high frequency, the hydrolysis to a fragment of surplus acetylation (corresponding to the intermediate) is not sufficient, and a peptide fragment regenerated in an ideal form is very slight and below the measurement limit.

10. A case wherein the two peaks of the peptide fragments (i) and (iv) are observed.

11. A case wherein the two kinds of peaks of the peptide fragments (iii) and (iv) are observed; that is, a case wherein a peptide fragment subjected to "dehydration" is a main fragment, a peptide fragment subjected to "dehydration" and having surplus acetylation can be observed, but both an ideal peptide fragment and a peptide fragment having surplus acetylation are below the measurement limit.

12. A case wherein only the peak of the peptide fragment (i) is observed; that is, a case wherein neither amino acid residue subjectable to surplus acetylation nor amino acid residue subjectable to "dehydration" is contained.

13. A case wherein only the peak of the peptide fragment (ii) is observed; that is, a case wherein no amino acid residue subjectable to "dehydration" is contained, surplus acetylation has taken place at a high frequency, and a peptide fragment regenerated in an ideal form is very slight and below the measurement limit.

14. A case wherein only the peak of the peptide fragment (iii) is observed; that is, a case wherein an amino acid residue subjectable to surplus acetylation is not contained, "dehydration" as seen in the scheme (VI) has taken place at a high frequency, and both residual intermediates and a peptide fragment regenerated in an ideal form are very slight and below the measurement limit.

15. A case wherein only the peak of the peptide fragment (iv) is observed; that is, a case wherein "dehydration" and surplus acetylation have proceeded excessively and other peptide fragments are very slight and below the measurement limit.

In the above were shown representative cases which are conceivable.

Sub-step 4-1 Identification of Ion Species Peaks of the Four Kinds of Peptide Fragments (i) to (iv)

First, the element peaks of the peak set $S_0$ to be analyzed are divided into the following sub-sets.

(a) Of the peak group which is in a relation of distance 42, a peak set positioned at a larger mass side is designated as S (42), and a peak set positioned at a smaller mass side is designated as S (0,42).

(b) Of the peak group which is in a relation of distance 18, a peak set positioned at a smaller mass side is designated as S (−18), and a peak set positioned at a larger mass side is designated as S (0,−18).

(c) Of the peak group which is in a relation of distance 24, a peak set positioned at a larger mass side is designated as S (24), and a peak set positioned at a smaller mass side is designated as S (0,24).

(d) Of the peak group which is in a relation of distance 60, a peak set positioned at a larger mass side is designated as S (60), and a peak set positioned at a smaller mass side is designated as S (0,60).

In said step for forming the sub-sets (a) to (d), each 2 to 4 peaks observed as one group for the classes 1 to 11 are selected as a member included in either of the sub-sets.

Specifically explaining, the selection is summarized as follows.

Class 1. Four Kinds of Peaks of (i) to (iv) are Observed:

Peak of (ii) of Class 1∈{S(60)∩S(42)∩S(0,18)}=S(Ac)$_1$

Peak of (iv) of Class 1∈{S(42)∩S(24)∩S(18)}=S(Ac–H$_2$O)$_1$

Peak of (i) of Class 1 of ∈{S(0,42)∩S(0,24)∩S(0,18)}=S(0)$_1$

Peak of (iii) of Class 1∈{S(18)∩S(0,60)∩S(0,24)}=S(–H$_2$O)$_1$

Class 2. Three Kinds of Peaks of (i), (ii) and (iii) are Observed:

Peak of (ii) of Class 2∈{[S(60)∩S(42)]\[S(60)∩S(42)∩S(0,18)]}=S(Ac)$_2$

Peak of (i) of Class 2∈{[S(0,42)∩S(0,18)]\[S(0,42)∩S(0,24)∩S(0,18)]}=S(0)$_2$

Peak of (iii) of Class 2∈{[S(0,60)∩S(0,18)]\[S(18)∩S(0,60)∩S(0,24)]}=S(–H$_2$O)$_2$ Class 3. Three Kinds of Peaks of (i), (ii) and (iv) are Observed:

Peak of (ii) of Class 3∈{[S(42)∩S(0,18)]\[S(60)∩S(42)∩S(0,18)]}=S(Ac)$_3$

Peak of (iv) of Class 3∈{[S(24)∩S(18)]\[S(42)∩S(24)∩S(18)]}=S(Ac–H$_2$O)$_3$

Peak of (i) of Class 3∈{[S(0,42)∩S(0,24)]\[S(0,42)∩S(0,24)∩S(0,18)]}=S(0)$_3$

Class 4. Three Kinds of Peaks of (i), (iii) and (iv) are Observed:

Peak of (iv) of Class 4∈{[S(42)∩S(24)]\[S(42)∩S(24)∩S(18)]}=S(Ac–H$_2$O)$_4$

Peak of (i) of Class 4∈{[S(0,42)∩S(0,18)]\[S(0,42)∩S(0,24)∩S(0,18)]}=S(0)$_4$

Peak of (iii) of Class 4∈{[S(18)∩S(0,42)]\[S(18)∩S(0,60)∩S(0,24)]}=S(–H$_2$O)$_4$ Class 5. Three Kinds of Peaks of (ii), (iii) and (iv) are Observed:

Peak of (ii) of Class 5∈{[S(60)∩S(0,18)]\[S(60)∩S(42)∩S(0,18)]}=S(Ac)$_5$

Peak of (iv) of Class 5∈{[S(42)∩S(18)]\[S(42)∩S(24)∩S(18)]}=S(Ac–H$_2$O)$_5$

Peak of (iii) of Class 5∈{[S(0,60)∩S(0,42)]\[S(18)∩S(0,60)∩S(0,24)]}=S(–H$_2$O)$_5$ Class 9. Two Kinds of Peaks of (ii) and (iii) are Observed:

Peak of (ii) of Class 9∈{S(60)\[S(Ac)$_1$∪S(Ac)$_2$∪S(Ac)$_5$]}=S(Ac)$_9$

Peak of (iii) of Class 9∈{[S(0,60)\[S(–H$_2$O)$_1$∪S(—H$_2$O)$_2$∪S(–H$_2$O)$_5$]}=S(–H$_2$O)$_9$ Class 10. Two Kinds of Peaks of (i) and (iv) are Observed:

Peak of (i) of Class 10∈{S(0,24)\[S(0)$_1$∪S(0)$_3$∪S(0)$_4$]}=S(0)$_{10}$

Peak of (iv) of Class 10∈{S(24)\[S(Ac–H$_2$O)$_1$∪S(Ac—H$_2$O)$_3$∪S(Ac–H$_2$O)$_4$]}=S(Ac–H$_2$O)$_{10}$ Class 6. Two Kinds of Peaks of (i) and (ii) are Observed:

Class 11. Two Kinds of Peaks of (iii) and (iv) are Observed:

Peak of (ii) of Class 6 or peak of (iv) of Class 11∈{S(42)\[S(Ac)$_1$∪S(Ac)$_2$∪S(Ac)$_3$∪S(Ac–H$_2$O)$_1$∪S(Ac–H$_2$O)$_4$∪S(Ac–H$_2$O)$_5$]}={S(Ac)$_6$∪S(Ac–H$_2$O)$_{11}$}≈S(Ac)$_6$ Peak of (i) of Class 6 or peak of (iii) of Class 11∈{S(0,42)\[S(0)$_1$∪S(0)$_2$∪S(0)$_3$∪S(–H$_2$O)$_1$∪S(–H$_2$O)$_4$ S(—H$_2$O)$_5$]}={S(0)$_6$∪S(–H$_2$O)$_{11}$}≈S(0)$_6$ Incidentally, the near-complete occurrence of "dehydration" in Class 11 is extremely rare in the present invention. Meanwhile, remaining of surplus acetylation in ideal peptide fragment as in Class 6 is highly probable.

Class 7. Two Kinds of Peaks of (i) and (iii) are Observed:

Class 8. Two Kinds of Peaks of (ii) and (iv) are Observed:

Peak of (iii) of Class 7 or peak of (iv) of Class 8∈{S(18)\[S(–H$_2$O)$_1$∪S(–H$_2$O)$_2$∪S(–H$_2$O)$_4$∪S(Ac–H$_2$O)$_1$∪S(Ac—H$_2$O)$_3$∪S(Ac–H$_2$O)$_5$]}={S(–H$_2$O)$_7$∪S(Ac–H$_2$O)$_8$}

Peak of (i) of Class 7 or peak of (ii) of Class 8∈{S(0,18)\[S(0)$_1$∪S(0)$_2$∪S(0)$_4$∪S(Ac)$_1$∪S(Ac)$_3$∪S(Ac)$_5$]}={S(0)$_7$∪S(Ac)$_8$}

The presence, for a main peak from ideal fragment, of an associated peak which is corresponding to a "dehydrated" fragment thereof, as observed in Class 7, is highly probable. Meanwhile, a case wherein surplus acetylation and "dehydration" have taken place, as described as for Class 8, is very rare in the present invention. However, it is impossible to separate $S(-H_2O)_7 \cup S(Ac-H_2O)_8$ and $S(0)_7 \cup S(Ac)_8$ further into $S(-H_2O)_7$ and $S(Ac-H_2O)_8$, and $S(0)_7$ and $S(Ac)_8$, respectively. It is impossible to make much more detailed assignment.

In the above classification, the results of the following series of set calculations are utilized.

(d) Peaks which are in a relation of distance 60, are a peak of a fragment having surplus acetylation and a peak of a fragment subjected to "dehydrated", in each of Classes 1, 2, 5 and 9.

$$S(60)=S(Ac)_1 \cup S(Ac)_2 \cup S(Ac)_5 \cup S(Ac)_9$$

$$S(0,60)=S(-H_2O)_1 \cup S(-H_2O)_2 \cup S(-H_2O)_5 \cup S(-H_2O)_9$$

(c) Peaks which are in a relation of distance 24, are a peak of a fragment having surplus acetylation and subjected to "dehydration" and a peak of an ideal fragment, in each of Classes 1, 3, 4 and 10.

$$S(0,24)=S(0)_1 \cup S(0)_3 \cup S(0)_4 \cup S(0)_{10}$$

$$S(24)=S(Ac-H_2O)_1 \cup S(Ac-H_2O)_3 \cup S(Ac-H_2O)_4 \cup S(Ac-H_2O)_{10}$$

(a) Peaks which are in a relation of distance 42, are a peak of a fragment having surplus acetylation and a peak of an ideal fragment, in each of Classes 1, 2, 3 and 6; and a peak of a fragment having surplus acetylation and subjected to "dehydration" and a peak of a fragment subjected to "dehydration", in each of Classes 1, 4, 5 and 11.

$$S(42)=\{S(Ac)_1 \cup S(Ac)_2 \cup S(Ac)_3 \cup S(Ac)_6\} \cup \{S(Ac-H_2O)_1 \cup S(Ac-H_2O)_4 \cup S(Ac-H_2O)_5 \cup S(Ac-H_2O)_{11}\}$$

$$S(0,42)=\{S(0)_1 \cup S(0)_2 \cup S(0)_3 \cup S(0)_6\} \cup \{S(-H_2O)_1 \cup S(-H_2O)_4 \cup S(-H_2O)_5 \cup S(-H_2O)_{11}\}$$

(b) Peaks which are in a relation of distance 18, are a peak of a fragment subjected to "dehydration" a and a peak of an ideal fragment, in each of Classes 1, 2, 4 and 7; and a peak of a fragment having surplus acetylation and a peak of a fragment having surplus acetylation and subjected to "dehydration", in each of Classes 1, 3, 5 and 8.

$$S(18)=\{S(-H_2O)_1 \cup S(-H_2O)_2 \cup S(-H_2O)_4 \cup S(-H_2O)_7\} \cup \{S(Ac-H_2O)_1 \cup S(Ac-H_2O)_3 \cup S(Ac-H_2O)_5 \cup S(Ac-H_2O)_8\}$$

$$S(0,18)=\{S(0)_1 \cup S(0)_2 \cup S(0)_4 \cup S(0)_7\} \cup \{S(Ac)_1 \cup S(Ac)_3 \cup S(Ac)_5 \cup S(Ac)_8\}$$

Product sets, when examined, come out to be as follows.

(1) $S(60) \cap S(42) = (S(Ac)_1:+Ac$ peak of Class 1$) \cup (S(Ac)_2:+Ac$ peak of Class 2)

(2) $S(60) \cap S(0,18) = (S(Ac)_1:+Ac$ peak of Class 1$) \cup (S(Ac)_5:+Ac$ peak of Class 5)

(3) $S(42) \cap S(24) = (S(Ac-H_2O)_1:+Ac-H_2O$ peak of Class 1$) \cup (S(Ac-H_2O)_4:+Ac-H_2O$ peak of Class 4)

(4) $S(42) \cap S(18) = (S(Ac-H_2O)_1:+Ac-H_2O$ peak of Class 1$) \cup (S(Ac-H_2O)_5:+Ac-H_2O$ peak of Class 5)

(5) $S(42) \cap S(0,18) = (S(Ac)_1:+Ac$ peak of Class 1$) \cup (S(Ac)_3:+Ac$ peak of Class 3)

(6) $S(24) \cap S(18) = (S(Ac-H_2O)_1:+Ac-H_2O$ peak of Class 1$) \cup (S(Ac-H_2O)_3:+Ac-H_2O$ peak of Class 3)

(7) $S(18) \cap S(0,42) = (S(-H_2O)_1:-H_2O$ peak of Class 1$) \cup (S(-H_2O)_4:-H_2O$ peak of Class 4)

(8) $S(0,60) \cap S(0,42) = (S(-H_2O)_1:-H_2O$ peak of Class 1$) \cup (S(-H_2O)_5:-H_2O$ peak of Class 5)

(9) $S(0,60) \cap S(0,18) = (S(-H_2O)_1:-H_2O$ peak of Class 1$) \cup (S(-H_2O)_2:-H_2O$ peak of Class 2)

(10) $S(0,42) \cap S(0,24) = (S(O)_1:$ideal peak of Class 1$) \cup (S(O)_3:$ideal peak of Class 3)

(11) $S(0,42) \cap S(0,18) = (S(O)_1:$ideal peak of Class 1$) \cup (S(O)_2:$ideal peak of Class 2)

(12) $S(0,24) \cap S(0,18) = (S(O)_1:$ideal peak of Class 1$) \cup (S(O)_4:$ideal peak of Class 4)

(13) $S(60) \cap S(42)_{109} S(0,18) = (S(Ac)_1:+Ac$ peak of Class 1)

(14) $S(42) \cap S(24) \cap S(18) = (S(Ac-H_2O)_1:+Ac-H_2O$ peak of Class 1)

(15) $S(0,42) \cap S(0,42) \cap S(0,18) = (S(O)_1:$ideal peak of Class 1)

(16) $S(18) \cap S(0,60) \cap S(0,24) = (S(-H_2O)_1:-H_2O$ peak of Class 1)

Incidentally, all product sets of other combinations become empty sets.

Each peak of Class 1 is given as (13) to (16).

In seeking each peak of Classes 2, 3, 4 and 5, each peak of Class 2 is given as odd set from (1), (9), (11), (13) to (16).

Each peak of Class 3 is given as odd set from (5), (6), (10), (13) to (16).

Each peak of Class 4 is given as odd set from (3), (7), (12), (13) to (16).

Each peak of Class 5 is given as odd set from (2), (4), (8), (13) to (16).

Each peak of Class 9, each peak of Class 10, each peak of Class 6 and Class 11, and each peak of Class 7 and Class 8 are given as odd set sequentially.

Incidentally, if the frequency of Class 11 is substantially negligible, $$S(Ac)_6 \cup S(Ac-H_2O)_{11} \approx S(Ac)_6$$

$$S(0)_6 \cup S(-H_2O)_{11} \approx S(0)_6$$

Since the remaining Classes 12 to 15 are each observed as a single peak, they remain as those not included in any of the sub-sets (a) to (d). However, correspondence of these single peaks to any of the Classes 12 to 15 is impossible to judge at this stage.

Each peak having accompanying peaks, which is classified into either of Classes 1 to 11, is further classified and designated as follows.

$S(0)_p$: a set of ion species peaks derived from the peptide fragments (i), having accompanying peaks $$S(0)_p \equiv S(0)_1 \cup S(0)_2 \cup S(0)_3 \cup S(0)_4 \cup S(0)_8 \cup S(0)_6 \cup S(0)_{10} \cup [S(0)_7 \cup S(Ac)_8]$$

$S(+Ac)_p$: a set of ion species peaks derived from the peptide fragments (ii), having accompanying peaks $$S(+Ac)_p \equiv S(Ac)_1 \cup S(Ac)_2 \cup S(Ac)_3 \cup S(Ac)_5 \cup S(Ac)_6 \cup S(Ac)_9 \cup [S(0)_7 \cup S(Ac)_8]$$

$S(-H_2O)_p$: a set of ion species peaks derived from the peptide fragments (iii), having accompanying peaks $$S(-H_2O)_p \equiv S(-H_2O)_1 \cup S(-H_2O)_2 \cup S(-H_2O)_4 \cup S(-H_2O)_5 \cup S(-H_2O)_9 \cup [S(-H_2O)_7 \cup S(Ac-H_2O)_8]$$

$S(+Ac,-H_2O)_p$: a set of ion species peaks derived from the peptide fragments (iv), having accompanying peaks $$S(+Ac,-H_2O)_p \equiv S(Ac-H_2O)_1 \cup S(Ac-H_2O)_3 \cup S(Ac-H_2O)_4 \cup S(Ac-H_2O)_5 \cup S(Ac-H_2O)_{10} \cup [S(-H_2O)_7 \cup S(Ac-H_2O)_8]$$

Incidentally, with respect to Class 6 and Class 11, they are classified as Class 6 and not as Class 11, in view of the possibility. Meanwhile, with respect to Class 7 and Class 8, the possibility of Class 7 is high but no further judgment is made; the peaks belonging to $S(0)_7 \cup S(Ac)_8$ is classified into $S(0)_p$ and $S(+Ac)_p$ and the peaks belonging to $S(-H_2O)_7 \cup S(Ac-H_2O)_8$ are classified into $S(-H_2O)_p$ and $S(+Ac,-H_2O)_p$.

By the aforementioned formation of the sub-sets classified, is complete the assignment of peaks recognized as those having accompanying peaks in the m/Z range to be analyzed.

Next, of the peaks contained in the main peak set M, those contained in the above-mentioned four kinds of sub-sets are selected and designated as follows.

$S(0)_{PM}$: a set of ion species peaks derived from the peptide fragments (i), which are classified as $S(0)_p$ of the main peak set M.

$$S(0)_{PM} \equiv \{M \cap S(0)_p\}$$

$S(+Ac)_{PM}$: a set of ion species peaks derived from the peptide fragments (ii), which are classified as $S(+Ac)_p$ of the main peak set M.

$$S(+Ac)_{PM} \equiv \{M \cap S(+Ac)_p\}$$

$S(-H_2O)_{PM}$: a set of ion species peaks derived from the peptide fragments (iii), which are classified as $S(-H_2O)_p$ of the main peak set M.

$$S(-H_2O)_{PM} \equiv \{M \cap S(-H_2O)_p\}$$

$S(+Ac,-H_2O)_{PM}$: a set of ion species peaks derived from the peptide fragments (iv), which are classified as $S(+Ac,-H_2O)_p$ of the main peak set M.

$$S(+Ac,-H_2O)_{PM} = \{M \cap S(+Ac,-H_2O)_p\}$$

By the above constitution of sub-sets is complete the assignment of "main peaks" recognized as those having accompanying peaks in the m/Z range to be analyzed.

Calculation of Average Peak Intensities

The above-selected peak sets are each calculated for average peak intensity.

The average peak intensity of the peaks belonging to $S(0)_p$ is named as $I_0$.

The average peak intensity of the peaks belonging to $S(+Ac)_p$ is named as $I_{Ac}$.

The average peak intensity of the peaks belonging to $S(-H_2O)_p$ is named as $I_{-H2O}$.

The average peak intensity of the peaks belonging to $S(+Ac,-H_2O)_p$ is named as $I_{Ac-H2O}$.

The "single peak" sets remaining unassigned in the above assignment operation include each peak of Classes 12 to 15, for example, a peak derived from an ideal fragment wherein there is no side reaction giving an accompanying peak.

These peaks are predicted to have the maximum average peak intensity I.

(Step 5) Selection of Main Peaks to be Analyzed

With respect to those peaks which, as the results of above classification and assignment, appear, in the ion species peaks derived from the peptide fragments obtained by digestion by trypsin, as a group of two or more ion species peaks derived from the above-mentioned four kinds of peptide fragments all having the same amino acid sequence, which are classified as either of Classes 1 to 11, and whose assignment has been made, there is selected a representative peak of each group and it is used as a main peak to be analyzed. Specifically explaining, there is selected, as the representative peak of each group, a peak having the maximum peak intensity.

Sub-step 5-1 Identification of Accompanying Peaks Having Trifluoroacetylation and Their Removal from Peaks to be Analyzed As a result of the side reactions occurring in the successive release of C-terminal amino acids, there may appear, on the spectra obtained, accompanying peaks of trifluoroacetylation (in place of acetylation) caused by trifluoroacetic acid present together, in the Classes 1, 2, 3, 5, 6, 8, 9, etc. containing peaks of accompanying ion species having surplus acetylation. That is, the spectra may additionally include ion species peaks derived from:

(v) peptide fragments having an amino acid residue(s) having surplus trifluoroacetylation but having no amino acid residue subjected to "dehydration", ad (vi) peptide fragments having an amino acid residue(s) having surplus trifluoroacetylation and an amino acid residue(s) subjected to "dehydration".

With respect to the peaks remaining unassigned in the Step 4, the presence of the ion species peaks derived from the peptide fragments (v) or (vi) is judged based on the ion species peaks derived from the peptide fragments (ii) having surplus acetylation, classified in the Classes 1, 2, 3, 5, 6, 8, 9, etc. Prior to this judgment of the presence, it is confirmed that the peak intensities of the ion species peaks derived from the peptide fragments (v) or (vi) are at least lower than the peak intensities of the ion species peaks derived from the peptide fragments (ii) having surplus acetylation.

If there have been identified the ion species peaks derived from the peptide fragments (v) or (vi), they are designated as S(CF): a set of peaks having surplus trifluoroacetylation. Meanwhile, they are removed from the set of peaks remaining unassigned in the Step 4 and excluded from target peaks to be analyzed in the following steps.

Sub-Step 5-2 Selection of Main Peaks to be Analyzed

With respect to the peaks which are classified as either of the Classes 1 to 11 and whose assignments for situation thereof have been made, a representative peak is selected from each group and used as a main peak to be analyzed. Specifically speaking, since the reliability and accuracy of the peak position (the center value of peak) which has been read, are ordinarily higher as its peak intensity is higher, there is selected a peak having the maximum peak intensity as the representative peak of each group which is utilized in the analysis of molecular weight difference (peak position difference) of the amino acids released.

With respect to the accompanying peaks present in addition to each selected peak, these peaks are summed up with the selected peak in each group, and the resulting summed-up peak intensity is utilized in the later analysis. Specifically explaining, in order to search the amino acids released successively from the C-terminus of peptide, accompanying peaks are integrated into a peak of the highest signal in calculation of distances between peaks, and such search is conducted.

Hence, the following typing is made and there is shown an example of the operation for integrating accompanying peaks into each representative peak selected.

Incidentally, a possibility is low that the ion species peaks derived from the peptide fragments (iv) having an amino acid residue(s) having surplus acetylation and an amino acid residue(s) subjected to "dehydration" have each the highest peak intensity, and such ion species peaks are not considered here. That is, it is assumed that there is no case of $I_{Ac-H2O} = \text{Max}(I_0, I_{Ac}, I_{-H2O}, I_{Ac-H2O})$.

(a) A Case wherein Ion Species Peaks Derived from the Peptide Fragments (ii) Having an Amino Acid Residue(s) Having Surplus Acetylation But Having no Amino Acid Residue Subjected to "Dehydration" are Significant.

If $I_{Ac} = \text{Max}(I_0, I_{Ac}, I_{-H2O}, I_{Ac-H2O})$ ⇒ the peaks of all the peptide fragments are piled up to the peaks of fragments (ii) of surplus acetylation.

This piling up operation is conducted according to the following procedure.

a-1: Operation for Piling Up of Peak of Fragment (iii) Subjected to "Dehydration" and Peak of Fragment (iv) Subjected to "Dehydration" and Having Surplus Acetylation With respect to each pair of peaks which are in relation of distance 18, $(P_i, P_j):d_{ij}=18$, a peak positioned at a lower mass side relative to the set S (−18) is translated by 18 to a higher mass side to fit to a peak positioned at a higher mass side relative to the set S(0,−18). By this piling up operation, the peak of fragment (iii) subjected to "dehydration" and the peak of fragment (iv) subjected to "dehydration" and having surplus acetylation are piled up to the respective corresponding peaks not subjected to "dehydration".

Next, with respect to each pair of peaks which are in relation of distance 60 relative to the peak of fragment (iii) subjected to "dehydration", not contained in the set S(−18), i.e. $(P_i, P_j):d_{ij}=60$, a peak positioned at a lower mass side relative to the set S(0,60) is translated by 60 to a higher mass side to fit to a peak of acetylated fragment positioned at a higher mass side relative to the set S(60). In this operation, piling up is made only for the peaks of fragment (iii) subjected to "dehydration, which are contained in the set S(0,60) but not contained in the set (−18).

a-2: Operation for Piling Up of Peak Derived from Ideal Peptide Fragment (i) Having Neither Amino Acid Residue Having Surplus Acetylation nor Amino Acid Residue Subjected to "Dehydration"

With respect to each pair of peaks which are in relation of distance 42, $(P_i,P_j):d_{ij}=42$, a peak positioned at a lower mass side relative to the set S (0,42) is translated by 42 to a higher mass side to fit to a peak (of acetylated peptide fragment) positioned at a higher mass side relative to the set S (42). By this piling up operation, the peak of ideal peptide fragment (i) is piled up to the peak of acetylated peptide fragment (ii).

a-3: With Respect to Peak of Peptide Fragment (iv) Subjected to "Dehydration" and Having Surplus Acetylation In the piling up operation a-1, each peak of peptide fragment (iv) has been piled up to the peak of acetylated peptide fragment (ii).

By effecting the piling up operations in the above order of a-1, a-2 and a-3, the majority of the peaks of dehydrated peptide fragments (iii) are piled up once to each peak of ideal peptide fragment (i) and further to each peak of acetylated peptide fragment (ii) together with the peak of ideal peptide fragment (i). As a result, each accompanying peak is piled up to the peak of acetylated peptide fragment (ii) which becomes a representative peak. Incidentally, the peaks translated are removed one by one from the peak set $S_0$ to be analyzed. Finally, in the Classes having peaks of acetylated peptide fragments (ii), only the representative peak thereof is selected as a peak to be analyzed. At that time, simultaneously with the piling up operation, integration of peak intensities is made to the peak intensity of the representative peak of acetylated peptide fragment (ii).

(b) A Case wherein Ion Species Peaks Derived from the Peptide Fragments (iii) Having an Amino Acid Residue(s) Subjected to "Dehydration" But Having no Amino Acid Residue Having Surplus Acetylation are Significant.

If $I_{-H2O}=\text{Max}(I_0, I_{Ac}, I_{-H2O}, I_{Ac-H2O})$ ⇒the peaks of all the peptide fragments are piled up to the peaks of "acetylated" fagments (iii).

This piling up operation is conducted according to the following procedure.

b-1: Operation for Piling Up of Peak of Ideal Peptide Fragment (i) and Peak of Peptide Fragment (ii) Having Surplus Acetylation With Respect to each pair of peaks which are in relation of distance 18, $(P_i,P_j):d_{ij}=18$, a peak positioned at a higher mass side relative to the set S (0,−18) is translated by 18 to a lower mass side to fit to a peak positioned at a lower mass side relative to the set S(−18). By this piling up operation, the peak of ideal peptide fragment (i) is piled up to the peak of "dehydrated" peptide fragment (iii), and the peak of peptide fragment (ii) having surplus acetylation is piled up to the peak of peptide fragment (iv) subjected to "dehydration" and having surplus acetylation.

b-2: Operation for Piling Up of Peak of Peptide Fragment (ii) Having Surplus Acetylation and Peak of Peptide Fragment (iv) Subjected to "Dehydration" and Having Surplus Acetylation With respect to each pair of peaks which are in relation of distance 42, $(P_i,P_j):d_{ij}=42$, a peak positioned at a higher mass side relative to the set S (42) is translated by 42 to a lower mass side to fit to a peak positioned at a lower mass side relative to the set S(0,42). As a result, the peak of peptide fragment (ii) having surplus acetylation, piled up, in the above b-1, to the peak of peptide fragment (iv) subjected to "dehydration" and having surplus acetylation, and the peak of peptide fragment (iv) subjected to "dehydration" and having surplus acetylation are piled up together to the peak of peptide fragment (iii) subjected to "dehydration".

Incidentally, in the Classes containing no peak of peptide fragment (iii) subjected to "dehydration", the peak of peptide fragment (ii) having surplus acetylation is piled up to the peak of ideal peptide fragment (i).

b-3: Operation for Piling Up of Remaining Peak of Peptide Fragment (iv) Subjected to "Dehydration" and Having Surplus Acetylation Incidentally, in the Classes containing no peak of peptide fragment (iii) subjected to "dehydration", peaks of peptide fragment (iv) subjected to "dehydration" and having surplus acetylation remain even after the operations of b-1 and b-2.

With respect to each pair of peaks which are in relation of distance 24, a peak positioned at a higher mass side relative to the set S(24) is translated by 42 to a lower mass side to fit to a peak positioned at a lower mass side relative to the set S(0,24). Accordingly, in the Classes containing no peak of peptide fragment (iii) subjected to "dehydration", a peak of peptide fragment (iv) subjected to "dehydration" and having surplus acetylation is piled up to a peak of ideal peptide fragment (i).

By effecting the piling up operation in the above order of b-1, b-2 and b-3, each accompanying peak is piled up, in the Classes containing peaks of peptide fragment (iii) subjected to "dehydration", to the peak of peptide fragment (iii) subjected to "dehydration" which becomes a representative peak. Incidentally, the peaks translated are removed one by one from the peak set $S_0$ to be analyzed. Finally, in the Classes having peaks of "dehydrated" peptide fragments (iii), only the representative peak of "dehydrated" peptide fragment (iii) is selected as a peak to be analyzed. At that time, simultaneously with the piling up operation, integration of peak intensities is made to the representative peak of "dehydrated" peptide fragment (c) A Case wherein Ion Species Peaks Derived from Ideal Peptide Fragments (i) Having Neither Amino Acid Residue Having Surplus Acetylation nor Amino Acid Residue Subjected to "Dehydration" are Significant If $I_O=\text{Max}(I_0, I_{Ac}, I_{-H2O}, I_{Ac-H2O})$ ⇒the peaks of all the peptide fragments are piled up to the peaks of ideal peptide fragments (i).

c-1: Operation for Piling Up of Peak of "Dehydrated" Peptide Fragment (iii) and Peak of Peptide Fragment (iv) Subjected to "Dehydration" and Having Surplus Acetylation With respect to each pair of peaks which are in relation of distance 18, $(P_i,P_j):d_{ij}=18$, a peak positioned at a lower mass side relative to the peak set S(−18) is translated by 18 to a higher mass side to fit to a peak positioned at a higher mass side relative to the peak set S(0,−18). By this piling up operation, the peak of "dehydrated" peptide fragment (iii) is piled up to the peak of ideal peptide fragment (i), and the peak of peptide fragment (iv) subjected to "dehydration" and having surplus acetylation is piled up to the peak of peptide fragment (ii) having surplus acetylation.

c-2: Operation for Piling Up of Peak of Peptide Fragment (ii) Having Surplus Acetylation With respect to each pair of peaks which are in relation of distance 42, $(P_i,P_j):d_{ij}=42$, a peak positioned at a higher mass side relative to the peak set S(42) is translated by 42 to a lower mass side to fit to a peak positioned at a lower mass side relative to the peak set S(0,42). As a result, the peak of peptide fragment (iv) subjected to "dehydration" and having surplus acetylation, piled up, in the above b-1, to the peak of peptide fragment (ii) having surplus acetylation, and the peak of peptide fragment (ii) having surplus acetylation are piled up together to the peak of ideal peptide fragment (i).

Incidentally, in the Classes containing no peak of peptide fragment (ii) having surplus acetylation, the peak of peptide fragment (iv) subjected to "dehydration" and having surplus acetylation is not piled up because, in the previous stage, the peak of peptide fragment (iii) has been piled up and excluded.

c-3: Operation for Piling Up of Remaining Peak of Peptide Fragment (iv) Subjected to "Dehydration" and Having Surplus Acetylation Incidentally, in the Classes containing no peak of peptide fragment (iii) subjected to "dehydration" or in the Classes containing no peak of peptide fragment (ii) having surplus acetylation, peaks of peptide fragment (iv) subjected to "dehydration" if and having surplus acetylation remain even after the operations c-1 and c-2.

With respect to each pair of peaks which are in relation of distance 24, a peak positioned at a higher mass side relative to the peak set S(24) is translated by 24 to a lower mass side to fit to a peak positioned at a lower mass side relative to the peak set S(0,24). Accordingly, in the Classes containing no peak of peptide fragment (iii) subjected to "dehydration" or in the Classes containing no peak of peptide fragment (ii) having surplus acetylation, each peak of peptide fragment (iv) subjected to "deydration" and having surplus acetylation is piled up to the peak of ideal peptide fragment (i) in this stage.

By effecting the piling up operation in the above order of c-1, c-2 and c-3, accompanying peaks are piled up to the peak of ideal peptide fragment (i) which becomes a representative peak, in the Classes containing peaks of ideal peptide fragments (i). Incidentally, the peaks translated are removed one by one from the peak set $S_0$ to be analyzed. Finally, in the Classes containing peaks of ideal peptide fragments (i), only the representative peak of peptide fragment (i) is selected as a peak to be analyzed. At that time, simultaneously with the piling up operation, integration of peak intensities is made to the representative peak of ideal peptide fragment (i).

By the above piling up operation, each representative peak selected is left in the peak set $S_0$, each peak translated is removed, and the resulting peak set to be analyzed in the later analysis is designated as $S_1$.

Sub-Step 5-3: Calculation of Indicator of the Possibility of Peaks Derived from Sample Protein For each peak contained in the peak set $S_0$ as well as in the peak set $S_1$ to be analyzed, obtained after the above piling up operation, there is calculated the indicator of the possibility of each peak derived from sample protein, as follows.

For the peak $P_i$ contained in either of the sub-groups selected based on the classification and assignment of the above Step 4, that is, $S(0)_{PM}$: a set of ion species peaks derived from the peptide fragments (i) classified as $S(0)_p$ in the main peak set M;

$$S(0)_{PM} \equiv \{M \cap S(0)_p\}$$

$S(+Ac)_{PM}$: a set of ion species peaks derived from the peptide fragments (ii) classified as $S(+Ac)_p$ in the main peak set M;

$$S(+Ac)_{PM} \equiv \{M \cap S(+Ac)_p\}$$

$S(-H_2O)_{PM}$: a set of ion species peaks derived from the peptide fragments (iii) classified as $S(-H_2O)_p$ in the main peak set M;

$$S(-H_2O)_{PM} \equiv \{(M \cap S(-H_2O)_p\}$$

$S(+Ac,-H_2O)_{PM}$: a set of ion species peaks derived from the peptide fragments (iv) classified as $S(+Ac,-H_2O)_p$ in the main peak set M;

$$S(+Ac,-H_2O)_{PM} \equiv \{M \cap S(+Ac,-H_2O)_p\}$$

the indicator $r_i$ of possibility is set as follows:

if $P_i \in S(0)_{PM} \rightarrow r_i = 3$ if $P_i \in S(+Ac)_{PM} \rightarrow r_i = 3$ if $P_i \in S(-H_2O)_{PM} \rightarrow r_i = 3$ if $P_i \in S(+Ac,-H_2O)_{PM} \rightarrow r_i = 3$ For the peak $P_i$ contained in the set of peaks of surplus trifluoroacetylation, S(CF), identified as the ion species peaks derived from the peptide fragments (v) or (vi), the indicator $r_i$ of possibility is set as follows:

if $P_i \in S(CF) \rightarrow r_i = 2$ the $P_i$ not contained in the main peak set M but contained in either of:

$S(0)_p$: a set of ion species peaks derived from the peptide fragments (i), having accompanying peaks, $S(+Ac)_p$: a set of ion species peaks derived from the peptide fragments (ii), having accompanying peaks, $S(-H_2O)_p$: a set of ion species peaks derived from the peptide fragments (iii), having accompanying peaks, and $S(+Ac-H_2O)_p$: a set of ion species peaks derived from the peptide fragments (iv), having accompanying peaks, the indicator $r_i$ of possibility is set as follows:

if $P_i \in S(0)_p \rightarrow r_i = 2$ if $P_i \in S(+Ac)_p \rightarrow r_i = 2$ if $P_i \in S(-H_2O)_{PM} \rightarrow r_i = 2$ if $P_i \in S(+Ac,-H_2O)_p \rightarrow r_i = 2$ For the $P_i$ recognized as "single peak" in the classification and assignment of the step 4 but contained in the main peak set M, the indicator $r_i$ of possibility is set as follows:

if $P_i \in M \rightarrow r_i = 1$

For other cases, the indicator $r_i$ of possibility is set at $r_i = 0$.

In the following Step 6, search of the amino acids released successively from C-termini is conducted for each peak contained in the peak set $S_1$ to be analyzed. Therefore, in calculating distances between peaks, analysis is preferentially effected in a range where each peak considered to be a corresponding cationic species or anionic species can be confirmed to have an indicator $r_i$ of at least 1.

(Step 6) Search of Amino Acids Successively Released from C-Terminus

Sub-step 6-1 Identification of Peaks derived from the N-Terminal Side Fragments and Intermediate Fragments, Resulted from Digestion by Trypsin In the N-terminal side fragments and intermediate fragments, obtained by digestion by trypsin, there is no elimination of amino acids, and these fragments are observed, at least on the spectra obtained by positive detection mode, as peaks contained in the main peak set M, in the to-be-analyzed peak set $S_1$ after the piling up operation. That is, since the C-termini of these fragments have arginine, the proportions of cationic species generated are ordinarily significantly larger than the proportions of corresponding anionic species generated;

therefore, these fragments are contained, on the spectra obtained by positive detection mode, in the product set $(S_1 \cap M)$ of peak set $S_1$ and main peak set M.

With respect to the peaks of the product set $\{S_1 \cap M\}$ on the spectra obtained by positive detection mode, there are selected those peaks of lower mass side or higher mass side each having a molecular weight difference corresponding to elimination of amino acid and not detected in the peak set $S_1$, and they are designated as sub-set positive $S_2$. Then, there are identified, on the spectra obtained by negative detection mode, anionic species peaks corresponding to the individual peaks of the sub-set positive $S_2$, and they are designated as sub-set negative $S_2$. With respect to the peaks of the sub-set negative $S_2$, there are selected those peaks of lower mass side or higher mass side each having a molecular weight difference ($\Delta A[i]$) corresponding to elimination of amino acid and not detected in the peak set $S_1$, and they are designated as sub-set negative $S_3$.

Each peak of the sub-set negative $S_3$ has no "daughter" fragment formed by elimination of amino acid, in any of cationic species or anionic species and further is observed as a main peak on the spectra obtained by positive detection mode and, therefore, satisfies the necessary condition for the peak of a N-terminal side fragment or an intermediate fragment, both obtained by digestion by trypsin. Hence, $S_3$ is identified as a set of peaks derived from the N-terminal side fragments and intermediate fragments all obtained by digestion by trypsin.

Values of specific peak shifts corresponding to elimination of amino acids

| | | $\Delta A[i]$ | |
|---|---|---|---|
| 0 | G | 57 | |
| 1 | S* | 69: | Serine residue subjected to "dehydration" |
| 2 | A | 71 | |
| 3 | T* | 83: | Threonine residue subjected to "dehydration" |
| 4 | S | 87 | |
| (5 | P | 98): | no elimination of cyclic amino acid proline takes place in the present invention. |
| 6 | V | 99 | |
| 7 | T | 101 | |
| 8 | C | 103 | |
| 9 | L | 113 | |
| 10 | I | 113 | |
| 11 | D | 115 | |
| 12 | N | 116 | |
| 13 | E | 127 | |
| 14 | K | 128 | |
| 15 | S—Ac | 129: | Serine residue having surplus acetylation |
| 16 | Q | 130 | |
| 17 | M | 131 | |
| 18 | H | 137 | |
| 19 | H* | 138: | hydrogenated Histidine residue |
| 20 | T-Ac | 143: | Threonine residue having surplus acetylation |
| 21 | F | 147 | |
| 22 | Y | 148 | |
| 23 | R | 156 | |
| 24 | K—Ac | 170: | Lysine N-acetylated at the side chain |
| 25 | H—Ac | 179: | Histidine residue having surplus acetylation |
| 26 | W | 186 | |
| 27 | Y—Ac | 191: | Tyrosine residue having surplus acetylation |

Sub-Step 6-2 Identification of Peaks derived from C-Terminal Side Fragments

On the spectra obtained by negative detection mode, the peaks derived from C-terminal side fragments are contained in an odd set $\{S_1 \backslash \text{negative } S_3\}$ which is the peak set $S_1$ minus the sub-set negative $S_3$.

In the odd set $\{S_1 \backslash \text{negative } S_3\}$, a peak having the largest peak position (m/Z) is designated as $P^-_{max}$. Using this $P^-_{max}$ as a starting point $P^-(0)$, there is searched, in the peak set $S_1$, the presence of peaks of lower mass side each having a molecular weight difference ($\Delta A[i]$) corresponding to elimination of amino acid. That is, for the C-terminal side fragments obtained by successive release of amino acids from C-termini, it is assumed that there is observed a sequential peak series each having a molecular weight difference $\{\Delta A[i]\}$ corresponding to elimination of amino acid. In this case, the molecular weight difference $\{\Delta A[i]\}$ corresponding to elimination of amino acid is in a range of 57 to 191 as explained previously, and search is advanced orderly for the peaks of lower mass side which are in a range of peak position difference ($\Delta m/z$) of 200 or less.

In the peak set $S_1$ are included "assigned peaks" wherein the above-mentioned classification and assignment are complete and further the piling up operation is complete, and "independent peaks" to which no piling up operation has been made. In calculating the peak position difference ($\Delta m/z$) between "assigned peaks", consideration is the whether or not there is present surplus acetylation and/or "dehydration", based on respective assignments, and there is judged whether or not the peak position difference ($\Delta m/z$) corresponds to a molecular weight difference ($\Delta A[i]$) caused by the elimination of amino acid. Incidentally, as to the independent peaks", judgement is made for all the possibilities of the Classes 12 to 15.

(a) A Case wherein the Starting Peak is a Peak of Peptide Fragment (ii) Having Surplus Acetylation Search is made on whether or not a peak(s) belonging to the peak set $S_1$ is (are) present at a mass side which is lower from P(0) by a distance $\Delta A[i]$ (i=0, 1, ..., 27). If present, the peak (peaks) is (are) designated as P(1). When the P(1) is plural, a peak of larger $r_i$ is selected preferentially and search is advanced for a peak series formed by the gradual elimination of amino acids. Then, similar search for peak series is advanced also on other P(1).

Finally, when a plurality of possible peak series have been searched, a peak series of higher possibility is selected by considering the indicator $r_i$ of possibility of each peak constituting each peak series and further considering that the possibility that the peak of each "daughter fragment" formed by elimination of amino acid is a peak of peptide fragment (ii) having surplus acetylation, is also high.

a-0: A case wherein only peaks of peptide fragments (ii) having surplus acetylation are present at the lower mass side in a range of peak position difference ($\Delta m/Z$) of 200 or less.

Search is made on whether or not peaks are present at a mass side lower from P(0) by distances $\Delta A[i]$ (i=0, 1, ..., 27).

When each "daughter fragment" searched is a fragment formed by elimination of amino acid having surplus acetylation, from a "parent fragment", it can be judged as selection of low possibility. Also, when each "daughter fragment" searched is afagment formed by elimination of amino acid subjected to "dehydration" at the side chain, it can be judged as selection of low possibility, as well. Incidentally, when each "daughter fragment" searched is a fragment formed by elimination of amino acid free from surplus acetylation or "dehydration", it can be judged as selection of higher possibility.

a-1; A case wherein only peaks of ideal fragments (i) are present at a lower mass side in a range of peak position difference ($\Delta$m/z) of 200 or less.

Search is made on whether or not peaks are present at a mass side lower from P(0) by distances $\Delta$A[i]+42 (i=0, 1, ..., 27).

When each "daughter fragment" searched is a fragment formed by elimination of amino acid having surplus acetylation, from a "parent fragment", it can be judged as selection of high possibility. Meanwhile, when each "daughter fragment" searched is a fragment formed by elimination of amino acid subjected to "dehydration" at the side chain, it can be judged as selection of low possibility. Also, when each "daughter fragment" searched is a fragment formed by elimination of amino acid free from surplus acetylation or "dehydration", it can be judged as selection of low possibility.

a-2: A case wherein only peaks of peptide fragments (iii) subjected to "dehydration" are present at a lower mass side in a range of peak position difference ($\Delta$m/z) of 200 or less.

Search is made on whether or not peaks are present at a mass side lower from P(0) by distances $\Delta$A[i]+60 (i=0, 1, ..., 27).

When each "daughter fragment" searched is a fragment formed by elimination of amino acid having surplus acetylation, from a "parent fragment", it can be judged as selection of possibility. Meanwhile, when each "daughter fragment" searched is a fragment formed by elimination of amino acid subjected to "dehydration" at the side chain, it can be judged as selection of lower possibility. Also, when each "daughter fragment" searched is a fragment formed by elimination of amino acid free from surplus acetylation or "dehydration", it can be judged as selection of low possibility.

(b) A Case wherein the Starting Peak is a Peak of Ideal Peptide Fragment (i)

Search is made on whether or not a peak(s) belonging to the peak set $S_1$ is (are) present at a mass side which is lower from P(0) by a distance $\Delta$A[i] (i=0, 1, ..., 27). If present, the peak (peaks) is (are) designated as P(1). When the P(1) is plural, a peak of larger $r_i$ is selected preferentially and search is advanced for a peak series formed by the gradual elimination of amino acids. Then, similar search for peak series is advanced also on other P(1).

Finally, when a plurality of possible peak series have been searched, a peak series of higher possibility is selected by considering the indicator $r_i$ of possibility of each peak constituting each peak series and further considering that the possibility that the peak of each "daughter fragment" formed by elimination of amino acid is a peak of ideal peptide fragment (i), is also high.

b-0: A case wherein only peaks of ideal peptide fragments (i) are present at a lower mass side in a range of peak position difference ($\Delta$m/z) of 200 or less.

Search is made on whether or not peaks are present at a mass side lower from P(0) by distances $\Delta$A[i] (i=0, 1, ..., 27).

When each "daughter fragment" searched is a fragment formed by elimination of amino acid free from surplus acetylation or "dehydration", from a "parent fragments", it can be judged as selection of high possibility. Meanwhile, when each "daughter fragment" searched is a fragment formed by elimination of amino acid subjected to "dehydration" at the side chain, it can be judged as selection of low possibility. Also, when each "daughter fragment" searched is a fragment formed by elimination of amino acid having surplus acetylation, it can be judged as selection of low possibility.

b-1: A case wherein only peaks of peptide fragments (iii) subjected to "dehydration" are present at a lower mass side in a range of peak position difference ($\Delta$m/z) of 200 or less.

Search is made on whether or not peaks are present at a mass side lower from P(0) by distances $\Delta$A[i]+18 (i=0, 1, ..., 27).

When each "daughter fragment" searched is a fragment formed by elimination of amino acid free from surplus acetylation or "dehydration", from a "parent fragment", it can be judged as selection of possibility. Meanwhile, when each "daughter fragment" searched is a fragment formed by elimination of amino acid subjected to "dehydration" at the side chain, it can be judged as selection of lower possibility. Also, when each "daughter fragment" searched is a fragment formed by elimination of amino acid having surplus acetylation, it can be judged as selection of low possibility b-2: A case wherein only peaks of peptide fragments (ii) having surplus acetylation are present at a lower mass side in a range of peak position difference ($\Delta$m/z) of 200 or less.

Search is made on whether or not peaks are present at a mass side lower from P(0) by distances $\Delta$A[i]−42 (i=0, 1, ..., 27).

When each "daughter fragment" searched is a fragment formed by elimination of amino acid free from surplus acetylation or "dehydration", from a "parent fragment", it can be judged as selection of possibility. When each "daughter fragment" searched is a fragment formed by elimination of amino acid subjected to "dehydration" at the side chain, it can be judged as selection of low possibility. When each "daughter fragment" searched is a fragment formed by elimination of amino acid having surplus acetylation, it can be judged as selection of low possibility.

(c) A Case wherein the Starting Peak is a Peak of Peptide Fragment (iii) Subjected to "Dehydration"

Search is made on whether or not a peak(s) belonging to the peak set $S_1$ is (are) present at a mass side which is lower from P(0) by a distance $\Delta$A[i] (i=0, 1, ..., 27). If present, the peak (peaks) is (are) designated as P(1). When the P(1) is plural, a peak of larger $r_i$ is selected preferentially and search is advanced for a peak series formed by the gradual elimination of amino acids. Then, similar search for peak series is advanced also on other P(1).

Finally, when a plurality of possible peak series have been searched, a peak series of higher possibility is selected by considering the indicator $r_i$ of possibility of each peak constituting each peak series and further considering that the possibility that the peak of each "daughter fragment" formed by elimination of amino acid is a peak of peptide fragment (iii) subjected to "dehydration", is also high.

c-0: A case wherein only peaks of peptide fragments (iii) subjected to dehydration" are present at a lower mass side in a range of peak position difference ($\Delta$m/z) of 200 or less.

Search is made on whether or not peaks are present at a mass side lower from P(0) by distances $\Delta$A[i] (i=0, 1, ..., 27).

When each "daughter fragment" searched is a fragment formed by elimination of amino acid free from surplus acetylation or "dehydration", from a "parent fragments", it can be judged as selection of high possibility. Meanwhile, when each "daughter fragment" searched is a fragment formed by elimination of amino acid subjected to "dehydration" at the side chain, it can be judged as selection of low possibility. Also, when each "daughter fragment" searched is a fragment formed by elimination of amino acid having surplus acetylation, it can be judged as selection of lower possibility.

c-1: A case wherein only peaks of ideal peptide fragments (i) are present at a lower mass side in a range of peak position difference ($\Delta$m/z) of 200 or less.

Search is made on whether or not peaks are present at a mass side lower from P(0) by distances $\Delta$A[i]−18 (i=0, 1, ..., 27).

When each "daughter fragment" searched is a fragment formed by elimination of amino acid subjected to "dehydration" at the side chain, from a "parent fragment", it can be judged as selection of high possibility. Meanwhile, when each "daughter fragment" searched is a fragment formed by elimination of amino acid free from surplus acetylation or "dehydration", it can be judged as selection of possibility. Also, when each "daughter fragment" searched is a fragment formed by elimination of amino acid having surplus acetylation, it can be judged as selection of low possibility.

c-2: A case wherein only peaks of peptide fragments (ii) having surplus acetylation are present at a lower mass side in a range of peak position difference ($\Delta$m/z) of 200 or less.

Search is made on whether or not peaks are present at a mass side lower from P(0) by distances $\Delta A[i]-60$ (i=0, 1, ..., 27).

When each "daughter fragment" searched is a fragment formed by elimination of amino acid subjected to "dehydration" at the side chain, from a "parent fragment", it can be judged as selection of possibility. When each "daughter fragment" searched is a fragment formed by elimination of amino acid free from surplus acetylation or "dehydration", it can be judged as selection of low possibility. When each "daughter fragment" searched is a fragment formed by elimination of amino acid having surplus acetylation, it can be judged as selection of lower possibility.

Incidentally, a peak having the largest peak position (m/Z) in the odd set $\{S_1\backslash\text{negative } S_3\}$ is designated as $P^-_{max}$. Using this $P^-_{max}$ as a starting point $P^-(0)$, there is searched, in the peak set $S_1$, the presence of peaks of lower mass side each having a molecular weight difference ($\Delta A[i]$) corresponding to elimination of amino acid. When no peak corresponding to P(1) can be searched, similar search is made using, as a starting point $P^-(0)$, a peak having a peak position (m/Z) next to $P^-_{max}$ in the odd set $\{S_1\backslash\text{negative } S_3\}$.

Meanwhile, when search is made on whether or not peaks of peak set $S_1$ are present at a mass side lower by distance $\Delta A[i]$ (i=0, 1, ..., 27) and when judgment is made for "independent peaks" of lower mass side, "independent peaks" have all possibilities for belonging to either of the Classes 12 to 15; in this connection, each position difference may have two or more possible identifications. The two or more possible identifications for peak position difference (degeneracy) are summarized in the following Table 3.

TABLE 3

Degeneracy of peak shift

| $\Delta$m | Peak of ideal peptide fragment (i) | Peak of peptide fragment (iii) subjected to "dehydration" | Peak of peptide fragment (ii) having surplus acetylation | Peak of peptide fragment (iv) subjected to "dehydration" an having surplus acetylation |
|---|---|---|---|---|
| 69 | S* | S | | |
| 81 | | V | | G |
| 83 | T* | T | | |
| 95 | | I or L | | A |
| 98 | (P) | N | | |
| 99 | V | | G | |
| 111 | | S—Ac | S* | S |
| 113 | I or L | M | | |
| 125 | | T—Ac | T* | T |
| 127 | E | | | C |
| 129 | S—Ac | F | S | |
| 130 | Q | Y | | |
| 137 | H | | | I or L |
| 138 | H* | R | | |
| 140 | | | (P) | N |
| 143 | T—Ac | | T | |
| 152 | | K—Ac | | K |
| 161 | | H—Ac | | |
| 170 | K—Ac | | K | |
| 172 | | | Q | Y |
| 173 | | Y—Ac | M | |
| 179 | H—Ac | | H | |
| 180 | | | H* | R |

In the above example, there are compared the two kinds of spectra observed by positive detection mode and by negative detection mode in discrimination of the N-terminal side fragments and intermediate fragments obtained by the digestion by trypsin in the Step 6, from the group of C-terminal side fragments because the N-terminal side fragments and intermediate fragments have each arginine at the C-terminus thereof; thereby, the identification thereof is made in advance.

There is another method in which the change of elimination reaction with time is traced and the peaks each showing a significant change caused by the difference in reaction time are regarded as peaks from the group of C-terminal side fragments and utilized for selection thereof. That is, with a longer reaction time, a larger number of amino acids are released and peaks of a larger number of C-terminal side fragments are obtained; however, there takes place a reduction in original C-terminal side fragment per se which becomes a starting point in analysis of the amino acid sequence thereof. Therefore, it is easy to identify peaks of C-terminal side fragments formed by release of a larger number of amino acids while comparison is made with samples of relative short reaction time. In this case, the N-terminal side fragments and intermediate fragments appear on both the spectra obtained by positive detection mode and the spectra obtained by negative detection mode, and the peak intensity ratio of each fragment on the two spectra is essentially independent of the level of reaction time.

Incidentally, in the procedure for identifying the peaks of C-terminal side fragments and advancing identification of the kinds of amino acids released successively, a series of analyses can be carried out based on each of the following stages A to E.

A. Possible values of the peak position differences ($\Delta$m/Z) observed between peaks of C-terminal side fragments There is shown a procedure for determining the sequence of C-terminal amino acid at a higher accuracy based on the peaks of C-terminal side fragments, considering the previously mentioned "degeneracy of peak shift". When each peak of C-terminal side ideal fragment (i) obtained by successive release of amino acids is accompanied by a peak of acetylated fragment (ii) and a peak of "dehydrated" fragment (iii), the possible values of the peak position differences ($\Delta$m/Z) observed between these peaks can be indicated by the following sets.

They are specifically:

sets corresponding to the values of specific peak shift $\Delta A[i]$ corresponding to elimination of amino acids $$D_0 = \{\Delta A[i]: i=0, 1, \ldots, 27\}$$

sets derived from peak position differences ($\Delta m/Z$) observed between peak of ideal fragment (i) and peak of "dehydrated" fragment (iii)

$$D_1^{(+)} = \{\Delta A[i]+18: i=0, 1, \ldots, 27\}$$

$$D_1^{(-)} = \{\Delta A[i]-18: i=0, 1, \ldots, 27\}$$

sets derived from peak position differences ($\Delta m/Z$) observed between peak of ideal fragment (i) and peak of fragment (ii) having surplus acetylation:

$$D_2^{(+)} = \{\Delta A[i]+42: i=0, 1, \ldots, 27\}$$

$$D_2^{(-)} = \{\Delta A[i]-42: i=0, 1, \ldots, 27\}$$

sets derived from peak position differences ($\Delta m/Z$) observed between peak of fragment (ii) having surplus acetylation and peak of "dehydrated" fragment (iii)

$$D_3^{(+)} = \{\Delta A[i]+60: i=0, 1, \ldots, 27\}$$

$$D_3^{(-)} = \{\Delta A[i]-60: i=0, 1, \ldots, 27\}$$

As a summed-up set of the above 7 kinds of sets, i.e. $D_0, D_1^{(+)}, D_1^{(-)}, D_2^{(+)}, D_2^{(-)}, D_3^{(+)}$, and $D_3^{(-)}$, there is designated:

$$D = D_0 \cup (D_1^{(+)} \cup D_1^{(-)}) \cup (D_2^{(+)} \cup D_2^{(-)}) \cup (D_3^{(+)} \cup D_3^{(-)})$$

The products sets of these 7 kinds of sets are classified as follows.
(1) In the products sets of 5 or more kinds of sets, there is no product set having elements.
(2) In the product sets of 4 kinds of sets, those having elements:

$$F_1 = D_0 \cap D_1^{(-)} \cap D_2^{(+)} \cap D_3(+) = \{129\}$$

$$F_2 = D_0 \cap D_1^{(+)} \cap D_2^{(-)} \cap D_3(-) = \{87\}$$

$$F_3 = D_0 \cap D_1^{(+)} \cap D_3^{(-)} \cap D_3(+) = \{131\}$$

(3) In the product sets of 3 kinds of sets, those having elements:

$$T_1 = D_0 \cap D_1^{(-)} \cap D_2^{(+)} \backslash F_1 = \{113\}$$

$$T_2 = D_0 \cap D_1^{(-)} \cap D_3^{(-)} = \{69, 83\}$$

$$T_3 = D_0 \cap D_1^{(+)} \cap D_2^{(-)} \backslash F_2 = \{101\}$$

$$T_4 = D_0 \cap D_1^{(+)} \cap D_3^{(+)} = \{147\}$$

$$T_5 = D_0 \cap D_2^{(-)} \cap D_3^{(-)} = \{71\}$$

$$T_6 = D_0 \cap D_2^{(+)} \cap D_3^{(+)} = \{143\}$$

$$T_7 = D_1^{(-)} \cap D_1^{(+)} \cap D_3^{(-)} = \{119\}$$

$$T_8 = D_1^{(-)} \cap D_1^{(+)} \cap D_3^{(+)} = \{161\}$$

$$T_9 = D_1^{(-)} \cap D_2^{(+)} \cap D_3^{(+)} = \{119\}$$

(4) In the product sets of 2 kinds of sets, those having elements:

$$W_1 = D_0 \cap D_1^{(-)} \backslash [T_1 \cup T_2 \cup F_1] = \{98, 130, 138\}$$

$$W_2 = D_0 \cap D_1^{(+)} \backslash [T_3 \cup T_4 \cup F_2 \cup F_3] = \{116, 148, 156\}$$

$$W_3 = D_0 \cap D_2^{(-)} \backslash [T_3 \cup T_5 \cup F_2] = \{55, 128, 137\}$$

$$W_4 = D_0 \cap D_2^{(+)} \backslash [T_1 \cup T_6 \cup F_1] = \{99, 170, 179\}$$

$$W_5 = D_0 \cap D_3^{(-)} \backslash [T_4 \cup T_6 \cup F_1 \cup F_3] = \{191\}$$

$$W_6 = D_1^{(-)} \cap D_2^{(-)} = \{85, 95\}$$

$$W_7 = D_1^{(-)} \cap D_2^{(+)} \backslash [T_9 \cup F_1] = \{111, 125\}$$

$$W_8 = D_1^{(-)} \cap D_3^{(-)} \backslash [T_2 \cup T_7] = \{39, 53, 110\}$$

$$W_9 = D_1^{(+)} \cap D_2^{(-)} \backslash [T_3 \cup F_2] = \{89, 105, 149\}$$

$$W_{10} = D_1^{(+)} \cap D_2^{(+)} = \{145, 155\}$$

$$W_{11} = D_1^{(+)} \cap D_3^{(+)} \backslash [T_4 \cup T_8 \cup F_3] = \{117, 188, 197\}$$

$$W_{12} = D_2^{(+)} \cap D_3^{(+)} \backslash [T_6 \cup T_9 \cup F_1] = \{151, 188, 190, 198\}$$

$$W_{13} = D_2^{(-)} \cap D_3^{(-)} \backslash [T_5 \cup F_3] = \{27, 41, 45, 56, 88, 96\}$$

(5) Values of peak shifts having no "degeneracy $$Sh_0 = D_0 \backslash ([W_1 \cup W_2 \cup W_3 \cup W_4 \cup W_5] \cup [T_1 \cup T_2 \cup T_3 \cup T_4 \cup T_5] \cup [F_1 \cup F_2 \cup F_3]) = \{103, 115, 127, 186\}$$

$$Sh_1^{(+)} = D_1^{(+)} \backslash ([W_2 \cup W_9 \cup W_{10} \cup W_{11}] \cup [T_3 \cup T_4 \cup T_7 \cup T_8] \cup [F_2 \cup F_3]) = \{75, 121, 133, 134, 146, 165, 166, 174, 204, 209\}$$

$$Sh_1^{(-)} = D_1^{(-)} \backslash ([W_1 \cup W_6 \cup W_7 \cup W_8] \cup [T_1 \cup T_2 \cup T_7 \cup T_8 \cup T_9] \cup [F_1]) = \{51, 65, 80, 81, 97, 109, 112, 120, 152, 168\}$$

$$Sh_2^{(+)} = D_2^{(+)} \backslash ([W_4 \cup W_7 \cup W_{10} \cup W_{12}] \cup [T_1 \cup T_6 \cup T_9] \cup [F_1]) = \{140, 141, 169, 171, 172, 180, 185, 212, 221, 228, 233\}$$

$$Sh_2^{(-)} = D_2^{(-)} \backslash ([W_3 \cup W_6 \cup W_9 \cup W_{13}] \cup [T_3 \cup T_5] \cup [F_2]) = \{15, 29, 59, 61, 73, 74, 86, 106, 114, 144\}$$

$$Sh_3^{(+)} = D_3^{(+)} \backslash ([W_5 \cup W_{12}] \cup [T_4 \cup T_6 \cup T_8 \cup T_9] \cup [F_1 \cup F_3]) = \{159, 163, 175, 176, 187, 203, 207, 208, 216, 230, 239, 251, 256\}$$

$$Sh_3^{(-)} = D_3^{(-)} \backslash ([W_8 \cup W_{13}] \cup [T_2 \cup T_5 \cup T_7] \cup [F_2 \cup F_3]) = \{(-3), 9, 11, 23, 38, 67, 68, 70, 77, 78, 126\}$$

In the above procedure, the individual odd sets are classified so that they contain no common element.

Even when, as indicated above, each peak position difference ($\Delta m/Z$) coincides with one element d (d$\in$D) of the above-shown summed-up sets D, there may be more than one interpretation. Specifically explaining, for the element d (d$\in$D) of the summed-up sets D, there are present, in some cases, two or more elements of $k_0(d)$, $k_1^+(d)$, $k_1^-(d)$, $k_2^+(d)$, $k_2^-(d)$, $k_3^+(d)$ and $k_3^-(d)$ which satisfy the following relations:
(i) a value of k satisfying $d = \Delta A[k]$: $k_0(d)$,
(ii) a value of k satisfying $d = \Delta A[k]+18$: $k_1^+(d)$,
a value of k satisfying $d = \Delta A[k]-18$: $k_1^-(d)$,
(iii) a value of k satisfying $d = \Delta A[k]+42$: $k_2^+(d)$,
a value of k satisfying $d = \Delta A[k]-42$: $k_2^-(d)$,
(iv) a value of k satisfying $d = \Delta A[k]+60$: $k_3^+(d)$,
a value of k satisfying $d = \Delta A[k]-60$: $k_3^-(d)$.

That is, with respect to the kinds of amino acids ($\Delta A[i]$: $i=0, 1, \ldots, 27$) released successively, when analysis thereof is advanced based only on the information of peak position differences ($\Delta m/Z$), there may be a plurality of interpretations.

Needless to say, with respect to the sub-sets of the values of peak shifts free from "degeneracy", a single k value corresponds to d, as shown below:
(1) for d$\in Sh_0$, $k_0(d)$,
(2) for d$\in Sh_1^{(+)}$, $k_1^+(d)$,
for d$\in Sh_1^{(-)}$, $k_1^-(d)$, (3) for $d\epsilon Sh_2^{+)}$, $k_2^+$ (d),
for $d\epsilon Sh_2^{(-)}$, $k_2^-$ (d),
(4) for $d\epsilon Sh_3^{(+)}$, $k_3^+$ (d),
for $d\epsilon Sh_3^{(-)}$, $k_3^-$ (d).

With respect to other sub-steps defined as product sets, a plurality of k values can be anticipated, as shown in the following (5) to (29):

(5) for $d\epsilon W_1$, $k_0(d)$ and $k_1^-$ (d),
(6) for $d\epsilon W_2$, $k_0(d)$ and $k_1^+$ (d),
(7) for $d\epsilon W_3$, $k_0(d)$ and $k_2^-$ (d),
(8) for $d\epsilon W_4$, $k_0(d)$ and $k_2^+$ (d),
(9) for $d\epsilon W_5$, $k_0(d)$ and $k_3^+$ (d),
(10) for $d\epsilon W_6$, $k_1^-$ (d) and $k_2^-$ (d),
(11) for $d\epsilon W_7$, $k_1^-$ (d) and $k_2^+$ (d),
(12) for $d\epsilon W_8$, $k_1^-$ (d) and $k_3^-$ (d),
(13) for $d\epsilon W_9$, $k_1^+$ (d) and $k_2^-$ (d),
(14) for $d\epsilon W_{10}$, $k_1^-$ (d) and $k_2^+$ (d),
(15) for $d\epsilon W_{11}$, $k_1^+$ (d) and $k_3^+$ (d),
(16) for $d\epsilon W_{12}$, $k_2^+$ (d) and $k_3^+$ (d),
(17) for $d\epsilon W_{13}$, $k_2^-$ (d) and $k_3^-$ (d),
(18) for $d\epsilon T_1$, $k_0(d)$, $k_1^-$ (d) and $k_2^+$ (d),
(19) for $d\epsilon T_2$, $k_0(d)$, $k_1^-$ (d) and $k_2^-$ (d),
(20) for $d\epsilon T_3$, $k_0(d)$, $k_1^+$ (d) and $k_2^-$ (d),
(21) for $d\epsilon T_4$, $k_0(d)$, $k_1^+$ (d) and $k_3^+$ (d),
(22) for $d\epsilon T_5$, $k_0(d)$, $k_2^-$ (d) and $k_3^-$ (d),
(23) for $d\epsilon T_6$, $k_0(d)$, $k_2^+$ (d) and $k_3^+$ (d),
(24) for $d\epsilon T_7$, $k_1^-$ (d), $k_1^+$ (d) and $k_3^-$ (d),
(25) for $d\epsilon T_8$, $k_1^-$ (d), $k_1^+$ (d) and $k_3^+$ (d),
(26) for $d\epsilon T_9$, $k_1^-$ (d), $k_2^+$ (d) and $k_3^+$ (d),
(27) for $d\epsilon F_1$, $k_0(d)$, $k_1^-$ (d), $k_2^+$ (d) and $k_3^+$ (d),
(28) for $d\epsilon F_2$, $k_0(d)$, $k_1^+$ (d), $k_2^-$ (d) and $k_3^-$ (d),
(29) for $d\epsilon F_3$, $k_0(d)$, $k_1^-$ (d), $k_3^-$ (d) and $k_3^+$ (d).

B. Categories of Peak Pairs Observed between C-Terminal Side Fragments

By, with respect to the peaks contained in the set of ion species peaks derived from peptide, i.e. $A_p \equiv A \backslash A_t$, advancing the classification and assignment of the ion species peaks derived from the peptide fragments formed by digestion by trypsin, according to the above-described procedure, there are identified, based on the presence of accompanying peaks, the following sets of ion species peaks:

$S(0)_p$: a set of ion species peaks derived from ideal peptide fragments (i), having accompanying peaks, $S(+Ac)_p$: a set of ion species peaks derived from secondary peptide fragments (ii) having surplus acetylation, $S(-H_2O)_p$: a set of ion species peaks derived from secondary peptide fragments (iii) subjected to "dehydration", $S(+Ac,-H_2O)_p$: a set of ion species peaks derived from secondary peptide fragments (iii) subjected to "dehydration" and having surplus acetylation Besides, there are present a set [S(single)] of ion species peaks derived from peptide fragments, which are not accompanied by any peak derived from secondary fragment and which show "independent peaks".

When a peak $P_i$ contained in the set $A_p$ is contained in either of the above 5 kinds of sub-sets, the indicator $r_{itype}$ indicating the assignment (category) of the peak is shown as follows.

(1) $P_i \epsilon S(0)_p \rightarrow r_{itype} = 0$
(2) $P_i \epsilon S(+Ac)_p \rightarrow r_{itype} = 1$
(3) $P_i \epsilon S(-H_2O)_p \rightarrow r_{itype} = 2$
(4) $P_i \epsilon S(single)_p \rightarrow r_{itype} = 3$
(5) $P_i \epsilon S(+Ac,-H_2O)_p \rightarrow r_{itype} = 4$ With respect to at least the peaks of the group of the C-terminal side fragments, they are observed as peaks of either of the sub-sets $S(0)_p$, $S(+Ac)_p$ and $S(-H_2O)_p$, derived from the peptide fragments having accompanying peaks, or as "independent peaks". Therefore, even if the peaks belonging to the sub-set $S(+Ac,-H_2O)_p$ are excluded from consideration, consideration is made as to the peaks belonging to either of the remaining sub-sets $S(0)_p$, $S(+Ac)_p$ and $S(-H_2O)_p$, which are peaks derived from peptide fragment and having accompanying peaks, and therefore, there is no problem.

Specifically explaining, with respect to the two peaks $P_i$ and $P_j$ belonging to either of the sub-sets $S(0)_p$, $S(+Ac)_p$, $S(-H_2O)_p$ and S(single), their category is as follows.

When $P_j$ is arbitrarily considered to be a peak of larger peak position m/Z, the indicator $R_{ij}$ indicating the category of the peak pair $(P_i, P_j)$ is expressed by $R_{ij} \equiv (r_{itype}, r_{jtype})$ wherein the $r_{itype}$ is an indicator indicating the assignment (category) of peak $P_i$ and the $r_{jtype}$ is an indicator indicating the assignment (category) of peak $P_j$.

(1) Peak Pair of Category 1

$P_i \epsilon S(0)_p, P_j \epsilon S(0)_p \rightarrow R_{ij} = (0,0)$ (2) Peak Pair of Category 2

$P_i \epsilon S(+Ac)_p, P_j \epsilon S(+Ac)_p \rightarrow R_{ij} = (1,1)$ (3) Peak Pair of Category 3

$P_i \epsilon S(-H_2O)_p, P_j \epsilon S(-H_2O)_p \rightarrow R_{ij} = (2,2)$ (4) Peak Pair of Category 4

$P_i \epsilon S(single), P_j \epsilon S(single) \rightarrow R_{ij} = (3,3)$ (5) Peak Pair of Category 5

$P_i \epsilon S(+Ac)_p, P_j \epsilon S(0)_p \rightarrow R_{ij} = (1,0)$ (6) Peak Pair of Category 6

$P_i \epsilon S(0)_p, P_j \epsilon S(+Ac)_p \rightarrow R_{ij} = (0,1)$ (7) Peak Pair of Category 7

$P_i \epsilon S(-H_2O)_p, P_j \epsilon S(0)_p \rightarrow R_{ij} = (2,0)$ (8) Peak Pair of Category 8

$P_i \epsilon S(0)_p, P_j \epsilon S(-H_2O)_p \rightarrow R_{ij} = (0,2)$ (9) Peak Pair of Category 9

$P_i \epsilon S(single), P_j \epsilon S(0)_p \rightarrow R_{ij} = (3,0)$

(10) Peak Pair of Category 10

$P_i \epsilon S(0)_p, P_j \epsilon S(single) \rightarrow R_{ij} = (0,3)$

(11) Peak Pair of Category 11

$P_i \epsilon S(-H_2O)_p, P_j \epsilon S(+Ac)_p \rightarrow R_{ij} = (2,1)$

(12) Peak Pair of Category 12

$P_i \epsilon S(+Ac)_p, P_j \epsilon S(-H_2O)_p \rightarrow R_{ij} = (1,2)$

(13) Peak Pair of Category 13

$P_i \epsilon S(single), P_j \epsilon S(+Ac)_p \rightarrow R_{ij} = (3,1)$

(14) Peak Pair of Category 14

$P_i \epsilon S(+Ac)_p, P_j \epsilon S(single) \rightarrow R_{ij} = (1,3)$

(15) Peak Pair of Category 15

$P_i \epsilon S(-H_2O)_p, P_j \epsilon S(single) \rightarrow R_{ij} = (2,3)$

(16) Peak Pair of Category 16

$P_i \epsilon S(single), P_j \epsilon S(-H_2O)_p \rightarrow R_{ij} = (3,2)$

C. Value of peak shift derived from elimination of one amino acid, which is observed between peaks of C-terminal side fragment and which may occur in peak pair of each category Next, with respect to the pair of two peaks $P_i$ and $P_j$ belonging to either of the sub-sets $S(0)_p$, $S(+Ac)_p$, $S(-H_2O)_p$ and S(single), the category thereof is considered and there is judged whether or not the peak position difference ($\Delta m/Z$) thereof is equivalent to the value of peak shift caused by elimination of one amino acid. In other words, at first, there is excluded each peak pair ($P_i$, $P_j$) giving a peak position difference ($\Delta m/Z$) which can never be corresponding to the value of peak shift caused by elimination of one amino acid.

The value d of the peak shift caused by elimination of one amino acid, which may be shown by each peak pair of the above-mentioned categories 1 to 16, is included in the following sub-sets of peak shifts.

| | |
|---|---|
| Peak pair of category 1 | $d \in D_0$ |
| Peak pair of category 2 | $d \in D_0$ |
| Peak pair of category 3 | $d \in D_0$ |
| Peak pair of category 4 | $d \in D$ (all possibilities remain.) |
| Peak pair of category 5 | $d \in D_2^{(-)}$ |
| Peak pair of category 6 | $d \in D_2^{(+)}$ |
| Peak pair of category 7 | $d \in D_1^{(+)}$ |
| Peak pair of category 8 | $d \in D_1^{(-)}$ |
| Peak pair of category 9 | $d \in D_0 \cup (D_1^{(+)} \cup D_2^{(-)})$ |
| Peak pair of category 10 | $d \in D_0 \cup (D_1^{(-)} \cup D_2^{(+)})$ |
| Peak pair of category 11 | $d \in D_3^{(+)}$ |
| Peak pair of category 12 | $d \in D_3^{(-)}$ |
| Peak pair of category 13 | $d \in D_0 \cup (D_2^{(+)} \cup D_3^{(+)})$ |
| Peak pair of category 14 | $d \in D_0 \cup (D_2^{(-)} \cup D_3^{(-)})$ |
| Peak pair of category 15 | $d \in D_0 \cup (D_1^{(+)} \cup D_2^{(+)})$ |
| Peak pair of category 16 | $d \in D_0 \cup (D_1^{(-)} \cup D_2^{(-)})$ |

In particular, as peak pairs having such possibility that they may be observed as a peak pair between the peaks of the group of the C-terminal fragments, pairs of which peak position difference ($\Delta m/Z$) is included in said subset of the possible value d of peak sift defined for the category thereof are selected from all the pairs of two peaks $P_i$ and $P_j$ that are belonging to either of the sub-set $S(0)_p$, $S(+Ac)_p$, $S(-H_2O)_p$ or S(single) to make up the set of target peak pairs ($P_i$, $P_j$) to be further analyzed therewith.

D. Estimation of kind of eliminated amino acid residue based on the value of peak shift caused by elimination of one amino acid, which may occur in each peak pair of each category With respect to each peak pair contained in the set of target peak pairs (Pi, $P_j$) formed by the above-mentioned selection and to be analyzed later, there is advanced the estimation of kind of released amino acid residue which causes the peak position difference ($\Delta m/Z$) of the peak pair. In this case, the k value corresponding to the kind of eliminated amino acid residue can be limited to types shown later, based on the peak position difference ($\Delta m/Z$) and the category of the peak pair.

First, with respect to the value of peak shift of $d \in D$, when the category $P_{type}$ of the peak pair, which may give the value d of the peak shift, is divided in more detail, the following division results. Incidentally, the category 4 of peak pair may have all possibilities formally and, therefore, is excluded in the following division.

When $d \in Sh_0$, $P_{type}$: 1 to 3
When $d \in Sh_1^{(+)}$, $P_{type}$: 7
When $d \in Sh_1^{(-)}$, $P_{type}$: 8
When $d \in Sh_2^{(+)}$, $P_{type}$: 6
When $d \in Sh_2^{(-)}$, $P_{type}$: 5
When $d \in Sh_3^{(+)}$, $P_{type}$: 11
When $d \in Sh_3^{(-)}$, $P_{type}$: 12
When $d \in W_1$,
  $P_{type}$: 1 to 3, 8
    9, 13, 14, 15 (when $d \in D_0$)
    10, 16 (when $d \in D_0 \cup D_1^{(-)}$)
When $d \in W_2$,
  $P_{type}$: 1 to 3, 7
    10, 13, 14, 16 (when $d \in D_0$)
    9, 15 (when $d \in D_0 \cup D_1^{(+)}$)
When $d \in W_3$,
  $P_{type}$: 1 to 3, 5
    10, 13, 15 (when $d \in D_0$)
    9, 14, 16 (when $d \in D_0 \cup D_2^{(-)}$)
When $d \in W_4$,
  $P_{type}$: 1 to 3, 6
    9, 14, 16 (when $d \in D_0$)
    10, 15 (when $d \in D_0 \cup D_2^{(+)}$)
When $d \in W_5$,
  $P_{type}$: 1 to 3, 11
    9, 10, 14, 15, 16 (when $d \in D_0$)
    13 (when $d \in D_0 \cup D_3^{(+)}$)
When $d \in W_6$,
  $P_{type}$: 5, 8
    10 (when $d \in D_1^{(-)}$)
    9, 14 (when $d \in D_2^{(-)}$)
    10, 15 (when $d \in D_1^{(-)} \cup D_2^{(-)}$)
When $d \in W_7$,
  $P_{type}$: 6, 8
    16 (when $d \in D_1^{(-)}$)
    13, 15 (when $d \in D_2^{(+)}$)
    10 (when $d \in D_1^{(-)} \cup D_2^{(+)}$)
When $d \in W_8$,
  $P_{type}$: 8, 12
    10, 16 (when $d \in D_1^{(-)}$)
    14 (when $d \in D_3^{(-)}$)
When $d \in W_9$,
  $P_{type}$: 5, 7
    15 (when $d \in D_1^{(+)}$)
    14, 16 (when $d \in D_2^{(-)}$)
    9 (when $d \in D_1^{(+)} \cup D_2^{(-)}$)
When $d \in W_{10}$,
  $P_{type}$: 6, 7
    9 (when $d \in D_1^{(+)}$)
    10, 13 (when $d \in D_2^{(+)}$)
    15 (when $d \in D_1^{(+)} \cup D_2^{(+)}$)
When $d \in W_{11}$,
  $P_{type}$: 7, 11
    9, 15 (when $d \in D_1^{(+)}$)
    13 (when $d \in D_3^{(+)}$)
When $d \in W_{12}$,
  $P_{type}$: 6, 11
    10, 15 (when $d \in D_2^{(+)}$)
    13 (when $d \in D_2^{(+)} \cup D_3^{(+)}$)
When $d \in W_{13}$,
  $P_{type}$: 5, 12
    9, 16 (when $d \in D_2^{(-)}$)
    14 (when $d \in D_2^{(-)} \cup D_3^{(-)}$)
When $d \in T_1$,
  $P_{type}$: 1 to 3, 6, 8
    9, 14 (when $d \in D_0$)
    16 (when $d \in D_0 \cup D_1^{(-)}$)
    13, 15 (when $d \in D_0 \cup D_2^{(+)}$)
    10 (when $d \in D_0 \cup D_1^{(-)} \cup D_2^{(+)}$)
When $d \in T_2$,
  $P_{type}$: 1 to 3, 8, 12
    9, 13, 15 (when $d \in D_0$)
    10, 16 (when $d \in D_0 \cup D_1^{(-)}$)
    14 (when $d \in D_0 \cup D_3^{(+)}$)
When $d \in T_3$,
  $P_{type}$: 1 to 3, 5, 7
    10, 13 (when $d \in D_0$)
    15 (when $d \in D_0 \cup D_1^{(+)}$)

14, 16 (when $d \in D_0 \cup D_2^{(-)}$)
9 (when $d \in D_0 \cup D_1^{(+)} \cup D_2^{(-)}$)
When $d \in T_4$,
  $P_{type}$: 1 to 3, 7, 11
  10, 14, 16 (when $d \in D_0$)
  9, 15 (when $d \in D_0 \cup D_1^{(+)}$)
  13 (when $d \in D_0 \cup D_3^{(+)}$)
When $d \in T_5$,
  $P_{type}$: 1 to 3, 5, 12
  10, 13, 15 (when $d \in D_0$)
  9, 16 (when $d \in D_0 \cup D_2^{(-)}$)
  14 (when $d \in D_0 \cup D_2^{(-)} \cup D_3^{(-)}$)
When $d \in T_6$,
  $P_{type}$: 1 to 3, 6, 11
  9, 14, 16 (when $d \in D_0$)
  10, 15 (when $d \in D_0 \cup D_2^{(+)}$)
  13 (when $d \in D_0 \cup D_2^{(+)} \cup D_3^{(+)}$)
When $d \in T_7$,
  $P_{type}$: 7, 8, 12
  10, 16 (when $d \in D_1^{(-)}$)
  9, 15 (when $d \in D_1^{(+)}$)
  14 (when $d \in D_3$)
When $d \in T_8$,
  $P_{type}$: 7, 8, 11
  10, 16 (when $d \in D_1^{(-)}$)
  9, 15 (when $d \in D_1^{(+)}$)
  13 (when $d \in D_3^{(+)}$)
When $d \in T_9$,
  $P_{type}$: 6, 8, 11
  16 (when $d \in D_1^{(-)}$)
  15 (when $d \in D_3^{(+)}$)
  10 (when $d \in D_1^{(-)} \cup D_2^{(+)}$)
  13 (when $d \in D_2^{(+)} \cup D_3^{(+)}$)
When $d \in F_1$,
  $P_{type}$: 1 to 3, 6, 8, 11
  9, 14 (when $d \in D_0$)
  16 (when $d \in D_0 \cup D_1^{(-)}$)
  15 (when $d \in D_0 \cup D_2^{(+)}$)
  10 (when $d \in D_0 \cup D_1^{(-)} \cup D_3^{(+)}$)
  13 (when $d \in D_0 \cup D_2^{(+)} \cup D_3^{(+)}$)
When $d \in F_2$,
  $P_{type}$: 1 to 3, 5, 7, 11
  10 (when $d \in D_0$)
  15 (when $d \in D_0 \cup D_1^{(+)}$)
  14, 16 (when $d \in D_0 \cup D_2^{(-)}$)
  9 (when $d \in D_0 \cup D_1^{(+)} \cup D_2^{(-)}$)
  13 (when $d \in D_0 \cup D_3^{(-)}$)
When $d \in F_3$,
  $P_{type}$: 1 to 3, 7, 11, 12
  10, 16 (when $d \in D_0$)
  9, 15 (when $d \in D_0 \cup D_1^{(+)}$)
  13 (when $d \in D_0 \cup D_3^{(+)}$)
  14 (when $d \in D_0 \cup D_3^{(-)}$)

With respect to the value of peak shift of $d \in D$, by linking said results rearranging the category $P_{type}$ of the peak pair, which may give the value d of the peak shift, for the sub-set being divided in detail to the results rearranging the possible k values for each of the sub-set being divided in detail as shown in the Examination Step A, the k values corresponding to the possible kinds of eliminated amino acid residues can be summarized in following types for each combination of the value of peak shift and the category $P_{type}$ of the peak pair.

| | | |
|---|---|---|
| When $d \in Sh_0$, $P_{type}$: | 1 to 3, 4 | $K_0(d)$ |
| When $d \in Sh_1^{(+)}$, $P_{type}$: | 7, 4 | $K_1^+(d)$ |
| When $d \in Sh_1^{(-)}$, $P_{type}$: | 8, 4 | $K_1^-(d)$ |
| When $d \in Sh_2^{(+)}$, $P_{type}$: | 6, 4 | $K_2^+(d)$ |
| When $d \in Sh_2^{(-)}$, $P_{type}$: | 5, 4 | $K_2^-(d)$ |
| When $d \in Sh_3^{(+)}$, $P_{type}$: | 11, 4 | $K_3^+(d)$ |
| When $d \in Sh_3^{(-)}$, $P_{type}$: | 12, 4 | $K_3^-(d)$ |
| When $d \in W_1$, $P_{type}$: | 1 to 3, 9, 13, 15 → | $k_0(d)$ |
| | 8 → | $k_1^-(d)$ |
| | 10, 16, 4 → | $k_0(d)$ or $k_1^-(d)$ |
| When $d \in W_2$, $P_{type}$: | 1 to 3, 10, 13, 14, 16 → | $k_0(d)$ |
| | 7 → | $k_1^+(d)$ |
| | 9, 15, 4 → | $k_0(d)$ or $k_1^+(d)$ |
| When $d \in W_3$, $P_{type}$: | 1 to 3, 10, 13, 15 → | $k_0(d)$ |
| | 5 | $k_2^-(d)$ |
| | 9, 14, 16, 4 → | $k_0(d)$ or $k_2^-(d)$ |
| When $d \in W_4$, $P_{type}$: | 1 to 3, 9, 14, 16 → | $k_0(d)$ |
| | 6 → | $k_2^+(d)$ |
| | 10, 15 → | $k_0(d)$ or $k_2^+(d)$ |
| When $d \in W_5$, $P_{type}$: | 1 to 3, 9, 10, 14 to 16 → | $k_0(d)$ |
| | 11 → | $k_3^+(d)$ |
| | 13 → | $k_0(d)$ or $k_3^+(d)$ |
| When $d \in W_6$, $P_{type}$: | 5, 10 → | $k_2^-(d)$ |
| | 8, 9, 14 → | $k_1^-(d)$ |
| | 16, 4 → | $k_2^-(d)$ or $k_1^-(d)$ |
| When $d \in W_7$, $P_{type}$: | 5, 13, 15 → | $k_2^+(d)$ |
| | 8, 16 → | $k_1^-(d)$ |
| | 10, 4 → | $k_2^+(d)$ or $k_1^-(d)$ |
| When $d \in W_8$, $P_{type}$: | 8, 10, 16 → | $k_1^-(d)$ |
| | 12, 14 → | $k_3^-(d)$ |
| | 4 → | $k_1^-(d)$ or $k_3^-(d)$ |
| When $d \in W_9$, $P_{type}$: | 5, 14, 16 → | $k_2^-(d)$ |
| | 7, 15 → | $k_1^+(d)$ |
| | 9, 4 → | $k_1^+(d)$ or $k_2^-(d)$ |
| When $d \in W_{10}$, $P_{type}$: | 6, 10, 13 → | $k_2^+(d)$ |
| | 7, 9 → | $k_1^+(d)$ |
| | 15, 4 → | $k_1^+(d)$ or $k_2^+(d)$ |

| | | |
|---|---|---|
| -continued | | |
| When d ∈ $W_{11}$, $P_{type}$: | 7, 9, 15 → | $k_1^+(d)$ |
| | 11, 13 → | $k_3^+(d)$ |
| | 4 → | $k_1^+(d)$ or $k_3^+(d)$ |
| When d ∈ $W_{12}$, $P_{type}$: | 6, 10, 15 → | $k_2^+(d)$ |
| | 11 → | $k_3^+(d)$ |
| | 13, 4 → | $k_2^+(d)$ or $k_3^+(d)$ |
| When d ∈ $W_{12}$, $P_{type}$: | 5, 9, 16 → | $k_2^-(d)$ |
| | 12 → | $k_3^-(d)$ |
| | 14, 4 → | $k_2^-(d)$ or $k_3^-(d)$ |
| When d ∈ $T_1$, $P_{type}$: | 1 to 3, 9, 15 → | $k_0(d)$ |
| | 6 → | $k_2^+(d)$ |
| | 8 → | $k_1^-(d)$ |
| | 16 → | $k_0(d)$ or $k_1^-(d)$ |
| | 13, 15 → | $k_0(d)$ or $k_2^+(d)$ |
| | 10, 4 → | $k_0(d)$ or $k_1^-(d)$ or $k_2^+(d)$ |
| When d ∈ $T_2$, $P_{type}$: | 1 to 3, 9, 13, 15 → | $k_0(d)$ |
| | 8 → | $k_1^-(d)$ |
| | 12 → | $k_3^-(d)$ |
| | 10, 16 → | $k_0(d)$ or $k_1^-(d)$ |
| | 14 → | $k_0(d)$ or $k_3^-(d)$ |
| | 4 → | $k_0(d)$ or $k_1^-(d)$ or $k_3^-(d)$ |
| When d ∈ $T_3$, $P_{type}$: | 1 to 3, 10, 13 → | $k_0(d)$ |
| | 5 → | $k_2^-(d)$ |
| | 7 → | $k_1^+(d)$ |
| | 15 → | $k_0(d)$ or $k_1^+(d)$ |
| | 14, 16 → | $k_0(d)$ or $k_2^-(d)$ |
| | 9, 4 → | $k_0(d)$ or $k_1^+(d)$ or $k_2^-(d)$ |
| When d ∈ $T_4$, $P_{type}$: | 1 to 3, 10, 14, 16 → | $k_0(d)$ |
| | 7 → | $k_1^+(d)$ |
| | 11 → | $k_3^+(d)$ |
| | 9, 15 → | $k_0(d)$ or $k_1^+(d)$ |
| | 13 → | $k_0(d)$ or $k_3^+(d)$ |
| | 4 → | $k_0(d)$ or $k_1^+(d)$ or $k_3^+(d)$ |
| When d ∈ $T_5$, $P_{type}$: | 1 to 3, 10, 13, 15 → | $k_0(d)$ |
| | 5 → | $k_2^-(d)$ |
| | 12 → | $k_3^-(d)$ |
| | 9, 16 → | $k_0(d)$ or $k_2^-(d)$ |
| | 14, 4 → | $k_0(d)$ or $k_2^-(d)$ or $k_3^-(d)$ |
| When d ∈ $T_6$ $P_{type}$: | 1 to 3, 9, 14, 16 → | $k_0(d)$ |
| | 6 → | $k_2^+(d)$ |
| | 11 → | $k_3^+(d)$ |
| | 10, 15 → | $k_0(d)$ or $k_2^+(d)$ |
| | 13, 4 → | $k_0(d)$ or $k_2^+(d)$ or $k_3^+(d)$ |
| When d ∈ $T_7$, $P_{type}$: | 7, 9, 15 → | $k_1^+(d)$ |
| | 8, 10, 16 → | $k_1^-(d)$ |
| | 12, 14 → | $k_3^-(d)$ |
| | 4 → | $k_1^-(d)$ or $k_1^+(d)$ or $k_3^-(d)$ |
| When d ∈ $T_8$, $P_{type}$: | 7, 9, 15 → | $k_1^+(d)$ |
| | 8, 10, 16 → | $k_1^-(d)$ |
| | 11, 13 → | $k_3^+(d)$ |
| | 4 → | $k_1^-(d)$ or $k_1^+(d)$ or $k_3^+(d)$ |
| When d ∈ $T_9$, $P_{type}$: | 6, 15 → | $k_2^+(d)$ |
| | 8, 16 → | $k_1^-(d)$ |
| | 11 → | $k_3^+(d)$ |
| | 10 → | $k_1^-(d)$ or $k_2^+(d)$ |
| | 13 → | $k_2^+(d)$ or $k_3^+(d)$ |
| | 4 → | $k_1^-(d)$ or $k_2^+(d)$ or $k_3^-(d)$ |
| When d ∈ $F_1$, $P_{type}$: | 1 to 3, 9, 14 → | $k_0(d)$ |
| | 6 → | $k_2^+(d)$ |
| | 8 → | $k_1^-(d)$ |
| | 11 → | $k_3^+(d)$ |
| | 16 → | $k_0(d)$ or $k_1^-(d)$ |
| | 15 → | $k_0(d)$ or $k_2^+(d)$ |
| | 10 → | $k_0(d)$ or $k_1^-(d)$ or $k_2^+(d)$ |
| | 13 → | $k_0(d)$ or $k_2^+(d)$ or $k_3^+(d)$ |
| | 4 → | $k_0, k_2^+, k_1^-$ or $k_3^+(d)$ |
| When d ∈ $F_2$, $P_{type}$: | 1 to 3, 10 → | $k_0(d)$ |
| | 5 → | $k_2^-(d)$ |
| | 7 → | $k_1^+(d)$ |
| | 11 → | $k_3^+(d)$ |
| | 15 → | $k_0(d)$ or $k_1^+(d)$ |
| | 14, 16 → | $k_0(d)$ or $k_2^-(d)$ |
| | 13 → | $k_0(d)$ or $k_3^+(d)$ |
| | 9 → | $k_0(d)$ or $k_1^+(d)$ or $k_2^-(d)$ |
| | 4 → | $k_0, k_1^+, k_2^-$ or $k_3^+(d)$ |
| When d ∈ $F_3$, $P_{type}$: | 1 to 3, 10, 16 → | $k_0(d)$ |
| | 7 → | $k_1^+(d)$ |
| | 11 → | $k_3^+(d)$ |
| | 12 → | $k_3^-(d)$ |

-continued

| | |
|---|---|
| 9, 15 → | $k_0$ (d) or $k_1^+$ (d) |
| 13 → | $k_0$ (d) or $k_3^+$ (d) |
| 14 → | $k_0$ (d) or $k_3^-$ (d) |
| 4 → | $k_0, k_1^+, k_3^-$ or $k_3^+$ (d) |

By applying the aforementioned examination results, the k values corresponding to the possible kinds of eliminated amino acid residues can be limited to small numbers for each combination of the value of peak shift and the category $P_{type}$ of the peak pair. Specifically, according to the Step C, as peak pairs having such possibility that they may be observed as a peak pair between the peaks of the group of the C-terminal fragments, pairs of which peak position difference ($\Delta$m/Z) is included in said subset of the possible value d of peak sift defined for the category thereof are beforehand selected from all the pairs of two peaks $P_i$ and $P_j$ that are belonging to either of the sub-set $S(0)_p, S(+Ac)_p, S(-H_2O)_p$ or S(single), and then as for the thus-selected set of target peak pairs ($P_i, P_j$) to be further analyzed, the kinds of eliminated amino acid residues (k values) corresponding to the value of peak shift which each peak pair included in said set can be determined or be limited to the well-defined four or less kinds.

E. Extraction of a group of sequential peak series showing reductions in peak position difference ($\Delta$m/Z) caused by successive release of amino acids In the above stage C were selected, from all the peak pairs $P_i, P_j$ belonging to either of the sub-sets $S(0)_p, S(+Ac)_p, S(-H_2O)_p$ and S(single), those peak pairs whose peak position differences ($\Delta$m/Z) correspond to the peak shifts d caused by elimination of one amino acid. From a set of these peak pairs $(P_i, P_j):P_D \equiv \{(P_i, P_j):d_{ij} \in D, P_i, P_j \in (S(0)_p \cup S(+Ac)_p \cup S(-H_2O)_p \cup S(single)\}$ are selected a group of sequential peak series reflecting the successive release of amino acids.

From the set of peak pairs $(P_i, P_j):P_D$ are formed a set of peaks $P_j$ of larger peak position of peak pair: $S_{pair-h0} \equiv \{P_j:(P_i, P_j) \in P_D\}$ and a set of peaks $P_i$ of smaller peak position of peak pair: $S_{pair-l0} \equiv \{P_i:(P_i, P_j) \in P_D\}$. Then, there is formed a product set $C_0: S_{pair-h0} \cap S_{pair-l0}$ of the set: $S_{pair-h0}$ and the set: $S_{pair-l0}$. This product set: $C_0$ is a set of peaks which are peaks of larger peak position in one peak pair and, in other peak pair, are peaks of smaller peak position.

There are further formed an odd set $B_0$ as $B_0 \equiv S_{pair-h0} \backslash C_0$ and an odd set $F_0$ as $F_0 \equiv S_{pair-l0} \backslash C_0$.

The peaks contained in the odd set $B_0$ means that there is not, at a peak position larger than those of such peaks, any peak capable of forming a peak pair such as contained in the set: $P_D$. Meanwhile, the peaks contained in the odd set $F_0$ means that there is not, at a peak position smaller than those of such peaks, any peak capable of forming a peak pair such as contained in the set: $P_D$. Incidentally, each peak contained in the product set: $C_0$ is a peak that is an intermediate point of a peak series consisting of at least three peaks and that has a peak position difference ($\Delta$m/Z) corresponding to the peak shift d caused by the elimination of one amino acid.

(E-1) Exclusion of Peak Pairs Forming No Peak Series Consisting of Three or More Peaks First, each peak contained in the odd set $B_0$ is selected as a peak of larger peak position and each peak contained in the odd set $F_0$ is selected as a peak of smaller peak position; there is formed a set of such peak pairs $P_{B0-F0} \equiv \{(P_i, P_j):P_i \in F_0, P_j \in B_0\}$; and there is produced a product set: $P_D \cap P_{B0-F0}$ of the set $P_D$ and the set $P_{B0-F0}$. Then, the product set: $P_D \cap P_{B0-F0}$ is removed from the set $P_D$ to produce an odd set $P_{D1} \equiv P_D \backslash (P_D \cap P_{B0-F0})$ In this odd set $P_{D1}$ is not contained any peak pair which has no possibility of forming a sequential peak series reflecting the successive release of amino acids. Meanwhile, the above-mentioned product set: $P_D \cap P_{B0-F0}$ corresponds to a set of peak pairs forming no peak series.

Once again, from the set of peak pairs $(P_i, P_j): P_{D1}$ are formed a set of peaks $P_j$ of larger peak position of peak pair: $S_{pair-h1} \equiv \{P_j:(P_i, P_j) \in P_{D1}\}$ and a set of peaks $P_i$ of smaller peak position of peak pair: $S_{pair-l1} \equiv \{P_i:(P_i, P_j) \in P_{D1}\}$. Then, there is formed a product set $C_1 \equiv S_{pair-h1} \cap S_{pair-l1}$ of the set $S_{pair-h1}$ and the set $S_{pair-l1}$. This product set: $C_1$ is a set of peaks which are peaks of larger peak position in one peak pair and, in other peak pair, are peaks of smaller peak position.

There are further formed an odd set $B_1$ as $B_1 \equiv S_{pair-h1} \backslash C_1$ and an odd set $F_1$ as $F_1 \equiv S_{pair-l1} \backslash C_1$.

The peaks contained in this odd set $B_1$ means that there is not, at a peak position larger than those of such peaks, any peak capable of forming a peak pair such as contained in the set: $P_{D1}$. Therefore, $B_1$ corresponds to a set of peaks (starting peaks) each having the largest peak position in each peak series consisting of at least three peaks and having a peak position difference ($\Delta$m/Z) corresponding to the peak shift d caused by the elimination of one amino acid. Meanwhile, the peaks contained in this odd set $F_1$ means that there is not, at a peak position smaller than those of such peaks, any peak capable of forming a peak pair such as contained in the set: $P_{D1}$. Therefore, $F_1$ corresponds to a set of peaks (final peaks) each having the smallest peak position in each peak series consisting of at least three peaks and having a peak position difference ($\Delta$m/Z) corresponding to the peak shift d caused by the elimination of one amino acid. Incidentally, the product set: $C_1$ is a set of intermediate peaks in each peak series consisting of at least three peaks, which has the above-mentioned starting peak and final peak at the termini and which has a peak position difference ($\Delta$m/Z) corresponding to the peak shift d caused by the elimination of one amino acid.

(E-2) Identification of Each Peak Series Comprising Three Peaks: Starting Peak→Intermediate Peak→Final Peak Next, each peak contained in the odd set $B_1$ is selected as a peak of larger peak position and each peak contained in the product set $C_1$ is selected as a peak of smaller peak position; there is formed a set of such peak pairs: $P_{B1-C1} \equiv \{(P_i, P_j): P_i \in C_1, P_j \in B_1\}$; and there is produced a product set: $P_{D1} \cap P_{B1-C1}$ of the set $P_{D1}$ and the set $P_{B1-C1}$. From the product set: $P_D \cap P_{B1-C1}$ of peak pairs $(P_i, P_j)$ is formed a set of peaks $P_i$ of smaller peak position of each peak pair, i.e. $S_{pair-l2} \equiv \{P_i:(P_i, P_j) \in P_{D1} \cap P_{B1-C1}\}$. This set $S_{pair-l2}$ corresponds to a set of peaks in the product set $C_1$, linking to each peak contained in the odd set $B_1$.

Meanwhile, each peak contained in the odd set $F_1$ is selected as a peak of smaller peak position and each peak contained in the product set $C_1$ is selected as a peak of larger peak position; there is formed a set of such peak pairs: $P_{C1-F1} \equiv \{(P_i, P_j): P_i \in F_1, P_j \in C_1\}$; and there is produced a product set: $P_{D1} \cap P_{C1-F1}$ of the set $P_{D1}$ and the set $P_{C1-F1}$. From the product set: $P_{D1} \cap P_{C1-F1}$ of peak pairs $(P_i, P_j)$ is formed a set of peaks $P_j$ of larger peak position of each peak pair, i.e. $S_{pair-h2} \equiv \{P_j:(P_i, P_j) \in P_{D1} \cap P_{C1-F1}\}$. This set $S_{pair-h2}$ corresponds to a set of peaks in the product set $C_1$, linking from each peak contained in the odd set $F_1$.

Next, there is formed a product set: $C_2 \equiv S_{pair-h2} \cap S_{pair-l2}$ of the set $S_{pair-h2}$ and the set $S_{pair-l2}$. This product set is a set of intermediate peaks in each peak series consisting of three peaks, which has the above-mentioned starting peak and final peak at the termini and which has a peak position difference ($\Delta$m/Z) corresponding to the peak shift d caused by the elimination of one amino acid. Further, each peak contained in the odd set $F_1$ is selected as a peak of smaller peak position and each peak contained in the product set $C_2$ is selected as a peak of higher peak position; there is formed a set of such peak pairs: $P_{C2-F1} \equiv \{(P_i, P_j) : P_i \in F_1, P_j \in C_2\}$; and there is produced a product set: $P_{D1} \cap P_{C2-F1}$ of the set $P_{D1}$ and the set $P_{C2-F1}$. From the product set: $P_{D1} \cap P_{C2-F1}$ of peak pairs $(P_i, P_j)$ is formed a set of peaks $P_j$ of smaller peak position of each peak pair, i.e. $F_{c2} \equiv \{P_i : (P_i, P_j) \in P_{D1} \cap P_{C2-F1}\}$. This set $F_{c2}$ corresponds to a set of peaks in the odd set $F_1$, linking to each peak contained in the set $C_2$. Further, each peak contained in the odd set $B_1$ is selected as a peak of higher peak position and each peak contained in the product set $C_2$ is selected as a peak of smaller peak position; there is formed a set of such peak pairs: $P_{B1-C2} \equiv \{(P_i, P_j) : P_i \in C_2, P_j \in F_1\}$; and there is produced a product set: $P_{D1} \cap P_{B1-C2}$ of the set $P_{D1}$ and the set $P_{B1-C2}$. From the product set: $P_{D1} \cap P_{B1-C2}$ of peak pairs $(P_i, P_j)$ is formed a set of peaks $P_j$ of larger peak position of each peak pair, i.e. $B_{C2} \equiv \{P_i : (P_i, P_j) \in P_{D1} \cap P_{B1-C1}\}$. This set $B_{C2}$ corresponds to a set of peaks in the odd set $B_1$, linking from each peak contained in the set $C_2$. As a result, there is identified each peak series consisting of three peaks, i.e. a starting peak in the set $B_{C2}$, an intermediate peak in the set $C_2$ and a final peak in the set $F_{C2}$.

(E-3) Identification of Each Peak Series Comprising Four Peaks: Starting Peak→First Intermediate Peak→Second Intermediate Peak→Final Peak First, each peak contained in the set $S_{pair-l2}$ is selected as a peak of larger peak position and each peak contained in the product set $C_1$ is selected as a peak of smaller peak position; there is formed a set of such peak pairs: $P_{Sl2-C1} \equiv \{(P_i, P_j) : P_i \in C_1, P_j \in S_{pair-l2}\}$; and there is produced a product set: $P_{D1} \cap P_{Sl2-C1}$ of the set $P_{D1}$ and the set $P_{Sl2-C1}$. From the product set: $P_{D1} \cap P_{Sl2-C1}$ of peak pairs $(P_i, P_j)$ is formed a set of peaks $P_i$ of smaller peak position of each peak pair, i.e. $S_{pair-l3} \equiv \{P_i : (P_i, P_j) \in P_{D1} \cap P_{Sl2-C1}\}$. This set $S_{pair-l3}$ corresponds to a set of peaks in the product set $C_1$, linking to each peak contained in the set $S_{pair-l2}$. Further, there is formed a product set: $C_{3/2} \equiv S_{pair-l3} \cap S_{pair-h2}$ of the set $S_{pair-l3}$ and the set $S_{pair-h2}$.

Further, each peak contained in the odd set $F_1$ is selected as a peak of smaller peak position and each peak contained in the product set $C_{3/2}$ is selected as a peak of higher peak position; there is formed a set of such peak pairs: $P_{C3/2-F1} \equiv \{(P_i, P_j) : P_i \in F_1, P_j \in C_{3/2}\}$; and there is produced a product set: $P_{D1} \cap P_{3/22-F1}$ of the set $P_{D1}$ and the set $P_{C3/2-F1}$. From the product set: $P_{D1} \cap P_{C3/2-F1}$ of peak pairs $(P_i, P_j)$ is formed a set of peaks $P_i$ of smaller peak position of each peak pair, i.e. $F_{c3} \equiv \{P_i : (P_i, P_j) \in P_{D1} \cap P_{3/2-F1}\}$. This set $F_{c3}$ corresponds to a set of peaks in the odd set $F_1$, linking to each peak contained in the set $C_{3/2}$.

Meanwhile, each peak contained in the set $S_{pair-h2}$ is selected as a peak of smaller peak position and each peak contained in the product set $C_1$ is selected as a peak of larger peak position; there is formed a set of such peak pairs: $P_{C1-Sh2} \equiv \{(P_i, P_j) : P_i \in S_{pair-h2}, P_j \in C_1\}$; and there is produced a product set: $P_{D1} \cap P_{C1-Sh2}$ of the set $P_{D1}$ and the set $P_{C1-Sh2}$. From the product set: $P_{D1} \cap P_{C1-Sh2}$ of peak pairs $(P_i, P_j)$ is formed a set of peaks $P_j$ of larger peak position of each peak pair, i.e. $S_{pair-h3} \equiv \{P_j : (P_i, P_j) \in P_{D1} \cap P_{C1-Sh2}\}$. This set $S_{pair-h3}$ corresponds to a set of peaks in the product set $C_1$, linking from each peak contained in the set $S_{pair-h2}$. Further, there is formed a product set: $C_{3/1} \equiv S_{pair-h3} \cap S_{pair-l2}$.

Further, each peak contained in the odd set $B_1$ is selected as a peak of larger peak position and each peak contained in the product set $C_{3/1}$ is selected as a peak of smaller peak position; there is formed a set of such peak pairs: $P_{B1-C3/1} \equiv \{(P_i, P_j) : P_i \in C_{3/1}, P_j \in F_1\}$; and there is produced a product set: $P_{D1} \cap P_{B1-C3/1}$ of the set $P_{D1}$ and the set $P_{B1-C3/1}$. From the product set: $P_{D1} \cap P_{B1-C3/1}$ of peak pairs $(P_i, P_j)$ is formed a set of peaks $P_j$ of larger peak position of each peak pair, i.e. $B_{c3} \equiv \{P_j : (P_i, P_j) \in P_{D1} \cap P_{B1-C3/1}\}$. This set $B_{C3}$ corresponds to a set of peaks in the odd set $B_1$, linking from each peak contained in the set $C_{3/1}$. As a result, there is identified each peak series consisting of four peaks, i.e. a starting peak in the set $B_{C3}$, a first intermediate peak in the set $C_{3/1}$, a second intermediate peak in the set $C_{3/2}$ and a final peak in the set $F_{C3}$.

(E-4) Identification of Each Peak Series Comprising Five Peaks: Starting Peak→First Intermediate Peak→Second Intermediate Peak→Third Intermediate Peak→Final Peak First, each peak contained in the set $S_{pair-l3}$ is selected as a peak of larger peak position and each peak contained in the product set $C_1$ is selected as a peak of smaller peak position; there is formed a set of such peak pairs: $P_{Sl3-C1} \equiv \{(P_i, P_j) : P_i \in C_1, P_j \in S_{pair-l3}\}$; and there is produced a product set: $P_{D1} \cap P_{Sl3-C1}$ of the set $P_{D1}$ and the set $P_{Sl3-C1}$. From the product set: $P_{D1} \cap P_{Sl3-C1}$ of peak pairs $(P_i, P_j)$ is formed a set of peaks $P_i$ of smaller peak position of each peak pair, i.e. $S_{pair-l4} \equiv \{P_i : (P_i, P_j) \in P_{D1} \cap P_{Sl3-C1}\}$. This set $S_{pair-l4}$ corresponds to a set of peaks in the product set $C_1$, linking to each peak contained in the set $S_{pair-l3}$. Further, there is formed a product set: $C_{4/3} \equiv S_{pair-l4} \cap S_{pair-h2}$ of the set $S_{pair-l4}$ and the set $S_{pair-h2}$.

Further, each peak contained in the odd set $F_1$ is selected as a peak of smaller peak position and each peak contained in the product set $C_{4/3}$ is selected as a peak of larger peak position; there is formed a set of such peak pairs: $P_{C4/3-F1} \equiv \{(P_i, P_j) : P_i \in F_1, P_j \in C_{4/3}\}$; and there is produced a product set: $P_{D1} \cap P_{C4/3-F1}$ of the set $P_{D1}$ and the set $P_{C4/3-F1}$. From the product set: $P_{D1} \cap P_{C4/3-F1}$ of peak pairs $(P_i, P_j)$ is formed a set of peaks $P_i$ of smaller peak position of each peak pair, i.e. $F_{C4} \equiv \{P_i : (P_i, P_j) \in P_{D1} \cap P_{C4/3-F1}\}$. This set $F_{C4}$ corresponds to a set of peaks in the odd set $F_1$, linking to each peak contained in the set $C_{4/3}$.

Meanwhile, each peak contained in the set $S_{pair-h3}$ is selected as a peak of smaller peak position and each peak contained in the product set $C_1$ is selected as a peak of larger peak position; there is formed a set of such peak pairs: $P_{C1-Sh3} \equiv \{(P_i, P_j) : P_i \in S_{pair-h3}, P_j \in C_1\}$; and there is produced a product set: $P_{D1} \cap P_{C1-Sh3}$ of the set $P_{D1}$ and the set $P_{C1-Sh3}$. From the product set: $P_{D1} \cap P_{C1-Sh3}$ of peak pairs $(P_i, P_j)$ is formed a set of peaks $P_j$ of larger peak position of each peak pair, i.e. $S_{pair-h4} \equiv \{P_j : (P_i, P_j) \in P_{D1} \cap P_{C1-Sh3}\}$. This set $S_{pair-h4}$ corresponds to a set of peaks in the product set $C_1$, linking from each peak contained in the set $S_{pair-h3}$. There is further formed a product set: $C_{4/1} \equiv S_{pair-h4} \cap S_{pair-l2}$ of the set $S_{pair-h4}$ and the set $S_{pair-l2}$.

Further, each peak contained in the odd set $B_1$ is selected as a peak of larger peak position and each peak contained in the product set $C_{4/1}$ is selected as a peak of smaller peak position; there is formed a set of such peak pairs: $P_{B1-C4/1} \equiv \{(P_i, P_j) : P_i \in C_{4/1}, P_j \in F_1\}$; and there is produced a product set: $P_{D1} \cap P_{B1-C4/1}$ of the set $P_{D1}$ and the set $P_{B1-C4/1}$. From the product set: $P_{D1} \cap P_{B1-C3/1}$ of peak pairs $(P_i, P_j)$ is formed a set of peaks $P_h$ of larger peak position of each peak pair, i.e.

$B_{C4/1} \equiv \{P_j:(P_i, P_j) \in P_{D1} \cap P_{B1-C4/1}\}$. This set $B_{C4}$ corresponds to a set of peaks in the odd set $B_1$, linking from each peak contained in the set $C_{4/1}$.

Further, there is produced a product set: $C_{4/2} \equiv S_{pair-h3} \cap S_{pair-l3}$ of the set $S_{pair-h3}$ and the set $S_{pair-l3}$. Each peak contained in the product set $C_{4/2}$ corresponds to a set of intermediate peaks which are each a peak in the set $S_{pair-h3}$, linking from each peak contained in the set $S_{pair-h2}$ and also a peak in the set $S_{pair-h3}$, linking to each peak contained in the set $S_{pair-l2}$.

As a result, there is identified each peak series consisting of five peaks, i.e. a starting peak in the set $B_{C4}$, a first intermediate peak in the set $C_{4/1}$, a second intermediate peak in the set $C_{4/2}$, a third intermediate peak in the set $C_{4/3}$ and a final peak in the set $F_{C4}$.

(E-5) Identification of Each Peak Series Comprising at Least 6 Peaks

Also with respect to each peak series of 6 or more peaks, there can be identified a plurality of sets of intermediate peaks, a set of corresponding starting peaks and a set of corresponding final peaks, in accordance with the procedures described in E-3 and E-5. Finally, when an increase of Nth stage {a peak series consisting of (N+1) peaks} has been reached, the peak set $S_{pair-lN}$ linking to starting peak side becomes an empty set and also the peak set $S_{pair-hN}$ linking from final peak side becomes an empty set; therefore, an increase of (N−1)th stage (a peak series consisting of N peaks) becomes the longest peak series.

Needless to say, when successive release of C-terminal amino acids has been achieved ideally, there are contained, in the set $P_{D1}$ of peak pairs $(P_i, P_j)$, only peak pairs of a series of C-terminal side peptide fragments caused by the successive release of C-terminal amino acids; therefore, in the above-mentioned transitional stages of E-2, E-3 and E-4, principally there is not found any peak series other than peak series consisting of N peaks. In the increase of (N−1)th stage (a peak series consisting of N peaks), there are selected, for the first time, a peak series reflecting the explicitly defined successive release of C-terminal amino acids.

However, in the successive release of C-terminal amino acids, when there are formed by-products by, for example, cleavage of peptide chain in the middle, successive release of C-terminal amino acids proceeds from these by-products and, resultantly, a series of peptide fragments are formed as by-products. Consequently, there are, in some cases, identified, besides main peak series of C-terminal side peptide fragments of (N−1) stages, secondary peak series of several stages. In this case, with respect to each peak pair of each peak series, the k value corresponding to the kind of eliminated amino acid residue is already known; using this k value, there is identified an eliminated amino acid residue series corresponding to a starting peak, a plurality of intermediate peaks, and a final peak; and secondary peak series are excluded taking into consideration the kinds of C-terminal amino acids and their peak intensities. That is, although the cleavage of peptide chain in the middle occurs at a certain probability, the total amount of the peptide fragments caused by such secondary reaction is generally small as compared to the total amount of main peptide fragments, and their peak intensities observed are relatively low. Therefore, the total peak intensity of each peak series of different stage is calculated based on the observed peak intensity of each peak series of different stage; such total peak intensities are compared with each other; a group of peak series of high total peak intensity is selected.

(E-7) Identification of Each Peak Series of an Identified Group of Peak Series Each Comprising N Peaks For a case of a group of peak series identified in the above E-4, each consisting of 5 peaks (a starting peak in the set $B_{C4}$, a first intermediate peak in the set $C_{4/1}$, a second intermediate peak in the set $C_{4/2}$, a third intermediate peak in the set $C_{4/3}$, and a final peak in the set $F_{C4}$), there is shown below a procedure for identification of each peak series.

First, a starting peak $P_{j0}$ contained in the set $B_{C4}$ is selected as a peak of larger peak position and a peak contained in the product set $C_{4/1}$ is selected as a peak of smaller peak position; there is formed a set of such peak pairs, i.e. $P_{BC4-C4/1}(P_{j0}) \equiv \{(P_i, P_{j0}):P_i \in C_{4/1}, P_{j0} \in B_{C4}\}$; there is produced a product set $P_{D1} \cap P_{BC4-C4/1}(P_{j0})$ of the set $P_{D1}$ and the set $P_{BC4-C4/1}(P_{j0})$. From the product set $P_{D1} \cap P_{BC4-C4/1}(P_{j0})$ of peak pairs $(P_i, P_{j0})$ is formed a set of peaks $P_i$ of smaller peak position of each peak pair, i.e. $C_{4/1}(P_{j0}) \equiv \{P_i:(P_i, P_{j0}) \in P_{D1} \cap P_{BC4-C4/1}(P_{j0})\}$. This set $C_{4/1}(P_{j0})$ corresponds to a set of peaks in the first intermediate peak set $C_{4/1}$ linking to each starting peak $P_{j0}$ contained in the set $B_{C4}$.

Then, a first intermediate peak $P_{jC4/1}(P_{j0})$ contained in the set $C_{4/1}(P_{j0})$ is selected as a peak of larger peak position and a peak contained in the product set $C_{4/2}$ is selected as a peak of smaller peak position; there is formed a set of such peak pairs, i.e. $P_{C4/1-C4/2}(Pn_{jC4/1}) \equiv \{(P_i, P_{jC4/1}(P_{j0})):P_i \in C_{4/2}, P_{jC4/1}(P_{j0}) \in C_{4/1}(P_{j0})\}$; there is produced a product set $P_{D1} \cap P_{C4/1-C4/2}(P_{jC4/1})$ of the set $P_{D1}$ and the set $P_{C4/1-C4/2}(P_{jC4/1})$. From the product set $P_{D1} \cap P_{C4/1-C4/2}(P_{jC4/1})$ of peak pairs $(P_i, P_{jC4/1}(P_{j0}))$ is formed a set of peaks $P_i$ of smaller peak position of each peak pair, i.e. $C_{4/2}(P_{j0}) \equiv \{P_i:(P_i, P_{jC4/1}(P_{j0})) \in P_{D1} \cap P_{C4/1-C4/2}(P_{jC4/1})\}$. This set $C_{4/2}(P_{j0})$ corresponds to a set of peaks in the second intermediate peak set $C_{4/2}$, linking to each first intermediate peak $P_{jC4/1}(P_{j0})$ contained in the set $C_{4/}1(P_{j0})$.

Further, a second intermediate peak $P_{jC4/2}(P_{j0})$ contained in the set $C_{4/2}(P_{j0})$ is selected as a peak of larger peak position and a peak contained in the product set $C_{4/3}$ is selected as a peak of smaller peak position; there is formed a set of such peak pairs, i.e. $P_{C4/2-C4/3}(P_{jC4/2}) \equiv \{(P_i, P_{jC4/2}(P_{j0})):P_i \in C_{4/3}, P_{jC4/2}(P_{j0}) \in C_{4/2}(P_{j0})\}$; there is produced a product set $P_{D1} \cap P_{C4/2-C4/3}(P_{jC4/2})$ of the set $P_{D1}$ and the set $P_{C4/2-C4/3}(P_{jC4/2})$. From the product set $P_{D1} \cap P_{C4/2-C4/2}(P_{jC4/2})$ of peak pairs $(P_i, P_{jC4/2}(P_{j0}))$ is formed a set of peaks $P_i$ of smaller peak position of each peak pair, i.e. $C_{4/3}(P_{j0}) \equiv \{(P_i:(P_i, P_{jC4/2}(P_{j0})) \in P_{D1} \cap P_{C4/2-C4/3}(P_{jC4/2})\}$. This set $C_{4/3}(P_{j0})$ corresponds to a set of peaks in the third intermediate peak set $C_{4/3}$, linking to each second intermediate peak $P_{jC4/2}(P_{j0})$ contained in the set $C_{4/2}(P_{j0})$.

Lastly, a third intermediate peak $P_{jC4/3}(P_{j0})$ contained in the set $C_{4/3}(P_{j0})$ is selected as a peak of larger peak position and a peak contained in the set $F_{C4}$ is selected as a peak of smaller peak position; there is formed a set of such peak pairs, i.e. $P_{C4/3-FC4}(P_{jC4/3}) \equiv \{(P_i, P_{jC4/3}(P_{j0})):P_i \in F_{C4}, P_{jC4/3}(P_{j0}) \in C_{4/3}(P_{j0})\}$; there is produced a product set $P_{D1} \cap P_{C4/3-FC4}(P_{jC4/3})$ of the set $P_{D1}$ and the set $P_{C4/3-FC4}(P_{jC4/3})$. From the product set $P_{D1} \cap P_{C4/3-FC4}(P_{jC4/3})$ of peak pairs $(P_i, P_{jC4/3}(P_{j0}))$ is formed a set of peaks $P_i$ of smaller peak position of each peak pair, i.e. $F_{C4}(P_{j0}) \equiv \{P_i:(P_i, P_{jC4/3}(P_{j0})) \in P_{D1} \cap P_{C4/4-FC4}(P_{jC4/3}))\}$. This set $F_{C4}(P_{j0})$ corresponds to a set of peaks in the final peak set $F_{C4}$, linking to each third intermediate peak $P_{jC4/3}(P_{j0})$ contained in the set $C_{4/3}(P_{j0})$.

As a result of completion of the above-described procedure for identification of "linking-to" peaks, there can be identified a group of peak series having a starting peak $P_{j0} \in B_{C4}$, from a group of peak series each consisting of 5 peaks. Incidentally, also when a peak accompanying to the starting peak $P_{j0} \in B_{C4}$ is used as a starting peak, there can be identified, as well, a group of peak series via intermediate peaks. This identification procedure of "linking-to" peaks starting with a starting peak and ending with a final peak via intermediate peaks is equivalent to the previously described analysis for identification of "peaks of daughter peak fragments" derived from the reaction products of successive release of amino acids, using the peak of largest peak position (a peak of parent peptide fragment) as a starting peak.

Meanwhile, since extraction has been beforehand made for a group of peak series each consisting of 5 peaks (a starting peak in the set $B_{C4}$, a first intermediate peak in the set $C_{4/1}$, a second intermediate peak in the set $C_{4/2}$, a third intermediate peak in the set $C_{4/3}$, and a final peak in the set $F_{C4}$), it is also possible to, by using a corresponding procedure, conduct identification of "linking-from" peaks starting with a final peak in the set $F_{C4}$ and ending with a starting peak via intermediate peaks. Needless to say, this identification procedure for "linking-from" peaks gives, in principle, the same result as the identification procedure for "linking-to" peaks.

When any of the above identification procedures is employed for a group of peak series, it is desired to advance analysis, with respect to "independent peaks" not accompanied by any secondary product peak, by assuming that the independent peaks are mainly ion species peaks of ideal peptide fragments (i). Meanwhile, when the "independent peaks" are judged to be ion species peaks of secondary peptide fragments (ii) having surplus acetylation or ion species peaks of secondary peptide fragments (iii) subjected to "dehydration" and the ion species peaks of ideal peptide fragments have peak intensities lower than the lower limit of observation, it is necessary to at least confirm, even in the "linking-from" peaks, that the ion species peaks of peptide fragments (ii) having surplus acetylation or the ion species peaks of "dehydrated" peptide fragments (iii) show higher peak intensities than the ion species peaks of ideal peptide fragments (i).

EXAMPLES

The present invention is described specifically below by way of Examples. These Examples are examples of the best mode for carrying out the present invention; however, the present invention is in no way restricted by such examples.

Example 1

In order to verify the usefulness of the method for analysis of the C-terminal amino acid sequence of peptide according to the first aspect of the present invention, analysis of C-terminal amino acid sequence was conducted for globin peptide chain, a protein portion of the horse myoglobin which is a heme protein comprising 153 amino acids.

The amino acid sequence possessed by the globin peptide chain of the horse myoglobin, which is a sample to be analyzed in this Example, is already known. Using this sample, the accuracy of the identification for analysis of C-terminal amino acid sequence identified by the analysis method according to the present invention was verified. In FIG. 1 is shown a flow of the process for successive release of C-terminal amino acids, employed in Example 1.

(Preparation of Isolated and Dried Peptide Powder Sample)

First, there is prepared, using a commercially available horse myoglobin standard sample, a peptide solution containing only the globin peptide chain portion thereof at a concentration of 1.0 µg/µl. Said peptide solution is taken into a test tube and lyophilized to prepare a dried peptide powder sample.

(Pre-Treatment Operation)

Next, a vial containing the dried peptide sample is set in a glass-made reactor of air-tight test tube type with fitting stopper, having an evacuation port equipped with a Teflon-made cock valve for sealing. Separately, a given amount of the following liquid reagent is placed in the glass-made reactor. As the reagent for pretreatment, there is used 300 µl of acetic anhydride with 5% by volume of acetic acid added thereto. After the vial containing the dried peptide sample is set in said glass-made reactor, the reactor inside is evacuated under cooling condition and then sealed in an air-tight state.

The whole reactor of air-tight state is kept at 50° C. for 2 hours to allow acetic anhydride and acetic acid both of vapor state, supplied from the liquid reagent in the reactor, to act on the dried peptide sample. By allowing acetic anhydride as an acylation reagent in the presence of acetic acid to act on the dried peptide sample, selective acetylation to the N-terminal amino group of the peptide proceeds. In addition, there take place N-acetylation to the $\epsilon$-position amino group of the lysine residue ($-NH-CH(CH_2CH_2CH_2CH_2NH_2)-CO-$); O-acetylation to the hydroxy groups present in the serine residue ($-NH-CH(CH_2OH)-CO-$) and the threonine reside ($-NH-CH(CH_3)OH)-CO-$); and O-acetylation to the phenolic hydroxy group of the tyrosine residue ($-NH-CH(CH_2-C_6H_4-OH)-CO-$), which residues are all contained in the peptide chain.

After this pre-treatment is completed, the unreacted acetic anhydride, acetic acid, etc. remaining in the reactor are removed away by distillation under reduced pressure, and the protected and modified globin peptide chain resulting therefrom is dried.

(Operation of Reaction for Release of C-Terminal Amino Acids)

Next, in a state that the vial holding the globin peptide chain that is modified and protected with acetyl roup is set in a glass-made reactor of air-tight test tube type with fitting stopper, a given amount of the following liquid reagent is placed anew in the glass-made reactor.

As the liquid reagent for the reaction of selective release of C-terminal amino acids, 300 µl of acetic anhydride with 1% by volume of heptafluorobutanoic acid (HFBA: $C_3F_7COOH$) added thereto is used. After the vial containing the dried peptide sample is set in said glass-made reactor, the reactor inside is evacuated under cooling condition and then sealed in an air-tight state.

The whole reactor of air-tight state is kept at 40° C. for 3 hours to allow acetic anhydride and HFBA both of vapor phase, supplied from the liquid reagent in the reactor, to act on the dried peptide sample. Since the HFBA and acetic anhydride are allowed to act on the C-terminus of peptide chain at said heated up temperature, the reactions for successive release of the C-terminal amino acids of peptide chain proceeds via the reaction path of the above-mentioned reaction schemes (Ia) to (II'). In this case, the C-terminus of peptide chain for each reaction product takes a form of the above-mentioned 5-oxazolone ring or a form of an asymmetric acid anhydride whereby activation of carboxy group is accomplished.

After the completion of the treatment for selective release of C-terminal amino acids, the unreacted acetic anhydride, HFBA, etc. remaining in the reactor are distilled off under reduced pressure, and a mixture of the remaining globin peptide chains and the reaction products obtained, which are all protected and modified by acetylaltion, is dried.

(Post-Treatment Operation)

Next, in a state that the vial holding the dried sample of a mixture containing the reaction products is set in a glass-made reactor of air-tight test tube type with fitting stopper, a given amount of the following liquid reagent is placed anew in the glass-made reactor.

As, in the above mixture, the C-termini of reaction product peptides are in a mixture state including those staying in the 5-oxazolone structure, or being advanced even to an asymmetric acid anhydride therefrom, other than those being converted into carboxy group, the post-treatment is a treatment mainly aiming to convert them into a state where all the C-termini of the peptides have turned carboxy groups by applying treatment for hydrolysis to them. That is, an aqueous solution (300 µl) dissolving 10% by volume of DMAE is used as a liquid reagent for post-treatment, and after the vial containing the dried peptide sample is set in said glass-made reactor, the reactor inside is evacuated under cooling condition and then sealed in an air-tight state.

The whole reactor of air-tight state is heated at 60° C. for 1 hour to allow the DMAE and water molecules in vapor phase, supplied from the liquid reagent in the reactor, to act on the dried sample. The asymmetric acid anhydride and the 5-oxazolone structure undergo hydrolysis by the action of water molecules in the presence of DMAE being an organic base, whereby they are converted into a form having a carboxy group at the C-terminus as illustrated in the above-shown reaction scheme (IV). Further, on the peptide chain modified and protected by acetyl group, the protection by O-acetylation to the hydroxy groups present in the serine residue (—NH—CH(CH$_2$OH)—CO—) and the threonine residue (—NH—CH(CH(CH$_3$)OH)—CO—) is hydrolyzed to be deprotected, and the protection by O-acetylation to the phenolic hydroxy group of tyrosine residue (—NH—CH(CH$_2$—C$_6$H$_4$—OH)—CO—) is also hydrolyzed almost completely. However, since the basicity of the organic base used is not high, deprotection of N-acetylation does not proceed and, after the post-treatment, there remain, at a high selectivity, the N-acetylation to N-terminal amino group and the N-acetylation to the ε-position amino group of lysine residue (—NH—CH(CH$_2$CH$_2$CH$_2$CH$_2$NH$_2$)—CO—). In some cases, there only slightly remains the O-acetylation to the phenolic hydroxy group of tyrosine residue (—NH—CH(CH$_2$—C$_6$H$_4$—OH)—CO—).

After such post-treatment, the water molecules, DMAE, etc. remaining in the reactor are distilled off under reduced pressure and the mixture of the reaction products after post-treatment is dried.

(Peptide Fragmentation with Use of the Digestion by Trypsin)

The globin peptide chain of horse myoglobin is composed of 153 amino acids and its molecular weight deviates from an appropriate molecular weight range in mass spectrometry; therefore, the treatment for peptide fragmentation by means of the digestion by trypsin is applied to it.

Specifically explaining, the dried sample of a mixture of said reaction products after post-treatment is placed in a container, and an aqueous solution containing trypsin is added to conduct fragmentation of peptide chain. In said aqueous solution containing trypsin, 0.1 µg/µl of trypsin is contained in a 3-pyridine acetate buffer (pH: 7). The enzymatic reaction for the digestion by trypsin is carried out at 37° C. for 8 hours with stirring.

Incidentally, in the original peptide chain and reaction products, the N-acetylation to N-terminal amino group and the N-acetylation to the ε-position amino group of lysine residue (—NH—CH(CH$_2$CH$_2$CH$_2$CH$_2$NH$_2$)—CO—) remain as such even after said deprotection in the post-treatment step; in the digestion by trypsin, the cleavage of the C-terminal side peptide bond of N-acetylated lysine residue does not take place and there progresses only the cleavage of the C-terminal side peptide bond of arginine residue. The amino acid sequence which the globin peptide of horse myoglobin has is already known, and the original peptide chain having 153 amino acids, as shown in FIG. 7, when subjected to the digestion by trypsin at the arginine residues, produces fragments each containing a partial amino acid sequences of 1-31 amino acids, of 32-139 amino acids or of 140-153 amino acids. Therefore, a series of reaction products produced by the above-mentioned successive release of C-terminal amino acids, give a series of mass spectrum peaks reflecting the differences of molecular weights of C-terminal amino acids, together with that of said C-terminal fragment containing a partial amino acid sequence of 140-153 amino acids.

After the digestion by trypsin, the reaction mixture is subjected to desalting using ZipTip and then to separation and recovery of peptide fragments. These peptide fragments are subjected to lyophilization.

(Identification of Reaction Products Processed by Post-Treatment and Peptide Fragmentization by Means of Trypsin Digestion)

The mixture of the reaction products processed by post-treatment and peptide fragmentization by means of trypsin digestion and the C-terminal fragments of globin peptide chain, which are obtained by completion of a series of treatments, is subjected to mass spectrometry to determine the molecular weight of each peptide fragment contained in the mixture.

In this Example, the masses of the main ion species peaks reflecting the molecular weights of individual fragments and the relative peak intensities of the main ion species peaks are measured for the dried sample of peptide fragment mixture by using MALDI-TOF-MS apparatus, and then compared threrebetween. Incidentally, in the measurement by means of MALDI-TOF-MS apparatus, there are conducted two kinds of measurements for separation of ion species, i.e. a negative mode detection wherein negatively charged ion species are introduced into a detector and a positive mode detection wherein positively charged ion species are introduced into a detector. That is, as for the main ion species reflecting the molecular weights of individual peptide fragments, there are obtained two types of spectra corresponding to cationic species raised by proton (H$^+$) addition, in the positive mode detection, and anionic species raised by proton (H$^+$) elimination, in the negative mode detection.

Figure 3:
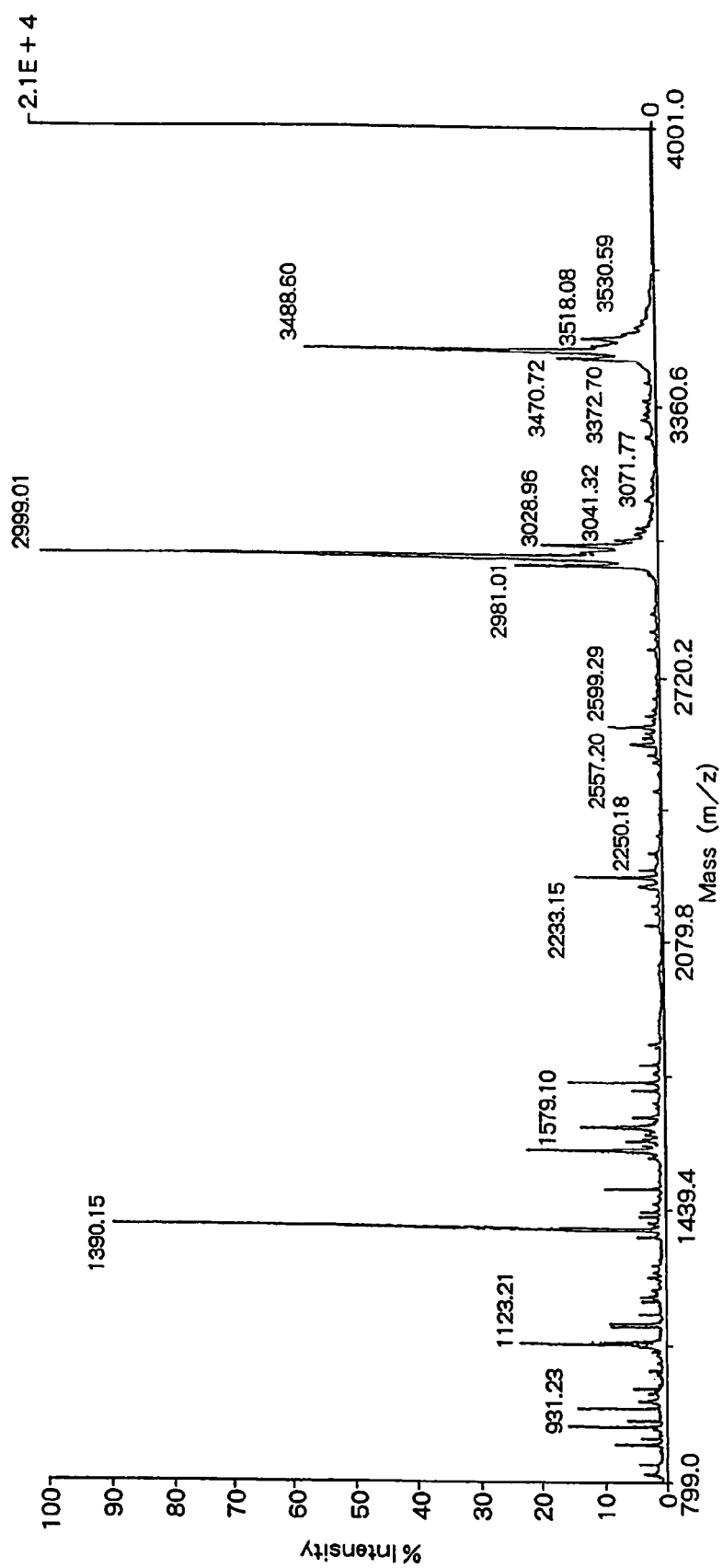
FIG. 3 is a chart showing an example of the mass spectrometry spectrum measured in cationic species detection mode by a MALDI-TOF-MS apparatus for the resulting peptide fragments that are obtained by the treatment process for successive release of C-terminal amino acids from the peptide according to the first aspect of the present invention, in which successive release of C-terminal amino acids of the globin peptide chain was conducted for a dry peptide sample of horse myoglobin, and then the obtained mixture of reaction products was subjected to the digestion by trypsin.
Figure 4:
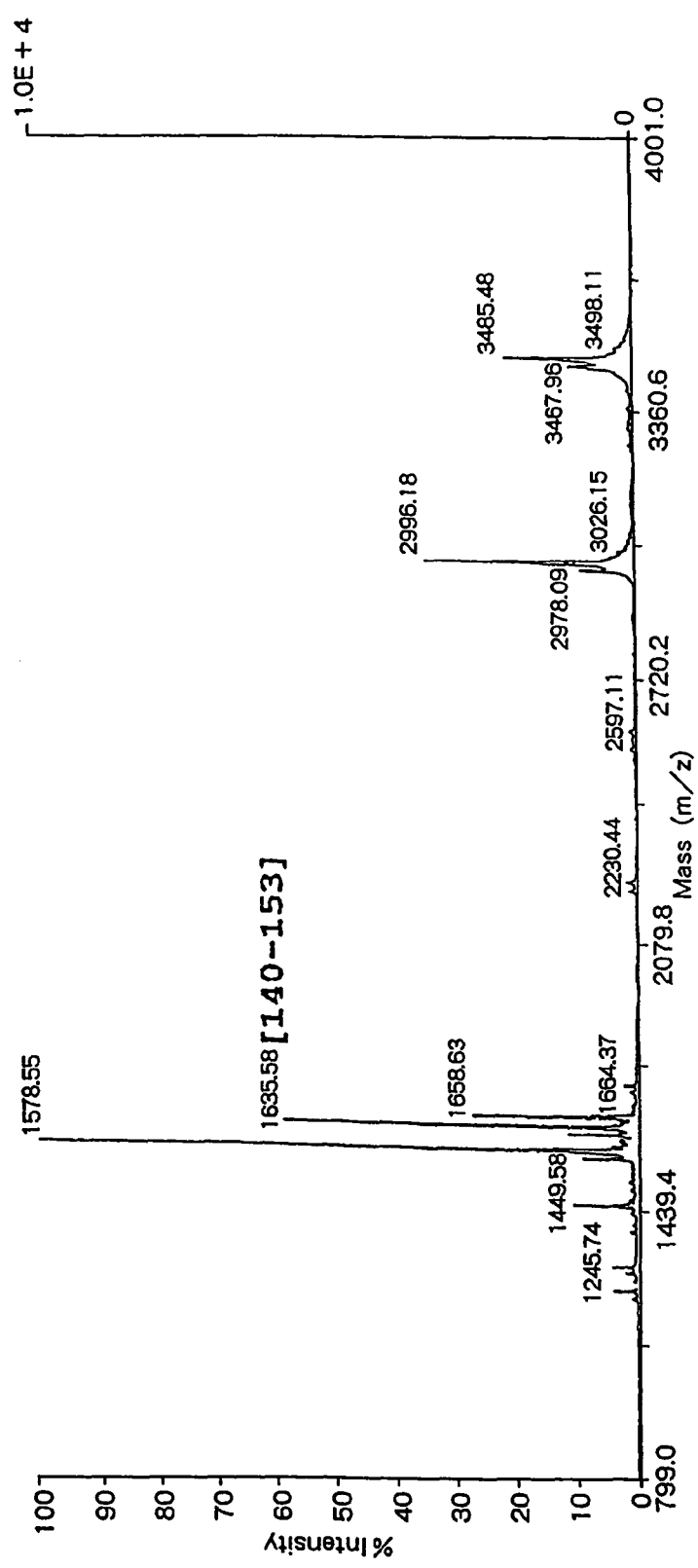
FIG. 4 is a chart showing an example of the mass spectrometry spectrum measured in anionic species detection mode by a MALDI-TOF-MS apparatus for the resulting peptide fragments that are obtained by the treatment process for successive release of C-terminal amino acids from the peptide according to the first aspect of the present invention, in which successive release of C-terminal amino acids of the globin peptide chain was conducted for a dry peptide sample of horse myoglobin, and then the obtained mixture of reaction products was subjected to the digestion by trypsin.

When there are compared the spectrum in the positive mode detection shown in FIG. 3 and the spectrum in the negative mode detection shown in FIG. 4, there are found, as two main peaks corresponding to the fragments due to digestion by trypsin, which are derived from the globin peptide chain of horse myoglobin, fragments each containing a partial amino acid sequence of 1-31 amino acids or a partial amino acid sequence of 140-153 amino acids, in such a molecular weight range. In the positive mode detection shown in FIG. 3, the peak of high relative intensity is judged to correspond to a N-terminal side peptide fragment having a partial amino acid sequence of 1-31 amino acids and having an arginine residue at the C-terminus and, in the negative mode detection shown in FIG. 4, the peak of high relative intensity is judged to correspond to a C-terminal side peptide fragment having a partial amino acid sequence of 140-153 amino acids and containing no arginine residue. There is further found a peptide fragment corresponding to a partial amino acid sequence of 78-102 amino acids, which is derived from partial amino acid sequence of 32-139 amino acids, by cleavage at the N-acetylation-dropped-off lysine residue therein; in the positive mode detection shown in FIG. 3, the intensity thereof exhibits a relatively high peak. Besides, peptide fragments resulting from trypsin autolysis are also found in such a molecular weight range and, in the positive mode detection shown in FIG. 3, their intensities give relatively high peaks as well.

In the peaks of the peptide fragments produced by trypsin autolysis, the half-widths are about 1.5. Each spike having a half-width extremely smaller than that is judged to be a spike-shaped noises and is not considered in the analysis which follows. Further, the mass spectrum information to be measured finally is recorded digitally and, prior to the reading of the central value of each peak, is subjected to removal of spike-shaped noises and a peak shape-smoothening treatment. In this case, there is selected a smoothening treatment which does not impair the shape and half-width of peak derived from trypsin, that is, a function approximation treatment of spectra shape. Further, the smoothening treatment after reading of each central value of peak, or the correction of the systematic reading error associated with the MALDI-TOF-MS apparatus used is conducted by applying an automatically programmed treatment based on the known central value of the peak derived from trypsin In the negative mode detection shown in FIG. 4, in addition to the C-terminal side peptide fragment of the partial amino acid sequence of 140-153 amino acids, the intensities for a series of C-terminal side peptide fragments derived from reaction products formed by successive release of C-terminal amino acids are also detected to be relatively high. In Table 4 is shown the result of identification of corresponding ion species conducted based on the measurements of FIG. 3 and FIG. 4. In Table 5 are shown the measured masses of the peaks, their differences from the mass of peak of C-terminal fragment of original globin peptide chain, as well as the amino acids identified therefrom which are removed in individual reaction product fragments and the forms of individual reaction products.

TABLE 4

| m/Z (M − H$^+$) | Relative peak intensity | m/Z (M + H$^+$) | Relative peak intensity | Assignment |
| --- | --- | --- | --- | --- |
|  |  | 931.23 | 16.03 | ? M = 930 |
|  |  | 1123.21 | 23.71 | ? M = 1122 |
| 1245.74 | 4.30 |  | Small peak | Mb C-term 140-149 |
| 1302.58 | Trace |  |  | Mb C-term 140-150 |
|  |  | 1388.13 | 15.14 |  |
|  |  | 1390.15 | 89.62 | ? M = 1389 |
|  |  | 1391.15 | 76.71 | +1 isotope |
|  |  | 1392.15 | 37.31 | +2 isotope |
| 1449.58 | 11.22 |  | Small peak | Mb C-term 140-151 |
| 1451.51 | 6.00 |  |  |  |
| 1559.48 | 8.76 |  |  |  |
| 1577.56 | 90.32 |  |  | −1(1578.55)? |
| 1578.55 | 100.00 | 1579.10 | 16.93 | Mb C-term 140-152 |
| 1579.53 | 67.34 |  |  | +1 isotope |
| 1616.59 | 10.91 |  |  |  |
| 1634.61 | 44.41 |  |  | −1(1635.58)? |
| 1635.58 | 59.08 |  | Small peak | Mb C-term 140-153 |
| 1636.55 | 42.72 |  |  | +1 isotope |
| 1658.63 | 27.62 |  |  |  |
| 1659.62 | 27.39 |  |  |  |
| 1664.37 | 3.32 |  |  |  |
|  |  | 1741.11 | 15.68 |  |
|  |  | 2119.11 | 3.08 |  |
| 2230.44 | 2.44 | 2233.15 | 14.43 |  |
|  |  | 2250.18 | 4.16 |  |
|  |  | 2557.20 | 4.99 |  |

TABLE 4-continued

| m/Z (M − H$^+$) | Relative peak intensity | m/Z (M + H$^+$) | Relative peak intensity | Assignment |
| --- | --- | --- | --- | --- |
| 2597.11 | 1.62 | 2599.28 | 8.66 |  |
| 2978.09 | 9.36 | 2981.00 | 23.21 |  |
| 2996.18 | 34.86 | 2999.01 | 100.00 | Mb 78-102 |
| 3026.15 | 3.32 | 3028.96 | 19.02 |  |
|  |  | 3041.32 | 7.10 | +42(2999)? |
|  |  | 3071.77 | 3.64 |  |
|  |  | 3372.70 | 2.06 |  |
| 3451.11 | 3.36 |  |  |  |
| 3467.96 | 10.87 | 3470.72 | 16.10 | −18(3488)? |
| 3485.48 | 21.33 | 3488.60 | 56.72 | Mb N-term 1-31 |
| 3498.11 | 4.57 | 3501.15 | 10.50 |  |
| 3514.96 | 3.44 | 3518.08 | 12.08 |  |
|  |  | 3530.59 | 5.55 |  |

TABLE 5

| m/Z | Δm | Assignment | Corresponding peptide structure |
| --- | --- | --- | --- |
| 1636.58 | — |  | NDIAAK(Ac)YK(Ac)ELGFGQ |
| 1578.55 | 58.03 | -Gly | NDIAAK(Ac)YK(Ac)ELGFG |
| 1449.58 | 187.00 | -Gln-Gly | NDIAAK(Ac)YK(Ac)ELGF |
| 1302.58 | 334.00 | -Phe-Gln-Gly | NDIAAK(Ac)YK(Ac)ELG |
| 1245.74 | 390.84 | -Gly-Phe-Gln-Gly | NDIAAK(Ac)YK(Ac)EL |

By the process for the treatment using a vapor-phase reagent used in the present example 1, a series of reaction products are obtained in which the four amino acids; i.e. glycine, glutamine, phenylalanine and glycine are sequentially eliminated from the C-termini thereof by the treatment for the successive release of C-terminal amino acids. Incidentally, in the negative mode detection shown in FIG. 4 are observed, besides these peaks including that of the C-terminal peptide fragment containing the partial amino acid sequence of 140-153 amino acids described above, two peaks (m.w.: 2996.18, 3485.48) corresponding to peptide fragments of 1-31 amino acid portion and 78-102 amino acid portion, produced by the digestion by trypsin. However, there is not found, in such a molecular weight range, any peptide fragment which can be judged to have been secondarily produced by digestion by trypsin in association with deprotection of lysine residue, other than the fragment of 78-102 amino acid portion. Therefore, by comparing the positive mode detection shown in FIG. 3 with the negative mode detection shown in FIG. 4, there can be easily distinguished the ion species corresponding to the peptide fragments each having an arginine residue at the C-terminus and the peptide fragments each having an N-acetylation-dropped-off lysine residue at the C-terminus, which are both produced by digestion by trypsin. On the other hand, many kinds of peptide fragments caused by digestion by trypsin at lysine residue do not co-exist in such a molecular weight range. Accordingly, when identifying intended C-terminal peptide fragments and a series of C-terminal peptide fragments associated therewith, which are treated for the successive release of C-terminal amino acids, it is easier to conduct such discrimination.

Example 2

In order to verify the usefulness of the method for analysis of the C-terminal amino acid sequence of peptide according to the second aspect of the present invention, analysis of C-terminal amino acid sequence of was conducted for globin peptide chain bound on the gel carrier, which is a protein component of horse myoglobin that is a heme protein comprising 153 amino acids.

In this Example, horse myoglobin, which is used as a sample to be analyzed, was subjected to gel electrophoresis by SDS-PAGE method, using a polyacrylamide gel, to separate the globin peptide chain thereof as a single spot. Then, the accuracy of the identification was verified for its C-terminal amino acid sequence determined by the method of analysis according the present invention.

(Isolation by Gel Electrophoresis)

First, as for a commercially available horse myoglobin standard product, a peptide solution is prepared which contains only the globin peptide chain portion thereof at a concentration of 0.2 μg/μl. Incidentally, the globin peptide chain portion of horse myoglobin contains no cystine residue unlike human myoglobin; however, if there is used a peptide containing cystine residue, like human myoglobin, an anti-oxidation treatment is applied beforehand in order to avoid formation of —S—S— bond due to the oxidation of the sulfanyl group (—SH) of the cystine residue, by, for example, adding a reducing reagent such as 2-sulfanylethanol (HS—$C_2H_2$—OH: 2-mercaptoethanol) or DTT (dithiothreitol: threo-1,4-disulfanyl-2,3-butanediol).

This peptide solution is spotted on a polyacrylamide gel with gel concentration of 12.5% by mass, followed by electrophoresis. Then, Coomassie staining was conducted to identify a band of intended globin peptide chain. In this Example, the stained band portion of gel is cut out and the resulting gel slice is subjected to a series of operations described below.

(Dehydration of Gel)

The gel slice is placed in an air-tight tube; 1 ml of acetonitrile is poured thereinto; stirring is made for 15 minutes. Then, the acetonitrile is discarded; 1 ml of acetonitrile is added newly; stirring is made again for 15 minutes. This extraction treatment of water included in the gel by using acetonitrile is repeated three times in total to complete dehydration treatment of the gel. With the dehydration treatment of the gel, the gel volume contracts.

(Pre-Treatment Operation)

Next, to the dehydrated gel slice in the tube is added 1 ml of a solution containing 10% by volume of acetic anhydride in formamide. The tube that is sealed up tightly in a dry atmosphere, and then the temperature of whole tube is heated up to 50° C. with stirring. It is further held at that temperature for 3 hours.

During this period for keeping in the heated-up condition, the gel in contraction reswells owing to the infiltration of formamide solvent and returns to its original volume. The acetic anhydride solute acts on the globin peptide chain bound on the reswollen gel at said heated-up temperature. As a result, there proceeds selective acetylation reaction to the N-terminal amino group of the peptide. In addition, there take place coincidentally N-acetylation to the $\epsilon$-position amino group of the lysine residue (—NH—CH(CH$_2$CH$_2$CH$_2$CH$_2$NH$_2$)—CO—) contained in the peptide chain; O-acetylation to the hydroxy groups present in the serine residue (—NH—CH(CH$_2$OH)—CO—) and the threonine reside (—NH—CH(CH$_3$)OH)—CO—); and O-acetylation to the phenolic hydroxy group of the tyrosine residue (—NH—CH(CH$_2$—C$_6$H$_4$—OH)—CO—).

After performing the above-mentioned protection with N-acetylation to N-terminal amino group as well as N-acetylation/O-acetylations to side chains of amino acid residues, the solution of acetic anhydride in formamide is removed; 1 ml of acetonitrile is poured into the tube; stirring is conducted for 15 minutes. Then, the acetonitrile is discarded; 1 ml of acetonitrile is added newly; stirring is made again for 15 minutes. This extraction of formamide solution included in the gel by using acetonitrile is conducted three times in total to complete the treatment for removing the solvent (formamide) in the reswollen gel. With the treatment for solvent removal, the gel volume contracts and simultaneously the gel is dehydrated.

(Operation of the Reaction for Release of C-Terminal Amino Acids)

Next, as shown in the process of FIG. 2, there is conducted reswelling of the gel contracted by said dehydration treatment and infiltration of reaction reagent into gel. Specifically explaining, into the tube containing the gel slice, in which the globin peptide chain that is subjected to modification and protection by means of acetylation is kept in a bound state on gel, is poured 1 ml of a solution containing 1% by volume of heptafluorobutanoic acid (HFBA: $C_3F_7COOH$) and 10% by volume of acetic anhydride in formamide. The tube that is sealed up tightly in a dry atmosphere, and then the temperature of whole tube is heated up to 40° C. with stirring. It is further held at the same temperature for 16 hours.

During this period for keeping in the heated-up condition, the gel in contraction reswells owing to the infiltration of formamide solvent and returns to its original volume. HFBA and acetic anhydride act on the C-terminus of the peptide chain bound on the reswollen gel, at said heated-up temperature, whereby the reaction for selective release of C-terminal amino acids of peptide chain proceeds. It is presumed specifically that the reaction of successive release of C-terminal amino acids of peptide chain via formation of 5-oxazolone ring may progress through the stages of reaction shown by the reaction schemes (Ia) to (II') illustrated above. At each of the reaction stages of successive release, reaction is promoted by the catalysis of HFBA, which functions as a proton donor in formamide that is a dipolar solvent.

The reaction for successive release of C-terminal amino acids proceeds in the gel and, as a result, there remains, in a state bound on the gel carrier, a mixture containing a series of reaction products, from which C-terminal amino acids are eliminated stepwisely, and an original peptide chain with modification and protection by acetylation, which is left yet in the stage of converting into the 5-oxazolone structure for the initial step. The formamide solution containing unreacted acetic anhydride, HFBA, etc., remaining in the tube is removed; 1 ml of acetonitrile is poured into the tube; stirring is made for 15 minutes. Then, the acetonitrile is discarded; 1 ml of acetonitrile is poured newly; stirring is conducted again for 15 minutes. This extraction of formamide solution included in the gel by using acetonitrile is carried out three times in total to remove the solvent (formamide) in the reswollen gel. With the treatment for solvent removal, the gel volume contracts and simultaneously the gel is dehydrated.

(Post-Treatment Operation)

Next, into the tube containing a gel slice in a state that the mixture containing the reaction products is bound thereon is poured 1 ml of an aqueous solution containing 10% by volume of DMAE ((CH$_3$)$_2$N—CH$_2$CH$_2$OH). The tube is sealed tightly and then the whole tube is heated up to 60° C., and kept at the temperature for 1 hour with stirring. In this case, the dehydrated gel reswells quickly owing to the infiltration of water solvent and returns to its original volume. Water molecules act, in the presence of the basic nitrogen-containing organic compound and at said heated-up temperature, on the peptide chain and reaction products bound on the reswollen gel, whereby treatment for hydration proceeds.

As, in said mixture, the C-termini of the reaction product peptides are in a mixture state including those staying in the 5-oxazolone structure, or being advanced even to conversion into an asymmetric acid anhydride therefrom, other than those being converted into carboxy group, the treatment for hydration of the post-treatment is a treatment mainly aiming to convert them into a state where all the C-termini of the peptides have turned carboxy groups by applying treatment for hydrolysis to them. Further, since the basic nitrogen-containing organic compound functions as a basic catalyst, there occur, on the peptide chain modified and protected by acetyl group, hydrolysis of the O-acetylation protection to the hydroxy groups present in the serine residue (—NH—CH(CH$_2$OH)—CO—) and the threonine residue (—NH—CH(CH(CH$_3$)OH)—CO—) to finish deprotection thereof; similarly, hydrolysis of the O-acetylation protection to the phenolic hydroxy group of tyrosine residue (—NH—CH(CH$_2$—C$_6$H$_4$—OH)—CO—) proceeds as well. However, since the basicity of the organic base used is not high, deprotection of N-acetylation protection does not proceed and, after the post-treatment, there remain, at a higher selectivity, the N-acetylation to N-terminal amino group and the N-acetylation to the $\epsilon$-position amino group of lysine residue (—NH—CH(CH$_2$CH$_2$CH$_2$CH$_2$NH$_2$)—CO—). In some cases, there only slightly remains the O-acetylation to the phenolic hydroxy group of tyrosine residue (—NH—CH(CH$_2$—C$_6$H$_4$—OH)—CO—).

After the end of such post-treatment, the aqueous solution remaining in the tube is removed; 1 ml of acetonitrile is poured into the tube; stirring is made for 15 minutes. Then, the acetonitrile is discarded; 1 ml of acetonitrile is poured newly; stirring is made again for 15 minutes. This extraction of aqueous solution included in the gel by using acetonitrile is conducted three times in total to complete the treatment for dehydration of the reswollen gel. With the treatment for dehydration, the gel volume contracts.

(Fragmentization of Peptide by Digestion with Trypsin)

The globin peptide chain of horse myoglobin is composed of 153 amino acids and its molecular weight deviates from an appropriate molecular weight range in mass spectrometry; therefore, the treatment for peptide fragmentation by means of the digestion by trypsin is applied to it.

Specifically explaining, into the tube containing the gel slice dehydrated by application of said post-treatment is added an aqueous solution containing trypsin and, in a state of peptide chain bound on gel carrier, fragmentation of the peptide chain is carried out. As said aqueous solution containing trypsin is containing trypsin at a concentration of 0.067 µg/µl in an ammonium bicarbonate buffer (pH 8), the enzymatic reaction is performed at 37° C. for 4 hours with stirring to achieve the digestion by trypsin. In this case, the dehydrated gel reswells quickly owing to the infiltration of water solvent and returns to its original volume. At the heated-up temperature, said trypsin, together with the buffer solution, penetrates into the gel and acts on the peptide chain and reaction products bound on the reswollen gel, whereby trypsin-specific enzymatic digestion proceeds.

Incidentally, in the peptide chain and reaction products, the N-acetylation to N-terminal amino group and the N-acetylation to the $\epsilon$-position amino group of lysine residue (—NH—CH(CH$_2$CH$_2$CH$_2$CH$_2$NH$_2$)—CO—) remain as such even after said deprotection in the step of the post-treatment; in the digestion by trypsin, the cleavage of the C-terminal side peptide bond of the N-acetylated lysine residue does not take place and there proceeds the cleavage of the C-terminal side peptide bond of arginine residue. The amino acid sequence that the globin peptide chain of horse myoglobin has is already known as shown in FIG. 7, and as the result of cleavage of the C-terminal side peptide bond of arginine residue, the original peptide chain composed of 153 amino acids is digested by trypsin into the fragments each containing partial amino acid sequences of 1-31 amino acids, of 32-139 amino acids and of 140-153 amino acids. Incidentally, in FIG. 7, the lysine residues to be protected by N-acetylation in the pre-treatment operation are shown in a dotted state; and the partial amino acid sequences of N-terminal side 1-31 amino acids and C-terminal side 140-153 amino acids, which are to be produced by the cleavage of C-terminal side peptide bond of each arginine residue due to the digestion by trypsin, are shown in bold type.

When the fragmentization is made by digestion by trypsin, the peptide fragments are easily eluted from the gel carrier and dissolve away into the trypsin solution in the tube. Incidentally, in the step of the treatment for digestion by trypsin, together with the C-terminal fragment containing a partial amino acid sequence of 140-153 amino acids, the C-terminal fragments that are derived from a series of reaction products formed by the treatment for successive release of C-terminal amino acids dissolve away into the trypsin solution in the tube. Therefore, the digestion treatment by trypsin makes it possible to cleave off the C-terminal portion from the peptide chains of long amino acid length, resulting in the peptide fragments ranging within a desired molecular weight range suitable for mass spectrometry and also makes it possible to elute these peptide fragments away from inside the gel and recover in high yield.

At the end of step of digestion treatment by trypsin, peptide fragments dissolving into the trypsin solution in the tube are recovered from inside the gel. The solution containing a mixture of peptide fragments recovered is subjected to desalting and then lyophilized.

(Identification of Reaction Products Processed by Post-Treatment and Peptide Fragmentation by Means of Trypsin Digestion)

The mixture of the reaction products processed by post-treatment and peptide fragmentation by means of trypsin digestion and the C-terminal fragments of globin peptide chain, which are obtained by completion of a series of treatments, is subjected to mass spectrometry to determine the molecular weight of each peptide fragment contained in the mixture.

In this Example as well, the masses of the main ion species peaks reflecting the molecular weights of individual fragments and the relative peak intensities of the main ion species peaks are measured for the desalted and dried sample of peptide fragment mixture by using MALDI-TOF-MS apparatus, and then compared threrebetween. Incidentally, in the measurement by means of MALDI-TOF-MS apparatus, there are conducted two kinds of measurements for separation of ion species, i.e. a negative mode detection wherein negatively charged ion species are introduced into a detector and a positive mode detection wherein positively charged ion species are introduced into a detector. That is, as for the main ion species reflecting the molecular weights of individual peptide fragments, there are obtained two types of spectra corresponding to cationic species raised by proton (H$^+$) addition, in the positive mode detection, and anionic species raised by proton (H$^+$) elimination, in the negative mode detection.

Figure 5:
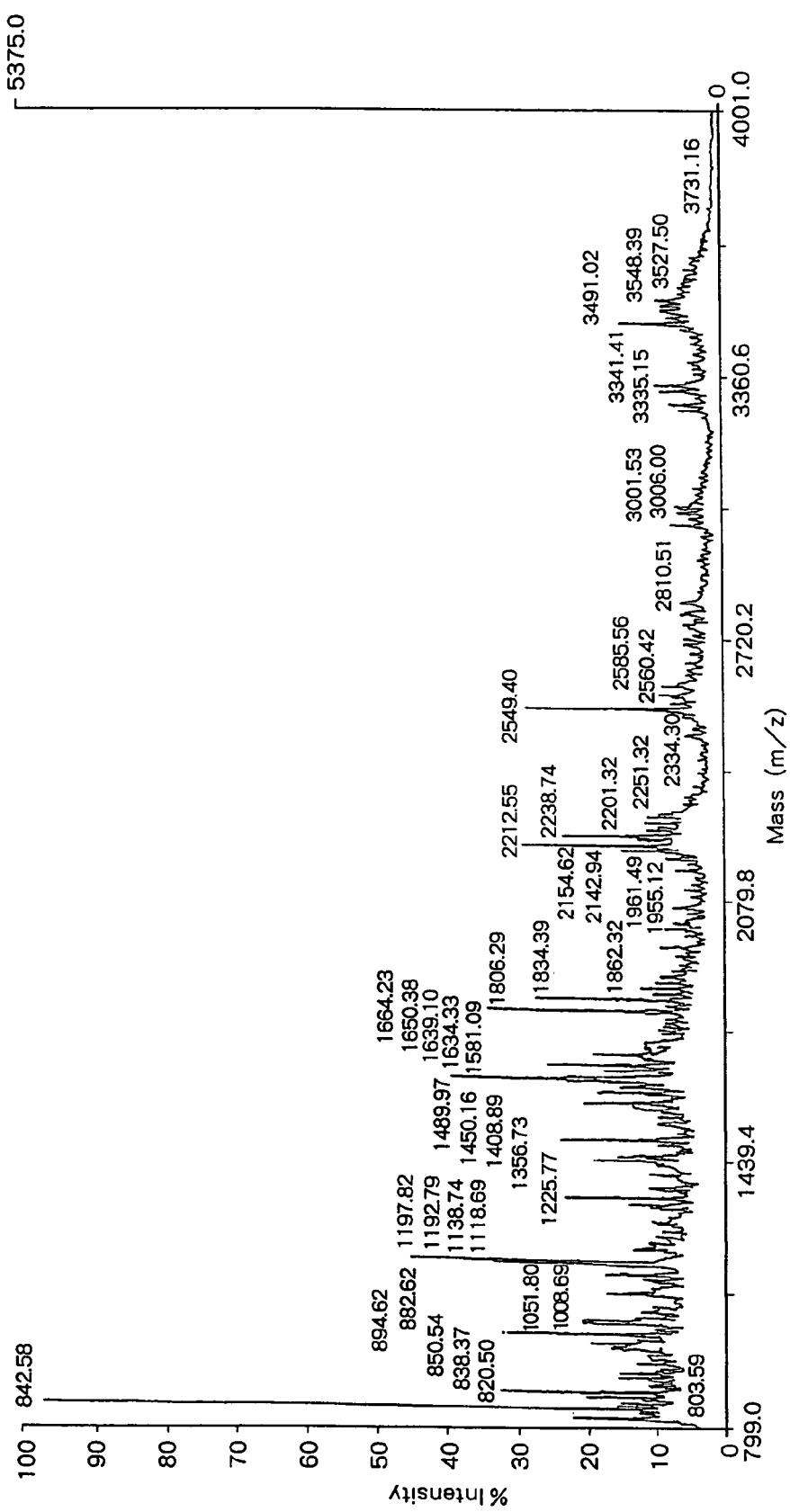
FIG. 5 is a chart showing an example of the mass spectrometry spectrum measured in cationic species detection mode by a MALDI-TOF-MS apparatus for the resulting peptide fragments that are obtained by the treatment process for successive release of C-terminal amino acids from the peptide according to the second aspect of the present invention, in which successive release of C-terminal amino acids of the globin peptide chain was conducted for a sample of horse myoglobin bound on the gel, and then the obtained mixture of reaction products was subjected to the digestion by trypsin.
Figure 6:
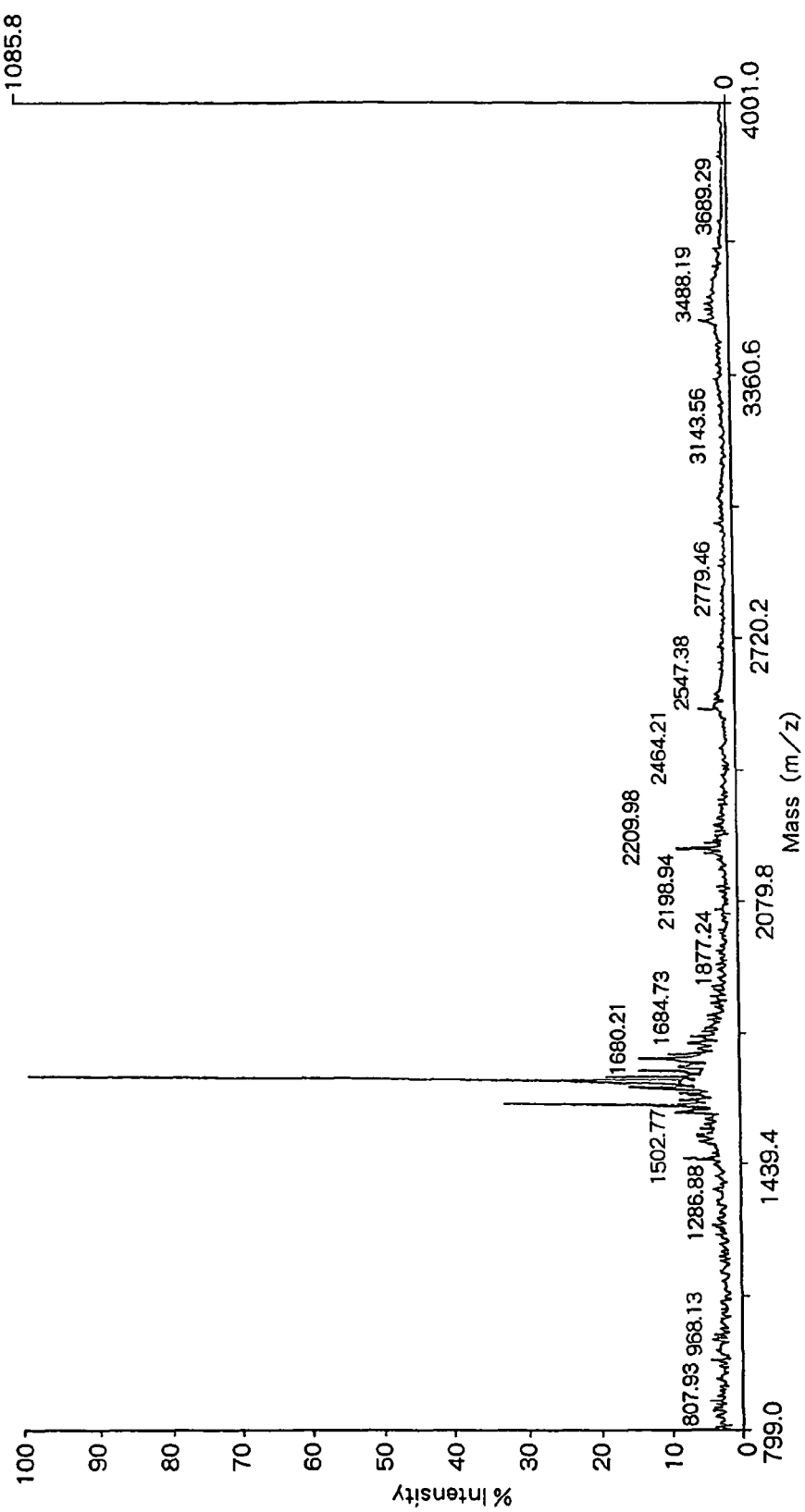
FIG. 6 is a chart showing an example of the mass spectrometry spectrum measured in anionic species detection mode by a MALDI-TOF-MS apparatus for the resulting peptide fragments that are obtained by the treatment process for successive release of C-terminal amino acids from the peptide according to the second aspect of the present invention, in which successive release of C-terminal amino acids of the globin peptide chain was conducted for a sample of horse myoglobin bound on the gel, and then the obtained mixture of reaction products was subjected to the digestion by trypsin.

In Example 2 as well, when there are compared the spectrum in the positive mode detection shown in FIG. 5 and the spectrum in the negative mode detection shown in FIG. 6, there are found, as two main peaks corresponding to the fragments due to digestion by trypsin, which are derived from the globin peptide chain of horse myoglobin, fragments each containing a partial amino acid sequence of 1-31 amino acids or a partial amino acid sequence of 140-153 amino acids, in such a molecular weight range. In the positive mode detection shown in FIG. 5, the peak of high relative intensity is judged to correspond to a N-terminal side peptide fragment having a partial amino acid sequence of 1-31 amino acids and having an arginine residue at the C-terminus and, in the negative mode detection shown in FIG. 6, the peak of high relative intensity is judged to correspond to a C-terminal side peptide fragment having a partial amino acid sequence of 140-153 amino acids and containing no arginine residue. There is further found a peptide fragment corresponding to a partial amino acid sequence of 78-102 amino acids, which is derived from partial amino acid sequence of 32-139 amino acids, by cleavage at the N-acetylation-dropped-off lysine residue therein; in the positive mode detection shown in FIG. 5, the intensity thereof exhibits a relatively high peak. Besides, peptide fragments resulting from trypsin autolysis are also found in such a molecular weight range and, in the positive mode detection shown in FIG. 5, their intensities give relatively high peaks as well.

In the negative mode detection shown in FIG. 6, in addition to the C-terminal side peptide fragment of the partial amino acid sequence of 140-153 amino acids, the intensities for a series of C-terminal side peptide fragments derived from reaction products formed by successive release of C-terminal amino acids are also detected to be relatively high. In Table 6 are shown the measured masses of the peaks, their differences from the mass of peak of C-terminal fragment of original globin peptide chain, as well as the amino acids identified therefrom which are removed in individual reaction product fragments and the forms of individual reaction products.

TABLE 6

| m/Z | Δm | Assignment | Corresponding peptide structure |
|---|---|---|---|
| 1636.55 | — |  | NDIAAK(Ac)YK(Ac)ELGFGQ |
| 1578.49 | 58.06 | -Gly | NDIAAK(Ac)YK(Ac)ELGFG |
| 1450.52 | 186.03 | -Gln-Gly | NDIAAK(Ac)YK(Ac)ELGF |

In the process for treatment with use of a reaction reagent solution using a dipolar aprotic solvent of the present Example 2, there are identified as well peaks derived from the reaction products in which the two amino acids; i.e. glycine and glutamine are sequentially eliminated from the C-termini thereof by the treatment for the successive release of C-terminal amino acids. That is, it is verified that the to-be-analyzed peptide chain that is separated as a band on the aforementioned gel slice is indeed a globin peptide chain and the successive release of C-terminal amino acids can be conducted in a bound-on-gel state.

It is confirmed that also when there is employed the method for analysis of C-terminal amino acid sequence according to the second aspect of the present invention and the successive release of C-terminal amino acids is conducted in a state that the peptide chain to be analyzed is bound on a gel, substantially comparable analysis accuracy is achieved.

Reference Example 1

In the method for analysis of the C-terminal amino acid sequence of peptide according to the present invention, a peptide chain is subjected to digestion by trypsin in a state that the side chain of lysine residue has been protected by N-acylation and, as a result, whereby the obtained common peptide fragments of N-terminal side amino acid sequence are all the peptide fragments having an arginine residue at the C-terminus; this phenomenon is utilized for distinguishment of them from the C-terminal side peptide fragments. It was verified that even if a peptide chain to be analyzed has arginine at the C-terminus, C-terminal side peptide fragments derived from a series of reaction products can be identified by obtaining, as the spectra of the main ion species reflecting the molecular weights of individual peptide fragments in measurement by means of MALDI-TOF-MS apparatus, spectra of proton ($H^+$)-added cationic species in the positive mode detection and spectra of proton ($H^+$)-eliminated anionic species in the negative mode detection and then comparing those two with each other.

In this Reference Example, analysis of the C-terminal amino acid sequence of peptide was conducted for a peptide composed of 14 amino acids wherein the N-terminal amino group of the peptide had been protected by N-acetylation, i.e. an N-acetylated $Glu^1$-Fibrino peptide fragment.

(Operation for Successive Release of C-Terminal Amino Acids)

A vial holding a dried sample of said peptide (Ac-EGVNDNEEGFFSAR) obtained by the treatment for N-acetylation is set in a glass-made reactor of air-tight test tube type with fitting stopper. Into this glass-made reactor is added a predetermined amount of the following liquid reagent.

As the liquid reagent for selective release of C-terminal amino acids, there is used 300 μl of acetic anhydride with 5% by volume of trifluoroacetic acid added thereto. After the vial containing the dried peptide sample is set in the glass-made reactor, the reactor inside is evacuated under cooling condition and then sealed in an air-tight state.

The whole reactor of air-tight state is kept at 40° C. for 16 hours to allow acetic anhydride and trifluoroacetic acid both of vapor phase, supplied from the liquid reagent in the reactor, to act on the dried sample.

After finishing the treatment for selective release of C-terminal amino acids, the unreacted acetic anhydride, trifluoroacetic acid, etc. remaining in the reactor are distilled off under reduced pressure and the resulting mixture of residual N-acetylated $Glu^1$-Fibrino peptide sample and the obtained reaction products is dried.

(Post-Treatment Operation)

Next, in a state that the vial holding the dried sample of a mixture containing the reaction products is set in a glass-made reactor of air-tight test tube type with fitting stopper, a given amount of the following liquid reagent is placed anew in the glass-made reactor.

In this Reference Example 1, as the liquid reagent for the post-treatment for hydrolysis, there is used 300 μl of an aqueous solution in which 10% by volume of pyridine is dissolved; and after the vial containing the dried peptide sample is set in said glass-made reactor, the reactor inside is evacuated under cooling condition and then sealed in an air-tight state.

The whole reactor of air-tight state is kept at 100° C. for 30 minutes to allow pyridine and water molecules both of vapor phase, supplied from the liquid reagent in the reactor, to act on the dried sample. Under such conditions, the protection with O-acetylation to serine residue is deprotected, but hydrolysis for the amide bond of N-terminal protection with N-acetylation does not take place. Therefore, the reaction products obtained by this post-treatment are N-acetylated peptides, which are modified with an acetyl group at the N-termini thereof.

After such post-treatment, the water molecules, pyridine, etc. remaining in the reactor are distilled off under reduced pressure and the resulting mixture of N-acetylated Glu¹-Fibrino peptide fragments and the obtained reaction products after post-treatment is dried.

(Identification of Reaction Products Processed by the Post-Treatment)

As for the mixture of the reaction products after post-treatment and the original peptide fragment, which is obtained by the above-mentioned series of chemical treatments, there are obtained by using MALDI-TOF-MS apparatus, two kinds of corresponding spectra as to the main ion species reflecting the molecular weights of individual peptide fragments; i.e. in the positive mode detection, as to proton ($H^+$)-added cationic species and, in the negative mode detection, as to proton ($H^+$)-eliminated anionic species.

The two kinds of spectra shown in FIG. 8 are compared. In the positive mode detection, the intensity for the original peptide fragment having a 1-14 amino acid sequence is relatively high, and it is confirmed that it contains an arginine residue. Furthermore, in the negative mode detection is observed a peak corresponding to the molecular weight in which an arginine residue is eliminated by release; however, in the positive mode detection, no corresponding peak is found clearly. Accordingly, it is confirmed that the original peptide fragment having a 1-14 amino acid sequence has an arginine residue at the C-terminus and the intensity therefor is relatively high in the positive mode detection but, in the negative mode detection, ion species from a series of reaction products, which are accompanying therewith, are found and also there is included a peak corresponding to the molecular weight in which an arginine residue is eliminated by release, which indicates that they undergo the successive release of C-terminal amino acids. In Table 7 are shown the masses of measured peaks, their differences from the mass of peak originated from the original peptide chain, as well as the amino acids identified therefrom which are removed in individual reaction product fragments and the forms of individual reaction products.

TABLE 7

| m/Z | Δm | Assignment | Corresponding peptide structure |
| --- | --- | --- | --- |
| 1610.68 | — | 1-14 | Ac-EGVNDNEEGFFSAR |
| 1454.58 | 156.10 | -Arg | Ac-EGVNDNEEGFFSA |
| 1383.54 | 227.14 | -Ala-Arg | Ac-EGVNDNEEGFFS |
| 1296.51 | 314.17 | -Ser-Ala-Arg | Ac-EGVNDNEEGFF |
| 1149.44 | 461.24 | -Phe-Ser-Ala-Arg | Ac-EGVNDNEEGF |

Thus, even when the amino acid sequence of original peptide chain has arginine at the C-terminus, it is verified that whether it is C-terminal side peptide fragment thereof or other peptide fragments derived from N-terminal side amino acid sequence can be judged at a high accuracy by scrutinizing the presence of the peak indicating the molecular weight decrease corresponding to the elimination of arginine residue, which is associated with the C-terminal side peptide fragment obtained by digestion by trypsin.

INDUSTRIAL APPLICABILITY

In the method for analysis of the C-terminal amino acid sequence of peptide according to the present invention, at the step of successive release of C-terminal amino acids of peptide, employed is such a process in which, in a state that protection with N-acylation is provided beforehand to the N-terminal amino group of the peptide chain and the amino group of the side chain of lysine residue side, and whereby coincidently protection with O-acylation is also provided to the hydroxy groups present in the serine residue (—NH—CH($CH_2OH$)—CO—) and the threonine residue (—NH—CH(CH($CH_3$)OH)—CO—), by acting a reaction reagent that is a combination of an alkanoic acid anhydride and a small amount of a perfluoroalkanoic on a target peptide in a dry atmosphere under a mild temperature condition, release of C-terminal amino acid, which is associated to cleavage of the 5-oxazolone ring following to formation of 5-oxazolone structure, is carried out to prepare a series of reaction products. In such a technique, since the reactivity of the alkanoic acid anhydride used is low, any unnecessary side reaction such as cleavage of amide bond in the middle of peptide is not initiated thereby, and the successive release of C-terminal amino acids of peptide can be performed under a mild heated-up condition therewith. Further, since there is no cleavage of amide bond in the middle of peptide, it is possible to avoid incorporation of peptide fragments secondarily formed by cleavage of amide bond in the middle of peptide or reaction products originating from such secondary peptide fragments into the reaction products obtained. Furthermore, in the post-treatment, hydrolysis is conducted, in the presence of an organic basic compound, for the series of reaction products obtained by means of the reaction of such mild conditions, whereby they are converted to the fragments having each a carboxy group at the C-terminus, in which the protection with o-acylation is deprotected, but the protection with N-acylation on the N-terminal amino group of peptide chain and the amino group of the side chain of lysine residue is kept. Finally, digestion by trypsin is effected to conduct cleavage at the C-terminal side of each arginine residue while avoiding cleavage at the C-terminal side of lysine residue protected with N-acylation, to prepare, from a peptide chain of large amino acid length, C-terminal side peptide fragments of a molecular weight range suitable for detection by means of MALDI-TOF-MS apparatus; thereafter, there can be determined, at a high accuracy, a C-terminal amino acid sequence which is shortened by the successive release of C-terminal amino acids, based on a series of molecular weight decreases in the C-terminal side peptide fragments.

In addition, in the above-mentioned chemical treatment for successive release of C-terminal amino acids, the change in the amino acid length of peptide chain is at most about 10 amino acids; therefore, it is also possible to separate a target peptide by gel electrophoresis and, in a state that the peptide is bound on a gel carrier, advance the afore-mentioned chemical treatments for the peptide. Meanwhile, when digestion by trypsin is effected to give rise to peptide fragmentation, those peptide fragments having remarked short amino acid length can be no longer held on the gel carrier stably and thus it is possible to elute them easily from the gel carrier and recover thereby. Accordingly, since the present method has such advantages as excellent controllability in the successive release of C-terminal amino acids of peptide and mild reaction conditions, for instance, broad width of acceptable variation for the reaction temperature, and enables the analysis of C-terminal amino acid sequence at a high accuracy even for a peptide chain having long amino acid length, the method for analysis of the C-terminal amino acid sequence of peptide according to the present invention can be used as analyzing procedure with wider applicability.

The invention claimed is:

1. A method for analyzing, by means of mass spectrometry, the C-terminal amino acid sequence of a peptide to be examined, which method comprises the following steps:

a step of preparing a mixture containing a series of reaction products that are obtained from an original peptide to be examined by releasing the C-terminal amino acids successively by chemical means and the remains of the original peptide, a step of analyzing the differences in molecular weight between said series of reaction products and the original peptide by means of mass spectrometry to measure the decreases in molecular weight associated with the successive release of the C-terminal amino acids, and a step of identifying a series of the amino acids removed successively, based on a series of the measured decreases in molecular weight and arranging them from the C-terminus to obtain the information of the C-terminal amino acid sequence of the peptide, wherein said process for releasing the C-terminal amino acids successively comprises at least the following steps:

a pretreatment step for providing the protection by means of N-acylation in which N-acylation with the acyl group derived from the alkanoic acid anhydride is applied to the N-terminal amino group of the peptide as well as to the amino group on the side chain of the lysine residue which may be included in the peptide, a step of allowing an alkanoic acid anhydride to act on the dry sample of said peptide to be examined after N-acylation protection in the presence of a catalytic amount of a perfluoroalkanoic acid to release the C-terminal amino acids in association with a process that at the C-terminus of the peptide, the formation of a 5-oxazolone structure represented by the following general formula (III):

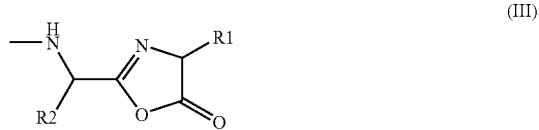

wherein R1 is a side chain of the C-terminal amino acid of the peptide and R2 is a side chain of the amino acid residue positioned just before the C-terminal amino acid, is followed by the cleavage of the 5-oxazolone ring, wherein the formation of the 5-oxazolone structure and the cleavage of the 5-oxazolone ring is carried out in parallel at the same temperature by using the alkanoic acid anhydride in the presence of the catalytic amount of the perfluoroalkanoic acid to successively release the C-terminal amino acids, and a hydrolysis treatment step which comprises applying, to a mixture containing a series of reaction products obtained in said step of releasing the C-terminal amino acids successively, a post-treatment of removing said remaining alkanoic acid anhydride and perfluoroalkanoic acid therefrom, and then allowing water molecules to act thereto in the presence of a catalytic amount of a basic, nitrogen-containing, aromatic compound or a tertiary amine compound to give rise to a hydrolysis reaction, wherein the hydrolysis reaction is carried out by using the water molecules in the presence of a catalytic amount of the basic, nitrogen-containing, aromatic compound or the tertiary amine compound, whereby the mixture containing the series of reaction products having a carboxyl group at their C-terminal as well as the remains of the original peptide having a carboxyl group at its C-terminus are prepared as a sample to be used for the analysis by means of MALDI-TOF-MS, wherein said step of measuring the decreases in molecular weight associated with the successive release of the C-terminal amino acids employs a technique which comprises:

allowing trypsin to act on the sample in a buffer solution to carry out the treatment for the enzymatic digestion specific to trypsin of said peptide chain which holds N-acylation protection as for the N-terminal amino group of the peptide chain as well as to the amino group on the side chain of the lysine residue that may be contained in the peptide chain, and thereby, conducting selective cleavage of the C-terminal side peptide bond of each arginine residue that present in the peptide chain to complete peptide fragmentization, applying a desalting treatment to remove the buffer solution component, followed by recovering and drying the peptide fragments after the digestion treatment by trypsin, next, conducting, as for the dried mixture containing said peptide fragments recovered after the digestion treatment by trypsin, molecular weight measurement for the cationic species of $(M+H)^+$ as well as molecular weight measurement for the anionic species of $(M-H)^-$ both of which are generated from the ionization treatment by means of MALDI-TOF-MS, with respect to the corresponding mass spectra of the ion species, which are measured in said molecular weight measurement for the cationic species of $(M+H)^+$ as well as molecular weight measurement for the anionic species of $(M-H)^-$, judging that the peaks of the peptide fragments each having an arginine residue at the C-terminus, which fragments are produced by said digestion treatment by trypsin, are peaks that give such intensities that the intensity in the molecular weight measurement for the cationic species of $(M+H)^+$ is relatively larger in comparison with the intensity in the molecular weight measurement for the anionic species of $(M-H)^-$, and judging that the peaks of the C-terminal peptide fragment derived from the original peptide and the C-terminal peptide fragments derived from a series of the reaction products that are obtained by successive release of the C-terminal amino acids, which fragments are produced by said digestion treatment by trypsin, are peaks that give such intensities that the intensity in the molecular weight measurement for the anionic species of $(M-H)^-$ is relatively larger in comparison with the intensity in the molecular weight measurement for the cationic species of $(M+H)^+$, and based on a series of the peaks that gives a relatively larger intensity in the molecular weight measurement for the anionic species of $(M-H)^-$, measuring the decreases in molecular weight associated with the successive release of the C-terminal amino acids;

wherein the step of analysis of the spectra, in which the range to be analyzed for the analysis operation of spectra is selected within m/z value of 4,000 or less, comprises the following Steps 1 to 9:

(Step 1) a step for identification of internal standard peaks derived from trypsin, which comprises:

with respect to the peptide fragments derived from the autolysis of trypsin having a known molecular weight, which are concomitant with the digestion treatment with trypsin used for peptide fragmentization, and incorporated into the dry mixture containing the peptide fragments, identifying the peaks of the cationic species of $(M+H)^+$ due to the peptide fragments derived from trypsin autolysis, in a m/z value range of 4,000 to 500 of the result of the molecular weight measurements for the cationic species of $(M+H)^+$, then, identifying the peaks of the corresponding anionic species of $(M-H)^-$ due to the peptide fragments resulting from trypsin autolysis in a m/z range of 4,000 to 500 of the result of the molecular weight measurements for the anionic species of $(M-H)^-$;

(Step 2) a step for identification of major ion species peaks, which comprises:

excluding said peaks assigned for the cationic species leaks derived from trypsin from the result of molecular weight measurements for cationic species, identifying the highest peak of cationic species having the highest peak intensity, in a m/z value range of 4,000 to 500, and by using the peak intensity of the highest peak of cationic species as a basis, selecting peaks of cationic species each having a peak intensity of 1/40 or more relative to the basis to make up the first group of cationic species peaks therewith, next to that, excluding said peaks assigned for the anionic species peaks derived from trypsin from the result of molecular weight measurements for anionic species identifying the highest peak of anionic species having the highest peak intensity, in a m/z value range of 4,000 to 500, and by using the peak intensity of the highest peak of anionic species as a basis, selecting anionic species peaks each having a peak intensity of 1/40 or more relative to the basis to make up the first group of anionic species peaks therewith, (Step 3) a step for identification of counter ion species peaks for the major ion species peaks, which comprises:

identifying, in the result of the molecular weight measurements for anionic species, peaks due to anionic species each corresponding to each peak of said first group of cationic species peaks to make up the second group of anionic species peaks therewith, next to that, identifying, in the result of the molecular weight measurements for cationic species, peaks due to cationic species each corresponding to each peak of said first group of anionic species peaks to make up the second group of cationic species peaks therewith, (Step 4) a step for identification of major ion species peaks having significant counter-ionic species, which comprises:

making up the overlapping group between the first group of anionic species peaks and the second of anionic species peaks to define it as the third group of anionic species peaks, and also making up the sum group of the first group of anionic species peaks and the second group of anionic species peaks to define it as the fourth group of anionic species peaks, next to that, making up the overlapping group between the first group of cationic species peaks and the second group of cationic species peaks to define it as the third group of cationic species peaks, and also making up the sum group of the first group of cationic species peaks and the second group of cationic species peaks to define it as the fourth group of cationic species peaks, with respect to each cationic species peak corresponding to each peak of said third group of anionic species peaks, calculating the relative peak intensity on the basis of said peak intensity of the highest cationic species peak identified at the Step 2 and, with respect to each anionic species peak of said third group of anionic species peaks, calculating the relative peak intensity on basis of said peak intensity of the highest anionic species peak identified at the Step 2, and comparing the two relative peak intensities with each other, identifying those corresponding cationic species peaks each having a relative intensity which is 3/2 or more relative to that of the peak of the third group of anionic species peaks to make up the fifth group of cationic species peaks therewith, meanwhile, identifying those anionic species peaks each having a relative intensity which is 3/2 or more relative to that of the corresponding cationic species peaks to make up the fifth group of anionic species peaks therewith, (Step 5) a step for identification of major ion species peaks caused by peptide fragments derived from target peptide to be analyzed, which comprises:

based on the m/z value of each cationic species peak of the fourth group of cationic species peaks, calculating the differences in the m/z value between each adjacent peaks thereof, meanwhile based on the m/z value of each anionic species peak of the fourth group of anionic species peaks, calculating the differences in the m/z value between each adjacent peaks thereof, with respect to each peak of the fifth group of cationic species peaks, examining said peak as to the following criteria:

(5a-1) a cationic species peak having a m/z value smaller than the m/z value of said peak by the molecular weight of 18 corresponding to loss of one water molecule is present in the fifth group of cationic species peaks;

(5a-2) a cationic species peak having a m/z value larger than the m/z value of said peak by the molecular weight excess equivalent to the formula weight of the acyl group used for said N-acylation protection is present in the fifth group of cationic species peaks and (5a-3) a cationic species peak having a ink value larger than the m/z value of said peak by the combination of the molecular weight decrease of 18 corresponding to loss of one water molecule and excess equivalent to the formula weight of the acyl group used for said N-acylation protection is present in the fifth group of cationic species peaks;

to select those cationic species peaks each satisfying at least one of said requirements (5a-1) to (5a-3), and then making up the sixth group of cationic species peaks therewith, meanwhile, with respect to each peak of the fifth group of anionic species peaks, examining said peak as to the following criteria:

(5b-1) an anionic species peak having a m/z value smaller than the ink value of said peak by the molecular weight of 18 corresponding to loss of one water molecule is present in the fifth group of anionic species peaks;

(5b-2) an anionic species peak having a m/z value larger than the m/z value of said peak by the molecular weight excess equivalent to the formula weight of the acyl group used for said N-acylation protection is present in the fifth group of anionic species peaks; and (5b-3) an anionic species peak having a ink value larger than the m/z value of said peak by the combination of the molecular weight decrease of 18 corresponding to loss of one water molecule and excess equivalent to the formula weight of the acyl group used for said N-acylation protection is present in the fifth group of anionic species peaks;

to select those anionic species peaks each satisfying at least one of said requirements (5b-1) to (5b-3), and then making up the sixth group of anionic species peaks therewith, judging that the seventh group of cationic species peaks are a group of cationic species peaks caused by peptide fragments per se derived from the target peptide to be analyzed, and judging also that the seventh group of anionic species peaks are a group of anionic species groups caused by peptide fragments per se derived from the target peptide to be analyzed, (Step 7) a step for identification of peptide fragments each having arginine at the C-terminus of its peptide chain, produced by the digestion treatment by trypsin, which comprises:

selecting each anionic species peak which corresponds to each cationic species peak of the seventh group of cationic species peaks, from the peaks being present in the fourth group of anionic species peaks, to make up the eighth group of anionic species peaks therewith, with respect to each peak of the eighth group of anionic species peaks, selecting group of anionic species peaks of which a m/z value difference from the fiducial m/z value of the said anionic species peak is found within the range of less than 200, based on set of the m/z value differences between adjacent peaks that are calculated in the Step 5, from the peaks being present in the fourth group of anionic species peaks, and confirming that there is not present, in the thus-selected groups, any peak whose m/z value difference between those peaks is equivalent to the formula weight of natural chain a-amino acid residue: —NH—CH(R)—CO— (R is a side chain of said amino acid residue) or of a-amino acid residue protected by acylation wherein the hydroxy group or amino group of its side chain is modified by substitution with the acyl group used in said N-acylation protection, and thus judging that said eighth group of anionic species peaks are the group of anionic species peaks from peptide fragments each having arginine at the C-terminus of its peptide chain, which are derived from the target peptide to be examined and produced by the treatment for digestion by trypsin, judging that the sixth group of cationic species peaks selected thereby are a group of cationic species peaks caused by peptide fragments derived from the target peptide to be analyzed, and judging also that the six group of anionic species peaks selected thereby are a group of anionic species peaks caused by peptide fragments derived from the target peptide to be analyzed, (Step 6) a step identification ion species peaks of peptide fragments per se derived from target peptide to be analyzed, which comprises:

with respect to each peak of the sixth group of cationic species peaks, in comparison with the relative intensities of its accompanying cationic species peaks that are relevant to at least one of said relationships (5a-1) to (5a-3) for said peak, selecting peaks whose relative intensities are superior to their accompanying cationic species peaks, and then from the group of the selected peaks, further selecting peaks which is not one of accompanying cationic species peaks that are relevant to at least one of said relationships (5a-1) to (5a-3) for other peak included in said group of the selected peaks and have an inferior relative intensity to other peak, and making up the seventh group of cationic species peaks therewith, meanwhile, with respect to each peak of the sixth group of anionic species peaks, in comparison with the relative intensities of its accompanying anionic species peaks that are relevant to at least one of said relationships (5b-1) to (5b-3) for said peak, selecting peaks whose relative intensities are superior to their accompanying anionic species peaks, and then from the group of the selected peaks, further selecting peaks which is not one of accompanying anionic species peaks that are relevant to at least one of said relationships (5b-1) to (5b-3) for other peak included in said group of the selected peaks and have an inferior relative intensity to other peak, and making up the seventh group of anionic species peaks therewith, (Step 8) a step for identification of group of C-terminal side peptide fragments that are produced from target peptide and a series of reaction products thereof by the treatment for digestion by trypsin, which comprises:

with respect to each anionic species peak of the seventh group of anionic species peaks, selecting group of anionic species peaks of which a m/z value difference from the fiducial m/z value of the said anionic species peak is found within the range of less than 200, based on set of the m/z value differences between adjacent peaks that are calculated in the Step 5, from the peaks being present in the fourth group of anionic species peaks, and identifying those anionic species peaks being included in the seventh group of anionic species group, for which there is present, in the thus-selected groups, a peak whose m/z value difference between those peaks is equivalent to the formula weight of natural chain a-amino acid residue: —NH—CH(R)—CO— (R is a side chain of said amino acid residue) or of a-amino acid residue protected by acylation wherein the hydroxy group or amino group of its side chain is modified by substitution with the acyl group used in said N-acylation protection, and then making up the ninth group of anionic species peaks therewith, forming the summed-up group of each anionic species peak of the ninth group of anionic species peaks and each of said anionic species peaks being present in the fourth group of anionic species peaks whose m/z value difference between those peaks has been confirmed in said operation of identification, to be equivalent to the formula weight of amino acid residue, and then defining the group as the tenth group of anionic species peaks, from said largest m/z peak, selecting, in the tenth group of anionic species peaks, an anionic species peak having the largest m/z value, successively identifying, from the tenth group of anionic species peaks, a series of anionic specie peaks each having a m/z value difference between peaks that is equal to the formula weight of amino acid residue, by using, as the finducial point, the m/z value which the anionic species peak with the largest m/z value shows, and then judging that the series of thus-identified peaks as the group consisting of the anionic species peak of C-terminal peptide fragment derived from the original peptide and the anionic species peaks of C-terminal peptides derived from a series of reaction products that are obtained by successive release of C-terminal amino acids of original peptide, which fragments are all produced by the treatment for digestion by trypsin, and (Step 9) a step for assignment of C-terminal amino acid sequence, which comprises:

according to a series of said formula weights of amino acid residues that are corresponding to the m/z differences between the anionic species peaks, which have been sequentially assigned in Step 8, based on the identified group consisting of the anionic species peaks of C-terminal peptide fragments that are derived from the original peptide and a series of reaction products resulted from successive release of C-terminal amino acids, which fragments are all produced by the treatment for digestion by trypsin, identifying the sequence of partial amino acids which have been released successively from the C-terminus thereof, wherein the mass spectra used to measure the decreases in molecular weight associated with said successive release of the C-terminal amino acids, are said results of the molecular weight measurements based on the cationic species of $(M+H)^+$ as well as of molecular weight measurements based on the anionic species of $(M-H)^-$, by means of MALDI-TOF-MS, wherein said process for releasing the C-terminal amino acids successively, as for the sample of the target peptide that has been subjected to separation by gel electrophoresis and is maintained in a state that it is bound on a polyacrylamide gel carrier, comprises the following steps:

a step of removing the water solvent impregnated into the polyacrylamide gel carrier by dilution with use of a polar aprotic solvent having no solvency for the polyacrylamide gel substance and having affinity for water, to conduct a dehydration treatment for the polyacrylamide gel carrier, a pretreatment step for the target peptide sample that is still bound on the polyacrylamide gel carrier after carrying out said step for dehydration treatment, in which pretreatment step applying N-acylation protection by the acyl group derived from the alkanoic acid constituting said alkanoic acid anhydride, to the N-terminal amino group of the target peptide with use of a solution of an alkanoic acid anhydride dissolved in a dipolar aprotic solvent that is capable of infiltrating into the polyacrylamide gel substance and keeping it in a swollen state is conducted by immersing, at a temperature selected in a range of 30° C. to 80° C., the polyacrylamide gel carrier in the solution of the alkanoic acid anhydride to allow the alkanoic acid anhydride to act on the target peptide sample that is kept in the bound state; and then removal of said solution is carried out by dilution with use of a polar aprotic solvent having no solvency for the polyacrylamide gel substance and having affinity for the alkanoic acid anhydride as well as the dipolar aprotic solvent, to conduct termination of the N-acylation reaction and removal of the reaction reagent therefor;

a step of treatment as for the target peptide sample bound on the polyacrylamide gel carrier, after the pretreatment step of N-acylation protection, comprising steps of immersing, at a temperature selected in a range of 30° C. to 80° C., the polyacrylamide gel carrier in a mixed solution of an alkanoic acid anhydride added with a small amount of a perfluoroalkanoic acid in relative ratio thereto dissolved in a dipolar aprotic solvent that is capable of infiltrating into the polyacrylamide gel substance and keeping it in a swollen state, to allow the alkanoic acid anhydride and in the presence of the small amount of the perfluoroalkanoic acid to act on the target peptide sample being kept in the bound state; thereby, successive release of the C-terminal amino acids results from the reaction process with use of the mixed solution in which formed is a 5-oxazolone-ring structure represented by the following general formula (III):

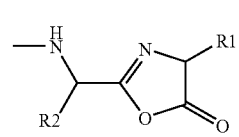

(III)

wherein R1 is a side chain of the C-terminal amino acid of the peptide and R2 is a side chain of the amino acid residue positioned just before the C-terminal amino acid, followed by the cleavage of the 5-oxazolone-ring, wherein the formation of the 5-oxazolone structure and the cleavage of the 5-oxazolone ring is carried out in parallel at the same temperature by using the alkanoic acid anhydride in the presence of the small amount of the perfluoroalkanoic acid to successively release the C-terminal amino acids, and removing the mixed solution used in the reaction for successive release of C-terminal amino acids, by dilution with use of a polar aprotic solvent having no solvency for the polyacrylamide gel substance and having affinity for the perfluoroalkanoic acid and the alkanoic acid anhydride as well as the dipolar aprotic solvent, to conduct termination of the releasing reaction and removal of the reaction reagents therefor; and an additional step for hydrolysis treatment and then redehydration treatment, in which step the hydrolysis treatment for said mixture comprising a series of reaction products obtained by the reaction for successive release of C-terminal amino acids is conducted by immersing the polyacrylamide gel carrier in an aqueous solution dissolving a basic nitrogen-containing aromatic compound or a tertiary amine compound therein to allow a water molecule to act, in the presence of said basic nitrogen-containing organic compound, on said peptides of the reaction products being still bound on the polyacrylamide gel carrier, wherein the hydrolysis reaction is carried out by using the water molecule in the presence of the basic, nitrogen-containing, aromatic compound or the tertiary amine compound, whereby the mixture containing the series of reaction products having a carboxyl group at their C-terminal as well as the remains of the original peptide having a carboxyl group at its C-terminus are prepared as the sample to be used for the analysis by means of MALDI-TOF-MS, and then the redehydration treatment for the polyacrylamide gel carrier is performed by removing said aqueous solution infiltrated into the polyacrylamide gel carrier by dilution with use of a polar aprotic solvent having no solvency for the polyacrylamide gel substance and having affinity for water; and wherein said step of measuring the decreases in molecular weight associated with the successive release of the C-terminal amino acids employs a method which comprises:

allowing trypsin being soluble in a buffer solution to act on said mixture, after the re-dried up treatment, containing a series of the reaction products finished by hydrolysis treatment to carry out the treatment for the enzymatic digestion specific to trypsin of said peptide chain which holds N-acylation protection as for the N-terminal amino group of the peptide chain as well as to the amino group on the side chain of the lysine residue that may be contained in the peptide chain, and thereby, conducting selective cleavage of the C-terminal side peptide bond of each arginine residue that present in the peptide chain to complete peptide fragmentization, applying a desalting treatment to remove the buffer solution component, followed by recovering and drying the peptide fragments after the digestion treatment by trypsin, followed by drying, next, conducting, as for the dried mixture containing said peptide fragments recovered after the digestion treatment by trypsin, molecular weight measurement for the cationic species of $(M+H)^+$ as well as molecular weight measurement for anionic species of $(M-H)^-$, both of which are generated from the ionization treatment, by means of MALDI-TOF-MS.

2. A method for analysis claimed in claim 1, wherein, in said combination of a perfluoroalkanoic acid and an alkanoic acid anhydride, used for the formation of 5-oxazolone structure and subsequently for the reaction for release of C-terminal amino acids in association with cleavage of the 5-oxazolone ring, there is used, as the alkanoic acid anhydride, a symmetric anhydride of an alkanoic acid having 2 to 4 carbon atoms.

3. A method for analysis claimed in claim 2, wherein there is used, as the symmetric anhydride of an alkanoic acid of 2 to 4 carbon acids, a symmetric anhydride of a linear-chain alkanoic acid having 2 to 4 carbon atoms.

4. A method for analysis claimed in claim 1, wherein, in said combination of a perfluoroalkanoic acid and an alkanoic acid anhydride, used for the formation of 5-oxazolone structure and subsequently for the reaction for release of C-terminal amino acids in association with cleavage of the 5-oxazolone ring, there is used acetic anhydride as the alkanoic acid anhydride.

5. A method for analysis claimed in claim 1, wherein, in said combination of a perfluoroalkanoic acid and an alkanoic acid anhydride, used for the formation of 5-oxazolone structure and subsequently for the reaction for release of C-terminal amino acids in association with cleavage of the 5-oxazolone ring, there is used, as the perfluoroalkanoic acid, a perfluoroalkanoic acid of which pKa is in a range of 0.3 to 2.5.

6. A method for analysis claimed in claim 1, wherein, in said combination of a perfluoroalkanoic acid and an alkanoic acid anhydride, used for the formation of 5-oxazolone structure and subsequently for the reaction for release of C-terminal amino acids in association with cleavage of the 5-oxazolone ring, there is used, as the perfluoroalkanoic acid, a perfluoroalkanoic acid having 2 to 4 carbon atoms.

7. A method for analysis claimed in claim 1, wherein, in said combination of a perfluoroalkanoic acid and an alkanoic acid anhydride, used for the formation of 5-oxazolone structure and subsequently for the reaction for release of C-terminal amino acids in association with cleavage of the 5-oxazolone ring, the content ratio of the alkanoic acid anhydride and the perfluoroalkanoic acid is selected in a range of 1 to 20 volumes per 100 volumes of the alkanoic acid anhydride.

8. A method for analysis claimed in claim 1, wherein, there is used, as the alkanoic acid anhydride used in said pretreatment step of applying N-acylation protection, a symmetric anhydride of an alkanoic acid having 2 to 4 carbon atoms.

9. A method for analysis claimed in claim 8, wherein there is used, as the symmetric anhydride of an alkanoic acid having 2 to 4 carbon atoms, a symmetric anhydride of a linear-chain alkanoic acid having 2 to 4 carbon atoms.

10. A method for analysis claimed in claim 1, wherein, as the alkanoic acid anhydride used in said pretreatment step of applying N-acylation protection, there is used acetic anhydride.

11. A method for analysis claimed in claim 1, wherein there is used acetic anhydride as the alkanoic acid anhydride used in said pretreatment step of applying N-acylation protection and also as the alkanoic acid anhydride employed in the combination of a perfluoroalkanoic acid and an alkanoic acid anhydride, used for the formation of 5-oxazolone structure and subsequently for the reaction for release of C-terminal amino acids in association with the cleavage of the 5-oxazolone ring.

12. A method for analysis claimed in claim 1, wherein, after Step 1 being the step for identification of internal standard peaks derived from trypsin, there is employed a step for noise removal and smoothening treatment, which comprises:

with respect to each cationic species peak of the peptide fragments derived from trypsin autolysis, identified in the result of the molecular weight measurements for cationic species, determining its peak m/z value and calculating its apparent full-width of half maximum, by using said apparent full-width of half maximum calculated as the datum width, conducting, for the spectra of molecular weight measurement for cationic species peak, a treatment of removing noise peaks each showing an apparent full-width of half maximum which is ¼ or less of the datum width, then, conducting, for the spectra after the treatment for noise removal, a smoothing treatment such that the asymmetry of peak shape and the integrated intensity of peak as for each cationic species peak of the peptide fragments derived from trypsin autolysis can be well-retained, which are evaluated based on the determined peak m/z values and the two m/z values used in calculation of said apparent full-width of half maximum and, meanwhile, with respect to each anionic species peak of the peptide fragments derived from trypsin autolysis, identified in the result of the molecular weight measurements for anionic species, determining its peak m/z value and calculating its apparent full-width of half maximum, by using said apparent full-width of half maximum calculated as the datum width, conducting, for the spectra of molecular weight measurement for anionic species peak, a treatment of removing noise peaks each showing an apparent full-width of half maximum which is ¼ or less of the datum width, conducting, for said anionic species peak, a treatment of removing noise peaks each having an apparent half width which is ¼ or less of the above-calculated apparent half width, then, conducting, for the spectra after the treatment for noise removal, a smoothing treatment such that the asymmetry of peak shape and the integrated intensity of peak as for each anionic species peak of the peptide fragments derived from trypsin autolysis can be well-retained, which are evaluated based on the determined peak m/z values and the two m/z values used in calculation of said apparent full-width of half maximum.

13. A method for analysis claimed in claim 1 or 12, wherein, after Step 1 being the step for identification of internal standard peaks derived from trypsin, there is employed a step for systematic error correction for peak m/z value, which comprises:

with respect to the cationic species peak of each peptide fragment derived from the trypsin autolysis, identified in the result of molecular weight measurements based on cationic species, calculating the m/z value of said cationic species based on the known molecular weight of said peptide fragment, comparing it with the peak m/z value measured therefor on the spectra and, based on their difference, making a correction of systematic error for the m/z value measured in spectra of the molecular weight measurements based on cationic species, meanwhile, with respect to the anionic species peak of each peptide fragment derived from the trypsin autolysis, identified in the result of molecular weight measurements based on anionic species, calculating the m/z value of said anionic species based on the known molecular weight of said peptide fragment, comparing it with the peak m/z value measured therefor on the spectra and, based on their difference, making a correction of systematic error for the m/z value measured in spectra of the molecular weight measurements based on anionic species.

14. A method for analysis claimed in claim 1, wherein, in Step 9 being the step for assignment of C-terminal amino acid sequence, when the assigned sequence of partial amino acids which have been released successively from the C-terminus of original peptide, has arginine as the C-terminal amino acid, there is optionally employed a step for reconfirming the assignment such that its C-terminal fragment is a peptide fragment having arginine at the C-terminus of its peptide chain, which comprises:

with respect to the anionic species peak having the largest m/z value in the tenth group of anionic species peaks, which is used as the fiducial peak for the assignment of partial amino acid sequence, finding, in the result of the molecular weight measurement based on cationic species, a cationic species peak corresponding thereto, as for the corresponding cationic species peak, selecting group of cationic species peaks of which a m/z value is larger than the fiducial m/z value of the said anionic species peak and the m/z value difference therebetween is found within the range of less than 200, based on set of the m/z value differences between adjacent peaks that are calculated in the Step 5, from the peaks being present in the fourth group of cationic species peaks, and confirming that there is not present, in the thus-selected groups, any peak whose m/z value difference between those peaks is equivalent to the formula weight of natural chain a-amino acid residue: —NH—CH(R)—CO— (R is a side chain of said amino acid residue) or of a-amino acid residue protected by acylation wherein the hydroxy group or amino group of its side chain is modified by substitution with the acyl group used in said N-acylation protection.

* * * * *